US009181340B2

(12) United States Patent
St. Croix et al.

(10) Patent No.: US 9,181,340 B2
(45) Date of Patent: Nov. 10, 2015

(54) TEM8 ANTIBODIES, CONJUGATES THEREOF, AND THEIR USE

(75) Inventors: Brad St. Croix, Frederick, MD (US); Tony Fleming, Stow, MA (US); Amit Chaudhary, Frederick, MD (US); Saurabh Saha, Leawood, KS (US); Xiaoyan Michelle Zhang, Lexington, MA (US); Rou-fun Kwong, Cambridge, MA (US); Mary Beth Hilton, Thurmont, MD (US)

(73) Assignees: The United States of America, as represented by the Secretary, Department of Health and Human Services, Washington, DC (US); Novartis AG, Basel (CH)

( * ) Notice: Subject to any disclaimer, the term of this patent is extended or adjusted under 35 U.S.C. 154(b) by 0 days.

(21) Appl. No.: 14/126,372

(22) PCT Filed: Jun. 13, 2012

(86) PCT No.: PCT/US2012/042315
§ 371 (c)(1),
(2), (4) Date: Dec. 13, 2013

(87) PCT Pub. No.: WO2012/174160
PCT Pub. Date: Dec. 20, 2012

(65) Prior Publication Data
US 2014/0134179 A1    May 15, 2014

Related U.S. Application Data

(60) Provisional application No. 61/496,986, filed on Jun. 14, 2011, provisional application No. 61/496,737, filed on Jun. 14, 2011.

(51) Int. Cl.
C07K 16/30 (2006.01)
C07K 16/28 (2006.01)
A61K 39/00 (2006.01)

(52) U.S. Cl.
CPC ............ *C07K 16/28* (2013.01); *C07K 16/2863* (2013.01); *C07K 16/30* (2013.01); *A61K 2039/505* (2013.01); *A61K 2039/507* (2013.01); *C07K 2317/21* (2013.01); *C07K 2317/24* (2013.01); *C07K 2317/33* (2013.01); *C07K 2317/55* (2013.01); *C07K 2317/732* (2013.01); *C07K 2317/734* (2013.01); *C07K 2317/76* (2013.01)

(58) Field of Classification Search
None
See application file for complete search history.

(56) References Cited

U.S. PATENT DOCUMENTS

| 6,543,210 | B2 | 4/2003 | Rostoucher |
| 7,074,913 | B2 | 7/2006 | Young et al. |
| 7,393,932 | B2 | 7/2008 | Carson-Walter et al. |
| 2003/0017157 | A1 | 1/2003 | St. Croix et al. |
| 2003/0220287 | A1 | 11/2003 | Phillips et al. |
| 2005/0196407 | A1 | 9/2005 | Young et al. |
| 2005/0281830 | A1 | 12/2005 | Morrow et al. |
| 2006/0083746 | A1 | 4/2006 | Young et al. |
| 2007/0020271 | A1 | 1/2007 | Teicher et al. |
| 2007/0028314 | A1* | 2/2007 | Komori et al. .............. 800/18 |

FOREIGN PATENT DOCUMENTS

| CN | 101591395 | 12/2009 |
| WO | WO 02/46228 | 6/2002 |
| WO | WO 2008/000734 | 1/2008 |
| WO | WO 2012/065161 | 5/2012 |
| WO | WO 2012/172495 | 12/2012 |

OTHER PUBLICATIONS

Carson-Walter, el al. "Cell surface tumor endothelial markers are conserved in mice and humans." *Cancer research*, 61.18 (2001): 6649-6655.
Chaudhary, et al. "TEM8/ANTXR1 blockade inhibits pathological angiogenesis and potentiates tumoricidal responses against multiple cancer types." *Cancer cell*, 21.2 (2012): 212-226.
Cullen, et al. "Host-derived tumor endothelial marker 8 promotes the growth of melanoma." *Cancer research*, 69.15 (2009): 6021-6026.
Davies, et al. "Elevated levels of tumour endothelial marker-8 in human breast cancer and its clinical significance." *International journal of oncology*, 29.5 (2006): 1311-1317.
Fernando, et al. "Targeting tumor endothelial marker 8 in the tumor vasculature of colorectal carcinomas in mice." *Cancer research*, 69.12 (2009): 5126-5132.
International Search Report for application No. PCT/IB2012/052990, mailed by the International Searching Authority on Oct. 24, 2012.
Nanda, et al. "TEM8 interacts with the cleaved C5 domain of collagen α3 (VI)." *Cancer research*, 64.3 (2004): 817-820.
Nanda, et al. "Tumor endothelial markers: new targets for cancer therapy." *Current opinion in oncology*, 16.1 (2004): 44-49.
St. Croix, et al. "Genes expressed in human tumor endothelium." *Science*, 289.5482 (2000): 1197-1202.
Yang, el al. "The cell surface structure of tumor endothelial marker 8 (TEM8) is regulated by the actin cytoskeleton," *Biochimica et Biophysica Acta (BBA)- Molecular Cell Research*, 1813.1 (2011): 39-49.

(Continued)

*Primary Examiner* — Brad Duffy
*Assistant Examiner* — Nelson B Moseley, II
(74) *Attorney, Agent, or Firm* — Klarquist Sparkman, LLP

(57) ABSTRACT

Antibodies that specifically bind TEM8 protein, and conjugates thereof, are disclosed herein. In some examples the conjugates and antibodies are useful for methods of detecting and treating pathogenic angiogenesis. In other examples the conjugates and antibodies are useful for methods of detecting and treating cancer. In additional examples, the conjugates and antibodies are useful for methods of decreasing binding of Anthrax protective antigen to a cell.

37 Claims, 26 Drawing Sheets

(56) References Cited

OTHER PUBLICATIONS

Li, et al. "The inhibition of the interaction between the anthrax toxin and its cellular receptor by an anti-receptor monoclonal antibody." *Biochemical and biophysical research communications* 385 (2009): 591-595.

Carter, et al. "Antibody-drug conjugates for cancer therapy." *The Cancer Journal*, 14.3 (2008): 154-169.

Cryan, et al. "Targeting the anthrax receptors, TEM-8 and CMG-2, for anti-angiogenic therapy." *Frontiers in bioscience: a journal and virtual library*, 16 (2011): 1574-1588.

McCarron, et al. "Antibody conjugates and therapeutic strategies." *Molecular interventions*, 5.6 (2005): 368-380.

Nanda, et al. "Identification of a binding partner for the endothelial cell surface proteins TEM7 and TEM7R." *Cancer research*, 64.23 (2004): 8507-8511.

Scobie, et al. "Human capillary morphogenesis protein 2 functions as an anthrax toxin receptor." *Proceedings of the National Academy of Sciences*, 100.9 (2003): 5170-5174.

Zhu, et at. "Quantitative high throughput screening identifies inhibitors of anthrax-induced cell death:" *Bioorg Med Chem.*, 17(14) (2009): 5139-5145.

Frankel, et al. "TEM8 Targeted Cancer Therapy." *Anti-cancer agents in medicinal chemistry*, 11.10 (2011): 983-992.

Lonberg. "Fully human antibodies from transgenic mouse and phage display platforms." *Current opinion in immunology*, 20.4 (2008): 450-459.

Rmali, et al. "Identification of microvessels using tumour endothelial marker-8 (TEM-8) in breast cancer and its correlation with tumour progression." *Breast Cancer Research and Treatment*, vol. 88. 233 (2004): p. S144.

Rmali, et al. "Tumour endothelial marker 8 (TEM-8) in human colon cancer and its association with tumour progression." *European Journal of Surgical Oncology* (*EJSO*), 30.9 (2004): 948-953.

* cited by examiner

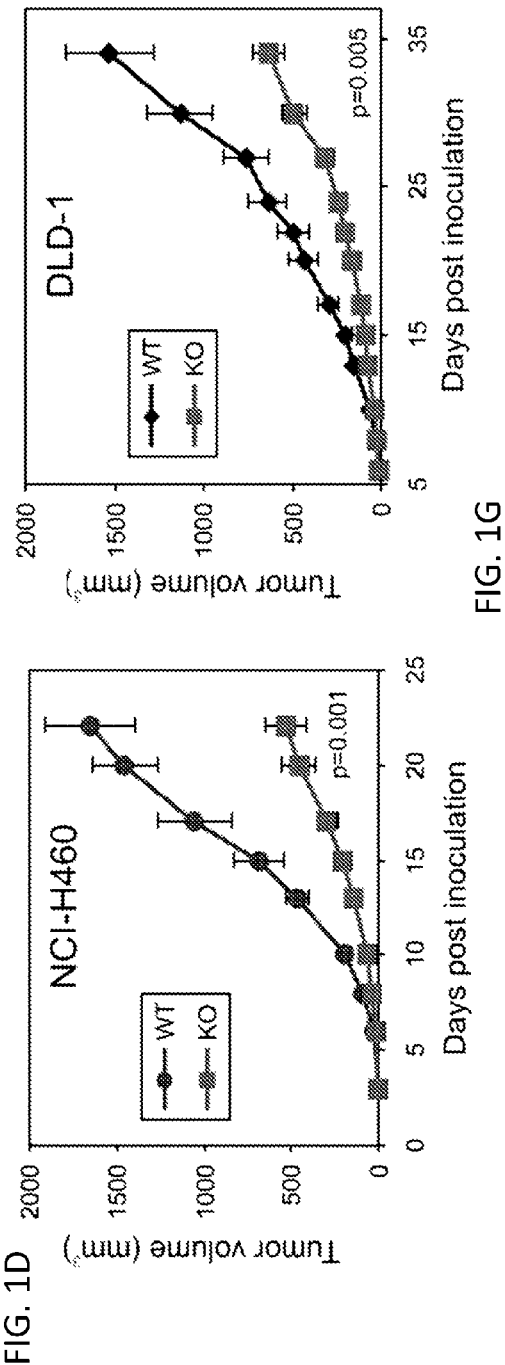
FIG. 1D
FIG. 1E
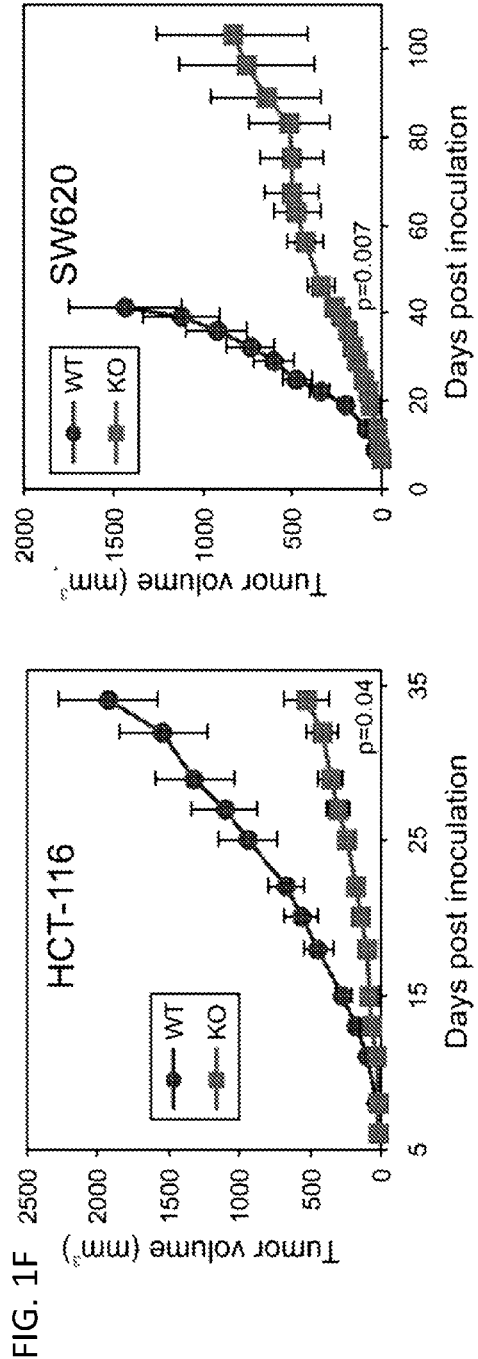
FIG. 1F
FIG. 1G

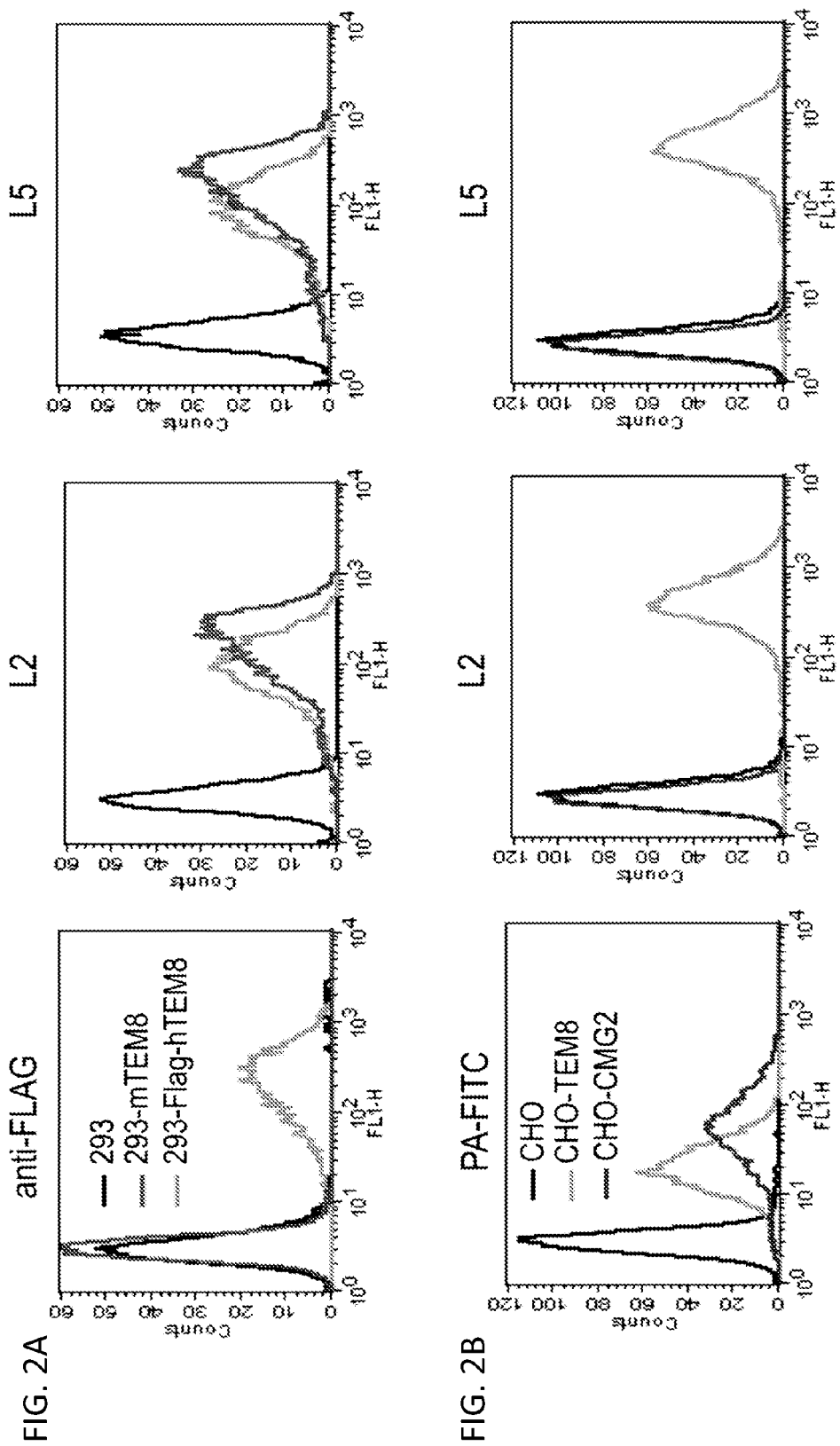

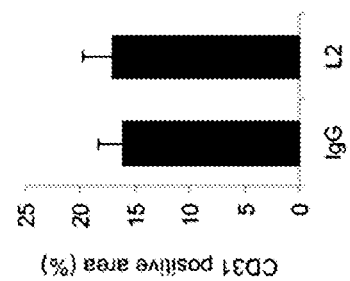
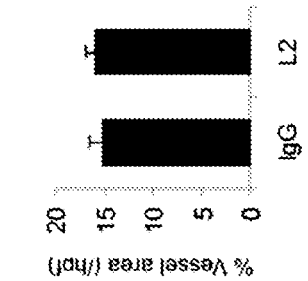
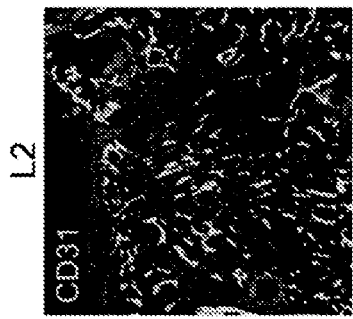
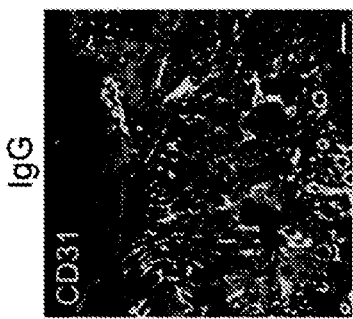
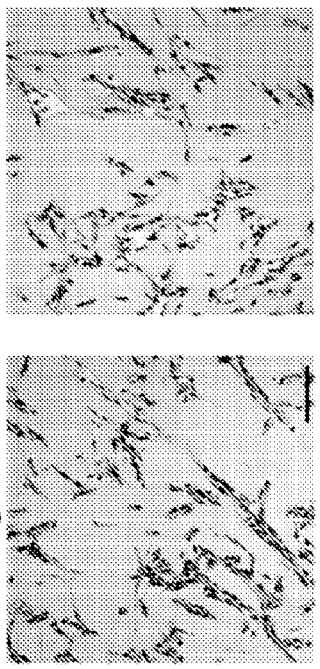
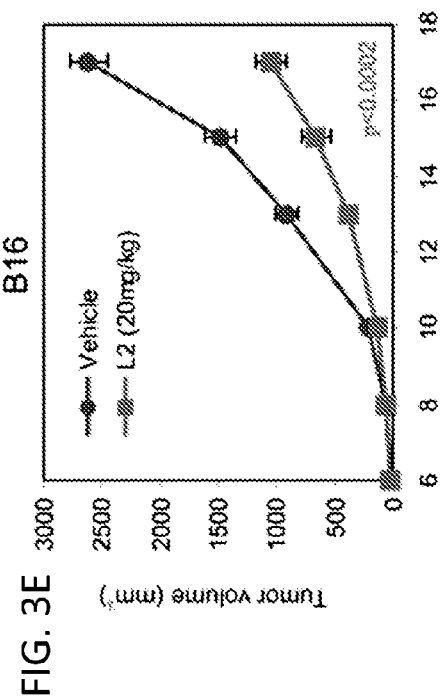
FIG. 3E
FIG. 3G
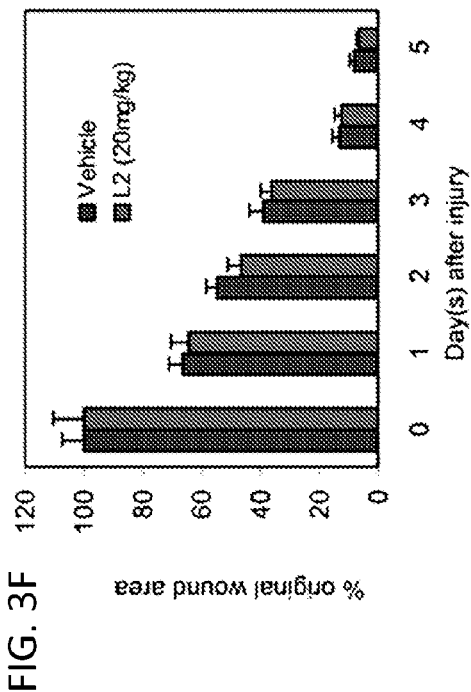
FIG. 3F
FIG. 3H

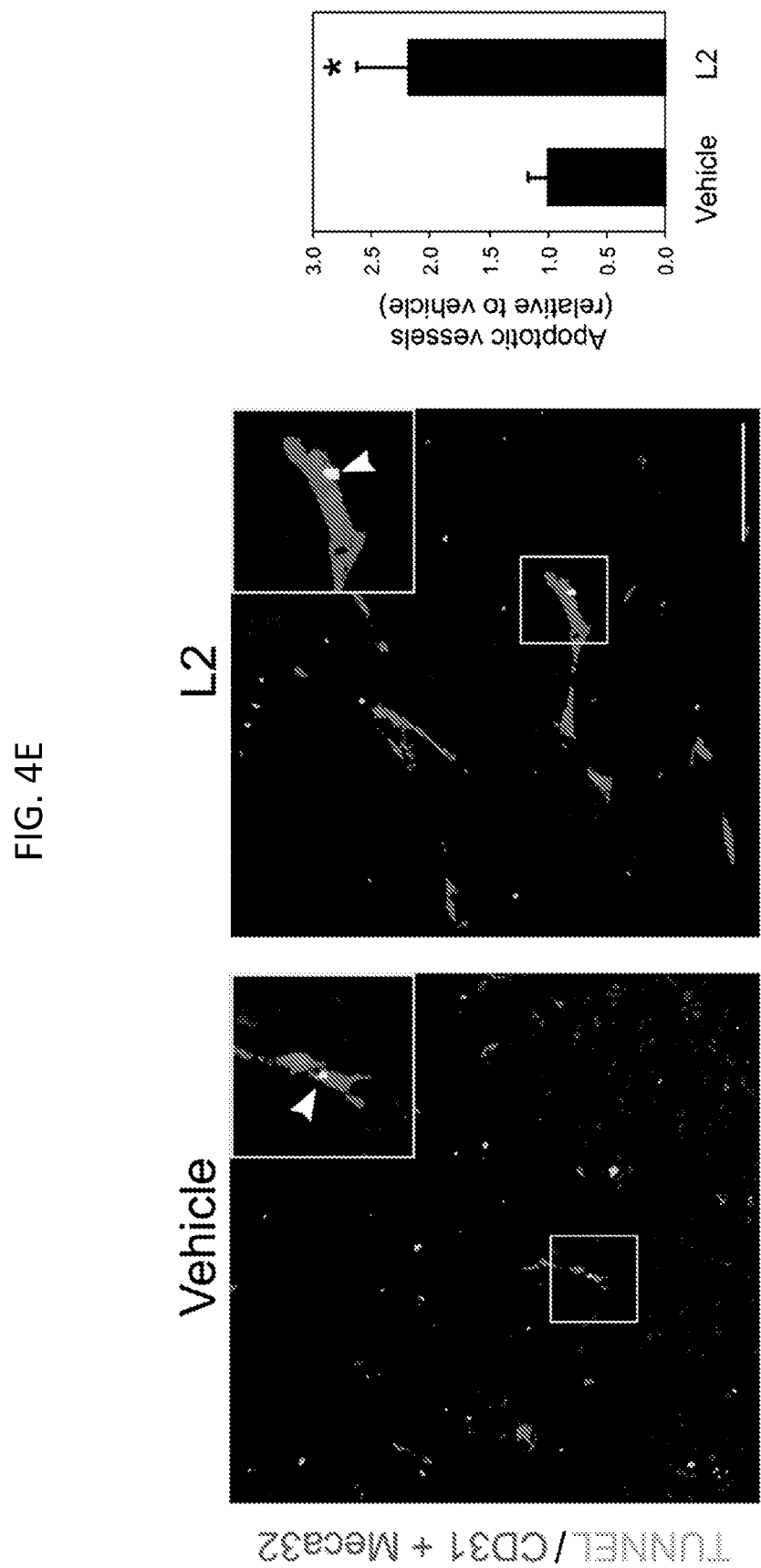

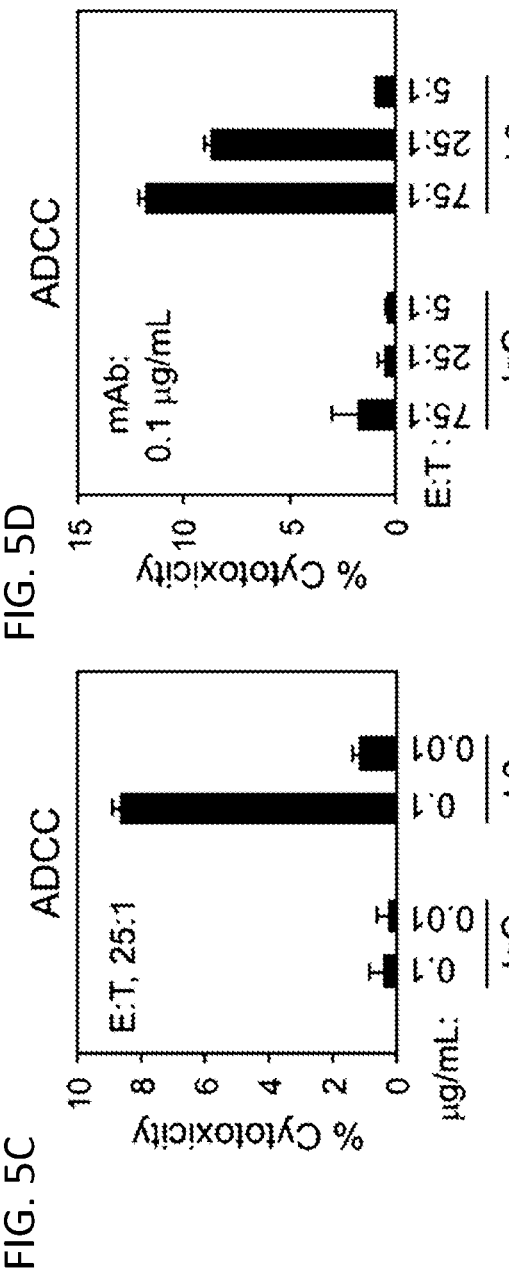
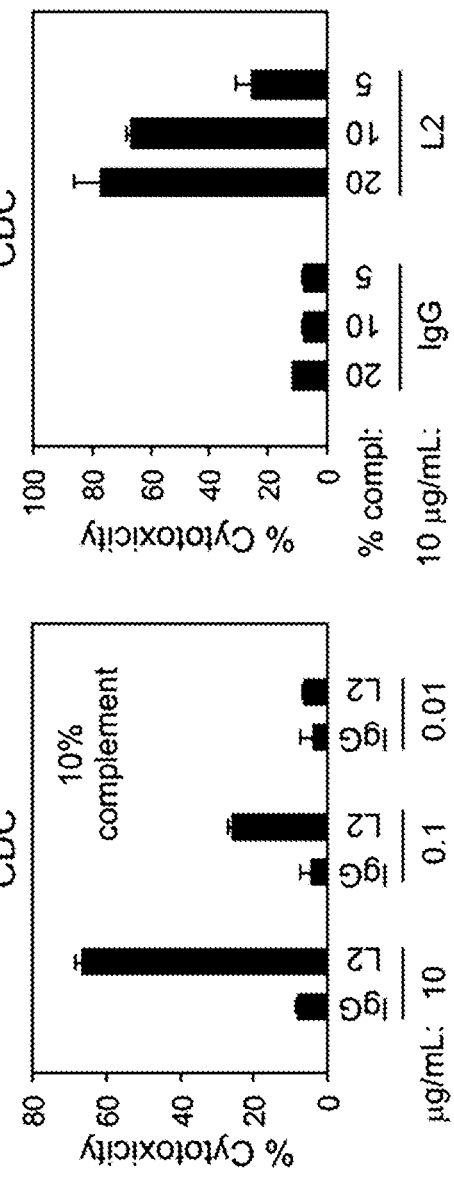
FIG. 5C
FIG. 5D
FIG. 5E
FIG. 5F

FIG. 8A  EC₅₀ (nM) for binding of anti-TEM8 Fabs to recombinant TEM8-ED by ELISA

| | L1 | L2 | L3 | L5 | 1D2 |
|---|---|---|---|---|---|
| hTEM8 | 0.18 | 0.24 | 0.33 | 0.24 | 7.6 |
| mTEM8 | 0.21 | 0.28 | 0.36 | 0.22 | 31.2 |

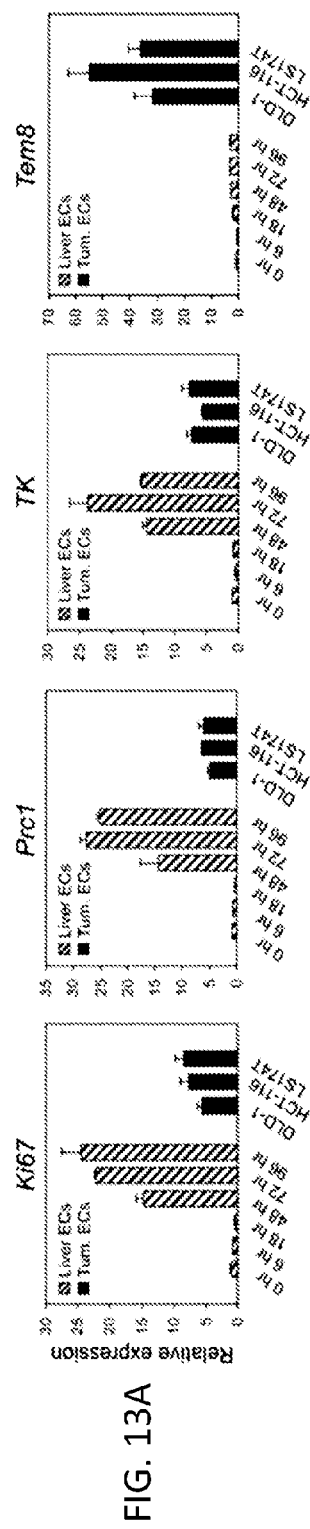
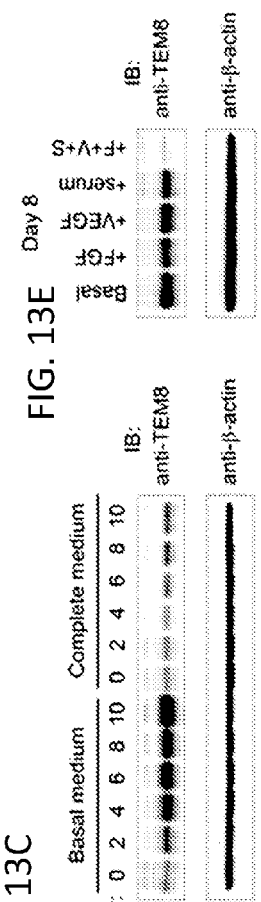
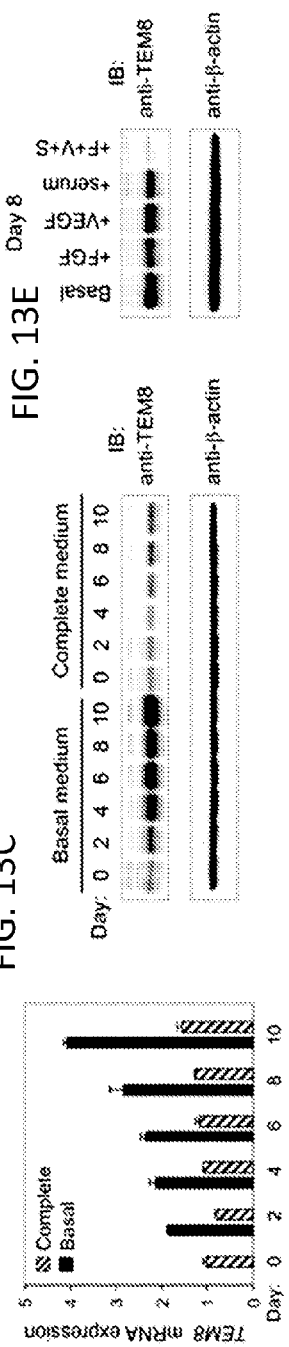
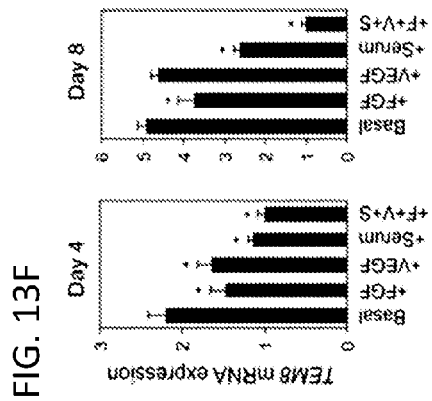
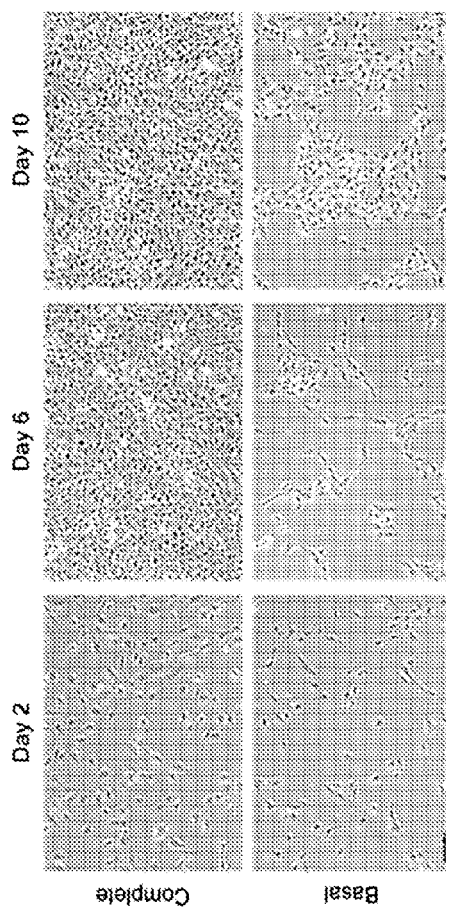
FIG. 13A
FIG. 13B
FIG. 13C
FIG. 13D
FIG. 13E
FIG. 13F

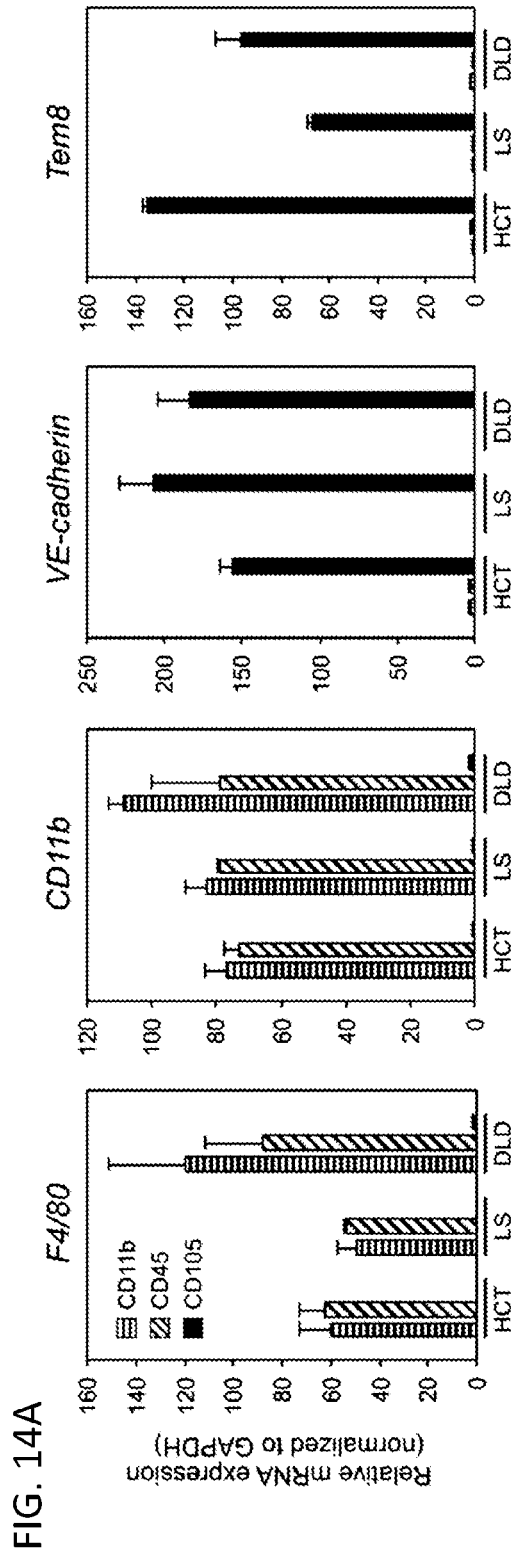
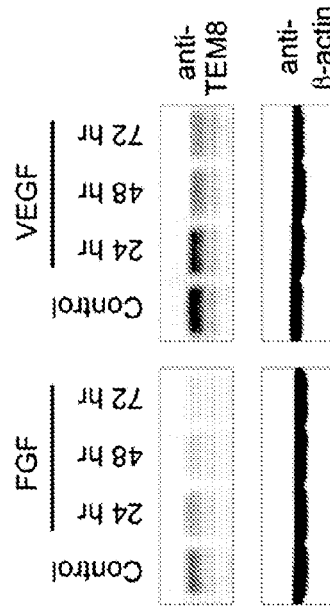
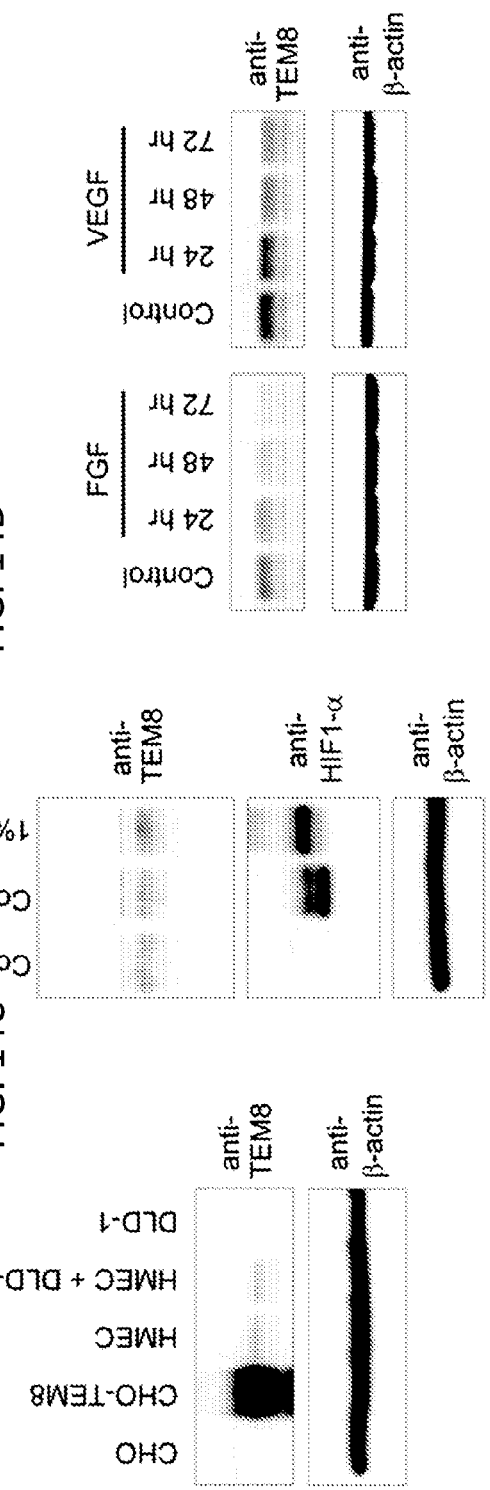
FIG. 14A
FIG. 14B
FIG. 14C
FIG. 14D

SEQUENCE LISTING

```
<160> NUMBER OF SEQ ID NOS: 48

<210> SEQ ID NO 1
<211> LENGTH: 117
<212> TYPE: PRT
<213> ORGANISM: Artificial Sequence
<220> FEATURE:
<223> OTHER INFORMATION: Antibody sequence

<400> SEQUENCE: 1

Gln Val Gln Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Gly Gly Val Ser Trp Ile Arg Gln Pro Pro Gly Lys Ala Leu Glu
        35                  40                  45

Trp Leu Ala His Ile Tyr Ser Asn Asp Asp Lys Ser Tyr Ser Thr Ser
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Gly Gly Tyr Phe Leu Asp Tyr Trp Gly Gln Gly Thr Leu
            100                 105                 110

Val Thr Val Ser Ser
        115

<210> SEQ ID NO 2
<211> LENGTH: 115
<212> TYPE: PRT
<213> ORGANISM: Artificial Sequence
```

<220> FEATURE:
<223> OTHER INFORMATION: Antibody sequence

<400> SEQUENCE: 2

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Ser Tyr
            20                  25                  30

Ala Met Ser Trp Val Arg Gln Ala Pro Gly Lys Gly Leu Glu Trp Val
        35                  40                  45

Ser Leu Ile Ser Ser Gly Ser Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Ala Gly Phe Lys Phe Asp Asn Trp Gly Gln Gly Thr Leu Val Thr
            100                 105                 110

Val Ser Ser
        115
```

<210> SEQ ID NO 3
<211> LENGTH: 121
<212> TYPE: PRT
<213> ORGANISM: Artificial Sequence
<220> FEATURE:
<223> OTHER INFORMATION: Antibody sequence

<400> SEQUENCE: 3

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Thr Asn
            20                  25                  30

Gly Ala Ala Trp Gly Trp Ile Arg Gln Ser Pro Gly Arg Gly Leu Glu
        35                  40                  45

Trp Leu Gly Arg Ile Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Met Pro Gly Gly Phe Leu Phe Asp Leu Trp Gly
            100                 105                 110

Gln Gly Thr Leu Val Thr Val Ser Ser
        115                 120
```

<210> SEQ ID NO 4
<211> LENGTH: 119
<212> TYPE: PRT
<213> ORGANISM: Artificial Sequence
<220> FEATURE:
<223> OTHER INFORMATION: Antibody sequence

<400> SEQUENCE: 4

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Ser Tyr
            20                  25                  30
```

Gly Leu Ser Trp Val Arg Gln Ala Pro Gly Lys Gly Leu Glu Trp Val
            35                  40                  45

Ser Asn Ile Ser Ser Asn Gly Ser Tyr Thr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Gly Tyr Gly Leu Phe Asp Val Trp Gly Gln Gly Thr Leu
            100                 105                 110

Val Thr Val Ser Ser Val Leu
            115

<210> SEQ ID NO 5
<211> LENGTH: 118
<212> TYPE: PRT
<213> ORGANISM: Artificial Sequence
<220> FEATURE:
<223> OTHER INFORMATION: Antibody sequence

<400> SEQUENCE: 5

Gln Val Gln Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Ser Trp Ile Arg Gln Pro Pro Gly Lys Ala Leu Glu
            35                  40                  45

Trp Leu Ala His Ile Asn Leu Asp Asp Asp Lys Tyr Tyr Ser Thr Ser
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Gly Gly Tyr Gly Asp Met Asp Val Trp Gly Gln Gly Thr
            100                 105                 110

Leu Val Thr Val Ser Ser
            115

<210> SEQ ID NO 6
<211> LENGTH: 106
<212> TYPE: PRT
<213> ORGANISM: Artificial Sequence
<220> FEATURE:
<223> OTHER INFORMATION: Antibody sequence

<400> SEQUENCE: 6

Asp Ile Glu Leu Thr Gln Pro Pro Ser Val Ser Val Ala Pro Gly Gln
1               5                   10                  15

Thr Ala Arg Ile Ser Cys Ser Gly Asp Asn Ile Gly Gly Ile Tyr Val
            20                  25                  30

His Trp Tyr Gln Gln Lys Pro Gly Gln Ala Pro Val Leu Val Ile Tyr
            35                  40                  45

Ala Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Tyr Asp Ile Thr Ser Leu Val
                85                  90                  95

```
Phe Gly Gly Gly Thr Lys Leu Thr Val Leu
            100                 105

<210> SEQ ID NO 7
<211> LENGTH: 108
<212> TYPE: PRT
<213> ORGANISM: Artificial Sequence
<220> FEATURE:
<223> OTHER INFORMATION: Antibody sequence

<400> SEQUENCE: 7

Asp Ile Glu Leu Thr Gln Pro Pro Ser Val Ser Val Ala Pro Gly Gln
1               5                   10                  15

Thr Ala Arg Ile Ser Cys Ser Gly Asp Ser Ile Pro Asn Tyr Ser Val
            20                  25                  30

Ser Trp Tyr Gln Gln Lys Pro Gly Gln Ala Pro Val Leu Val Ile Tyr
        35                  40                  45

Ala Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Tyr Asp Asn Thr Ser Pro Asp
                85                  90                  95

Leu Val Phe Gly Gly Gly Thr Lys Leu Thr Val Leu
            100                 105

<210> SEQ ID NO 8
<211> LENGTH: 106
<212> TYPE: PRT
<213> ORGANISM: Artificial Sequence
<220> FEATURE:
<223> OTHER INFORMATION: Antibody sequence

<400> SEQUENCE: 8

Asp Ile Glu Leu Thr Gln Pro Pro Ser Val Ser Val Ala Pro Gly Gln
1               5                   10                  15

Thr Ala Arg Ile Ser Cys Ser Gly Asp Asn Ile Arg Ser Tyr Tyr Ala
            20                  25                  30

His Trp Tyr Gln Gln Lys Pro Gly Gln Ala Pro Val Leu Val Ile Tyr
        35                  40                  45

Gly Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Ser Ser Tyr Ala Ser His Asp Tyr Val
                85                  90                  95

Phe Gly Gly Gly Thr Lys Leu Thr Val Leu
            100                 105

<210> SEQ ID NO 9
<211> LENGTH: 108
<212> TYPE: PRT
<213> ORGANISM: Artificial Sequence
<220> FEATURE:
<223> OTHER INFORMATION: Antibody sequence

<400> SEQUENCE: 9

Asp Ile Glu Leu Thr Gln Pro Pro Ser Val Ser Val Ala Pro Gly Gln
1               5                   10                  15
```

Thr Ala Arg Ile Ser Cys Ser Gly Asp Lys Leu Arg Glu Tyr Tyr Val
            20                  25                  30

His Trp Tyr Gln Gln Lys Pro Gly Gln Ala Pro Val Leu Val Ile Tyr
            35                  40                  45

Gly Asp Asn Lys Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Ser Ser Trp Ala Gly Ser Arg Ser Gly
                85                  90                  95

Thr Val Phe Gly Gly Gly Thr Lys Leu Thr Val Leu
            100                 105

<210> SEQ ID NO 10
<211> LENGTH: 108
<212> TYPE: PRT
<213> ORGANISM: Artificial Sequence
<220> FEATURE:
<223> OTHER INFORMATION: Antibody sequence

<400> SEQUENCE: 10

Asp Ile Glu Leu Thr Gln Pro Pro Ser Val Ser Val Ala Pro Gly Gln
1               5                   10                  15

Thr Ala Arg Ile Ser Cys Ser Gly Asp Asn Ile Arg Ser Met Phe Val
            20                  25                  30

His Trp Tyr Gln Gln Lys Pro Gly Gln Ala Pro Val Leu Val Ile Tyr
            35                  40                  45

Ala Asp Asn Lys Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Ser Ser Tyr Asp Tyr Asn Ala His Leu
                85                  90                  95

Val Val Phe Gly Gly Gly Thr Lys Leu Thr Val Leu
            100                 105

<210> SEQ ID NO 11
<211> LENGTH: 447
<212> TYPE: PRT
<213> ORGANISM: Artificial Sequence
<220> FEATURE:
<223> OTHER INFORMATION: Antibody sequence

<400> SEQUENCE: 11

Gln Val Gln Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Gly Gly Val Ser Trp Ile Arg Gln Pro Pro Gly Lys Ala Leu Glu
            35                  40                  45

Trp Leu Ala His Ile Tyr Ser Asn Asp Asp Lys Ser Tyr Ser Thr Ser
 50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Gly Gly Tyr Phe Leu Asp Tyr Trp Gly Gln Gly Thr Leu
            100                 105                 110

```
Val Thr Val Ser Ser Ala Lys Thr Thr Ala Pro Ser Val Tyr Pro Leu
            115                 120                 125
Ala Pro Val Cys Gly Asp Thr Thr Gly Ser Ser Val Thr Leu Gly Cys
        130                 135                 140
Leu Val Lys Gly Tyr Phe Pro Glu Pro Val Thr Leu Thr Trp Asn Ser
145                 150                 155                 160
Gly Ser Leu Ser Ser Gly Val His Thr Phe Pro Ala Val Leu Gln Ser
                165                 170                 175
Asp Leu Tyr Thr Leu Ser Ser Ser Val Thr Val Thr Ser Ser Thr Trp
            180                 185                 190
Pro Ser Gln Ser Ile Thr Cys Asn Val Ala His Pro Ala Ser Ser Thr
        195                 200                 205
Lys Val Asp Lys Lys Ile Glu Pro Arg Gly Pro Thr Ile Lys Pro Cys
    210                 215                 220
Pro Pro Cys Lys Cys Pro Ala Pro Asn Leu Leu Gly Gly Pro Ser Val
225                 230                 235                 240
Phe Ile Phe Pro Pro Lys Ile Lys Asp Val Leu Met Ile Ser Leu Ser
                245                 250                 255
Pro Ile Val Thr Cys Val Val Asp Val Ser Glu Asp Asp Pro Asp
            260                 265                 270
Val Gln Ile Ser Trp Phe Val Asn Asn Val Glu Val His Thr Ala Gln
        275                 280                 285
Thr Gln Thr His Arg Glu Asp Tyr Asn Ser Thr Leu Arg Val Val Ser
    290                 295                 300
Ala Leu Pro Ile Gln His Gln Asp Trp Met Ser Gly Lys Glu Phe Lys
305                 310                 315                 320
Cys Lys Val Asn Asn Lys Asp Leu Pro Ala Pro Ile Glu Arg Thr Ile
                325                 330                 335
Ser Lys Pro Lys Gly Ser Val Arg Ala Pro Gln Val Tyr Val Leu Pro
            340                 345                 350
Pro Pro Glu Glu Glu Met Thr Lys Lys Gln Val Thr Leu Thr Cys Met
        355                 360                 365
Val Thr Asp Phe Met Pro Glu Asp Ile Tyr Val Glu Trp Thr Asn Asn
    370                 375                 380
Gly Lys Thr Glu Leu Asn Tyr Lys Asn Thr Glu Pro Val Leu Asp Ser
385                 390                 395                 400
Asp Gly Ser Tyr Phe Met Tyr Ser Lys Leu Arg Val Glu Lys Lys Asn
                405                 410                 415
Trp Val Glu Arg Asn Ser Tyr Ser Cys Ser Val Val His Glu Gly Leu
            420                 425                 430
His Asn His His Thr Thr Lys Ser Phe Ser Arg Thr Pro Gly Lys
        435                 440                 445

<210> SEQ ID NO 12
<211> LENGTH: 1695
<212> TYPE: DNA
<213> ORGANISM: homo sapiens

<400> SEQUENCE: 12
atggccacgg cggagcggag agccctcggc atcggcttcc agtggctctc tttggccact      60
ctggtgctca tctgcgccgg gcaaggggga cgcaggagg atgggggtcc agcctgctac      120
ggcggatttg acctgtactt cattttggac aaatcaggaa gtgtgctgca ccactggaat      180
gaaatctatt actttgtgga acagttggct cacaaattca tcagcccaca gttgagaatg      240
```

-continued

```
tcctttattg ttttctccac ccgaggaaca accttaatga aactgacaga agacagagaa      300
caaatccgtc aaggcctaga agaactccag aaagttctgc caggaggaga cacttacatg      360
catgaaggat ttgaaagggc cagtgagcag atttattatg aaaacagaca agggtacagg      420
acagccagcg tcatcattgc tttgactgat ggagaactcc atgaagatct cttttttctat     480
tcagagaggg aggctaatag gtctcgagat cttggtgcaa ttgtttactg tgttggtgtg      540
aaagatttca atgagacaca gctggccggg attgcggaca gtaaggatca tgtgtttccc      600
gtgaatgacg gctttcaggc tctgcaaggc atcatccact caattttgaa gaagtcctgc      660
atcgaaattc tagcagctga accatccacc atatgtgcag agagtcatt tcaagttgtc       720
gtgagaggaa acggcttccg acatgcccgc aacgtggaca gggtcctctg cagcttcaag      780
atcaatgact cggtcacact caatgagaag cccttttctg tggaagatac ttatttactg      840
tgtccagcgc ctatcttaaa agaagttggc atgaaagctg cactccaggt cagcatgaac      900
gatggcctct cttttatctc cagttctgtc atcatcacca ccacacactg ttctgacggt      960
tccatcctgg ccatcgccct gctgatcctg ttcctgctcc tagccctggc tctcctctgg    1020
tggttctggc ccctctgctg cactgtgatt atcaaggagg tccctccacc ccctgccgag    1080
gagagtgagg aagaagatga tgatggtctg cctaagaaaa agtggccaac ggtagacgcc    1140
tcttattatg gtgggagagg cgttggaggc attaaaagaa tggaggttcg ttggggagaa    1200
aagggctcca cagaagaagg tgctaagttg gaaaaggcaa agaatgcaag agtcaagatg    1260
ccggagcagg aatatgaatt ccctgagccg cgaaatctca acaacaatat gcgtcggcct    1320
tcttcccccc ggaagtggta ctctccaatc aagggaaaac tcgatgcctt gtgggtccta    1380
ctgaggaaag gatatgatcg tgtgtctgtg atgcgtccac agccaggaga cacggggcgc    1440
tgcatcaact tcaccagggt caagaacaac cagccagcca agtacccact caacaacgcc    1500
taccacacct cctcgccgcc tcctgccccc atctacactc ccccacctcc tgcgccccac    1560
tgccctcccc cgcccccag cgccctacc cctcccatcc cgtccccacc ttccacccctt     1620
cccccctcctc cccaggctcc acctcccaac agggcacctc ctccctcccg ccctcctcca    1680
aggccttctg tctag                                                     1695
```

<210> SEQ ID NO 13
<211> LENGTH: 564
<212> TYPE: PRT
<213> ORGANISM: homo sapiens

<400> SEQUENCE: 13

```
Met Ala Thr Ala Glu Arg Arg Ala Leu Gly Ile Gly Phe Gln Trp Leu
1               5                   10                  15

Ser Leu Ala Thr Leu Val Leu Ile Cys Ala Gly Gln Gly Gly Arg Arg
            20                  25                  30

Glu Asp Gly Gly Pro Ala Cys Tyr Gly Gly Phe Asp Leu Tyr Phe Ile
        35                  40                  45

Leu Asp Lys Ser Gly Ser Val Leu His His Trp Asn Glu Ile Tyr Tyr
    50                  55                  60

Phe Val Glu Gln Leu Ala His Lys Phe Ile Ser Pro Gln Leu Arg Met
65                  70                  75                  80

Ser Phe Ile Val Phe Ser Thr Arg Gly Thr Thr Leu Met Lys Leu Thr
                85                  90                  95

Glu Asp Arg Glu Gln Ile Arg Gln Gly Leu Glu Glu Leu Gln Lys Val
            100                 105                 110
```

```
Leu Pro Gly Gly Asp Thr Tyr Met His Glu Gly Phe Glu Arg Ala Ser
        115                 120                 125

Glu Gln Ile Tyr Tyr Glu Asn Arg Gln Gly Tyr Arg Thr Ala Ser Val
130                 135                 140

Ile Ile Ala Leu Thr Asp Gly Glu Leu His Glu Asp Leu Phe Phe Tyr
145                 150                 155                 160

Ser Glu Arg Glu Ala Asn Arg Ser Arg Asp Leu Gly Ala Ile Val Tyr
                165                 170                 175

Cys Val Gly Val Lys Asp Phe Asn Glu Thr Gln Leu Ala Arg Ile Ala
            180                 185                 190

Asp Ser Lys Asp His Val Phe Pro Val Asn Asp Gly Phe Gln Ala Leu
        195                 200                 205

Gln Gly Ile Ile His Ser Ile Leu Lys Lys Ser Cys Ile Glu Ile Leu
210                 215                 220

Ala Ala Glu Pro Ser Thr Ile Cys Ala Gly Glu Ser Phe Gln Val Val
225                 230                 235                 240

Val Arg Gly Asn Gly Phe Arg His Ala Arg Asn Val Asp Arg Val Leu
                245                 250                 255

Cys Ser Phe Lys Ile Asn Asp Ser Val Thr Leu Asn Glu Lys Pro Phe
            260                 265                 270

Ser Val Glu Asp Thr Tyr Leu Leu Cys Pro Ala Pro Ile Leu Lys Glu
        275                 280                 285

Val Gly Met Lys Ala Ala Leu Gln Val Ser Met Asn Asp Gly Leu Ser
290                 295                 300

Phe Ile Ser Ser Ser Val Ile Ile Thr Thr Thr His Cys Ser Asp Gly
305                 310                 315                 320

Ser Ile Leu Ala Ile Ala Leu Leu Ile Leu Phe Leu Leu Leu Ala Leu
                325                 330                 335

Ala Leu Leu Trp Trp Phe Trp Pro Leu Cys Cys Thr Val Ile Ile Lys
            340                 345                 350

Glu Val Pro Pro Pro Ala Glu Glu Ser Glu Glu Glu Asp Asp Asp
        355                 360                 365

Gly Leu Pro Lys Lys Lys Trp Pro Thr Val Asp Ala Ser Tyr Tyr Gly
370                 375                 380

Gly Arg Gly Val Gly Gly Ile Lys Arg Met Glu Val Arg Trp Gly Glu
385                 390                 395                 400

Lys Gly Ser Thr Glu Glu Gly Ala Lys Leu Glu Lys Ala Lys Asn Ala
                405                 410                 415

Arg Val Lys Met Pro Glu Gln Glu Tyr Glu Phe Pro Glu Pro Arg Asn
            420                 425                 430

Leu Asn Asn Asn Met Arg Arg Pro Ser Ser Pro Arg Lys Trp Tyr Ser
        435                 440                 445

Pro Ile Lys Gly Lys Leu Asp Ala Leu Trp Val Leu Leu Arg Lys Gly
450                 455                 460

Tyr Asp Arg Val Ser Val Met Arg Pro Gln Pro Gly Asp Thr Gly Arg
465                 470                 475                 480

Cys Ile Asn Phe Thr Arg Val Lys Asn Asn Gln Pro Ala Lys Tyr Pro
                485                 490                 495

Leu Asn Asn Ala Tyr His Thr Ser Ser Pro Pro Ala Pro Ile Tyr
            500                 505                 510

Thr Pro Pro Pro Ala Pro His Cys Pro Pro Pro Pro Ser Ala
        515                 520                 525
```

```
Pro Thr Pro Pro Ile Pro Ser Pro Pro Ser Thr Leu Pro Pro Pro Pro
        530                 535                 540

Gln Ala Pro Pro Asn Arg Ala Pro Pro Ser Arg Pro Pro
545                 550                 555                 560

Arg Pro Ser Val

<210> SEQ ID NO 14
<211> LENGTH: 351
<212> TYPE: DNA
<213> ORGANISM: Artificial Sequence
<220> FEATURE:
<223> OTHER INFORMATION: Antibody sequence

<400> SEQUENCE: 14
caggtgcaat tgaaagaaag cggcccggcc ctggtgaaac cgacccaaac cctgaccctg      60
acctgtacct tttccggatt tagcctgtct acttctggtg gtggtgtgtc ttggattcgc     120
cagccgcctg gaaagccct  cgagtggctg gctcatatct attctaatga tgataagtct     180
tatagcacca gcctgaaaac gcgtctgacc attagcaaag atacttcgaa aaatcaggtg     240
gtgctgacta tgaccaacat ggacccggtg gataccggcca cctattattg cgcgcgtggt    300 ggttatttc ttgattattg gggccaaggc accctggtga cggttagctc a               351

<210> SEQ ID NO 15
<211> LENGTH: 345
<212> TYPE: DNA
<213> ORGANISM: Artificial Sequence
<220> FEATURE:
<223> OTHER INFORMATION: Antibody sequence

<400> SEQUENCE: 15
caggtgcaat tggtggaaag cggcggcggc ctggtgcaac cgggcggcag cctgcgtctg      60
agctgcgcgg cctccggatt tacctttaat tcttatgcta tgtcttgggt gcgccaagcc    120
cctgggaagg gtctcgagtg ggtgagcctt atctcttctg gtagctctac ctattatgcg    180
gatagcgtga aaggccgttt taccatttca cgtgataatt cgaaaaacac cctgtatctg    240
caaatgaaca gcctgcgtgc ggaagatacg gccgtgtatt attgcgcgcg tgctggtttt    300
aagtttgata ttggggccca aggcacctg gtgacggtta gctca                     345

<210> SEQ ID NO 16
<211> LENGTH: 363
<212> TYPE: DNA
<213> ORGANISM: Artificial Sequence
<220> FEATURE:
<223> OTHER INFORMATION: Antibody sequence

<400> SEQUENCE: 16
caggtgcaat tgcaacagtc tggtccgggc ctggtgaaac cgagccaaac cctgagcctg      60
acctgtgcga tttccggaga tagcgtgagc actaatggtg ctgcttgggg ttggattcgc    120
cagtctcctg gcgtggcct  cgagtggctg ggccgtatct attatcgtag caagtggtat    180
aacgattatg cggtgagcgt gaaaagccgg attaccatca cccggatac ttcgaaaaac    240 cagtttagcc tgcaactgaa cagcgtgacc ccggaagata cggccgtgta ttattgcgcg     300
cgtatgcctg gtggttttct ttttgatctt tggggccaag gcaccctggt gacggttagc    360
tca                                                                    363

<210> SEQ ID NO 17
<211> LENGTH: 351
```

```
<212> TYPE: DNA
<213> ORGANISM: Artificial Sequence
<220> FEATURE:
<223> OTHER INFORMATION: Antibody sequence

<400> SEQUENCE: 17
caggtgcaat tggtggaaag cggcggcggc ctggtgcaac cgggcggcag cctgcgtctg      60
agctgcgcgg cctccggatt tacctttaat tcttatggtc tttcttgggt gcgccaagcc     120
cctgggaagg gtctcgagtg ggtgagcaat atctcttcta atggtagcta tacctattat     180
gcggatagcg tgaaaggccg ttttaccatt tcacgtgata attcgaaaaa caccctgtat     240
ctgcaaatga acagcctgcg tgcggaagat acggccgtgt attattgcgc gcgtgctggt     300
tatggtcttt ttgatgtttg gggccaaggc accctggtga cggttagctc a             351

<210> SEQ ID NO 18
<211> LENGTH: 354
<212> TYPE: DNA
<213> ORGANISM: Artificial Sequence
<220> FEATURE:
<223> OTHER INFORMATION: Antibody sequence

<400> SEQUENCE: 18
caggtgcaat tgaaagaaag cggcccggcc ctggtgaaac cgacccaaac cctgaccctg      60
acctgtacct tttccggatt tagcctgtct acttctggta tgggtgtgtc ttggattcgc     120
cagccgcctg ggaaagccct cgagtggctg gctcatatca atcttgatga tgataagtat     180
tatagcacca gcctgaaaac gcgtctgacc attagcaaag atacttcgaa aaatcaggtg     240
gtgctgacta tgaccaacat ggacccggtg atacggcca cctattattg cgcgcgtggt      300
ggttatggtg atatggatgt ttggggccaa ggcaccctgg tgacggttag ctca           354

<210> SEQ ID NO 19
<211> LENGTH: 318
<212> TYPE: DNA
<213> ORGANISM: Artificial Sequence
<220> FEATURE:
<223> OTHER INFORMATION: Antibody sequence

<400> SEQUENCE: 19
gatatcgaac tgacccagcc gccttcagtg agcgttgcac caggtcagac cgcgcgtatc      60
tcgtgtagcg gcgataatat cggtggtatt tatgttcatt ggtaccagca gaaacccggg     120
caggcgccag ttcttgtgat ttatgctgat tctaagcgtc cctcaggcat cccggaacgc     180
tttagcggat ccaacagcgg caacaccgcg accctgacca ttagcggcac tcaggcggaa     240
gacgaagcgg attattattg ccagtcttat gatattactt ctcttgtgtt tggcggcggc     300
acgaagttaa ccgtccta                                                  318

<210> SEQ ID NO 20
<211> LENGTH: 324
<212> TYPE: DNA
<213> ORGANISM: Artificial Sequence
<220> FEATURE:
<223> OTHER INFORMATION: Antibody sequence

<400> SEQUENCE: 20
gatatcgaac tgacccagcc gccttcagtg agcgttgcac caggtcagac cgcgcgtatc      60
tcgtgtagcg gcgattctat tcctaattat tctgttttct tggtaccagca gaaacccggg    120 caggcgccag ttcttgtgat ttatgctgat tctaatcgtc cctcaggcat cccggaacgc     180
```

| | |
|---|---|
| tttagcggat ccaacagcgg caacaccgcg accctgacca ttagcggcac tcaggcggaa | 240 |
| gacgaagcgg attattattg ccagtcttat gataatactt ctcctgatct tgtgtttggc | 300 |
| ggcggcacga agttaaccgt tctt | 324 |

<210> SEQ ID NO 21
<211> LENGTH: 318
<212> TYPE: DNA
<213> ORGANISM: Artificial Sequence
<220> FEATURE:
<223> OTHER INFORMATION: Antibody sequence

<400> SEQUENCE: 21

| | |
|---|---|
| gatatcgaac tgacccagcc gccttcagtg agcgttgcac caggtcagac cgcgcgtatc | 60 |
| tcgtgtagcg gcgataatat tcgttcttat tatgctcatt ggtaccagca gaaacccggg | 120 |
| caggcgccag ttcttgtgat ttatggtgat tctaagcgtc cctcaggcat cccggaacgc | 180 |
| tttagcggat ccaacagcgg caacaccgcg accctgacca ttagcggcac tcaggcggaa | 240 |
| gacgaagcgg attattattg ctcttcttat gcttctcatg attatgtgtt tggcggcggc | 300 |
| acgaagttaa ccgttctt | 318 |

<210> SEQ ID NO 22
<211> LENGTH: 324
<212> TYPE: DNA
<213> ORGANISM: Artificial Sequence
<220> FEATURE:
<223> OTHER INFORMATION: Antibody sequence

<400> SEQUENCE: 22

| | |
|---|---|
| gatatcgaac tgacccagcc gccttcagtg agcgttgcac caggtcagac cgcgcgtatc | 60 |
| tcgtgtagcg gcgataagct tcgtgagtat tatgttcatt ggtaccagca gaaacccggg | 120 |
| caggcgccag ttcttgtgat ttatggtgat aataagcgtc cctcaggcat cccggaacgc | 180 |
| tttagcggat ccaacagcgg caacaccgcg accctgacca ttagcggcac tcaggcggaa | 240 |
| gacgaagcgg attattattg ctcttcttgg gctggttctc gttctggtac tgtgtttggc | 300 |
| ggcggcacga agttaaccgt ccta | 324 |

<210> SEQ ID NO 23
<211> LENGTH: 324
<212> TYPE: DNA
<213> ORGANISM: Artificial Sequence
<220> FEATURE:
<223> OTHER INFORMATION: Antibody sequence

<400> SEQUENCE: 23

| | |
|---|---|
| gatatcgaac tgacccagcc gccttcagtg agcgttgcac caggtcagac cgcgcgtatc | 60 |
| tcgtgtagcg gcgataatat tcgttctatg tttgttcatt ggtaccagca gaaacccggg | 120 |
| caggcgccag ttcttgtgat ttatgctgat aataagcgtc cctcaggcat cccggaacgc | 180 |
| tttagcggat ccaacagcgg caacaccgcg accctgacca ttagcggcac tcaggcggaa | 240 |
| gacgaagcgg attattattg ctcttcttat gattataatg ctcatcttgt tgtgtttggc | 300 |
| ggcggcacga agttaaccgt tctt | 324 |

<210> SEQ ID NO 24
<211> LENGTH: 447
<212> TYPE: PRT
<213> ORGANISM: Artificial Sequence
<220> FEATURE:
<223> OTHER INFORMATION: Antibody sequence

<400> SEQUENCE: 24

```
Gln Val Gln Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Gly Gly Val Ser Trp Ile Arg Gln Pro Pro Gly Lys Ala Leu Glu
        35                  40                  45

Trp Leu Ala His Ile Tyr Ser Asn Asp Lys Ser Tyr Ser Thr Ser
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Gly Gly Tyr Phe Leu Asp Tyr Trp Gly Gln Gly Thr Leu
            100                 105                 110

Val Thr Val Ser Ser Ala Lys Thr Thr Ala Pro Ser Val Tyr Pro Leu
        115                 120                 125

Ala Pro Val Cys Gly Asp Thr Thr Gly Ser Ser Val Thr Leu Gly Cys
130                 135                 140

Leu Val Lys Gly Tyr Phe Pro Glu Pro Val Thr Leu Thr Trp Asn Ser
145                 150                 155                 160

Gly Ser Leu Ser Ser Gly Val His Thr Phe Pro Ala Val Leu Gln Ser
                165                 170                 175

Asp Leu Tyr Thr Leu Ser Ser Ser Val Thr Val Thr Ser Ser Thr Trp
            180                 185                 190

Pro Ser Gln Ser Ile Thr Cys Asn Val Ala His Pro Ala Ser Ser Thr
        195                 200                 205

Lys Val Asp Lys Lys Ile Glu Pro Arg Gly Pro Thr Ile Lys Pro Cys
210                 215                 220

Pro Pro Cys Lys Cys Pro Ala Pro Asn Leu Leu Gly Gly Pro Ser Val
225                 230                 235                 240

Phe Ile Phe Pro Pro Lys Ile Lys Asp Val Leu Met Ile Ser Leu Ser
                245                 250                 255

Pro Ile Val Thr Cys Val Val Asp Val Ser Glu Asp Asp Pro Asp
            260                 265                 270

Val Gln Ile Ser Trp Phe Val Asn Asn Val Glu Val His Thr Ala Gln
        275                 280                 285

Thr Gln Thr His Arg Glu Asp Tyr Asn Ser Thr Leu Arg Val Val Ser
290                 295                 300

Ala Leu Pro Ile Gln His Gln Asp Trp Met Ser Gly Lys Glu Phe Lys
305                 310                 315                 320

Cys Lys Val Asn Asn Lys Asp Leu Pro Ala Pro Ile Glu Arg Thr Ile
                325                 330                 335

Ser Lys Pro Lys Gly Ser Val Arg Ala Pro Gln Val Tyr Val Leu Pro
            340                 345                 350

Pro Pro Glu Glu Glu Met Thr Lys Lys Gln Val Thr Leu Thr Cys Met
        355                 360                 365

Val Thr Asp Phe Met Pro Glu Asp Ile Tyr Val Glu Trp Thr Asn Asn
370                 375                 380

Gly Lys Thr Glu Leu Asn Tyr Lys Asn Thr Glu Pro Val Leu Asp Ser
385                 390                 395                 400

Asp Gly Ser Tyr Phe Met Tyr Ser Lys Leu Arg Val Glu Lys Lys Asn
```

```
                    405                 410                 415
Trp Val Glu Arg Asn Ser Tyr Ser Cys Ser Val Val His Glu Gly Leu
            420                 425                 430

His Asn His His Thr Thr Lys Ser Phe Ser Arg Thr Pro Gly Lys
        435                 440                 445

<210> SEQ ID NO 25
<211> LENGTH: 211
<212> TYPE: PRT
<213> ORGANISM: Artificial Sequence
<220> FEATURE:
<223> OTHER INFORMATION: Antibody sequence

<400> SEQUENCE: 25

Asp Ile Glu Leu Thr Gln Pro Pro Ser Val Ser Val Ala Pro Gly Gln
1               5                   10                  15

Thr Ala Arg Ile Ser Cys Ser Gly Asp Asn Ile Gly Gly Ile Tyr Val
            20                  25                  30

His Trp Tyr Gln Gln Lys Pro Gly Gln Ala Pro Val Leu Val Ile Tyr
        35                  40                  45

Ala Asp Ser Lys Arg Pro Ser Gly Ile Pro Glu Arg Phe Ser Gly Ser
50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Tyr Asp Ile Thr Ser Leu Val
                85                  90                  95

Phe Gly Gly Gly Thr Lys Leu Thr Val Leu Gly Gln Pro Lys Ser Thr
            100                 105                 110

Pro Thr Leu Thr Val Phe Pro Pro Ser Ser Glu Glu Leu Lys Glu Asn
        115                 120                 125

Lys Ala Thr Leu Val Cys Leu Ile Ser Asn Phe Ser Pro Ser Gly Val
    130                 135                 140

Thr Val Ala Trp Lys Ala Asn Gly Thr Pro Ile Thr Gln Gly Val Asp
145                 150                 155                 160

Thr Ser Asn Pro Thr Lys Glu Gly Asn Lys Phe Met Ala Ser Ser Phe
                165                 170                 175

Leu His Leu Thr Ser Asp Gln Trp Arg Ser His Asn Ser Phe Thr Cys
            180                 185                 190

Gln Val Thr His Glu Gly Asp Thr Val Glu Lys Ser Leu Ser Pro Ala
        195                 200                 205

Glu Cys Leu
    210

<210> SEQ ID NO 26
<211> LENGTH: 219
<212> TYPE: PRT
<213> ORGANISM: Artificial Sequence
<220> FEATURE:
<223> OTHER INFORMATION: Antibody sequence

<400> SEQUENCE: 26

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Ser Tyr
            20                  25                  30

Ala Met Ser Trp Val Arg Gln Ala Pro Gly Lys Gly Leu Glu Trp Val
        35                  40                  45
```

```
Ser Leu Ile Ser Ser Gly Ser Ser Thr Tyr Tyr Ala Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Ala Gly Phe Lys Phe Asp Asn Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Glu Phe
210                 215

<210> SEQ ID NO 27
<211> LENGTH: 213
<212> TYPE: PRT
<213> ORGANISM: Artificial Sequence
<220> FEATURE:
<223> OTHER INFORMATION: Antibody sequence

<400> SEQUENCE: 27

Asp Ile Glu Leu Thr Gln Pro Pro Ser Val Ser Val Ala Pro Gly Gln
 1               5                  10                  15

Thr Ala Arg Ile Ser Cys Ser Gly Asp Ser Ile Pro Asn Tyr Ser Val
                 20                  25                  30

Ser Trp Tyr Gln Gln Lys Pro Gly Gln Ala Pro Val Leu Val Ile Tyr
             35                  40                  45

Ala Asp Ser Asn Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Gln Ser Tyr Asp Asn Thr Ser Pro Asp
                 85                  90                  95

Leu Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190
```

```
Tyr Ser Cys Gln Val Thr His Glu Gly Ser Thr Val Glu Lys Thr Val
        195                 200                 205

Ala Pro Thr Glu Ala
        210

<210> SEQ ID NO 28
<211> LENGTH: 225
<212> TYPE: PRT
<213> ORGANISM: Artificial Sequence
<220> FEATURE:
<223> OTHER INFORMATION: Antibody sequence

<400> SEQUENCE: 28

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Thr Asn
            20                  25                  30

Gly Ala Ala Trp Gly Trp Ile Arg Gln Ser Pro Gly Arg Gly Leu Glu
        35                  40                  45

Trp Leu Gly Arg Ile Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Met Pro Gly Gly Phe Leu Phe Asp Leu Trp Gly
            100                 105                 110

Gln Gly Thr Leu Val Thr Val Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Glu
    210                 215                 220

Phe
225

<210> SEQ ID NO 29
<211> LENGTH: 211
<212> TYPE: PRT
<213> ORGANISM: Artificial Sequence
<220> FEATURE:
<223> OTHER INFORMATION: Antibody sequence

<400> SEQUENCE: 29

Asp Ile Glu Leu Thr Gln Pro Pro Ser Val Ser Val Ala Pro Gly Gln
1               5                   10                  15

Thr Ala Arg Ile Ser Cys Ser Gly Asp Asn Ile Arg Ser Tyr Tyr Ala
            20                  25                  30

His Trp Tyr Gln Gln Lys Pro Gly Gln Ala Pro Val Leu Val Ile Tyr
        35                  40                  45
```

-continued

```
Gly Asp Ser Lys Arg Pro Ser Gly Ile Pro Glu Arg Phe Ser Gly Ser
        50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Ser Ser Tyr Ala Ser His Asp Tyr Val
                 85                  90                  95

Phe Gly Gly Gly Thr Lys Leu Thr Val Leu Gly Gln Pro Lys Ala Ala
            100                 105                 110

Pro Ser Val Thr Leu Phe Pro Pro Ser Ser Glu Glu Leu Gln Ala Asn
        115                 120                 125

Lys Ala Thr Leu Val Cys Leu Ile Ser Asp Phe Tyr Pro Gly Ala Val
    130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
        195                 200                 205

Thr Glu Ala
    210

<210> SEQ ID NO 30
<211> LENGTH: 447
<212> TYPE: PRT
<213> ORGANISM: Artificial Sequence
<220> FEATURE:
<223> OTHER INFORMATION: Antibody sequence

<400> SEQUENCE: 30

Gln Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Asn Ser Tyr
            20                  25                  30

Gly Leu Ser Trp Val Arg Gln Ala Pro Gly Lys Gly Leu Glu Trp Val
        35                  40                  45

Ser Asn Ile Ser Ser Asn Gly Ser Tyr Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ala Gly Tyr Gly Leu Phe Asp Val Trp Gly Gln Gly Thr Leu
            100                 105                 110

Val Thr Val Ser Ser Ala Lys Thr Thr Ala Pro Ser Val Tyr Pro Leu
        115                 120                 125

Ala Pro Val Cys Gly Asp Thr Thr Gly Ser Ser Val Thr Leu Gly Cys
    130                 135                 140

Leu Val Lys Gly Tyr Phe Pro Glu Pro Val Thr Leu Thr Trp Asn Ser
145                 150                 155                 160

Gly Ser Leu Ser Ser Gly Val His Thr Phe Pro Ala Val Leu Gln Ser
                165                 170                 175

Asp Leu Tyr Thr Leu Ser Ser Ser Val Thr Val Thr Ser Ser Thr Trp
            180                 185                 190
```

```
Pro Ser Gln Ser Ile Thr Cys Asn Val Ala His Pro Ala Ser Ser Thr
            195                 200                 205

Lys Val Asp Lys Lys Ile Glu Pro Arg Gly Pro Thr Ile Lys Pro Cys
            210                 215                 220

Pro Pro Cys Lys Cys Pro Ala Pro Asn Leu Leu Gly Gly Pro Ser Val
225                 230                 235                 240

Phe Ile Phe Pro Pro Lys Ile Lys Asp Val Leu Met Ile Ser Leu Ser
            245                 250                 255

Pro Ile Val Thr Cys Val Val Val Asp Val Ser Glu Asp Asp Pro Asp
            260                 265                 270

Val Gln Ile Ser Trp Phe Val Asn Asn Val Glu Val His Thr Ala Gln
            275                 280                 285

Thr Gln Thr His Arg Glu Asp Tyr Asn Ser Thr Leu Arg Val Val Ser
            290                 295                 300

Ala Leu Pro Ile Gln His Gln Asp Trp Met Ser Gly Lys Glu Phe Lys
305                 310                 315                 320

Cys Lys Val Asn Asn Lys Asp Leu Pro Ala Pro Ile Glu Arg Thr Ile
            325                 330                 335

Ser Lys Pro Lys Gly Ser Val Arg Ala Pro Gln Val Tyr Val Leu Pro
            340                 345                 350

Pro Pro Glu Glu Glu Met Thr Lys Lys Gln Val Thr Leu Thr Cys Met
            355                 360                 365

Val Thr Asp Phe Met Pro Glu Asp Ile Tyr Val Glu Trp Thr Asn Asn
            370                 375                 380

Gly Lys Thr Glu Leu Asn Tyr Lys Asn Thr Glu Pro Val Leu Asp Ser
385                 390                 395                 400

Asp Gly Ser Tyr Phe Met Tyr Ser Lys Leu Arg Val Glu Lys Lys Asn
            405                 410                 415

Trp Val Glu Arg Asn Ser Tyr Ser Cys Ser Val Val His Glu Gly Leu
            420                 425                 430

His Asn His His Thr Thr Lys Ser Phe Ser Arg Thr Pro Gly Lys
            435                 440                 445

<210> SEQ ID NO 31
<211> LENGTH: 213
<212> TYPE: PRT
<213> ORGANISM: Artificial Sequence
<220> FEATURE:
<223> OTHER INFORMATION: Antibody sequence

<400> SEQUENCE: 31

Asp Ile Glu Leu Thr Gln Pro Pro Ser Val Ser Val Ala Pro Gly Gln
1               5                   10                  15

Thr Ala Arg Ile Ser Cys Ser Gly Asp Lys Leu Arg Glu Tyr Tyr Val
            20                  25                  30

His Trp Tyr Gln Gln Lys Pro Gly Gln Ala Pro Val Leu Val Ile Tyr
            35                  40                  45

Gly Asp Asn Lys Arg Pro Ser Gly Ile Pro Glu Arg Phe Ser Gly Ser
        50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Ser Ser Trp Ala Gly Ser Arg Ser Gly
                85                  90                  95

Thr Val Phe Gly Gly Gly Thr Lys Leu Thr Val Leu Gly Gln Pro Lys
            100                 105                 110
```

Ser Thr Pro Thr Leu Thr Val Phe Pro Pro Ser Ser Glu Glu Leu Lys
        115                 120                 125

Glu Asn Lys Ala Thr Leu Val Cys Leu Ile Ser Asn Phe Ser Pro Ser
        130                 135                 140

Gly Val Thr Val Ala Trp Lys Ala Asn Gly Thr Pro Ile Thr Gln Gly
145                 150                 155                 160

Val Asp Thr Ser Asn Pro Thr Lys Glu Gly Asn Lys Phe Met Ala Ser
                165                 170                 175

Ser Phe Leu His Leu Thr Ser Asp Gln Trp Arg Ser His Asn Ser Phe
                180                 185                 190

Thr Cys Gln Val Thr His Glu Gly Asp Thr Val Glu Lys Ser Leu Ser
        195                 200                 205

Pro Ala Glu Cys Leu
        210

<210> SEQ ID NO 32
<211> LENGTH: 222
<212> TYPE: PRT
<213> ORGANISM: Artificial Sequence
<220> FEATURE:
<223> OTHER INFORMATION: Antibody sequence

<400> SEQUENCE: 32

Gln Val Gln Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Ser Trp Ile Arg Gln Pro Pro Gly Lys Ala Leu Glu
        35                  40                  45

Trp Leu Ala His Ile Asn Leu Asp Asp Asp Lys Tyr Tyr Ser Thr Ser
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Gly Gly Tyr Gly Asp Met Asp Val Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Glu Phe
        210                 215                 220

<210> SEQ ID NO 33
<211> LENGTH: 213
<212> TYPE: PRT
<213> ORGANISM: Artificial Sequence
<220> FEATURE:
<223> OTHER INFORMATION: Antibody sequence

<400> SEQUENCE: 33

```
Asp Ile Glu Leu Thr Gln Pro Pro Ser Val Ser Val Ala Pro Gly Gln
1               5                   10                  15

Thr Ala Arg Ile Ser Cys Ser Gly Asp Asn Ile Arg Ser Met Phe Val
            20                  25                  30

His Trp Tyr Gln Gln Lys Pro Gly Gln Ala Pro Val Leu Val Ile Tyr
        35                  40                  45

Ala Asp Asn Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Ser Ser Tyr Asp Tyr Asn Ala His Leu
                85                  90                  95

Val Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Ala
    210
```

<210> SEQ ID NO 34
<211> LENGTH: 1341
<212> TYPE: DNA
<213> ORGANISM: Artificial Sequence
<220> FEATURE:
<223> OTHER INFORMATION: Antibody sequence

<400> SEQUENCE: 34

```
caggtgcaat tgaaagaaag cggcccggcc ctggtgaaac cgacccaaac cctgaccctg      60
acctgtacct tttccggatt tagcctgtct acttctggtg gtggtgtgtc ttggattcgc     120
cagccgcctg gaaagcccct cgagtggctg gctcatatct attctaatga tgataagtct    180
tatagcacca gcctgaaaac gcgtctgacc attagcaaag atacttcgaa aaatcaggtg    240
gtgctgacta tgaccaacat ggacccggtg gatacggcca ctattattg cgcgcgtggt    300
ggttattttc ttgattattg gggccaaggc accctggtga cggttagctc agccaaaaca    360
acagccccat cggtctatcc actggcccct gtgtgtggag atacaactgg ctcctcggtg    420
actctaggat gcctggtcaa gggttatttc cctgagccag tgaccttgac ctggaactct    480
ggatccctgt ccagtggtgt gcacaccttc ccagctgtcc tgcagtctga cctctacacc    540
ctcagcagct cagtgactgt aacctcgagc acctggccca gccagtccat cacctgcaat    600
gtggcccacc cggcaagcag caccaaggtg gacaagaaaa ttgagcccag agggcccaca    660
```

| | |
|---|---|
| atcaagccct gtcctccatg caaatgccca gcacctaacc tcttgggtgg accatccgtc | 720 |
| ttcatcttcc ctccaaagat caaggatgta ctcatgatct ccctgagccc catagtcaca | 780 |
| tgtgtggtgg tggatgtgag cgaggatgac ccagatgtcc agatcagctg gtttgtgaac | 840 |
| aacgtggaag tacacacagc tcagacacaa acccatagag aggattacaa cagtactctc | 900 |
| cgggtggtca gtgccctccc catccagcac caggactgga tgagtggcaa ggagttcaaa | 960 |
| tgcaaggtca acaacaaaga ccttccagcg cccatcgaga gaaccatctc aaaacccaaa | 1020 |
| gggtcagtaa gagctccaca ggtatatgtc ttgcctccac cagaagaaga gatgactaag | 1080 |
| aaacaggtca ctctgacctg catggtcaca gacttcatgc ctgaagacat ttacgtggag | 1140 |
| tggaccaaca acgggaaaac agagctaaac tacaagaaca ctgaaccagt cctggactct | 1200 |
| gatggttctt acttcatgta cagcaagctg agagtggaaa agaagaactg ggtggaaaga | 1260 |
| aatagctact cctgttcagt ggtccacgag ggtctgcaca tcaccacac gactaagagc | 1320 |
| ttctcccgga ctccgggtaa a | 1341 |

<210> SEQ ID NO 35
<211> LENGTH: 633
<212> TYPE: DNA
<213> ORGANISM: Artificial Sequence
<220> FEATURE:
<223> OTHER INFORMATION: Antibody sequence

<400> SEQUENCE: 35

| | |
|---|---|
| gatatcgaac tgacccagcc gccttcagtg agcgttgcac caggtcagac cgcgcgtatc | 60 |
| tcgtgtagcg gcgataatat cggtggtatt tatgttcatt ggtaccagca gaaacccggg | 120 |
| caggcgccag ttcttgtgat ttatgctgat tctaagcgtc cctcaggcat cccggaacgc | 180 |
| tttagcggat ccaacagcgg caacaccgcg accctgacca ttagcggcac tcaggcggaa | 240 |
| gacgaagcgg attattattg ccagtcttat gatattactt ctcttgtgtt tggcggcggc | 300 |
| acgaagttaa ccgtcctagg tcagcccaag tccactccca ctctcaccgt gtttccacct | 360 |
| tcctctgagg agctcaagga aaacaaagcc acactggtgt gtctgatttc aacttttcc | 420 |
| ccgagtggtg tgacagtggc ctggaaggca aatggtacac ctatcaccca gggtgtggac | 480 |
| acttcaaatc ccaccaaaga gggcaacaag ttcatggcca gcagcttcct acatttgaca | 540 |
| tcggaccagt ggagatctca aacagttttt acctgtcaag ttacacatga aggggacact | 600 |
| gtggagaaga gtctgtctcc tgcagaatgt ctc | 633 |

<210> SEQ ID NO 36
<211> LENGTH: 657
<212> TYPE: DNA
<213> ORGANISM: Artificial Sequence
<220> FEATURE:
<223> OTHER INFORMATION: Antibody sequence

<400> SEQUENCE: 36

| | |
|---|---|
| caggtgcaat tggtggaaag cggcggcggc ctggtgcaac cgggcggcag cctgcgtctg | 60 |
| agctgcgcgg cctccggatt tacctttaat tcttatgcta tgtcttgggt gcgccaagcc | 120 |
| cctgggaagg gtctcgagtg gtgagccctt atctcttctg gtagctctac ctattatgcg | 180 |
| gatagcgtga aaggccgttt taccatttca cgtgataatt cgaaaaacac cctgtatctg | 240 |
| caaatgaaca gcctgcgtgc ggaagatacg gccgtgtatt attgcgcgcg tgctggtttt | 300 |
| aagtttgata ttggggcca aggcaccctg gtgacggtta gctcagcgtc gaccaaaggt | 360 |
| ccaagcgtgt ttccgctggc tccgagcagc aaaagcacca gcggcggcac ggctgccctg | 420 |

```
ggctgcctgg ttaaagatta tttcccggaa ccagtcaccg tgagctggaa cagcggggcg      480
ctgaccagcg gcgtgcatac ctttccggcg gtgctgcaaa gcagcggcct gtatagcctg      540
agcagcgttg tgaccgtgcc gagcagcagc ttaggcactc agacctatat ttgcaacgtg      600
aaccataaac cgagcaacac caaagtggat aaaaaagtgg aaccgaaaag cgaattc         657
```

```
<210> SEQ ID NO 37
<211> LENGTH: 639
<212> TYPE: DNA
<213> ORGANISM: Artificial Sequence
<220> FEATURE:
<223> OTHER INFORMATION: Antibody sequence

<400> SEQUENCE: 37
gatatcgaac tgacccagcc gccttcagtg agcgttgcac caggtcagac cgcgcgtatc       60
tcgtgtagcg gcgattctat tcctaattat tctgtttctt ggtaccagca gaaacccggg      120
caggcgccag ttcttgtgat ttatgctgat tctaatcgtc cctcaggcat cccggaacgc      180
tttagcggat ccaacagcgg caacaccgcg accctgacca ttagcggcac tcaggcggaa      240
gacgaagcgg attattattg ccagtcttat gataatactt ctcctgatct tgtgtttggc      300
ggcggcacga agttaaccgt tcttggccag ccgaaagccg caccgagtgt gacgctgttt      360
ccgccgagca gcgaagaatt gcaggcgaac aaagcgaccc tggtgtgcct gattagcgac      420
ttttatccgg gagccgtgac agtggcctgg aaggcagata gcagcccgt caaggcggga       480 gtggagacca ccacaccctc caaacaaagc aacaacaagt acgcggccag cagctatctg      540
agcctgacgc ctgagcagtg gaagtcccac agaagctaca gctgccaggt cacgcatgag      600
gggagcaccg tggaaaaaac cgttgcgccg actgaggcc                             639
```

```
<210> SEQ ID NO 38
<211> LENGTH: 675
<212> TYPE: DNA
<213> ORGANISM: Artificial Sequence
<220> FEATURE:
<223> OTHER INFORMATION: Antibody sequence

<400> SEQUENCE: 38
caggtgcaat tgcaacagtc tggtccgggc ctggtgaaac cgagccaaac cctgagcctg       60
acctgtgcga tttccggaga tagcgtgagc actaatggtg ctgcttgggg ttggattcgc      120
cagtctcctg gcgtggcct cgagtggctg ggccgtatct attatcgtag caagtggtat      180
aacgattatg cggtgagcgt gaaaagccgg attaccatca cccggatac ttcgaaaaac       240 cagtttagcc tgcaactgaa cagcgtgacc ccggaagata cggccgtgta ttattgcgcg      300
cgtatgcctg gtggttttct ttttgatctt tggggccaag gcaccctggt gacggttagc      360
tcagcgtcga ccaaaggtcc aagcgtgttt ccgctggctc cgagcagcaa agcaccagc       420 ggcggcacgg ctgccctggg ctgcctggtt aaagattatt tcccggaacc agtcaccgtg      480
agctggaaca gcggggcgct gaccagcggc gtgcataccT ttccggcggt gctgcaaagc      540
agcggcctgt atagcctgag cagcgttgtg accgtgccga gcagcagctt aggcactcag      600
acctatattt gcaacgtgaa ccataaaccg agcaacacca agtggataa aaaagtggaa       660 ccgaaaagcg aattc                                                       675
```

```
<210> SEQ ID NO 39
<211> LENGTH: 633
<212> TYPE: DNA
```

<213> ORGANISM: Artificial Sequence
<220> FEATURE:
<223> OTHER INFORMATION: Antibody sequence

<400> SEQUENCE: 39

```
gatatcgaac tgacccagcc gccttcagtg agcgttgcac caggtcagac cgcgcgtatc      60
tcgtgtagcg gcgataatat tcgttcttat tatgctcatt ggtaccagca gaaacccggg     120
caggcgccag ttcttgtgat ttatggtgat tctaagcgtc cctcaggcat cccggaacgc     180
tttagcggat ccaacagcgg caacaccgcg accctgacca ttagcggcac tcaggcggaa     240
gacgaagcgg attattattg ctcttcttat gcttctcatg attatgtgtt tggcggcggc     300
acgaagttaa ccgttcttgg ccagccgaaa gccgcaccga gtgtgacgct gtttccgccg     360
agcagcgaag aattgcaggc gaacaaagcg accctggtgt gcctgattag cgacttttat     420
ccgggagccg tgacagtggc ctggaaggca gatagcagcc ccgtcaaggc gggagtggag     480
accaccacac cctccaaaca aagcaacaac aagtacgcgg ccagcagcta tctgagcctg     540
acgcctgagc agtggaagtc ccacagaagc tacagctgcc aggtcacgca tgaggggagc     600
accgtggaaa aaaccgttgc gccgactgag gcc                                  633
```

<210> SEQ ID NO 40
<211> LENGTH: 1341
<212> TYPE: DNA
<213> ORGANISM: Artificial Sequence
<220> FEATURE:
<223> OTHER INFORMATION: Antibody sequence

<400> SEQUENCE: 40

```
caggtgcaat tggtggaaag cggcggcggc ctggtgcaac cgggcggcag cctgcgtctg      60
agctgcgcgg cctccggatt tacctttaat tcttatggtc tttcttgggt gcgccaagcc     120
cctgggaagg gtctcgagtg ggtgagcaat atctcttcta atggtagcta tacctattat     180
gcggatagcg tgaaaggccg ttttaccatt tcacgtgata attcgaaaaa cacccctgtat     240
ctgcaaatga acagcctgcg tgcggaagat acggccgtgt attattgcgc gcgtgctggt     300
tatggtcttt ttgatgtttg gggccaaggc accctggtga cggttagctc agccaaaaca     360
acagccccat cggtctatcc actggcccct gtgtgtggag atacaactgg ctcctcggtg     420
actctaggat gcctggtcaa gggttatttc cctgagccag tgaccttgac ctggaactct     480
ggatccctgt ccagtggtgt gcacaccttc ccagctgtcc tgcagtctga cctctacacc     540
ctcagcagct cagtgactgt aacctcgagc acctggccca gccagtccat cacctgcaat     600
gtggcccacc cggcaagcag caccaaggtg gacaagaaaa ttgagcccag agggcccaca     660
atcaagccct gtcctccatg caaatgccca gcacctaacc tcttgggtgg accatccgtc     720
ttcatcttcc ctccaaagat caaggatgta ctcatgatct ccctgagccc catagtcaca     780
tgtgtggtgg tggatgtgag cgaggatgac ccagatgtcc agatcagctg gtttgtgaac     840
aacgtggaag tacacacagc tcagacacaa acccatagag aggattacaa cagtactctc     900
cgggtggtca gtgccctccc catccagcac caggactgga tgagtggcaa ggagttcaaa     960
tgcaaggtca caacaaagga ccttccagcg cccatcgaga accatctc aaacccaaa       1020
gggtcagtaa gagctccaca ggtatatgtc ttgcctccac cagaagaaga gatgactaag    1080
aaacaggtca ctctgacctg catggtcaca gacttcatgc ctgaagacat ttacgtggag    1140
tggaccaaca cgggaaaac agagctaaac tacaagaaca ctgaaccagt cctggactct    1200
gatggttctt acttcatgta cagcaagctg agagtggaaa agaagaactg gtggaaaga    1260
```

```
aatagctact cctgttcagt ggtccacgag ggtctgcaca atcaccacac gactaagagc    1320
ttctcccgga ctccgggtaa a                                              1341
```

<210> SEQ ID NO 41
<211> LENGTH: 639
<212> TYPE: DNA
<213> ORGANISM: Artificial Sequence
<220> FEATURE:
<223> OTHER INFORMATION: Antibody sequence

<400> SEQUENCE: 41

```
gatatcgaac tgacccagcc gccttcagtg agcgttgcac caggtcagac cgcgcgtatc      60
tcgtgtagcg gcgataagct tcgtgagtat tatgttcatt ggtaccagca gaaacccggg     120
caggcgccag ttcttgtgat ttatggtgat aataagcgtc cctcaggcat cccggaacgc     180
tttagcggat ccaacagcgg caacaccgcg accctgacca ttagcggcac tcaggcggaa     240
gacgaagcgg attattattg ctcttcttgg gctggttctc gttctggtac tgtgtttggc     300
ggcggcacga agttaaccgt cctaggtcag cccaagtcca ctcccactct caccgtgttt     360
ccaccttcct ctgaggagct caaggaaaac aaagccacac tggtgtgtct gatttccaac     420
ttttccccga gtggtgtgac agtggcctgg aaggcaaatg gtacacctat cacccagggt     480
gtggacactt caaatcccac caaagagggc aacaagttca tggccagcag cttcctacat     540
ttgacatcgg accagtggag atctcacaac agttttacct gtcaagttac acatgaaggg     600
gacactgtgg agaagagtct gtctcctgca gaatgtctc                           639
```

<210> SEQ ID NO 42
<211> LENGTH: 666
<212> TYPE: DNA
<213> ORGANISM: Artificial Sequence
<220> FEATURE:
<223> OTHER INFORMATION: Antibody sequence

<400> SEQUENCE: 42

```
caggtgcaat tgaaagaaag cggcccggcc ctggtgaaaa cgacccaaac cctgaccctg      60
acctgtacct tttccggatt tagcctgtct acttctggta tgggtgtgtc ttggattcgc     120
cagccgcctg ggaaagccct cgagtggctg gctcatatca atcttgatga tgataagtat     180
tatagcacca gcctgaaaac gcgtctgacc attagcaaag atacttcgaa aaatcaggtg     240
gtgctgacta tgaccaacat ggacccggtg atacggcca cctattattg cgcgcgtggt     300
ggttatggtg atatgatgt tgggccaa ggcaccctgg tgacggttag ctcagcgtcg     360
accaaaggtc caagcgtgtt tccgctggct ccagcagca aaagcaccag cggcggcacg     420
gctgccctgg gctgcctggt taaagattat ttcccgaac cagtcaccgt gagctggaac     480
agcggggcgc tgaccagcgg cgtgcatacc tttccggcgg tgctgcaaag cagcggcctg     540
tatagcctga gcagcgttgt gaccgtgccg agcagcagct taggcactca gacctatatt     600
tgcaacgtga accataaacc gagcaacacc aaagtggata aaaaagtgga accgaaaagc     660
gaattc                                                               666
```

<210> SEQ ID NO 43
<211> LENGTH: 639
<212> TYPE: DNA
<213> ORGANISM: Artificial Sequence
<220> FEATURE:
<223> OTHER INFORMATION: Antibody sequence

<400> SEQUENCE: 43
gatatcgaac tgacccagcc gccttcagtg agcgttgcac caggtcagac cgcgcgtatc 60
tcgtgtagcg gcgataatat tcgttctatg tttgttcatt ggtaccagca gaaacccggg 120
caggcgccag ttcttgtgat ttatgctgat aataagcgtc cctcaggcat cccggaacgc 180
tttagcggat ccaacagcgg caacaccgcg accctgacca ttagcggcac tcaggcggaa 240
gacgaagcgg attattattg ctcttcttat gattataatg ctcatcttgt tgtgtttggc 300
ggcggcacga agttaaccgt tcttggccag ccgaaagccg caccgagtgt gacgctgttt 360
ccgccgagca gcgaagaatt gcaggcgaac aaagcgaccc tggtgtgcct gattagcgac 420
ttttatccgg gagccgtgac agtggcctgg aaggcagata gcagccccgt caaggcggga 480
gtggagacca ccacaccctc caaacaaagc aacaacaagt acgcggccag cagctatctg 540
agcctgacgc ctgagcagtg gaagtcccac agaagctaca gctgccaggt cacgcatgag 600
gggagcaccg tggaaaaaac cgttgcgccg actgaggcc 639

<210> SEQ ID NO 44
<211> LENGTH: 345
<212> TYPE: PRT
<213> ORGANISM: Artificial Sequence
<220> FEATURE:
<223> OTHER INFORMATION: Pseudomonas endotoxin sequence

<400> SEQUENCE: 44

Gly Gly Ser Leu Ala Ala Leu Thr Ala His Gln Ala Cys His Leu Pro
1 5 10 15

Leu Glu Thr Phe Thr Arg His Arg Gln Pro Arg Gly Trp Glu Gln Leu
20 25 30

Glu Gln Cys Gly Tyr Pro Val Gln Arg Leu Val Ala Leu Tyr Leu Ala
35 40 45

Ala Arg Leu Ser Trp Asn Gln Val Asp Gln Val Ile Arg Asn Ala Leu
50 55 60

Ala Ser Pro Gly Ser Gly Gly Asp Leu Gly Glu Ala Ile Arg Glu Gln
65 70 75 80

Pro Glu Gln Ala Arg Leu Ala Leu Thr Leu Ala Ala Ala Glu Ser Glu
85 90 95

Arg Phe Val Arg Gln Gly Thr Gly Asn Asp Glu Ala Gly Ala Ala Asn
100 105 110

Gly Pro Ala Asp Ser Gly Asp Ala Leu Leu Glu Arg Asn Tyr Pro Thr
115 120 125

Gly Ala Glu Phe Leu Gly Asp Gly Gly Asp Val Ser Phe Ser Thr Arg
130 135 140

Gly Thr Gln Asn Trp Thr Val Glu Arg Leu Leu Gln Ala His Arg Gln
145 150 155 160

Leu Glu Glu Arg Gly Tyr Val Phe Val Gly Tyr His Gly Thr Phe Leu
165 170 175

Glu Ala Ala Gln Ser Ile Val Phe Gly Gly Val Arg Ala Arg Ser Gln
180 185 190

Asp Leu Asp Ala Ile Trp Arg Gly Phe Tyr Ile Ala Gly Asp Pro Ala
195 200 205

Leu Ala Tyr Gly Tyr Ala Gln Asp Gln Glu Pro Asp Ala Arg Gly Arg
210 215 220

Ile Arg Asn Gly Ala Leu Leu Arg Val Tyr Val Pro Arg Ser Ser Leu
225 230 235 240

```
Pro Gly Phe Tyr Arg Thr Ser Leu Thr Leu Ala Ala Pro Glu Ala Ala
                245                 250                 255

Gly Glu Val Glu Arg Leu Ile Gly His Pro Leu Pro Leu Arg Leu Asp
            260                 265                 270

Ala Ile Thr Gly Pro Glu Glu Gly Gly Arg Leu Glu Thr Ile Leu
                275                 280                 285

Gly Trp Pro Leu Ala Glu Arg Thr Val Val Ile Pro Ser Ala Ile Pro
        290                 295                 300

Thr Asp Pro Arg Asn Val Gly Gly Asp Leu Asp Pro Ser Ser Ile Pro
305                 310                 315                 320

Asp Lys Glu Gln Ala Ile Ser Ala Leu Pro Asp Tyr Ala Ser Gln Pro
                325                 330                 335

Gly Lys Pro Pro Arg Glu Asp Leu Lys
        340                 345

<210> SEQ ID NO 45
<211> LENGTH: 230
<212> TYPE: PRT
<213> ORGANISM: Artificial Sequence
<220> FEATURE:
<223> OTHER INFORMATION: Pseudomonas endotoxin sequence

<400> SEQUENCE: 45

Arg His Arg Gln Pro Arg Gly Trp Glu Gln Leu Pro Thr Gly Ala Glu
1               5                   10                  15

Phe Leu Gly Asp Gly Gly Asp Val Ser Phe Ser Thr Arg Gly Thr Gln
                20                  25                  30

Asn Trp Thr Val Glu Arg Leu Leu Gln Ala His Arg Gln Leu Glu Glu
            35                  40                  45

Arg Gly Tyr Val Phe Val Gly Tyr His Gly Thr Phe Leu Glu Ala Ala
    50                  55                  60

Gln Ser Ile Val Phe Gly Gly Val Arg Ala Arg Ser Gln Asp Leu Asp
65                  70                  75                  80

Ala Ile Trp Arg Gly Phe Tyr Ile Ala Gly Asp Pro Ala Leu Ala Tyr
                85                  90                  95

Gly Tyr Ala Gln Asp Gln Glu Pro Asp Ala Arg Gly Arg Ile Arg Asn
            100                 105                 110

Gly Ala Leu Leu Arg Val Tyr Val Pro Arg Ser Ser Leu Pro Gly Phe
        115                 120                 125

Tyr Arg Thr Ser Leu Thr Leu Ala Ala Pro Glu Ala Ala Gly Glu Val
    130                 135                 140

Glu Arg Leu Ile Gly His Pro Leu Pro Leu Arg Leu Asp Ala Ile Thr
145                 150                 155                 160

Gly Pro Glu Glu Gly Gly Arg Leu Glu Thr Ile Leu Gly Trp Pro
                165                 170                 175

Leu Ala Glu Arg Thr Val Val Ile Pro Ser Ala Ile Pro Thr Asp Pro
            180                 185                 190

Arg Asn Val Gly Gly Asp Leu Asp Pro Ser Ser Ile Pro Asp Lys Glu
        195                 200                 205

Gln Ala Ile Ser Ala Leu Pro Asp Tyr Ala Ser Gln Pro Gly Lys Pro
    210                 215                 220

Pro Arg Glu Asp Leu Lys
225                 230

<210> SEQ ID NO 46
<211> LENGTH: 230
```

```
<212> TYPE: PRT
<213> ORGANISM: Artificial Sequence
<220> FEATURE:
<223> OTHER INFORMATION: Pseudomonas endotoxin sequence

<400> SEQUENCE: 46
```

Arg His Arg Gln Pro Arg Gly Trp Glu Gln Leu Pro Thr Gly Ala Glu
1               5                   10                  15

Phe Leu Gly Asp Gly Gly Asp Val Ser Phe Ser Thr Arg Gly Thr Gln
            20                  25                  30

Asn Trp Thr Val Glu Arg Leu Leu Gln Ala His Arg Gln Leu Glu Glu
        35                  40                  45

Gly Gly Tyr Val Phe Val Gly Tyr His Gly Thr Phe Leu Glu Ala Ala
    50                  55                  60

Gln Ser Ile Val Phe Gly Gly Val Arg Ala Arg Ser Gln Asp Leu Asp
65                  70                  75                  80

Ala Ile Trp Ala Gly Phe Tyr Ile Ala Gly Asp Pro Ala Leu Ala Tyr
                85                  90                  95

Gly Tyr Ala Gln Asp Gln Glu Pro Asp Ala Ala Gly Arg Ile Arg Asn
            100                 105                 110

Gly Ala Leu Leu Arg Val Tyr Val Pro Arg Ser Ser Leu Pro Gly Phe
        115                 120                 125

Tyr Ala Thr Ser Leu Thr Leu Ala Ala Pro Glu Ala Ala Gly Glu Val
    130                 135                 140

Glu Arg Leu Ile Gly His Pro Leu Pro Leu Arg Leu Asp Ala Ile Thr
145                 150                 155                 160

Gly Pro Glu Glu Ser Gly Gly Arg Leu Glu Thr Ile Leu Gly Trp Pro
                165                 170                 175

Leu Ala Glu Arg Thr Val Val Ile Pro Ser Ala Ile Pro Thr Asp Pro
            180                 185                 190

Arg Asn Val Gly Gly Asp Leu Asp Pro Ser Ser Ile Pro Asp Ser Glu
        195                 200                 205

Gln Ala Ile Ser Ala Leu Pro Asp Tyr Ala Ser Gln Pro Gly Lys Pro
    210                 215                 220

Pro Arg Glu Asp Leu Lys
225                 230

```
<210> SEQ ID NO 47
<211> LENGTH: 230
<212> TYPE: PRT
<213> ORGANISM: Artificial Sequence
<220> FEATURE:
<223> OTHER INFORMATION: Pseudomonas endotoxin sequence
<220> FEATURE:
<221> NAME/KEY: MISC_FEATURE
<222> LOCATION: (23)..(23)
<223> OTHER INFORMATION: X is G, A, or S
<220> FEATURE:
<221> NAME/KEY: MISC_FEATURE
<222> LOCATION: (49)..(49)
<223> OTHER INFORMATION: X is G, A, or S
<220> FEATURE:
<221> NAME/KEY: MISC_FEATURE
<222> LOCATION: (84)..(84)
<223> OTHER INFORMATION: X is G, A, or S
<220> FEATURE:
<221> NAME/KEY: MISC_FEATURE
<222> LOCATION: (107)..(107)
<223> OTHER INFORMATION: X is G, A, or S
<220> FEATURE:
<221> NAME/KEY: MISC_FEATURE
<222> LOCATION: (130)..(130)
<223> OTHER INFORMATION: X is G, A, or S
```

```
<220> FEATURE:
<221> NAME/KEY: MISC_FEATURE
<222> LOCATION: (165)..(165)
<223> OTHER INFORMATION: X is G, A, or S
<220> FEATURE:
<221> NAME/KEY: MISC_FEATURE
<222> LOCATION: (207)..(207)
<223> OTHER INFORMATION: X is G, A, or S
<220> FEATURE:
<221> NAME/KEY: MISC_FEATURE
<222> LOCATION: (209)..(209)
<223> OTHER INFORMATION: X is G, A, or S

<400> SEQUENCE: 47
```

Arg His Arg Gln Pro Arg Gly Trp Glu Gln Leu Pro Thr Gly Ala Glu
1               5                   10                  15

Phe Leu Gly Asp Gly Gly Xaa Val Ser Phe Ser Thr Arg Gly Thr Gln
            20                  25                  30

Asn Trp Thr Val Glu Arg Leu Leu Gln Ala His Arg Gln Leu Glu Glu
        35                  40                  45

Xaa Gly Tyr Val Phe Val Gly Tyr His Gly Thr Phe Leu Glu Ala Ala
    50                  55                  60

Gln Ser Ile Val Phe Gly Val Arg Ala Arg Ser Gln Asp Leu Asp
65                  70                  75                  80

Ala Ile Trp Xaa Gly Phe Tyr Ile Ala Gly Asp Pro Ala Leu Ala Tyr
                85                  90                  95

Gly Tyr Ala Gln Asp Gln Glu Pro Asp Ala Xaa Gly Arg Ile Arg Asn
            100                 105                 110

Gly Ala Leu Leu Arg Val Tyr Val Pro Arg Ser Ser Leu Pro Gly Phe
        115                 120                 125

Tyr Xaa Thr Ser Leu Thr Leu Ala Ala Pro Glu Ala Ala Gly Glu Val
    130                 135                 140

Glu Arg Leu Ile Gly His Pro Leu Pro Leu Arg Leu Asp Ala Ile Thr
145                 150                 155                 160

Gly Pro Glu Glu Xaa Gly Gly Arg Leu Glu Thr Ile Leu Gly Trp Pro
                165                 170                 175

Leu Ala Glu Arg Thr Val Val Ile Pro Ser Ala Ile Pro Thr Asp Pro
            180                 185                 190

Arg Asn Val Gly Gly Asp Leu Asp Pro Ser Ser Ile Pro Asp Xaa Glu
        195                 200                 205

Xaa Ala Ile Ser Ala Leu Pro Asp Tyr Ala Ser Gln Pro Gly Lys Pro
    210                 215                 220

Pro Arg Glu Asp Leu Lys
225             230

```
<210> SEQ ID NO 48
<211> LENGTH: 230
<212> TYPE: PRT
<213> ORGANISM: Artificial Sequence
<220> FEATURE:
<223> OTHER INFORMATION: Pseudomonas endotoxin sequence

<400> SEQUENCE: 48
```

Arg His Arg Gln Pro Arg Gly Trp Glu Gln Leu Pro Thr Gly Ala Glu
1               5                   10                  15

Phe Leu Gly Asp Gly Gly Ala Val Ser Phe Ser Thr Arg Gly Thr Gln
            20                  25                  30

Asn Trp Thr Val Glu Arg Leu Leu Gln Ala His Arg Gln Leu Glu Glu
        35                  40                  45

-continued

```
Gly Gly Tyr Val Phe Val Gly Tyr His Gly Thr Phe Leu Glu Ala Ala
     50              55                  60
Gln Ser Ile Val Phe Gly Gly Val Arg Ala Arg Ser Gln Asp Leu Asp
 65              70                  75              80
Ala Ile Trp Ala Gly Phe Tyr Ile Ala Gly Asp Pro Ala Leu Ala Tyr
             85                  90                  95
Gly Tyr Ala Gln Asp Gln Glu Pro Asp Ala Ala Gly Arg Ile Arg Asn
             100                 105             110
Gly Ala Leu Leu Arg Val Tyr Val Pro Arg Ser Ser Leu Pro Gly Phe
         115             120                 125
Tyr Ala Thr Ser Leu Thr Leu Ala Ala Pro Glu Ala Ala Gly Glu Val
         130             135             140
Glu Arg Leu Ile Gly His Pro Leu Pro Leu Arg Leu Asp Ala Ile Thr
145             150                 155                 160
Gly Pro Glu Glu Ser Gly Gly Arg Leu Glu Thr Ile Leu Gly Trp Pro
                 165             170                 175
Leu Ala Glu Arg Thr Val Val Ile Pro Ser Ala Ile Pro Thr Asp Pro
             180             185                 190
Arg Asn Val Gly Gly Asp Leu Asp Pro Ser Ser Ile Pro Asp Ser Glu
             195             200                 205
Ala Ala Ile Ser Ala Leu Pro Asp Tyr Ala Ser Gln Pro Gly Lys Pro
         210             215             220
Pro Arg Glu Asp Leu Lys
225             230
```

TEM8 ANTIBODIES, CONJUGATES THEREOF, AND THEIR USE

CROSS REFERENCE TO RELATED APPLICATIONS

This is the U.S. National Stage of International Application No. PCT/US2012/042315, filed Jun. 13, 2012, which was published in English under PCT Article 21(2), which in turn claims the benefit of U.S. Provisional Application Nos. 61/496,986, filed Jun. 14, 2011, and 61/496,737, filed Jun. 14, 2011, each of which is incorporated herein in its entirety.

FIELD

This application relates to the fields of cancer and bacterial infection, particularly to antibodies and antibody conjugates that specifically bind TEM8.

PARTIES TO A JOINT RESEARCH AGREEMENT

This invention was made under Public Health Service Cooperative Research and Development Agreement (PHS-CRADA) No. 02350 between the National Institutes of Health National Cancer Institute and Novartis Institutes for BioMedical Research, Inc.

BACKGROUND

Angiogenesis, the process of developing a hemovascular network from pre-existing blood vessels, is essential for the growth of solid tumors and is a component of normal wound healing and growth processes. It also has been implicated in the pathophysiology of many diseases and conditions, including atherogenesis, arthritis, psoriasis, corneal neo-vascularization, and diabetic retinopathy. Angiogenesis factors play an important role in the development of malignancies.

Tumor Endothelial Marker 8 (TEM8), also known as Anthrax Toxin Receptor 1 (ANTXR1), is a single pass, cell surface glycoprotein originally identified, along with a number of other unrelated Tumor Endothelial Markers, based on its over-expression in the endothelial cells that line the tumor vasculature of human colorectal cancer. TEM8 also functions as a cell surface receptor for Anthrax toxin, and shares 58% amino acid identity with CMG2 (also known as ANTXR2), a second receptor for Anthrax toxin protein. Unlike VEGF, VEGFRs, and many other key angiogenesis regulators, TEM8 is not required for developmental angiogenesis, wound healing or normal physiological angiogenesis of the corpus luteum. TEM8 is up-regulated on tumor vessels of various tumor types in both mice and humans, and, in some tumors, is also expressed by the tumor cells. However, a need remains for chemotherapeutic agents that target TEM8, and for high affinity antibodies that specifically bind TEM8 on the cell surface.

SUMMARY

Isolated human monoclonal neutralizing antibodies that specifically bind to TEM8 on the cell surface, antigen binding fragments of such antibodies, conjugates thereof, and methods of using these molecules, are provided. In some embodiments, the conjugates include an effector molecule or detectable marker covalently linked to a monoclonal antibody, or an antigen binding fragment thereof, that specifically binds TEM8. In some embodiments, the antibodies or conjugates are used in methods for the detection of an endothelial cell from a subject that expresses TEM8. In some embodiments, detection of an endothelial cell from a subject that expresses TEM8 detects pathological angiogenesis in a subject. In other embodiments, the antibodies and conjugates are used in methods of detecting and treating a tumor, for example a carcinoma. In still other embodiments, the antibodies and conjugates are used in methods of decreasing Anthrax protective antigen (PA) binding to a cell.

It will be understood that the antibodies and conjugates and methods of their use are useful beyond the specific circumstances that are described in detail herein. For instance, the methods are expected to be useful for a variety of situations, for example to detect an endothelial cell expressing TEM8 in a subject, treat a tumor in a subject or to decrease binding of Anthrax PA to a cell.

The foregoing and features and advantages of the disclosure will become more apparent from the following detailed description, which proceeds with reference to the accompanying figures.

BRIEF DESCRIPTION OF THE FIGURES

FIGS. 1A-1G show a series of graphs and a digital image illustrating that the growth of human tumor xenografts is impaired in TEM8 KO mice. Xenografts of (A-B) Melanoma (UACC, LOX), (C) breast (MDA-MB-231), (D) Lung (NCI-H460), and (E-G) colon (DLD-1, HCT-116, and SW620) cancer cell lines were injected subcutaneously into TEM8 wildtype (WT, circles) or knockout (KO, squares) mice and tumor volume monitored over time. The physical appearance of the resected UACC tumors is shown in A. (G) In the SW620 study tumors in the TEM8 KO group required over 100 days to reach an average size of 800 mm$^3$, versus only 35 days in the TEM8 WT group. p-values were calculated from the final tumor measurement (A-F) or at day 41 (G) when the WT group reached its maximum size and had to be euthanized (Student's t-test). Bar=10 mm.

FIGS. 2A-2G show a series of graphs and digital images illustrating that the L2-mIgG2a and L5-mIgG2a antibodies react selectively with cells expressing TEM8, but not CMG2, and block binding and toxicity of Anthrax toxin proteins. (A) Flow cytometry staining with L2-mIgG2a antibody revealed reactivity with 293 cells stably transfected with mouse TEM8 (293-mTEM8) or a flag-tagged human TEM8 (293-Flag-hTEM8), but not parent 293 cells. (B) L2-mIgG2a and L5-mIgG2a stained Chinese Hamster Ovary (CHO) cells stably transfected with human TEM8 (CHO-TEM8) but not CMG2 (CHO-CMG2), whereas FITC-labeled PA (PA-FITC) labeled both cell types. (C) Western blot analysis confirmed the over-expression of TEM8 and CMG2 in stably transfected CHO-TEM8 and CHO-CMG2 cells. (D) Immunofluorescence staining with L2-mIgG2a reveals cell surface labeling of CHO-TEM8 cells. (E) L2-mIgG2a and L5-mIgG2a antibodies blocked binding of PA-FITC to CHO-TEM8 cells in a dose-dependent manner as measured by flow cytometry. (F) Lethal toxin selectively killed CHO-TEM8 cells, but not parent CHO cells. (G) L2-mIgG2a and L5-mIgG2a antibodies protect cells from toxicity following treatment with 1 µg/ml mg of lethal toxin. In this assay the $EC_{50}$ for L2-mIgG2a was 292 ng/mL and 2575 ng/mL for L5-mIgG2a.

FIGS. 3A-3H show a series of graphs and a digital image illustrating that the L2-mIgG2a and L5-mIgG2a antibodies inhibit the growth of human tumor xenografts, but do not delay wound healing. Nude mice were inoculated subcutaneously with UACC (FIGS. 3A and 3D), LS174T (FIG. 3B), HCT-116 (FIG. 3C) or B16 (FIG. 3E) tumor cells and the resulting tumor growth monitored. Treatments with phosphate buffered saline (PBS) (vehicle), anti-VEGFR2 antibodies, or L2-mIgG2a anti-TEM8 antibodies were administered 3 times per week and were initiated when tumors reached a size of 50 mm³ (arrow). FIG. 3A shows that L2-mIgG2a treatment inhibited UACC tumor growth. The digital image shows the physical appearance of the melanoma tumors at the end of the study following surgical excision. Bar=10 mm FIG. 3B shows that L2-mIgG2a treatment inhibited LS174T tumor growth to a level similar to that of VEGFR2 antibodies. FIG. 3C shows that L5-mIgG2a treatment inhibited HCT-116 tumor growth. FIG. 3D shows that L2-mIgG2a and L5-mIgG2a inhibited the growth of UACC tumors in a dose-dependent manner. L2-mIgG2a administered at 2 mg/kg was similar to L5-mIgG2a administered at 15 mg/kg. FIG. 3E shows that L2-mIgG2a treatment inhibited B16 melanoma tumor growth. FIG. 3F shows that wound closure rates were not affected following treatment with L2 compared to vehicle (PBS) alone. Wounds were generated in the same tumor-bearing mice as shown in FIG. 3E. FIG. 3G shows CD31-immunofluorescence staining of granulation tissue vasculature in control and L2 treated groups. Control mice received non-specific IgG in this experiment (n=6 wounds per group). FIG. 3H shows Matrigel Plug vascularization assessed following treatment with non-specific IgG or L2 anti-TEM8 antibodies. Vessels areas were calculated from 6 plugs per group. Values in represent mean±SE. Bar in FIGS. 3G and 3H: 100 μm. Tumors were excised at the end of the study to calculate final tumor weights (insets in A, B and C). *P=0.00005, P=0.002, **P=0.02. A Student's t-test was used to calculate p-values between the vehicle and L2 treatment groups at the final tumor measurement.

FIGS. 4A-4E show a set of graphs and digital images illustrating that L2-mIgG2a-mediated suppression of tumor growth and vascular density depend upon host-derived TEM8 expression. (FIG. 4A) Non-specific antibodies (IgG control) or L2-mIgG2a anti-TEM8 antibodies administered to TEM8 wild-type (T8-WT) or TEM8 knockout (T8-KO) nude mice at 20 mg/kg three times per week beginning one day post subcutaneous inoculation of TEM8 negative DLD-1 tumor cells. The L2-mIgG2a antibody only inhibited tumor growth in TEM8 WT mice. (FIG. 4B) Immunofluorescence staining revealed a lower tumor vessel density in the L2-mIgG2a treated WT, the IgG treated KO, and the L2-mIgG2a treated KO groups, compared to the WT IgG control group. In TEM8 KO mice, L2-mIgG2a treatment did not significantly reduce tumor vessel density compared to the IgG control. Right panel, quantification of CD31 positive vessel area. * P<0.05 between each of the groups and the IgG WT control group (one-way ANOVA). (FIG. 4C) Flow cytometry staining of dispersed tumor tissues was used to determine the percent of CD31-positive cells in L2-treated tumors from Tem8 WT mice (WT-L2), IgG treated tumors from Tem8 KO mice (KO-IgG) and IgG treated tumors from Tem8 wild-type mice (WT-IgG). The dot plots show representative data for each of the groups and the bar graph displays the average percent CD31-positive cells (n=6 per group). Both the WT-L2 and KO-IgG groups had significantly fewer cells than the WT-IgG group as determined by a one-way ANOVA. (FIG. 4D) The effect of L2 treatment on proliferation of DLD1 tumor-associated ECs was assessed by immunofluorescence staining for phospho-histone H3 (PHH3), a marker of proliferating cells. Vessels were stained with both CD31 and Meca32 antibodies. Arrowheads point to PHH3 positive vessels (inset). To calculate the relative amount of vessel specific proliferation in the vehicle (PBS) or L2 treated tumors (graph), the co-localization area (indicated by the arrow) was calculated as a percent of the total vessel area. (FIG. 4E) The effect of L2 treatment on apoptosis of DLD1 tumor-associated ECs was measured using the TUNEL-based assay that detects DNA fragmentation by incorporating digoxigenin-labeled nucleotides onto DNA fragments using the TdT enzyme, followed by detection with a FITC-labeled anti-digoxigenin antibody. Vessels were stained with anti-Meca32 and anti-CD31. Arrowheads point to TUNEL positive vessel nuclei (inset). To calculate the amount of apoptosis in the vehicle (PBS) or L2 treated tumors (graph), the co-localization area (indicated by the arrow) was calculated as a fraction of the total vessel area. Values were normalized to the vehicle group. *p<0.02. All sections in FIGS. 4D and 4E were counterstained with DAPI. Values in (C) and (D) represent means±SE. Bar in FIGS. 4D and 4E: 100 μm.

FIGS. 5A-5F show a set of digital images and graphs illustrating that L2 targets tumor vasculature in vivo and engages antibody-dependent cellular cytotoxicity (ADCC) and complement dependent cytotoxicity (CDC) in vitro. FIGS. 5A and 5B show that a conjugate of FITC covalently linked to the L2-mIgG2a antibody specifically labels tumor stroma in vivo in TEM8 WT mice, but is undetectable in normal tissues of TEM8 WT mice. (A) TEM8 WT mice were inoculated with DLD-1 colon cancer cells. Following growth of the resulting tumor, the mice were treated with intravenous injection of the FITC-L2-mIgG2a antibody conjugate, which was allowed to circulate for three hours. Following treatment, brain, heart, intestine, liver, muscle, spleen, stomach and tumor tissue was harvested, frozen in OCT, cryosectioned, and processed for immunofluorescence staining with Meca-32 (a pan-endothelial antibody) and DAPI (a nuclei stain), and examined using immunofluorescence microscopy. FITC immunofluorescence partially overlapped with Meca-32 immunofluorescence in tumor tissue of TEM8 WT, but was undetectable in normal tissue. (B) TEM8 WT and TEM8-KO mice were treated as in (A). FITC immunofluorescence overlapped with Meca-32 immunofluorescence in tumor tissue of TEM8 WT, but not TEM8-KO mice, indicated that the FITC-L2-mIgG2a staining of tumor stroma is TEM8 specific. FIGS. 5C-5F illustrate that that the L2 antibody engages ADCC and CDC in vitro. (C-D) NK-mediated toxicity against TEM8 expressing target cells was measured in the presence of L2 or control IgG. The effector to target cell ratio (E:T) in (c) was 25:1; the results using different E:T ratios are shown in (D). (E) Complement-dependent cytotoxicity (CDC) was assessed using varying amounts of L2 or control IgG. (F) To evaluate complement dependency, variable amounts of complement (compl.) were added to the CDC assay. Values in (FIGS. 5C-5F) represent mean±SE.

FIGS. 8A-8C show a table and a series of digital images and graphs illustrating that the antibody binding fragments of L1, L2, L3, L5, and 1D2 bind mouse and human TEM8. (A) An Enzyme Linked Immunosorbent Assay (ELISA) was used to identify Fabs that were able to react with purified recombinant hTEM8(ED)-Fc fusion protein. The half maximum concentration (EC$_{50}$) of the indicated Fabs needed to bind TEM8 is shown. (B) The indicated Fabs were screened for their ability to bind 293 cells expressing human TEM8 (293/Flag-hTEM8) by immunofluorescence staining. (C) Flow cytometry was used to screen the indicated Fabs for their ability to bind the native extracellular domain of mouse (293/mTEM8) or human (293/Flag-hTEM8) TEM8. The pooled population of 293/Flag-hTEM8 cells used has a uniform high level expression of TEM8 because they had been enriched for surface expression by FACS using anti-Flag antibodies prior to screening. The stably-transfected 293/mTEM8 cells, on the other hand, had not been enriched, and therefore express a heterogeneous (bimodal) pattern of mouse TEM8 staining. Following FACS enrichment of 293/mTEM8 cells with an independent anti-TEM8 antibody (AF344), the pattern of mouse TEM8 staining became similar to that of 293/Flag-hTEM8 cells (for example, see FIG. 2).

FIG. 9A shows that the L1, L2, L3, and L5 anti-TEM8 Fabs inhibit binding of the PA subunit of Anthrax toxin to cells expressing TEM8. CHO cells expressing TEM8 were pre-incubated with the indicated anti-TEM8 Fabs, followed by incubation with FITC conjugated PA and analyzed by flow cytometry. The examined Fabs blocked the binding of PA to TEM8 expressing CHO cells in a dose-dependent manner. The Fab concentrations required to inhibit half of the maximum binding (EC$_{50}$) is shown. FIG. 9B shows that the L2 and L5 full IgGs bind to TEM8 on the cell surface. The L2 and L5 IgGs were tested in flow cytometry by incubating 293/Flag-hTEM8 cells with various concentrations of the antibodies, followed by FITC-labeled anti-mouse secondary antibodies. The concentration of antibody required for EC$_{50}$ is shown in the legend. Values represent means±SE.

FIGS. 13A-13F are a series of graphs and digital images illustrating that TEM8 is selectively up-regulated on tumor vasculature and is elevated in cultured Human dermal microvascular endothelial cells (HMECs) in response to growth factor deprivation. FIG. 13A shows the results of quantitative real-time PCR (QPCR) assays used to evaluate the expression of the indicated genes in endothelial cells isolated from resting adult liver (0 hr), regenerating liver taken 6 hrs, 18 hrs, 48 hrs, 72 hrs, or 96 hrs following 70% partial hepatectomy, or from DLD1, HCT116, or LS174T colon cancer xenografts. FIG. 13B shows TEM8 mRNA levels over the course of 10 days in HMECs grown in EBM-2 (EBM) basal medium or in complete medium (EBM supplemented with FGF (F), VEGF (V) and 5% fetal bovine serum (S)). FIG. 13C shows TEM8 protein levels over the course of 10 days in HMECs grown in basal medium or in complete medium. The media are the same as in FIG. 13B. FIG. 13D shows the appearance of the cells used in FIGS. 13B and 13C. HMECs became confluent by day 6 in complete medium, but formed only small colonies by day 10 in basal medium. The media are the same as in FIG. 13B. Bar=100 µm. FIGS. 13E and 13F show the effect of supplementation of basal growth medium with FGF, VEGF, or serum alone or all three together on the expression of TEM8 protein (FIG. 13E) and mRNA (FIG. 13F) (*$p<0.05$). Values in FIGS. 13A, 13B and 13F represent mean±SD.

FIGS. 14A-14D illustrate that TEM8 is expressed by tumor endothelium and is regulated by Fibroblast Growth Factor (FGF) and Vascular Endothelial Cell Growth Factor (VEGF) in cultured HMECs. FIG. 14A shows the results of QPCR assays used to monitor Tem8 gene expression in $CD11b^+$ (myeloid), $CD45^+$ (hematopoietic) or $CD105^+$ (endothelial) cells isolated from HCT116 (HCT), LS174T (LS), or DLD1 (DLD) tumors. The macrophage marker F4/80 and the myeloid cell marker CD11b were highly enriched in both the $CD11b^+$ and $CD45^+$ fractions, while the endothelial marker VE-cadherin was highly enriched only in the $CD105^+$ fraction, confirming the purity of the isolated cells. Values represent means±SD. FIG. 14B shows results of Western blotting used to assess the impact of tumor cells on TEM8 expression in HMECs. HMECs cultured alone express a low but detectable level of TEM8 protein (lane 3). Lane 4 represents isolated HMECs that were enriched by magnetic bead selection from 48-hour co-cultures of HMECs and DLD1 cells. CHO cells transfected with human TEM8 (CHO-TEM8) served as a control for antibody specificity. TEM8 migrated at 80-85 kDa in HMECs and CHO-TEM8 cells. FIG. 14C shows the results of Western blotting used to assess the impact of hypoxia (1% $O_2$) or the hypoxia mimetic cobalt chloride ($CoCl_2$) on TEM8 protein expression levels in HMECs. HIF-1α was used as a positive control. FIG. 14D shows the results of Western blotting used to assess TEM8 protein levels in HMECs following exposure to VEGF and FGF. HMECs cultured in EBM-2 basal medium containing 1% FBS were stimulated with VEGF or FGF for 0 hr (control), 24 hrs, 48 hrs, or 72 hrs.

SEQUENCE LISTING

Figure 1A:
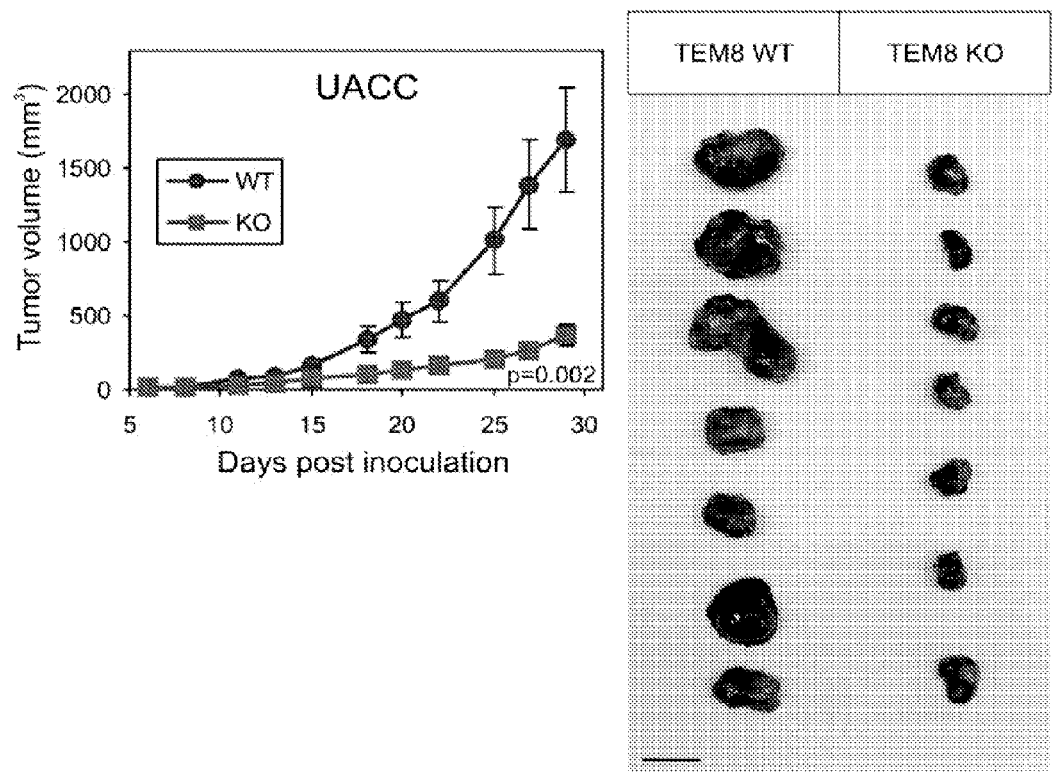

The nucleic and amino acid sequences provided herein are shown using standard letter abbreviations for nucleotide bases, and three letter codes for amino acids, as defined in 37 C.F.R. 1.822. Only one strand of each nucleic acid sequence is shown, but the complementary strand is understood as included by any reference to the displayed strand. The Sequence Listing is submitted as an ASCII text file in the form of the file named "Sequence.txt" (~76 kb), which was created on Jan. 22, 2014, which is incorporated by reference herein. In the accompanying sequence listing:

SEQ ID NO: 1 is the amino acid sequence of the heavy chain variable region of the L2 mAb.

SEQ ID NO: 2 is the amino acid sequence of the heavy chain variable region of the L1 mAb.

SEQ ID NO: 3 is the amino acid sequence of the heavy chain variable region of the L3 mAb.

SEQ ID NO: 4 is the amino acid sequence of the heavy chain variable region of the L5 mAb.

SEQ ID NO: 5 is the amino acid sequence of the heavy chain variable region of the 1D2 mAb.

SEQ ID NO: 6 is the amino acid sequence of the light chain of the L2 mAb.

SEQ ID NO: 7 is the amino acid sequence of the light chain of the L1 mAb.

SEQ ID NO: 8 is the amino acid sequence of the light chain of the L3 mAb.

SEQ ID NO: 9 is the amino acid sequence of the light chain of the L5 mAb.

SEQ ID NO: 10 is the amino acid sequence of the light chain of the 1D2 mAb.

SEQ ID NO: 11 is the amino acid sequence of the heavy chain of the L2-mIgG2a mAb.

SEQ ID NO: 12 is an exemplary cDNA sequence encoding human TEM8 protein.

SEQ ID NO: 13 is the protein sequence of human TEM8.

SEQ ID NO: 14 is an exemplary cDNA sequence encoding the heavy chain variable region of the L2 mAb.

SEQ ID NO: 15 is an exemplary cDNA sequence encoding the heavy chain variable region of the L1 mAb.

SEQ ID NO: 16 is an exemplary cDNA sequence encoding the heavy chain variable region of the L3 mAb.

SEQ ID NO: 17 is an exemplary cDNA sequence encoding the heavy chain variable region of the L5 mAb.

SEQ ID NO: 18 is an exemplary cDNA sequence encoding the heavy chain variable region of the 1D2 mAb.

SEQ ID NO: 19 is an exemplary cDNA sequence encoding the light chain variable region of the L2 mAb.

SEQ ID NO: 20 is an exemplary cDNA sequence encoding the light chain variable region of the L1 mAb.

SEQ ID NO: 21 is an exemplary cDNA sequence encoding the light chain variable region of the L3 mAb.

SEQ ID NO: 22 is an exemplary cDNA sequence encoding the light chain variable region of the L5 mAb.

SEQ ID NO: 23 is an exemplary cDNA sequence encoding the light chain variable region of the 1D2 mAb.

SEQ ID NO: 24 is the amino acid sequence of the heavy chain of the L2 Fab isolated as described in Example 2.

SEQ ID NO: 25 is the amino acid sequence of the light chain of the L2 Fab isolated as described in Example 2.

SEQ ID NO: 26 is the amino acid sequence of the heavy chain of the L1 Fab isolated as described in Example 2.

SEQ ID NO: 27 is the amino acid sequence of the light chain of the L1 Fab isolated as described in Example 2.

SEQ ID NO: 28 is the amino acid sequence of the heavy chain of the L3 Fab isolated as described in Example 2.

SEQ ID NO: 29 is the amino acid sequence of the light chain of the L3 Fab isolated as described in Example 2.

SEQ ID NO: 30 is the amino acid sequence of the heavy chain of the L5 Fab isolated as described in Example 2.

SEQ ID NO: 31 is the amino acid sequence of the light chain of the L5 Fab isolated as described in Example 2.

SEQ ID NO: 32 is the amino acid sequence of the heavy chain of the 1D2 Fab isolated as described in Example 2.

SEQ ID NO: 33 is the amino acid sequence of the light chain of the 1D2 Fab isolated as described in Example 2.

SEQ ID NO: 34 is an exemplary cDNA sequence encoding the heavy chain of the L2 Fab isolated as described in Example 2.

SEQ ID NO: 35 is an exemplary cDNA sequence encoding the light chain of the L2 Fab isolated as described in Example 2.

SEQ ID NO: 36 is an exemplary cDNA sequence encoding the heavy chain of the L1 Fab isolated as described in Example 2.

SEQ ID NO: 37 is an exemplary cDNA sequence encoding the light chain of the L1 Fab isolated as described in Example 2.

SEQ ID NO: 38 is an exemplary cDNA sequence encoding the heavy chain of the L3 Fab isolated as described in Example 2.

SEQ ID NO: 39 is an exemplary cDNA sequence encoding the light chain of the L3 Fab isolated as described in Example 2.

SEQ ID NO: 40 is an exemplary cDNA sequence encoding the heavy chain of the L5 Fab isolated as described in Example 2.

SEQ ID NO: 41 is an exemplary cDNA sequence encoding the light chain of the L5 Fab isolated as described in Example 2.

SEQ ID NO: 42 is an exemplary cDNA sequence encoding the heavy chain of the 1D2 Fab isolated as described in Example 2.

SEQ ID NO: 43 is an exemplary cDNA sequence encoding the light chain of the 1D2 Fab isolated as described in Example 2.

SEQ ID NO: 44 is the amino acid sequence of a pseudomonas endotoxin.

SEQ ID NO: 45 is the amino acid sequence of a pseudomonas endotoxin.

SEQ ID NO: 46 is the amino acid sequence of a pseudomonas endotoxin.

SEQ ID NO: 47 is the amino acid sequence of a pseudomonas endotoxin.

SEQ ID NO: 48 is the amino acid sequence of a pseudomonas endotoxin.

DETAILED DESCRIPTION

I. Abbreviations

ADCC antibody mediated cell-mediated cytotoxicity
CDR complementarity determining region
DMXAA 5,6-dimethylxanthenone-4-acetic acid
dsFv disulfide stabilized fragment of a variable region
ED extracellular domain
EF Anthrax edema factor
EM effector molecule
Fab antigen binding immunoglobulin fragment
F(ab)$_2$ divalent antigen binding immunoglobulin fragment
FACS fluorescence activated cell sorting
FITC fluoroscein istothiocyanate
Fv fragment of a variable region
kDa kilodaltons
KO knock-out
L-CDR light chain complementarity determining region
LF Anthrax lethal factor
H-CDR heavy chain complementarity determining region
HMEC Human dermal microvascular endothelial cells
IgG immunoglobulin
mAb monoclonal antibody
MMAE Monomethyl Auristatin E
MMAF Monomethyl Auristatin F
MVD mean vessel density
PBS phosphate buffered saline
PA Anthrax protective antigen
QPCR Quantitative real-time PCR
scFv single chain fragment of a variable region
SDR specificity determining residues
SDS-PAGE sodium dodecyl (lauryl) sulfate-polyacrylamide gel electrophoresis
TEM8 tumor endothelial marker 8
$V_H$ variable region of a heavy chain
$V_L$ variable region of a light chain II. Terms Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8). The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes."

All publications, patent applications, patents, and other references mentioned herein are incorporated by reference in their entirety. All GenBank Accession numbers are herein incorporated by reference as they appeared in the database on May 12, 2011. In case of conflict, the present specification, including explanations of terms, will control. In addition, the materials, methods, and examples are illustrative only and not intended to be limiting. In order to facilitate review of the various embodiments of this disclosure, the following explanations of specific terms are provided:

Administration: To provide or give to a subject an agent, for example, a composition that includes a monoclonal antibody that specifically binds TEM8, such as a conjugate, by any effective route. Exemplary routes of administration include, but are not limited to, oral, injection (such as subcutaneous, intramuscular, intradermal, intraperitoneal, and intravenous), sublingual, rectal, transdermal (for example, topical), intranasal, vaginal, and inhalation routes.

Agent: Any substance or any combination of substances that is useful for achieving an end or result; for example, a substance or combination of substances useful for decreasing or reducing pathological angiogenesis in a subject. Agents include effector molecules and detectable markers. In some embodiments, the agent is a detectable marker, chemotherapeutic agent, toxin or anti-angiogenic agent. The skilled artisan will understand that particular agents may be useful to achieve more than one result; for example, an agent may be useful as both a detectable marker and an anti-angiogenic agent.

Angiogenesis: A biological process leading to the generation of new blood vessels through sprouting or growth from pre-existing blood vessels. The process involves the migration and proliferation of endothelial cells from preexisting vessels. Angiogenesis occurs during pre- and post-natal development, and in the adult. Angiogenesis occurs during the normal cycle of the female reproductive system, wound healing, and during pathological processes such as cancer, where it is essential for the growth of solid tumors (for review, see Battegay, *J. Molec. Med.*, 73(7): 333-346, 1995; Shchors and Evan, *Cancer Res.*, 67:1630-1633. 2007).

Anti-angiogenic agent: A molecule that decreases or reduces angiogenesis, for example, a molecule that decreases pathological angiogenesis. In some examples, antibodies that specifically bind TEM8 or conjugates including such antibodies are anti-angiogenic agents that decrease pathological angiogenesis. Additional anti-angiogenic agents include, but are not limited to, vascular endothelial growth factor receptor 2 (VEGFR2) antibodies such as DC101, produced by the DC101 hybridoma (ATCC No. HB-11534) or small molecules (such as DMXAA (also known as Vadimezan or 5,6-Dimethyl-9-oxo-9H-xanthen-4-yl)-acetic acid, available from Novartis International AG, Basal, CH, and Sigma Corp., St. Louis, Mo.). See also, Liu et al., *Seminars in Oncology*, 29(11): 96-103, 2002; Shepherd et al., *Lung Cancer* 34:S81-S89, 2001).

Antibody: A polypeptide ligand including at least the complementarity determining regions (CDRs) of a light chain or heavy chain immunoglobulin variable region which specifically binds an epitope of an antigen or a fragment thereof. Antibodies include intact immunoglobulins and the variants of them well known in the art, such as Fab', F(ab)'$_2$ fragments, single chain Fv proteins (scFv), and disulfide stabilized Fv proteins (dsFv). A scFv protein is a fusion protein in which a light chain variable region of an antibody and a heavy chain variable region of an antibody are bound by a linker, while in dsFvs, the chains have been mutated to introduce a disulfide bond to stabilize the association of the chains. The term also includes genetically engineered forms such as chimeric antibodies (for example, humanized murine antibodies) and heteroconjugate antibodies (such as, bispecific antibodies). See also, *Pierce Catalog and Handbook*, 1994-1995 (Pierce Chemical Co., Rockford, Ill.); Kuby, J., *Immunology*, 3$^{rd}$ Ed., W.H. Freeman & Co., New York, 1997.

Typically, a naturally occurring immunoglobulin has heavy (H) chains and light (L) chains interconnected by disulfide bonds. There are two types of light chains, lambda (λ) and kappa (κ). There are five main heavy chain classes (or isotypes) which determine the functional activity of an antibody molecule: IgM, IgD, IgG, IgA and IgE.

Each heavy and light chain contains a constant region and a variable region (the regions are also known as domains). References to "V$_H$" or "VH" refer to the variable region of an immunoglobulin heavy chain, including that of an Fv, scFv, dsFv or Fab. References to "V$_L$" or "VL" refer to the variable region of an immunoglobulin light chain, including that of an Fv, scFv, dsFv or Fab. In combination, the heavy and the light chain variable regions specifically bind the antigen. Light and heavy chain variable regions contain a framework region interrupted by three hypervariable regions, also called complementarity-determining regions or CDRs. The extent of the framework region and CDRs have been defined (see, for example, Kabat et al., (1991) *Sequences of Proteins of Immunological Interest*, 5$^{th}$ Edition, U.S. Department of Health and Human Services, Public Health Service, National Institutes of Health, Bethesda, Md. (NIH Publication No. 91-3242), which is hereby incorporated by reference). The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The precise amino acid sequence boundaries of a given CDR can be readily determined using any of a number of well-known schemes, including those described by Kabat et al. (1991), "Sequences of Proteins of Immunological Interest," 5th Ed. Public Health Service, National Institutes of Health, Bethesda, Md. ("Kabat" numbering scheme), and Al-Lazikani et al., (1997) JMB 273, 927-948 ("Chothia" numbering scheme). The CDRs of each chain are typically referred to as CDR1, CDR2, and CDR3, numbered sequentially starting from the N-terminus, and are also typically identified by the chain in which the particular CDR is located. Thus, a HCDR1 is the CDR1 from the variable domain of the heavy chain of the antibody in which it is found, whereas a LCDR1 is the CDR1 from the variable domain of the light chain of the antibody in which it is found. An antibody that specifically binds an antigen of interest has a specific V$_H$ region and V$_L$ region sequence, and thus specific CDR sequences. Antibodies with different specificities (due to different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

A monoclonal antibody is an antibody produced by a single clone of B-lymphocytes or by a cell into which nucleic acid encoding the light and heavy chains of a single antibody have been transfected, or a progeny thereof. Monoclonal antibodies are produced by methods known to those of skill in the art. Monoclonal antibodies include humanized monoclonal antibodies. Monoclonal antibodies can have conservative amino acid substitutions which have substantially no effect on antigen binding or other immunoglobulin functions. (See, for example, Harlow & Lane, *Antibodies, A Laboratory Manual*, Cold Spring Harbor Publications, New York (1988).)

A chimeric antibody is an antibody having amino acid residues derived from more than one species. For example, a chimeric antibody may include human heavy and light chain variable regions and a mouse constant region. Alternatively, a chimeric antibody may include framework residues from one species, such as human, and CDRs (which generally confer antigen binding) from another species.

A bi-specific antibody is a protein having at least two domains, each domain including a binding region capable of specifically binding to a target protein. In general, the two domains are genetically fused together, in that nucleic acid molecules that encode each protein domain are functionally linked together, for instance by a linker oligonucleotide, thereby producing a single fusion-encoding nucleic acid molecule. The translated product of such a fusion-encoding nucleic acid molecule is the bi-specific fusion protein.

A single-chain antibody (scFv) is a genetically engineered molecule containing the V$_H$ and V$_L$ domains of one or more antibody(ies) linked by a suitable polypeptide linker as a genetically fused single chain molecule (see, for example, Bird et al., *Science*, 242:423-426, 1988; Huston et al., *Proc. Natl. Acad. Sci.*, 85:5879-5883, 1988). Diabodies are bivalent, bispecific antibodies in which V$_H$ and V$_L$ domains are expressed on a single polypeptide chain, but using a linker that is too short to allow for pairing between the two domains on the same chain, thereby forcing the domains to pair with complementary domains of another chain and creating two antigen binding sites (see, for example, Holliger et al., *Proc. Natl. Acad. Sci.*, 90:6444-6448, 1993; Poljak et al., *Structure*, 2:1121-1123, 1994). A chimeric antibody is an antibody that contains one or more regions from one antibody and one or more regions from one or more other antibodies. An antibody may have one or more binding sites. If there is more than one binding site, the binding sites may be identical to one another or may be different. For instance, a naturally-occurring immunoglobulin has two identical binding sites, a single-chain antibody or Fab fragment has one binding site, while a bispecific or bifunctional antibody has two different binding sites.

The antibodies disclosed herein specifically bind only to a defined target (or multiple targets, in the case of a bi-specific antibody). Thus, an antibody that specifically binds to TEM8 is an antibody that binds substantially to TEM8, including cells or tissue expressing TEM8, substrate to which the TEM8 is attached, or TEM8 in a biological specimen. It is, of course, recognized that a certain degree of non-specific interaction may occur between an antibody or conjugate including an antibody (such as an antibody that specifically binds TEM8 or conjugate including such antibody) and a non-target (such as a cell that does not express TEM8). Typically, specific binding results in a much stronger association between the antibody and protein or cells bearing the antigen than between the antibody and protein or cells lacking the antigen. Specific binding typically results in greater than 2-fold, such as greater than 5-fold, greater than 10-fold, or greater than 100-fold increase in amount of bound antibody (per unit time) to a protein including the epitope or cell or tissue expressing the target epitope as compared to a protein or cell or tissue lacking this epitope. Specific binding to a protein under such conditions requires an antibody that is selected for its specificity for a particular protein. A variety of immunoassay formats are appropriate for selecting antibodies or other ligands specifically immunoreactive with a particular protein. For example, solid-phase ELISA immunoassays are routinely used to select monoclonal antibodies specifically immunoreactive with a protein. See Harlow & Lane, *Antibodies, A Laboratory Manual*, Cold Spring Harbor Publications, New York (1988), for a description of immunoassay formats and conditions that can be used to determine specific immunoreactivity.

The binding affinity of an antibody for a particular antigen may be calculated according to standard methods, for example by the modified Scatchard method described by Frankel et al., *Mol. Immunol.*, 16:101-106, 1979. Alternatively, binding affinity is measured by an antigen/antibody dissociation rate, or competition radioimmunoassay. In several examples, a binding affinity is at least about $1\times10^{-8}$ M. In other embodiments, a binding affinity is at least about $1.5\times10^{-8}$M, at least about $2.0\times10^{-8}$M, at least about $2.5\times10^{-8}$M, at least about $3.0\times10^{-8}$M, at least about $3.5\times10^{-8}$M, at least about $4.0\times10^{-8}$M, at least about $4.5\times10^{-8}$M, at least about $5.0\times10^{-8}$ M or at least about $1.0\times10^{-9}$ M.

Anthrax: An acute disease caused by the bacterium *Bacillus anthracis*, and in particular the toxin it produces. Anthrax toxin is a mixture of three protein components: (i) protective antigen (PA), (ii) edema factor (EF), and (iii) lethal factor (LF). Cellular entry of Anthrax toxin requires PA binding to one of its two cell-surface receptors, ANTXR1 (aka TEM8) or ANTXR2 (also known as CMG2 receptor), on the host cell (see, for example, Van der Goot and Young, *Mol. Aspects. Med.*, 30(6):406-412, 2009; Moayeri and Leppla, *Curr Opin Microbiol* 7(1):19-24, 2004).

Anthrax protective antigen (PA): The protein secreted by *Bacillus anthracis* that forms the Anthrax toxin with edema factor (EF) and lethal factor (LF). Cellular entry of Anthrax toxin requires PA binding to one of its two cell-surface receptors, ANTXR1 (also known as TEM8) or ANTXR2 (also known as CMG2 receptor), on the host cell (see, for example, Van der Goot and Young, *Mol. Aspects. Med.*, 30(6):406-412, 2009; Moayeri and Leppla, *Curr Opin Microbiol* 7(1):19-24, 2004). After protease cleavage, PA binds to the two toxic enzymes (EF and LF) and mediates their transportation into the cytosol where they exert their pathogenic effects (Bradley et al., *Nature* 414:225, 2001). The smaller cleaved 63 kD PA remnant ($PA_{63}$) oligomerizes, exposing a second binding domain and binds to either EF, an 89 kD protein, to form edema toxin, or LF, a 90 kD protein, to form lethal toxin (LeTx) (Leppla et al., *Salisbury Med. Bull. Suppl.* 68:41-43, 1990), and the complex is internalized into the cell where it enters the endosomal system (Singh et al., *Infect. Immun.* 67:1853, 1999; Friedlander, *J. Biol. Chem.* 261:7123, 1986). From these endosomes, the $PA_{63}$ channel enables translocation of LF and EF to the cytosol by a pH- and voltage-dependent mechanism (Zhao et al., *J. Biol. Chem.*, 270:18626, 1995). In some embodiments, the TEM8 specific antibodies or conjugates including TEM8 specific antibodies disclosed herein are capable of blocking PA binding to TEM8. In one example, PA includes an amino acid sequence set forth in GENBANK® Accession No. AAF86457, as accessed on May 23, 2011.

Biological sample: A sample obtained from a subject. Biological samples include all clinical samples useful for detection of disease or infection (for example, cancer or Anthrax infection) in subjects, including, but not limited to, cells, tissues, and bodily fluids, such as blood, derivatives and fractions of blood (such as serum), cerebrospinal fluid; as well as biopsied or surgically removed tissue, for example tissues that are unfixed, frozen, or fixed in formalin or paraffin. In a particular example, a biological sample is obtained from a subject having or suspected of having a tumor; for example, a subject having or suspected of having breast, colorectal, lung, or skin cancer. In some examples, the subject has or is suspected of having a carcinoma.

Breast cancer: A neoplastic tumor of breast tissue that is or has potential to be malignant. The most common type of breast cancer is breast carcinoma, such as ductal carcinoma. Ductal carcinoma in situ is a non-invasive neoplastic condition of the ducts. Lobular carcinoma is not an invasive disease but is an indicator that a carcinoma may develop. Infiltrating (malignant) carcinoma of the breast can be divided into stages (I, IIA, IIB, IIIA, IIIB, and IV). See, for example, Bonadonna et al., (eds), *Textbook of Breast Cancer: A clinical Guide the Therapy*, 3*rd*; London, Tayloy & Francis, 2006.

Carcinoma: A malignant tumor including transformed epithelial cells. Non-limiting examples of carcinomas include adenocarcinoma, squamous cell carcinoma, anaplastic carcinoma and large and small cell carcinoma. In some examples, a carcinoma is a breast carcinoma, colorectal carcinoma, lung carcinoma or melanoma.

Chemotherapeutic agents: Any chemical agent with therapeutic usefulness in the treatment of diseases characterized by abnormal cell growth. For example, chemotherapeutic agents are useful for the treatment of cancer, including breast, colorectal, lung, and skin cancer. In one embodiment, a chemotherapeutic agent is an agent of use in treating a carcinoma. Particular examples of additional therapeutic agents that can be used include microtubule binding agents, DNA intercalators or cross-linkers, DNA synthesis inhibitors, DNA and RNA transcription inhibitors, antibodies, enzymes, enzyme inhibitors, gene regulators, and angiogenesis inhibitors. In one embodiment, a chemotherapeutic agent is a radioactive compound. Other examples include the anti-neoplastic drugs 5-fluorouracil (5-FU) and IRT. In particular examples, such chemotherapeutic agents are administered in combination with a treatment that decreases or reduces angiogenesis (for example before, during, or after administration of a therapeutically effective amount of one or more antibodies that specifically bind to TEM8 or a conjugate thereof). One of skill in the art can readily identify a chemotherapeutic agent of use (see for example, Slapak and Kufe, *Principles of Cancer Therapy*, Chapter 86 in Harrison's Principles of Internal Medicine, 14th edition; Perry et al., *Chemotherapy*, Ch. 17 in Abeloff, Clinical Oncology 2$^{nd}$ ed., ©2000 Churchill Livingstone, Inc; Baltzer, L., Berkery, R. (eds): *Oncology Pocket Guide to Chemotherapy*, 2nd ed. St. Louis, Mosby-Year Book, 1995; Fischer, D. S., Knobf, M. F., Durivage, H. J. (eds): *The Cancer Chemotherapy Handbook*, 4th ed. St. Louis, Mosby-Year Book, 1993; Chabner and Longo, *Cancer Chemotherapy and Biotherapy: Principles and Practice* (4th ed.). Philadelphia: Lippincott Willians & Wilkins, 2005; Skeel, *Handbook of Cancer Chemotherapy* (6th ed.). Lippincott Williams & Wilkins, 2003). Combination chemotherapy is the administration of more than one agent to treat cancer.

Colorectal cancer: A neoplastic tumor of colon, rectum or anus tissue that is or has the potential to be malignant. The main types of colorectal cancer include colorectal carcinomas such as adenocarcinoma and squamous cell carcinoma. Infiltrating (malignant) carcinoma of the colon can be divided into stages (I, II, III and IV). See, for example, Blake et al. (eds.), *Gastrointestinal Oncology: A practical Guide*, Berlin: Springer-Verlag, 2011.

Conjugate: A complex of two molecules linked together, for example, linked together by a covalent bond. In one embodiment, an antibody is linked to an effector molecule; for example, an antibody that specifically binds to TEM8 covalently linked to an effector molecule. The linkage can be by chemical or recombinant means. In one embodiment, the linkage is chemical, wherein a reaction between the antibody moiety and the effector molecule has produced a covalent bond formed between the two molecules to form one molecule. A peptide linker (short peptide sequence) can optionally be included between the antibody and the effector molecule. Because conjugates can be prepared from two molecules with separate functionalities, such as an antibody and an effector molecule, they are also sometimes referred to as "chimeric molecules."

Conservative variants: "Conservative" amino acid substitutions are those substitutions that do not substantially decrease the binding affinity of an antibody for an antigen (for example, the binding affinity of an antibody for TEM8). For example, a human antibody that specifically binds TEM8 can include at most about 1, at most about 2, at most about 5, at most about 10, or at most about 15 conservative substitutions and specifically bind the TEM8 polypeptide. The term conservative variation also includes the use of a substituted amino acid in place of an unsubstituted parent amino acid, provided that antibody retains binding affinity for TEM8. Non-conservative substitutions are those that reduce an activity or binding to TEM8.

Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Contacting: Placement in direct physical association, for example solid, liquid or gaseous forms. Contacting includes, for example, direct physical association of fully- and partially-solvated molecules.

Decrease or Reduce: To reduce the quality, amount, or strength of something; for example a reduction in tumor burden. In one example, a therapy reduces a tumor (such as the size of a tumor, the number of tumors, the metastasis of a tumor, or combinations thereof), or one or more symptoms associated with a tumor (such as pathological angiogenesis of the tumor or tumors), for example as compared to the response in the absence of the therapy. In a particular example, a therapy decreases the size of a tumor, the number of tumors, the metastasis of a tumor, or combinations thereof, subsequent to the therapy, such as a decrease of at least 10%, at least 20%, at least 30%, at least 40%, at least 50%, at least 60%, at least 70%, at least 80%, or at least 90%. Such decreases can be measured using the methods disclosed herein.

Degenerate variant: In the context of the present disclosure, a "degenerate variant" refers to a polynucleotide encoding a protein (for example, an antibody that specifically binds TEM8) that includes a sequence that is degenerate as a result of the genetic code. There are twenty natural amino acids, most of which are specified by more than one codon. Therefore, all degenerate nucleotide sequences are included as long as the amino acid sequence of the antibody that binds TEM8 encoded by the nucleotide sequence is unchanged.

Detectable marker: A detectable molecule (also known as a label) that is conjugated directly or indirectly to a second molecule, such as an antibody, to facilitate detection of the second molecule. For example, the detectable marker can be capable of detection by ELISA, spectrophotometry, flow cytometry, microscopy or diagnostic imaging techniques (such as CT scans, MRIs, ultrasound, fiberoptic examination, and laparoscopic examination). Specific, non-limiting examples of detectable markers include fluorophores, chemiluminescent agents, enzymatic linkages, radioactive isotopes and heavy metals or compounds (for example super paramagnetic iron oxide nanocrystals for detection by MRI). Methods for using detectable markers and guidance in the choice of detectable markers appropriate for various purposes are discussed for example in Sambrook et al. (Molecular Cloning: A Laboratory Manual, Cold Spring Harbor, N.Y., 1989) and Ausubel et al. (In Current Protocols in Molecular Biology, John Wiley & Sons, New York, 1998).

Detecting: To identify the existence, presence, or fact of something. General methods of detecting are known to the skilled artisan and may be supplemented with the protocols and reagents disclosed herein. For example, included herein are methods of detecting an endothelial cell that expresses TEM8 in a subject. In some examples, detecting an endothelial cell that expresses TEM8 detects pathological angiogenesis in the subject.

Effective amount: The amount of an agent (such as a TEM8 specific antibody or a conjugate including a TEM8 specific antibody) that alone, or together with one or more additional agents, induces the desired response, such as, for example formation of a detectable immune complex with TEM8.

Effector molecule: A molecule intended to have or produce a desired effect; for example, a desired effect on a cell to which the effector molecule is targeted. Effector molecules include such molecules as polypeptides, radioisotopes and small molecules. Non-limiting examples of effector molecules include toxins, chemotherapeutic agents and anti-angiogenic agents. The skilled artisan will understand that some effector molecules may have or produce more than one desired effect. In one example, an effector molecule is the portion of a chimeric molecule, for example a chimeric molecule that includes a disclosed antibody or fragment thereof, that is intended to have a desired effect on a cell to which the chimeric molecule is targeted.

Endothelial cell: A cell from the endothelium, which is the thin layer of cells that line the interior surface of blood vessels.

Epitope: An antigenic determinant. These are particular chemical groups or peptide sequences on a molecule that are antigenic, for example, that elicit a specific immune response. An antibody specifically binds a particular antigenic epitope on a polypeptide.

Immune complex: The binding of antibody to a soluble antigen forms an immune complex. The formation of an immune complex can be detected through conventional methods known to the skilled artisan, for instance immunohistochemistry, immunoprecipitation, flow cytometry, immunofluorescence microscopy, ELISA, immunoblotting (for example, Western blot), magnetic resonance imaging, CT scans, X-ray and affinity chromatography Immunological binding properties of selected antibodies may be quantified using methods well known in the art.

Isolated: A biological component (such as a nucleic acid, peptide, protein or protein complex, for example an antibody) that has been substantially separated, produced apart from, or purified away from other biological components in the cell of the organism in which the component naturally occurs, that is, other chromosomal and extra-chromosomal DNA and RNA, and proteins. Thus, isolated nucleic acids, peptides and proteins include nucleic acids and proteins purified by standard purification methods. The term also embraces nucleic acids, peptides and proteins prepared by recombinant expression in a host cell, as well as, chemically synthesized nucleic acids. A isolated nucleic acid, peptide or protein, for example an antibody, can be at least 50%, at least 60%, at least 70%, at least 80%, at least 90%, at least 95%, at least 96%, at least 97%, at least 98%, or at least 99% pure.

Linker: A bi-functional molecule that can be used to link two molecules into one contiguous molecule, for example, to link an effector molecule to an antibody. In some embodiments, the provided conjugates include a linker between the effector molecule or detectable marker and an antibody. In some embodiments, the linker is cleavable under intracellular conditions, such that cleavage of the linker releases the effector molecule or detectable marker from the antibody in the intracellular environment. In yet other embodiments, the linker is not cleavable and the effector molecule or detectable marker can be released, for example, by antibody degradation. In some cases, a linker is a peptide within an antibody binding fragment (such as an Fv fragment) which serves to indirectly bond the variable heavy chain to the variable light chain.

The terms "conjugating," "joining," "bonding," "labeling" or "linking" refer to making two molecules into one contiguous molecule; for example, linking two polypeptides into one contiguous polypeptide, or covalently attaching an effector molecule or detectable marker radionuclide or other molecule to a polypeptide, such as an scFv. In the specific context, the terms include reference to joining a ligand, such as an antibody moiety, to an effector molecule. The linkage can be either by chemical or recombinant means. "Chemical means" refers to a reaction between the antibody moiety and the effector molecule such that there is a covalent bond formed between the two molecules to form one molecule.

Lung cancer: A neoplastic tumor of lung tissue that is or has the potential to be malignant. The main types of lung cancer are lung carcinomas: adenocarcinoma, small cell carcinoma, squamous cell carcinoma, or non-small cell carcinoma. Lung cancer is typically staged from I to IV; other classifications are also used, for example small-cell lung carcinoma can be classified as limited stage if it is confined to one half of the chest and within the scope of a single radiotherapy field; otherwise, it is extensive stage. See, for example, Hansen (ed.), *Textbook of Lung Cancer, 2nd*, London: Informa Healthcare, 2008.

Neoplasia, cancer, or tumor: A neoplasm is an abnormal growth of tissue or cells that results from excessive cell division. Neoplastic growth can produce a tumor. The amount of a tumor in an individual is the "tumor burden" which can be measured as the number, volume, or weight of the tumor. A tumor that does not metastasize is referred to as "benign." A tumor that invades the surrounding tissue or can metastasize (or both) is referred to as "malignant."

Tumors of the same tissue type are primary tumors originating in a particular organ (such as colon, skin, breast, prostate, bladder or lung). Tumors of the same tissue type may be divided into tumors of different sub-types. For examples, lung carcinomas can be divided into an adenocarcinoma, small cell, squamous cell, or non-small cell tumors.

Examples of solid tumors, such as sarcomas (connective tissue cancer) and carcinomas (epithelial cell cancer), include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colorectal carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, and CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma).

Neutralizing antibody: An antibody that is able to specifically bind to a target protein in such a way as to inhibit a biological function associated with that target protein. In general, any protein that can perform this type of specific blocking activity is considered a neutralizing protein; neutralizing antibodies are therefore a specific class of neutralizing protein.

Operably linked: A first nucleic acid sequence is operably linked with a second nucleic acid sequence when the first nucleic acid sequence is placed in a functional relationship with the second nucleic acid sequence. For instance, a promoter, such as the CMV promoter, is operably linked to a coding sequence if the promoter affects the transcription or expression of the coding sequence. Generally, operably linked DNA sequences are contiguous and, where necessary to join two protein-coding regions, in the same reading frame.

Pathological angiogenesis: Angiogenesis that is medically undesired or harmful to a subject, such as angiogenesis associated with a tumor or the generation of blood vessels in or surrounding a tumor. Other examples of pathological angiogenesis include corneal or retinal angiogenesis (as in a corneal transplant or the retina of a subject with macular degeneration or diabetes).

Pharmaceutically acceptable carriers: The pharmaceutically acceptable carriers provided herein are conventional. *Remington's Pharmaceutical Sciences*, by E. W. Martin, Mack Publishing Co., Easton, Pa., 15th Edition (1975), describes compositions and formulations suitable for pharmaceutical delivery of the fusion proteins herein disclosed.

In general, the nature of the carrier will depend on the particular mode of administration being employed. For instance, parenteral formulations usually include injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polypeptide: A polymer in which the monomers are amino acid residues that are joined together through amide bonds. When the amino acids are alpha-amino acids, either the L-optical isomer or the D-optical isomer can be used, the L-isomers being preferred. The terms "polypeptide" or "protein" as used herein are intended to encompass any amino acid sequence and include modified sequences such as glycoproteins. A polypeptide includes both naturally occurring proteins, as well as those that are recombinantly or synthetically produced.

Conservative substitutions replace one amino acid with another amino acid that is similar in size, hydrophobicity, etc. Variations in the cDNA sequence that result in amino acid changes, whether conservative or not, should be minimized in order to preserve the functional and immunologic identity of the encoded protein. The immunologic identity of the protein may be assessed by determining if it is recognized by an antibody; a variant that is recognized by such an antibody is immunologically conserved. Any cDNA sequence variant will preferably introduce no more than twenty, and preferably fewer than ten amino acid substitutions into the encoded polypeptide. Variant amino acid sequences may, for example, be 80%, 90%, 95%, 98% or 99% identical to the native amino acid sequence.

Skin cancer: A neoplastic tumor of skin tissue that is or has the potential to be malignant. Melanoma is a skin cancer of transformed melanocytes (cells that make the pigment melanin). Melanocytes are found primary in the skin, but are also present in the bowel and eye. Melanoma in the skin includes superficial spreading melanoma, nodular melanoma, acral lentiginous melanoma, and lentigo maligna (melanoma). Any of the above types may produce melanin or can be amelanotic. Similarly, any subtype may show desmoplasia (dense fibrous reaction with neurotropism), which is a marker of aggressive behavior and a tendency for local recurrence. Other melanomas include clear cell sarcoma, mucosal melanoma and uveal melanoma. Melanoma is staged from I to IV. See, for example, Thompson et al. (eds), *Textbook of Melanoma: Pathology, Diagnosis and Management*, London: Taylor & Francis, 2004.

Subject: Any mammal, such as humans, non-human primates, pigs, sheep, cows, rodents, and the like. In two non-limiting examples, a subject is a human subject or a murine subject. Thus, the term "subject" includes both human and veterinary subjects.

Therapeutically effective amount: The amount of an agent (such as a TEM8 specific antibody or a conjugate including a TEM8 specific antibody) that alone, or together with one or more additional agents, induces the desired response, such as, for example treatment of a tumor, or treatment of Anthrax, in a subject. Ideally, a therapeutically effective amount provides a therapeutic effect without causing a substantial cytotoxic effect in the subject.

In one example, a desired response is to decrease the size, volume, or number (such as metastases) of a tumor in a subject. For example, the agent or agents can decrease the size, volume, or number of tumors by a desired amount, for example by at least 5%, at least 10%, at least 15%, at least 20%, at least 25%, at least 30%, at least 50%, at least 75%, at least 90%, or at least 95% as compared to a response in the absence of the agent.

Several preparations disclosed herein are administered in therapeutically effective amounts. A therapeutically effective amount of an antibody that specifically binds TEM8 or conjugate thereof (or a composition including one or more of these molecules) that is administered to a human or veterinary subject will vary depending upon a number of factors associated with that subject, for example the overall health of the subject. A therapeutically effective amount of the antibodies or conjugates can be determined by varying the dosage and measuring the resulting therapeutic response, such as the regression of a tumor. Therapeutically effective amounts also can be determined through various in vitro, in vivo or in situ immunoassays. The disclosed agents can be administered in a single dose, or in several doses, as needed to obtain the desired response. However, the therapeutically effective amount of can be dependent on the source applied, the subject being treated, the severity and type of the condition being treated, and the manner of administration.

Toxin: An effector molecule that induces cytotoxicity when it contacts a cell. Specific, non-limiting examples of toxins include, but are not limited to, abrin, ricin, auristatins (such as monomethyl auristatin E (MMAE; see for example, Francisco et al., Blood, 102: 1458-1465, 2003)) and monomethyl auristatin F (MMAF; see, for example, Doronina et al., BioConjugate Chem., 17: 114-124, 2006), maytansinoids (such as DM1; see, for example, Phillips et al., Cancer Res., 68:9280-9290, 2008), *Pseudomonas* exotoxin (PE, such as PE35, PE37, PE38, and PE40), diphtheria toxin (DT), botulinum toxin, saporin, restrictocin or gelonin, or modified toxins thereof, or other toxic agents that directly or indirectly inhibit cell growth or kill cells. For example, PE and DT are highly toxic compounds that typically bring about death through liver toxicity. PE and DT, however, can be modified into a form for use as an immunotoxin by removing the native targeting component of the toxin (such as the domain Ia of PE and the B chain of DT) and replacing it with a different targeting moiety, such as an antibody.

Treating or Treatment: A therapeutic intervention (for example, administration of a therapeutically effective amount of an antibody that specifically binds TEM8 or a conjugate thereof) that ameliorates a sign or symptom of a disease or pathological condition related to a disease (such as a tumor or Anthrax infection). Treatment can also induce remission or cure of a condition, such as a tumor or Anthrax infection. In particular examples, treatment includes preventing a tumor, for example by inhibiting the full development of a tumor, such as preventing development of a metastasis or the development of a primary tumor. Prevention does not require a total absence of a tumor.

Reducing a sign or symptom associated with a tumor (such as pathological angiogenesis) can be evidenced, for example, by a delayed onset of clinical symptoms of the disease in a susceptible subject (such as a subject having a tumor which has not yet metastasized), a reduction in severity of some or all clinical symptoms of the disease, a slower progression of the disease (for example by prolonging the life of a subject having tumor), a reduction in the number of relapses of the disease, an improvement in the overall health or well-being of the subject, or by other parameters well known in the art that are specific to the particular tumor.

Tumor burden: The total volume, number, metastasis, or combinations thereof of tumor or tumors in a subject.

Tumor Endothelial Marker 8 (TEM8): A protein also known as Anthrax Toxin Receptor 1 (ANTXR1). TEM8 is a cell-surface glycoprotein originally identified based on its over-expression in the endothelial cells that line the tumor vasculature of human colorectal cancer (St Croix et al., *Science,* 289(5482):1197-1202, 2000). Unlike VEGF, VEGFRs, and many other key angiogenesis regulators, TEM8 is not required for developmental angiogenesis, wound healing, or normal physiological angiogenesis of the corpus luteum (St Croix et al., *Science,* 289(5482):1197-1202, 2000; Nanda et al., *Cancer Res.,* 64(3):817-820, 2004). TEM8 is up-regulated on tumor vessels of various tumor types in both mice and humans (Nanda et al., *Cancer Res.,* 64(3):817-820, 2004; Carson-Walter et al., *Cancer Res.,* 61(18):6649-6655, 2001), and in some tumors is also expressed by the tumor cells themselves (Carson-Walter et al. *Cancer Res.,* 61(18):6649-6655, 2001; Yang et al., *Biochim Biophys Acta,* 1813(1):39-49, 2011). TEM8 also functions as a cell-surface receptor for Anthrax toxin, and shares 58% amino acid identify with CMG2 (also known as ANTXR2), which is a second receptor for Anthrax toxin protein (Scobie et al., *Proc. Natl. Acad. Sci. U.S.A.,* 100(9):5170-5174, 2003).

TEM8 protein sequence is known (see, for example, GEN-BANK® Accession No. AAK52094.1, incorporated by reference herein as present in the database on May 9, 2001). Additionally, exemplary nucleic acid sequences encoding TEM8 protein are known (see, for example, GENBANK® Accession No. AF279145.2, incorporated by reference herein as present in the database on May 9, 2001). In one example, TEM8 is a polypeptide having an amino acid sequence set forth as SEQ ID NO: 14.

Under conditions sufficient for: A phrase that is used to describe any environment that permits a desired activity. In one example the desired activity is formation of an immune complex. In particular examples the desired activity is treatment of a tumor.

III. Monoclonal Antibodies that Specifically Bind TEM8, and Antigen Binding Fragments Thereof Isolated human monoclonal neutralizing antibodies that specifically bind to TEM8 on the cell surface, antigen binding fragments of such antibodies, conjugates thereof, and methods of using these molecules, are provided. In some embodiments, the antibody includes a heavy chain variable region including a HCDR3 including the amino acid sequence of the HCDR3 of one of the L1, L2, L3, L5, or 1D2 antibodies as shown in Table 1 or Table 2, respectfully. In other embodiments, the antibody includes a heavy chain variable region including the amino acid sequence of the HCDR1, HCDR2 and/or HCDR3 of one of the L1, L2, L3, L5 or 1D2 antibodies as shown in Table 1 or Table 2, respectfully. In additional embodiments, the antibody includes a heavy chain variable region including the amino acid sequence of the HCDR1, HCDR2, and HCDR3 of one of the L1, L2, L3, L5, or 1D2 antibodies as shown in Table 1 or Table 2, respectfully.

In some embodiments, the antibody includes a light chain variable region including one or more of the light chain CDRs of the L1, L2, L3, L5, or 1D2 antibodies, respectively, listed in Table 1 or Table 2. In other embodiments, the antibody includes a light chain variable region including the amino acid sequence of the LCDR1, LCDR2, and/or LCDR3 of one of the L1, L2, L3, L5, or 1D2 antibodies as shown in Table 1 or Table 2. In additional embodiments, the antibody includes a light chain variable region including the amino acid sequence of the LCDR1, LCDR2, and LCDR3 of one of the L1, L2, L3, L5, or 1D2 antibodies, respectfully, as shown in Table 1 or Table 2.

In some embodiments, the antibody includes a heavy chain variable region including the amino acid sequence of the HCDR1, HCDR2 and/or HCDR3 of one of the L1, L2, L3, L5 or 1D2 antibodies as shown in Table 1 or Table 2, and a light chain variable region including the amino acid sequence of the LCDR1, LCDR2 and/or LCDR3 of one of the L1, L2, L3, L5 or 1D2 antibodies as shown in Table 1 or Table 2, respectfully. In other embodiments, the antibody includes a heavy chain variable region including the amino acid sequence of the HCDR1, HCDR2, and HCDR3 of one of the L1, L2, L3, L5, or 1D2 antibodies as shown in Table 1 or Table 2, respectfully, and a light chain variable region including the amino acid sequence of the LCDR1, LCDR2, and LCDR3 of one of the L1, L2, L3, L5, or 1D2 antibodies as shown in Table 1 or Table 2, respectfully.

In additional embodiments, the antibody includes a heavy chain variable region and a light chain variable region including the amino acid sequence of the HCDR1, HCDR2, and HCDR3, and the LCDR1, LCDR2, and LCD3, respectively, of the L1 antibody as shown in Table 1 or Table 2. In some embodiments, the antibody includes a heavy chain variable region and a light chain variable region including the amino acid sequence of the HCDR1, HCDR2, and HCDR3, and the LCDR1, LCDR2, and LCD3, respectively, of the L2 antibody as shown in Table 1 or Table 2. In further embodiments, the antibody includes a heavy chain variable region and a light chain variable region including the amino acid sequence of the HCDR1, HCDR2, and HCDR3, and the LCDR1, LCDR2, and LCD3, respectively, of the L3 antibody as shown in Table 1 or Table 2. In additional embodiments, the antibody includes a heavy chain variable region and a light chain variable region including the amino acid sequence of the HCDR1, HCDR2, and HCDR3, and the LCDR1, LCDR2, and LCD3, respectively, of the L5 antibody as shown in Table 1 or Table 2. In other embodiments, the antibody includes a heavy chain variable region and a light chain variable region including the amino acid sequence of the HCDR1, HCDR2, and HCDR3, and the LCDR1, LCDR2, and LCD3, respectively, of the 1D2 antibody as shown in Table 1 or Table 2.

TABLE 1

Locations of the CDRs in the L1, L2, L3, L5, and 1D2 antibodies (according to Kabat).

| Antibody | CDR | Kabat CDR | Residues |
|----------|-------|------------------|--------------------------------|
| L1 | HCDR1 | SYAMS | Residues 31-35 of SEQ ID NO: 2 |
|  | HCDR2 | LISSGSSTYYADSVKG | Residues 50-65 of SEQ ID NO: 2 |
|  | HCDR3 | AGFKFDN | Residues 96-102 of SEQ ID NO: 2 |
|  | LCDR1 | SGDSIPNYSVS | Residues 23-33 of SEQ ID NO: 7 |

TABLE 1-continued

Locations of the CDRs in the L1, L2, L3, L5, and 1D2 antibodies (according to Kabat).

| Antibody | CDR | Kabat CDR | Residues |
|---|---|---|---|
| | LCDR2 | ADSNRPS | Residues 49-55 of SEQ ID NO: 7 |
| | LCDR3 | QSYDNTSPDLV | Residues 88-98 of SEQ ID NO: 7 |
| L2 | HCDR1 | TSGGGVS | Residues 31-37 of SEQ ID NO: 1 |
| | HCDR2 | HIYSNDDKSYSTSLKT | Residues 52-67 of SEQ ID NO: 1 |
| | HCDR3 | GGYFLDY | Residues 100-106 of SEQ ID NO: 1 |
| | LCDR1 | SGDNIGGIYVH | Residues 23-33 of SEQ ID NO: 6 |
| | LCDR2 | ADSKRPS | Residues 49-55 of SEQ ID NO: 6 |
| | LCDR3 | QSYDITSLV | Residues 88-96 of SEQ ID NO: 6 |
| L3 | HCDR1 | TNGAAWG | Residues 31-37 of SEQ ID NO: 3 |
| | HCDR2 | RIYYRSKWYNDYAVSVKS | Residues 52-69 of SEQ ID NO: 3 |
| | HCDR3 | MPGGFLFDL | Residues 102-110 of SEQ ID NO: 3 |
| | LCDR1 | SGDNIRSYYAH | Residues 23-33 of SEQ ID NO: 8 |
| | LCDR2 | GDSKRPS | Residues 49-55 of SEQ ID NO: 8 |
| | LCDR3 | SSYASHDYV | Residues 88-96 of SEQ ID NO: 8 |
| L5 | HCDR1 | SYGLS | Residues 31-35 of SEQ ID NO: 4 |
| | HCDR2 | NISSNGSYTYYADSVKG | Residues 50-66 of SEQ ID NO: 4 |
| | HCDR3 | AGYGLFDV | Residues 99-106 of SEQ ID NO: 4 |
| | LCDR1 | SGDKLREYYVH | Residues 23-33 of SEQ ID NO: 9 |
| | LCDR2 | GDNKRPS | Residues 49-55 of SEQ ID NO: 9 |
| | LCDR3 | SSWAGSRSGTV | Residues 88-98 of SEQ ID NO: 9 |
| 1D2 | HCDR1 | TSGMGVS | Residues 31-37 of SEQ ID NO: 5 |
| | HCDR2 | HINLDDDKYYSTSLKT | Residues 52-67 of SEQ ID NO: 5 |
| | HCDR3 | GGYGDMDV | Residues 100-107 of SEQ ID NO: 5 |
| | LCDR1 | SGDNIRSMFVH | Residues 23-33 of SEQ ID NO: 10 |
| | LCDR2 | ADNKRPS | Residues 49-55 of SEQ ID NO: 10 |
| | LCDR3 | SSYDYNAHLVV | Residues 88-98 of SEQ ID NO: 10 |

TABLE 2

Locations of the CDRs in the L1, L2, L3, L5, and 1D2 antibodies (according to Chothia).

| Antibody | CDR | Chothia CDR | Residues |
|---|---|---|---|
| L1 | HCDR1 | GFTFNSY | Residues 26-32 of SEQ ID NO: 2 |
| | HCDR2 | SSGSS | Residues 52-56 of SEQ ID NO: 2 |
| | HCDR3 | AGFKFDN | Residues 96-102 of SEQ ID NO: 2 |
| | LCDR1 | DSIPNYS | Residues 25-31 of SEQ ID NO: 7 |
| | LCDR2 | ADS | Residues 49-51 of SEQ ID NO: 7 |
| | LCDR3 | YDNTSPDL | Residues 90-97 of SEQ ID NO: 7 |
| L2 | HCDR1 | GFSLSTSGG | Residues 26-34 of SEQ ID NO: 1 |
| | HCDR2 | YSNDD | Residues 54-58 of SEQ ID NO: 1 |
| | HCDR3 | GGYFLDY | Residues 100-106 of SEQ ID NO: 1 |
| | LCDR1 | DNIGGIY | Residues 25-31 of SEQ ID NO: 6 |
| | LCDR2 | ADS | Residues 49-51 of SEQ ID NO: 6 |
| | LCDR3 | YDITSL | Residues 90-95 of SEQ ID NO: 6 |
| L3 | HCDR1 | GDSVSTNGA | Residues 26-34 of SEQ ID NO: 3 |
| | HCDR2 | YYRSKWY | Residues 54-60 of SEQ ID NO: 3 |
| | HCDR3 | MPGGFLFDL | Residues 102-110 of SEQ ID NO: 3 |
| | LCDR1 | DNIRSYY | Residues 25-31 of SEQ ID NO: 8 |
| | LCDR2 | GDS | Residues 49-51 of SEQ ID NO: 8 |
| | LCDR3 | YASHDY | Residues 90-95 of SEQ ID NO: 8 |
| L5 | HCDR1 | GFTFNSY | Residues 26-32 of SEQ ID NO: 4 |
| | HCDR2 | SSNGSY | Residues 52-57 of SEQ ID NO: 4 |
| | HCDR3 | AGYGLFDV | Residues 100-106 of SEQ ID NO: 4 |
| | LCDR1 | DKLREYY | Residues 25-31 of SEQ ID NO: 9 |
| | LCDR2 | GDN | Residues 49-51 of SEQ ID NO: 9 |
| | LCDR3 | WAGSRSGT | Residues 90-97 of SEQ ID NO: 9 |
| 1D2 | HCDR1 | GFSLSTSGM | Residues 26-34 of SEQ ID NO: 5 |
| | HCDR2 | NLDDD | Residues 54-58 of SEQ ID NO: 5 |
| | HCDR3 | GGYGDMDV | Residues 100-107 of SEQ ID NO: 5 |
| | LCDR1 | DNIRSMF | Residues 25-31 of SEQ ID NO: 10 |
| | LCDR2 | ADN | Residues 49-51 of SEQ ID NO: 10 |
| | LCDR3 | YDYNAHLV | Residues 90-97 of SEQ ID NO: 10 |

In specific embodiments, the antibody includes a heavy chain variable region including a HCDR3 (according to Kabat) including the amino acid sequence set forth as amino acid residues 100-106 of SEQ ID NO: 1; amino acid residues 96-102 of SEQ ID NO: 2; amino acid residues 102-110 of SEQ ID NO: 3; amino acid residues 99-106 of SEQ ID NO: 4; or amino acid residues 100-107 of SEQ ID NO: 5. In other specific embodiments, the antibody includes a heavy chain variable region including a HCDR1, HCDR2, and HCDR3 (according to Kabat) including the amino acid sequence set forth as amino acid residues 31-37, 52-67, and/or 100-106 of SEQ ID NO: 1, respectively; amino acid residues 31-35, 50-65, and/or 96-102 of SEQ ID NO: 2, respectively; amino acid residues 31-37, 52-69, and/or 102-110 of SEQ ID NO: 3, respectively; amino acid residues 31-35, 50-66, and/or 99-106 of SEQ ID NO: 4, respectively; or amino acid residues 31-37, 52-6,7 and/or 100-107 of SEQ ID NO: 5, respectively. In additional specific embodiments, the antibody includes a heavy chain variable region including a HCDR1, HCDR2, and HCDR3 (according to Kabat) including the amino acid sequence set forth as amino acid residues 31-37, 52-6,7 and 100-106 of SEQ ID NO: 1, respectively; amino acid residues 31-35, 50-65, and 96-102 of SEQ ID NO: 2, respectively; amino acid residues 31-37, 52-69, and 102-110 of SEQ ID NO: 3, respectively; amino acid residues 31-35, 50-66, and 99-106 of SEQ ID NO: 4, respectively; or amino acid residues 31-37, 52-67, and 100-107 of SEQ ID NO: 5, respectively.

In specific embodiments, the antibody includes a light chain variable region including a LCDR1, LCDR2 and LCDR3 (according to Kabat) including the amino acid sequence set forth as amino acid residues 23-33, 49-55 and/or 88-96 of SEQ ID NO: 6, respectively; amino acid residues 23-33, 49-55 and/or 88-98 of SEQ ID NO: 7, respectively; amino acid residues 23-33, 49-55 and/or 88-96 of SEQ ID NO: 8, respectively; amino acid residues 23-33, 49-55 and/or 88-96 of SEQ ID NO: 9, respectively; or amino acid residues 23-33, 49-55 and/or 88-98 of SEQ ID NO: 10, respectively. In other specific embodiments, the antibody includes a light chain variable region including a LCDR1, LCDR2 and LCDR3 (according to Kabat) including the amino acid sequence set forth as amino acid residues 23-33, 49-55 and 88-96 of SEQ ID NO: 6, respectively; amino acid residues 23-33, 49-55 and 88-98 of SEQ ID NO: 7, respectively; amino acid residues 23-33, 49-55 and 88-96 of SEQ ID NO: 8, respectively; amino acid residues 23-33, 49-55 and 88-96 of SEQ ID NO: 9, respectively; or amino acid residues 23-33, 49-55 and 88-98 of SEQ ID NO: 10, respectively.

In specific embodiments, the antibody includes a heavy chain variable region including a HCDR1, HCDR2, and HCDR3 (according to Kabat) including the amino acid sequence set forth as amino acid residues 31-37, 52-67, and 100-106 of SEQ ID NO: 1, respectively, and a light chain variable region including a LCDR1, LCDR2, and LCDR3 (according to Kabat) including the amino acid sequence set forth as amino acid residues 23-33, 49-55, and 88-96 of SEQ ID NO: 6, respectively. In further specific embodiments, the antibody includes a heavy chain variable region including a HCDR1, HCDR2, and HCDR3 (according to Kabat) including the amino acid sequence set forth as amino acid residues 31-35, 50-65, and 96-102 of SEQ ID NO: 2, respectively, and a light chain variable region including a LCDR1, LCDR2, and LCDR3 (according to Kabat) including the amino acid sequence set forth as amino acid residues 23-33, 49-55, and 88-98 of SEQ ID NO: 7, respectively. In additional specific embodiments, the antibody includes a heavy chain variable region including a HCDR1, HCDR2, and HCDR3 (according to Kabat) including the amino acid sequence set forth as amino acid residues 31-37, 52-69, and 102-110 of SEQ ID NO: 3, respectively, and a light chain variable region including a LCDR1, LCDR2, and LCDR3 (according to Kabat) including the amino acid sequence set forth as amino acid residues 23-33, 49-55, and 88-96 of SEQ ID NO: 8, respectively. In another specific embodiments, the antibody includes a heavy chain variable region including a HCDR1, HCDR2, and HCDR3 (according to Kabat) including the amino acid sequence set forth as amino acid residues 31-35, 50-66, and 99-106 of SEQ ID NO: 4, respectively, and a light chain variable region including a LCDR1, LCDR2, and LCDR3 (according to Kabat) including the amino acid sequence set forth as amino acid residues 23-33, 49-55, and 88-98 of SEQ ID NO: 9, respectively. In more specific embodiments, the antibody includes a heavy chain variable region including a HCDR1, HCDR2, and HCDR3 (according to Kabat) including the amino acid sequence set forth as amino acid residues 31-37, 52-67, and 100-107 of SEQ ID NO: 5, respectively, and a light chain variable region including a LCDR1, LCDR2, and LCDR3 (according to Kabat) including the amino acid sequence set forth as amino acid residues 23-33, 49-55, and 88-98 of SEQ ID NO: 10, respectively.

In some embodiments, the antibody includes a heavy chain variable region including the amino acid sequence of the L1, L2, L3, L5, or 1D2 antibody heavy chain variable region set forth as SEQ ID NO: 2, SEQ ID NO: 1, SEQ ID NO: 3, SEQ ID NO: 4, or SEQ ID NO: 5, respectively. In other embodiments, the antibody includes a light chain variable region including the amino acid sequence of the L1, L2, L3, L5, or 1D2 antibody light chain variable region set forth as SEQ ID NO: 7, SEQ ID NO: 6, SEQ ID NO: 8, SEQ ID NO: 9, or SEQ ID NO: 10, respectively.

In further embodiments, the antibody includes a heavy chain variable region including the amino acid sequence of the L1 antibody set forth as SEQ ID NO: 2 and a light chain variable region including the amino acid sequence of the L1 antibody set forth as SEQ ID NO: 7. In some embodiments, the antibody includes a heavy chain variable region including the amino acid sequence of the L2 antibody set forth as SEQ ID NO: 1 and a light chain variable region including the amino acid sequence of the L2 antibody set forth as SEQ ID NO: 6. In some embodiments, the antibody includes a heavy chain variable region including the amino acid sequence of the L3 antibody set forth as SEQ ID NO: 3 and a light chain variable region including the amino acid sequence of the L3 antibody set forth as SEQ ID NO: 8. In other embodiments, the antibody includes a heavy chain variable region including the amino acid sequence of the L5 antibody set forth as SEQ ID NO: 4 and a light chain variable region including the amino acid sequence of the L5 antibody set forth as SEQ ID NO: 9. In additional embodiments, the antibody includes a heavy chain variable region including the amino acid sequence of the 1D2 antibody set forth as SEQ ID NO: 5 and a light chain variable region including the amino acid sequence of the 1D2 antibody set forth as SEQ ID NO: 10.

In some embodiments, the antibody includes a heavy chain variable region including an amino acid sequence at least 95%, 96%, 97%, 98%, or 99% identical to the amino acid sequence of the L1, L2, L3, L5, or 1D2 antibody heavy chain variable region set forth as SEQ ID NO: 2, SEQ ID NO: 1, SEQ ID NO: 3, SEQ ID NO: 4, or SEQ ID NO: 5, respectively, and a light chain variable region including an amino acid sequence at least 95%, 96%, 97%, 98%, or 99% identical to the amino acid sequence of the L1, L2, L3, L5, or 1D2 antibody heavy chain variable region set forth as SEQ ID NO: 7, SEQ ID NO: 6, SEQ ID NO: 8, SEQ ID NO: 9, or SEQ ID NO: 10, respectively.

In further embodiments, the antibody includes a heavy chain variable region including the amino acid sequence at least 95%, 96%, 97%, 98% or 99% identical to the amino acid sequence of the L1 antibody set forth as SEQ ID NO: 2 and a light chain variable region including the amino acid sequence at least 95%, 96%, 97%, 98% or 99% identical to the amino acid sequence of the L1 antibody set forth as SEQ ID NO: 7. In some embodiments, the antibody includes a heavy chain variable region including the amino acid sequence at least 95%, 96%, 97%, 98% or 99% identical to the amino acid sequence of the L2 antibody set forth as SEQ ID NO: 1 and a light chain variable region including the amino acid sequence at least 95%, 96%, 97%, 98% or 99% identical to the amino acid sequence of the L2 antibody set forth as SEQ ID NO: 6. In some embodiments, the antibody includes a heavy chain variable region including the amino acid sequence at least 95%, 96%, 97%, 98% or 99% identical to the amino acid sequence of the L3 antibody set forth as SEQ ID NO: 3 and a light chain variable region including the amino acid sequence at least 95%, 96%, 97%, 98% or 99% identical to the amino acid sequence of the L3 antibody set forth as SEQ ID NO: 8. In other embodiments, the antibody includes a heavy chain variable region including the amino acid sequence at least 95%, 96%, 97%, 98% or 99% identical to the amino acid sequence of the L5 antibody set forth as SEQ ID NO: 4 and a light chain variable region including the amino acid sequence at least 95%, 96%, 97%, 98% or 99% identical to the amino acid sequence of the L5 antibody set forth as SEQ ID NO: 9. In additional embodiments, the antibody includes a heavy chain variable region including the amino acid sequence at least 95%, 96%, 97%, 98% or 99% identical to the amino acid sequence of the 1D2 antibody set forth as SEQ ID NO: 5 and a light chain variable region including the amino acid sequence at least 95%, 96%, 97%, 98% or 99% identical to the amino acid sequence of the 1D2 antibody set forth as SEQ ID NO: 10.

TABLE 3

Protein sequence of the VH domain of the L1, L2, L3, L5 and 1D2 antibodies.

| Antibody ID | VH protein sequence |
| --- | --- |
| L1 | QVQLVESGGGLVQPGGSLRLSCAASGFTFNSYAMSWVRQAPGK GLEWVSLISSGSSTYYADSVKGRFTISRDNSKNTLYLQMNSLRAE DTAVYYCARAGFKFDNWGQGTLVTVSS (VH3) (SEQ ID NO: 2) |
| L2 | QVQLKESGPALVKPTQTLTLTCTFSGFSLSTSGGGVSWIRQPPGK ALEWLAHIYSNDDKSYSTSLKTRLTISKDTSKNQVVLTMTNMDP VDTATYYCARGGYFLDYWGQGTLVTVSS (VH2) (SEQ ID NO: 1) |
| L3 | QVQLQQSGPGLVKPSQTLSLTCAISGDSVSTNGAAWGWIRQSPG RGLEWLGRIYYRSKWYNDYAVSVKSRITINPDTSKNQFSLQLNS VTPEDTAVYYCARMPGGFLFDLWGQGTLVTVSS (VH6) (SEQ ID NO: 3) |
| L5 | QVQLVESGGGLVQPGGSLRLSCAASGFTFNSYGLSWVRQAPGK GLEWVSNISSNGSYTYYADSVKGRFTISRDNSKNTLYLQMNSLR AEDTAVYYCARAGYGLFDVWGQGTLVTVSS (VH3) (SEQ ID NO: 4) |
| 1D2 | QVQLKESGPALVKPTQTLTLTCTFSGFSLSTSGMGVSWIRQPPGK ALEWLAHINLDDDKYYSTSLKTRLTISKDTSKNQVVLTMTNMD PVDTATYYCARGGYGDMDVWGQGTLVTVSS (VH2) (SEQ ID NO: 5) |

TABLE 4

Protein sequence of the VL domain of the L1, L2, L3, L5 and 1D2 antibodies.

| Antibody ID | VL protein sequence |
| --- | --- |
| L1 | DIELTQPPSVSVAPGQTARISCSGDSIPNYSVSWYQQKPGQAPV LVIYADSNRPSGIPERFSGSNSGNTATLTISGTQAEDEADYYCQ SYDNTSPDLVFGGGTKLTVL (lambda 3) (SEQ ID NO: 7) |
| L2 | DIELTQPPSVSVAPGQTARISCSGDNIGGIYVHWYQQKPGQAP VLVIYADSKRPSGIPERFSGSNSGNTATLTISGTQAEDEADYYC QSYDITSLVFGGGTKLTVL (lambda 3) (SEQ ID NO: 6) |
| L3 | DIELTQPPSVSVAPGQTARISCSGDNIRSYYAHWYQQKPGQAP VLVIYGDSKRPSGIPERFSGSNSGNTATLTISGTQAEDEADYYC SSYASHDYVFGGGTKLTVL (lambda 3) (SEQ ID NO: 8) |
| L5 | DIELTQPPSVSVAPGQTARISCSGDKLREYYVHWYQQKPGQAP VLVIYGDNKRPSGIPERFSGSNSGNTATLTISGTQAEDEADYYC SSWAGSRSGTVFGGGTKLTVL (lambda 3) (SEQ ID NO: 9) |
| 1D2 | DIELTQPPSVSVAPGQTARISCSGDNIRSMFVHWYQQKPGQAP VLVIYADNKRPSGIPERFSGSNSGNTATLTISGTQAEDEADYYC SSYDYNAHLVVFGGGTKLTVL (lambda 3) (SEQ ID NO: 10) |

Generally, the monoclonal antibodies each include a variable heavy ($V_H$) and a variable light ($V_L$) chain and specifically bind TEM8. For example, the antibody can specifically bind TEM8 with an affinity of at least about $1.5 \times 10^{-8}$ M, at least about $2.0 \times 10^{-8}$ M, at least about $2.5 \times 10^{-8}$ M, at least about $3.0 \times 10^{-8}$ M, at least about $3.5 \times 10^{-8}$ M, at least about $4.0 \times 10^{-8}$ M, at least about $4.5 \times 10^{-8}$ M, at least about $5.0 \times 10^{-8}$ M or at least about $1.0 \times 10^{-9}$ M.

The monoclonal antibodies can be human monoclonal antibodies. Chimeric antibodies are also provided. The antibodies can include any suitable framework region, such as (but not limited to) a human framework region (for example, as listed in tables 3 and 4). Human framework regions, and mutations that can be made in a human antibody framework regions, are known in the art (see, for example, in U.S. Pat. No. 5,585,089, which is incorporated herein by reference). Alternatively, a heterologous framework region, such as, but not limited to a mouse framework region, can be included in the heavy or light chain of the antibodies. (See, for example, Jones et al., *Nature* 321:522, 1986; Riechmann et al., *Nature* 332:323, 1988; Verhoeyen et al., *Science* 239:1534, 1988; Carter et al., *Proc. Natl. Acad. Sci. U.S.A.* 89:4285, 1992; Sandhu, *Crit. Rev. Biotech.* 12:437, 1992; and Singer et al., *J. Immunol.* 150:2844, 1993.)

The antibodies or antibody fragments disclosed herein can be derivatized or linked to another molecule (such as another peptide or protein). In general, the antibodies or portion thereof is derivatized such that the binding to TEM8 is not affected adversely by the derivatization or labeling. For example, the antibody can be functionally linked (by chemical coupling, genetic fusion, noncovalent association or otherwise) to one or more other molecular entities, such as another antibody (for example, a bi-specific antibody or a diabody), a detectable marker, an effector molecule, or a protein or peptide that can mediate association of the antibody or antibody portion with another molecule (such as a streptavidin core region or a polyhistidine tag).

One type of derivatized antibody is produced by crosslinking two or more antibodies (of the same type or of different types, such as to create bispecific antibodies). Suitable crosslinkers include those that are heterobifunctional, having two distinctly reactive groups separated by an appropriate spacer (such as m-maleimidobenzoyl-N-hydroxysuccinimide ester) or homobifunctional (such as disuccinimidyl suberate). Such linkers are available from Pierce Chemical Company, Rockford, Ill.

The monoclonal antibodies disclosed herein can be of any isotype. The monoclonal antibody can be, for example, an IgM or an IgG antibody, such as $IgG_1$, $IgG_2$, $IgG_3$ or an $IgG_4$. The class of an antibody that specifically binds TEM8 can be switched with another (for example, IgG can be switched to IgM), according to well-known procedures. Class switching can also be used to convert one IgG subclass to another, such as from $IgG_1$ to $IgG_2$.

Antigen binding fragments of the above antibodies that specifically bind to TEM8 are also encompassed by the present disclosure, such as single-domain antibodies (for example, VH domain antibodies), Fab, F(ab')$_2$, and Fv. These antibody fragments retain the ability to specifically bind TEM8. These fragments include:

(1) Fab, the fragment which contains a monovalent antigen-binding fragment of an antibody molecule, can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, a genetically engineered fragment containing the variable region of the light chain and the variable region of the heavy chain expressed as two chains;

(5) Single chain antibody (such as scFv), a genetically engineered molecule containing the variable region of the light chain, the variable region of the heavy chain, linked by a suitable polypeptide linker as a genetically fused single chain molecule;

(6) A dimer of a single chain antibody (scFV$_2$), defined as a dimer of a scFV (also known as a "mini-antibody"); and (7) VH single-domain antibody, an antibody fragment consisting of the heavy chain variable domain.

Methods of making these fragments are known in the art (see for example, Harlow and Lane, *Antibodies: A Laboratory Manual*, Cold Spring Harbor Laboratory, New York, 1988).

In some cases, antibody fragments can be prepared by proteolytic hydrolysis of the antibody or by expression in a host cell (such as *E. coli*) of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly (see U.S. Pat. No. 4,036,945 and U.S. Pat. No. 4,331,647).

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

One of skill will realize that conservative variants of the antibodies can be produced. Such conservative variants employed in antibody fragments, such as dsFv fragments or in scFv fragments, will retain critical amino acid residues necessary for correct folding and stabilizing between the $V_H$ and the $V_L$ regions, and will retain the charge characteristics of the residues in order to preserve the low pI and low toxicity of the molecules. Amino acid substitutions (such as at most one, at most two, at most three, at most four, or at most five amino acid substitutions) can be made in the $V_H$ or the $V_L$ regions to increase yield. Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

In a further group of embodiments, the antibodies are Fv antibodies, which are typically about 25 kDa and contain a complete antigen-binding site with three CDRs per each heavy chain and each light chain. To produce these antibodies, the $V_H$ and the $V_L$ can be expressed from two individual nucleic acid constructs in a host cell. If the $V_H$ and the $V_L$ are expressed non-contiguously, the chains of the Fv antibody are typically held together by noncovalent interactions. However, these chains tend to dissociate upon dilution, so methods have been developed to crosslink the chains through glutaraldehyde, intermolecular disulfides, or a peptide linker. Thus, in one example, the Fv can be a disulfide stabilized Fv (dsFv), wherein the heavy chain variable region and the light chain variable region are chemically linked by disulfide bonds.

In an additional example, the Fv fragments include $V_H$ and $V_L$ chains connected by a peptide linker. These single-chain antigen binding proteins (scFv) are prepared by constructing a structural gene including DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing scFvs are known in the art (see Whitlow et al., *Methods: a Companion to Methods in Enzymology*, Vol. 2, page 97, 1991; Bird et al., *Science* 242:423, 1988; U.S. Pat. No. 4,946,778; Pack et al., *Bio/Technology* 11:1271, 1993; and Sandhu, supra). Dimers of a single chain antibody (scFV$_2$), are also contemplated.

Antibody fragments can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly (see U.S. Pat. No. 4,036,945 and U.S. Pat. No. 4,331,647, and references contained therein; Nisonhoff et al., *Arch. Biochem. Biophys.* 89:230, 1960; Porter, *Biochem. J.* 73:119, 1959; Edelman et al., *Methods in Enzymology*, Vol. 1, page 422, Academic Press, 1967; and Coligan et al. at sections 2.8.1-2.8.10 and 2.10.1-2.10.4).

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Also included are antibodies that bind to the same epitope on TEM8 to which the TEM8 specific antibodies provided herein bind. Antibodies that bind to such an epitope can be identified based on their ability to cross-compete (for example, to competitively inhibit the binding of, in a statistically significant manner) with the TEM8 specific antibodies provided herein in TEM8 binding assays (such as those described in the Examples). An antibody "competes" for binding when the competing antibody inhibits TEM8 binding of an antibody of the invention by more than 50%, in the presence of competing antibody concentrations higher than $10^6 \times K_D$ of the competing antibody. In a certain embodiment, the antibody that binds to the same epitope on TEM8 as the antibodies of the present invention is a human monoclonal antibody. Such human monoclonal antibodies can be prepared and isolated as described herein.

IV. Conjugates

Human monoclonal antibodies specific for TEM8, or antigen binding fragments thereof, can be conjugated to an agent, such as an effector molecule or detectable marker, using any number of means known to those of skill in the art. Both covalent and noncovalent attachment means may be used. Conjugates include, but are not limited to, molecules in which there is a covalent linkage of an effector molecule or a detectable marker to an antibody (or antigen binding fragment) that specifically binds TEM8. One of skill in the art will appreciate that various effector molecules and detectable markers can be used, including (but not limited to) chemotherapeutic agents, anti-angiogenic agents, toxins, radioactive agents such as $^{125}$I, $^{32}$P, $^{14}$C, $^3$H and $^{35}$S and other labels, target moieties and ligands, etc.

The choice of a particular effector molecule or detectable marker depends on the particular target molecule or cell, and the desired biological effect. Thus, for example, the effector molecule can be a cytotoxin that is used to bring about the death of a particular target cell (such as a tumor cell).

Effector molecules and detectable markers can be linked to an antibody (or antigen binding fragment) of interest using any number of means known to those of skill in the art. Both covalent and noncovalent attachment means may be used. The procedure for attaching an effector molecule or detectable marker to an antibody (or antigen binding fragment) varies according to the chemical structure of the effector. Polypeptides typically contain a variety of functional groups; such as carboxylic acid (COOH), free amine (—NH$_2$) or sulfhydryl (—SH) groups, which are available for reaction with a suitable functional group on an antibody to result in the binding of the effector molecule or detectable marker. Alternatively, the antibody (or antigen binding fragment) is derivatized to expose or attach additional reactive functional groups. The derivatization may involve attachment of any of a number of known linker molecules such as those available from Pierce Chemical Company, Rockford, Ill. The linker can be any molecule used to join the antibody (or antigen binding fragment) to the effector molecule or detectable marker. The linker is capable of forming covalent bonds to both the antibody (or antigen binding fragment) and to the effector molecule or detectable marker. Suitable linkers are well known to those of skill in the art and include, but are not limited to, straight or branched-chain carbon linkers, heterocyclic carbon linkers, or peptide linkers. Where the antibody (or antigen binding fragment) and the effector molecule or detectable marker are polypeptides, the linkers may be joined to the constituent amino acids through their side groups (such as through a disulfide linkage to cysteine) or to the alpha carbon amino and carboxyl groups of the terminal amino acids.

Additionally, in several embodiments, the linker can include a spacer element, which, when present, increases the size of the linker such that the distance between the effector molecule or the detectable marker and the antibody (or antigen binding fragment) is increased. Exemplary spacers are known to the person of ordinary skill, and include those listed in U.S. Pat. Nos. 7,964,566 7,498,298, 6,884,869, 6,323,315, 6,239,104, 6,034,065, 5,780,588, 5,665,860, 5,663,149, 5,635,483, 5,599,902, 5,554,725, 5,530,097, 5,521,284, 5,504,191, 5,410,024, 5,138,036, 5,076,973, 4,986,988, 4,978,744, 4,879,278, 4,816,444, and 4,486,414, as well as U.S. Pat. Pub. Nos. 20110212088 and 20110070248, each of which is incorporated by reference in its entirety.

Thus, in several embodiments, the conjugate includes a linker that connects the effector molecule or detectable marker to the TEM8-specific antibody or antigen binding fragment thereof. In some embodiments, the linker is cleavable under intracellular conditions, such that cleavage of the linker releases the effector molecule or detectable marker from the antibody (or antigen binding fragment) in the intracellular environment. In yet other embodiments, the linker is not cleavable and the effector molecule or detectable marker is released, for example, by antibody degradation. In some embodiments, the linker is cleavable by a cleaving agent that is present in the intracellular environment (for example, within a lysosome or endosome or caveolea). The linker can be, for example, a peptide linker that is cleaved by an intracellular peptidase or protease enzyme, including, but not limited to, a lysosomal or endosomal protease. In some embodiments, the peptide linker is at least two amino acids long or at least three amino acids long. However, the linker can be 4, 5, 6, 7, 8, 9, 10, 11, 12, 13, 14 or 15 amino acids long, such as 1-2, 1-3, 2-5, 3-10, 3-15, 1-5, 1-10, 1-15, amino acids long. Proteases can include cathepsins B and D and plasmin, all of which are known to hydrolyze dipeptide drug derivatives resulting in the release of active drug inside target cells (see, for example, Dubowchik and Walker, 1999, Pharm. Therapeutics 83:67-123). For example, a peptide linker that is cleavable by the thiol-dependent protease cathepsin-B, can be used (for example, a Phenylalanine-Leucine or a Glycine-Phenylalanine-Leucine-Glycine linker). Other examples of such linkers are described, for example, in U.S. Pat. No. 6,214,345, incorporated herein by reference. In a specific embodiment, the peptide linker cleavable by an intracellular protease is a Valine-Citruline linker or a Phenylalanine-Lysine linker (see, for example, U.S. Pat. No. 6,214,345, which describes the synthesis of doxorubicin with the Valine-Citruline linker).

In other embodiments, the cleavable linker is pH-sensitive, i.e., sensitive to hydrolysis at certain pH values. Typically, the pH-sensitive linker is hydrolyzable under acidic conditions. For example, an acid-labile linker that is hydrolyzable in the lysosome (for example, a hydrazone, semicarbazone, thiosemicarbazone, cis-aconitic amide, orthoester, acetal, ketal, or the like) can be used. (See, for example, U.S. Pat. Nos. 5,122,368; 5,824,805; 5,622,929; Dubowchik and Walker, 1999, Pharm. Therapeutics 83:67-123; Neville et al., 1989, Biol. Chem. 264:14653-14661.) Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, for example, a thioether attached to the therapeutic agent via an acylhydrazone bond (see, for example, U.S. Pat. No. 5,622,929).

In yet other embodiments, the linker is cleavable under reducing conditions (for example, a disulfide linker). A variety of disulfide linkers are known in the art, including, for example, those that can be formed using SATA (N-succinimidyl-S-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio) toluene)-, SPDB and SMPT. (See, for example, Thorpe et al., 1987, Cancer Res. 47:5924-5931; Wawrzynczak et al., In Immunoconjugates: Antibody Conjugates in Radioimagery and Therapy of Cancer (C. W. Vogel ed., Oxford U. Press, 1987); Phillips et al., Cancer Res. 68:92809290, 2008). See also U.S. Pat. No. 4,880,935.)

In yet other specific embodiments, the linker is a malonate linker (Johnson et al., 1995, Anticancer Res. 15:1387-93), a maleimidobenzoyl linker (Lau et al., 1995, Bioorg-Med-Chem. 3(10):1299-1304), or a 3'-N-amide analog (Lau et al., 1995, Bioorg-Med-Chem. 3(10):1305-12).

In yet other embodiments, the linker is not cleavable and the effector molecule or detectable marker is released by antibody degradation. (See U.S. Publication No. 2005/0238649 incorporated by reference herein in its entirety).

In several embodiments, the linker is resistant to cleavage in an extracellular environment. For example, no more than about 20%, no more than about 15%, no more than about 10%, no more than about 5%, no more than about 3%, or no more than about 1% of the linkers, in a sample of conjugate, are cleaved when the conjugate is present in an extracellular environment (for example, in plasma). Whether or not a linker is resistant to cleavage in an extracellular environment can be determined, for example, by incubating the conjugate containing the linker of interest with plasma for a predetermined time period (for example, 2, 4, 8, 16, or 24 hours) and then quantitating the amount of free effector molecule or detectable marker present in the plasma. A variety of exemplary linkers that can be used in conjugates are described in WO 2004-010957, U.S. Publication No. 2006/0074008, U.S. Publication No. 20050238649, and U.S. Publication No. 2006/0024317 (each of which is incorporated by reference herein in its entirety).

The antibodies or antibody fragments disclosed herein can be derivatized, for example, by cross-linking two or more antibodies (of the same type or of different types, such as to create bispecific antibodies). Suitable crosslinkers include those that are heterobifunctional, having two distinctly reactive groups separated by an appropriate spacer (such as m-maleimidobenzoyl-N-hydroxysuccinimide ester) or homobifunctional (such as disuccinimidyl suberate). Such linkers are commercially available.

In view of the large number of methods that have been reported for attaching a variety of radiodiagnostic compounds, radiotherapeutic compounds, labels (such as enzymes or fluorescent molecules), toxins, and other agents to antibodies one skilled in the art will be able to determine a suitable method for attaching a given agent to an antibody (or antigen binding fragment) or other polypeptide. For example, the antibody (or antigen binding fragment) can be conjugated with small molecular weight drugs such as Monomethyl Auristatin E (MMAE), Monomethyl Auristatin F (MMAF), maytansine, maytansine derivatives, including the derivative of maytansine known as DM1 (also known as mertansine), or other chemotherapeutic agents to make an antibody drug conjugate (ADC). In several embodiments, various chemotherapeutic agents described herein can be conjugated to the provided antibodies to generate a conjugate.

In several embodiments, conjugates of an antibody (or antigen binding fragment) and one or more small molecule toxins, such as a calicheamicin, maytansinoids, dolastatins, auristatins, a trichothecene, and CC1065, and the derivatives of these toxins that have toxin activity, are provided.

Maytansine compounds suitable for use as maytansinoid toxin moieties are well known in the art, and can be isolated from natural sources according to known methods, produced using genetic engineering techniques (see Yu et al (2002) PNAS 99:7968-7973), or maytansinol and maytansinol analogues prepared synthetically according to known methods. Maytansinoids are mitotic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533, each of which is incorporated herein by reference. Conjugates containing maytansinoids, methods of making same, and their therapeutic use are disclosed, for example, in U.S. Pat. Nos. 5,208,020; 5,416,064; 6,441,163 and European Patent EP 0 425 235 B1, the disclosures of which are hereby expressly incorporated by reference.

In one example, the conjugate includes a monoclonal antibody that specifically binds TEM8 (or antigen binding fragment thereof), a non-reducible thioester linker and the maytansinoid toxin DM1; for example the conjugate can include the structure set forth as (wherein "mAb" refers to the monoclonal antibody or antigen binding fragment thereof):

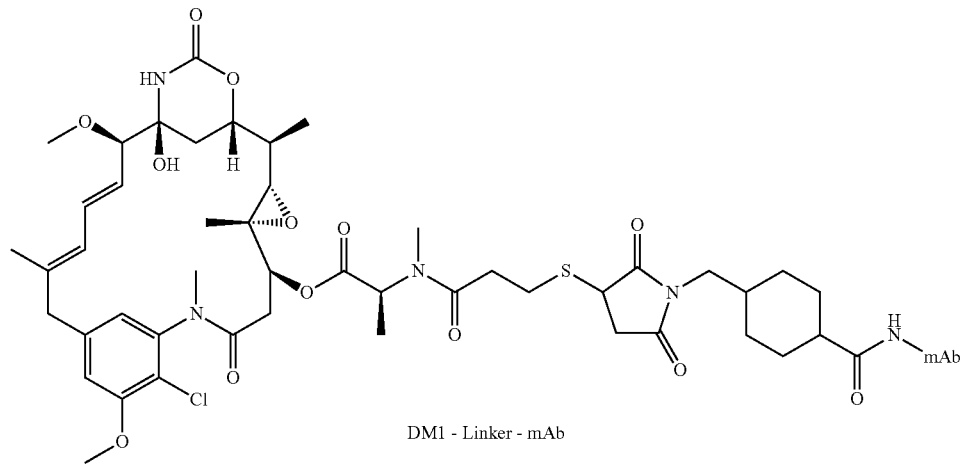

DM1 - Linker - mAb

In some embodiments, the effector molecule is an auristatin, such as auristatin E (also known in the art as a derivative of dolastatin-10) or a derivative thereof. The auristatin can be, for example, an ester formed between auristatin E and a keto acid. For example, auristatin E can be reacted with paraacetyl benzoic acid or benzoylvaleric acid to produce AEB and AEVB, respectively. Other exemplary auristatins include AFP, MMAF, and MMAE. The synthesis and structure of exemplary auristatins are described in U.S. Patent Application Publication No. 2003/0083263; International Patent Publication No. WO 04/010957, International Patent Publication No. WO 02/088172, and U.S. Pat. Nos. 7,498,298, 6,884,869, 6,323,315; 6,239,104; 6,034,065; 5,780,588; 5,665,860; 5,663,149; 5,635,483; 5,599,902; 5,554,725; 5,530,097; 5,521,284; 5,504,191; 5,410,024; 5,138,036; 5,076,973; 4,986,988; 4,978,744; 4,879,278; 4,816,444; and 4,486,414, each of which is incorporated by reference herein in its entirety. Auristatins have been shown to interfere with microtubule dynamics and nuclear and cellular division and have anticancer activity. Auristatins bind tubulin and can exert a cytotoxic or cytostatic effect on cells. There are a number of different assays, known in the art, which can be used for determining whether an auristatin or resultant conjugate exerts a cytostatic or cytotoxic effect on a desired cell line.

In one example, the conjugate includes a monoclonal antibody that specifically binds TEM8 (or antigen binding fragment thereof), a cleavable linker including a Valine-Citruline peptide cleavage site, a spacer, and the toxin MMAE; for example the conjugate can include the structure set forth as (wherein "mAb" refers to the monoclonal antibody or antigen binding fragment thereof):

Additional toxins can be employed with antibodies that specifically bind TEM8, and antigen binding fragment of these antibodies. Exemplary toxins include Pseudomonas exotoxin (PE), ricin, abrin, diphtheria toxin and subunits thereof, ribotoxin, ribonuclease, saporin, and calicheamicin, as well as botulinum toxins A through F. These toxins are well known in the art and many are readily available from commercial sources (for example, Sigma Chemical Company, St. Louis, Mo.). Contemplated toxins also include variants of the toxins (see, for example, see, U.S. Pat. Nos. 5,079,163 and 4,689,401). In some embodiments, these conjugates are of use for the treatment of a carcinoma, for example a breast carcinoma, colorectal carcinoma, lung carcinoma and melanoma.

Saporin is a toxin derived from Saponaria officinalis that disrupts protein synthesis by inactivating the 60S portion of the ribosomal complex (Stirpe et al., Bio/Technology, 10:405-412, 1992). However, the toxin has no mechanism for specific entry into cells, and therefore requires conjugation to an antibody (or antigen binding fragment) that recognizes a cell-surface protein that is internalized in order to be efficiently taken up by cells.

Diphtheria toxin is isolated from Corynebacterium diphtheriae. Typically, diphtheria toxin for use in immunotoxins is mutated to reduce or to eliminate non-specific toxicity. A mutant known as CRM107, which has full enzymatic activity but markedly reduced non-specific toxicity, has been known since the 1970's (Laird and Groman, J. Virol. 19:220, 1976), and has been used in human clinical trials. See, U.S. Pat. No. 5,792,458 and U.S. Pat. No. 5,208,021.

Ricin is the lectin RCA60 from Ricinus communis (Castor bean). For examples of ricin, see, U.S. Pat. No. 5,079,163 and U.S. Pat. No. 4,689,401. Ricinus communis agglutinin (RCA) occurs in two forms designated $RCA_{60}$ and $RCA_{120}$ accord-

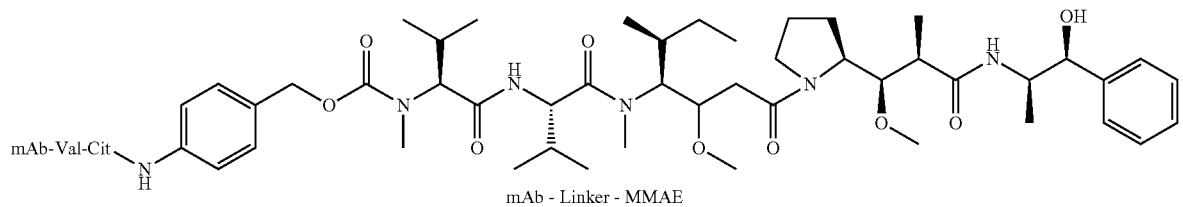

mAb - Linker - MMAE ing to their molecular weights of approximately 65 and 120 kD, respectively (Nicholson & Blaustein, J. Biochim Biophys. Acta 266:543, 1972). The A chain is responsible for inactivating protein synthesis and killing cells. The B chain binds ricin to cell-surface galactose residues and facilitates transport of the A chain into the cytosol (Olsnes et al., Nature 249:627-631, 1974 and U.S. Pat. No. 3,060,165).

Ribonucleases have also been conjugated to targeting molecules for use as immunotoxins (see Suzuki et al., Nat. Biotech. 17:265-70, 1999). Exemplary ribotoxins such as α-sarcin and restrictocin are discussed in, for example Rathore et al., Gene 190:31-5, 1997; and Goyal and Batra, Biochem. 345 Pt 2:247-54, 2000. Calicheamicins were first isolated from *Micromonospora echinospora* and are members of the enediyne antitumor antibiotic family that cause double strand breaks in DNA that lead to apoptosis (see, for example Lee et al., J. Antibiot. 42:1070-87, 1989). The drug is the toxic moiety of an immunotoxin in clinical trials (see, for example, Gillespie et al., Ann Oncol. 11:735-41, 2000).

Abrin includes toxic lectins from *Abrus precatorius*. The toxic principles, abrin a, b, c, and d, have a molecular weight of from about 63 and 67 kD and are composed of two disulfide-linked polypeptide chains A and B. The A chain inhibits protein synthesis; the B chain (abrin-b) binds to D-galactose residues (see, Funatsu et al., Agr. Biol. Chem. 52:1095, 1988; and Olsnes, Methods Enzymol. 50:330-335, 1978).

In one embodiment, the toxin is *Pseudomonas* exotoxin (PE) (U.S. Pat. No. 5,602,095). As used herein, PE includes full-length native (naturally occurring) PE or a PE that has been modified. Such modifications can include, but are not limited to, elimination of domain Ia, various amino acid deletions in domains Ib, II and III, single amino acid substitutions and the addition of one or more sequences at the carboxyl terminus (for example, see Siegall et al., J. Biol. Chem. 264: 14256-14261, 1989).

PE employed with the provided antibodies can include the native sequence, cytotoxic fragments of the native sequence, and conservatively modified variants of native PE and its cytotoxic fragments. Cytotoxic fragments of PE include those which are cytotoxic with or without subsequent proteolytic or other processing in the target cell. Cytotoxic fragments of PE include PE40, PE38, and PE35. For additional description of PE and variants thereof, see for example, U.S. Pat. Nos. 4,892,827; 5,512,658; 5,602,095; 5,608,039; 5,821,238; and 5,854,044; PCT Publication No. WO 99/51643; Pai et al., Proc. Natl. Acad. Sci. USA, 88:3358-3362, 1991; Kondo et al., J. Biol. Chem., 263:9470-9475, 1988; Pastan et al., Biochim. Biophys. Acta, 1333:C1-C6, 1997. In some examples, the PE is PE38 (SEQ ID NO: 44).

Also contemplated herein are protease-resistant PE variants and PE variants with reduced immunogenicity, such as, but not limited to PE-LR, PE-6X, PE-8X, PE-LR/6X and PE-LR/8X (see, for example, Weldon et al., Blood 113(16): 3792-3800, 2009; Onda et al., Proc. Natl. Acad. Sci. USA, 105(32):11311-11316, 2008; and PCT Publication Nos. WO 2007/016150, WO 2009/032954 and WO 2011/032022, which are herein incorporated by reference).

In some examples, the PE is a variant that is resistant to lysosomal degradation, such as PE-LR (SEQ ID NO: 45; Weldon et al., Blood 113(16):3792-3800, 2009; PCT Publication No. WO 2009/032954). In other examples, the PE is a variant designated PE-LR/6X (SEQ ID NO: 46; PCT Publication No. WO 2011/032022). In other examples, the PE variant is PE with reducing immunogenicity, such as a PE including an amino acid sequence set forth as SEQ ID NO: 47. In other examples, the PE is a variant designated PE-LR/8M (SEQ ID NO: 48; PCT Publication No. WO 2011/032022).

A monoclonal antibody that specifically binds TEM8 (or antigen binding fragment thereof) can also be conjugated with a detectable marker; for example, a detectable marker capable of detection by ELISA, spectrophotometry, flow cytometry, microscopy or diagnostic imaging techniques (such as computed tomography (CT), computed axial tomography (CAT) scans, magnetic resonance imaging (MRI), nuclear magnetic resonance imaging NMRI), magnetic resonance tomography (MTR), ultrasound, fiberoptic examination, and laparoscopic examination). Specific, non-limiting examples of detectable markers include fluorophores, chemiluminescent agents, enzymatic linkages, radioactive isotopes and heavy metals or compounds (for example super paramagnetic iron oxide nanocrystals for detection by MRI). For example, useful detectable markers include fluorescent compounds, including fluorescein, fluorescein isothiocyanate, rhodamine, 5-dimethylamine-1-napthalenesulfonyl chloride, phycoerythrin, lanthanide phosphors and the like. Bioluminescent markers are also of use, such as luciferase, Green fluorescent protein (GFP), Yellow fluorescent protein (YFP). An antibody (or antigen binding fragment) can also be conjugated with enzymes that are useful for detection, such as horseradish peroxidase, β-galactosidase, luciferase, alkaline phosphatase, glucose oxidase and the like. When an antibody (or antigen binding fragment) is conjugated with a detectable enzyme, it can be detected by adding additional reagents that the enzyme uses to produce a reaction product that can be discerned. For example, when the agent horseradish peroxidase is present the addition of hydrogen peroxide and diaminobenzidine leads to a colored reaction product, which is visually detectable. An antibody (or antigen binding fragment) may also be conjugated with biotin, and detected through indirect measurement of avidin or streptavidin binding. It should be noted that the avidin itself can be conjugated with an enzyme or a fluorescent label.

An antibody (or antigen binding fragment) may be conjugated with a paramagnetic agent, such as gadolinium. Paramagnetic agents such as superparamagnetic iron oxide are also of use as labels. Antibodies can also be conjugated with lanthanides (such as europium and dysprosium), and manganese. An antibody (or antigen binding fragment) may also be labeled with a predetermined polypeptide epitopes recognized by a secondary reporter (such as leucine zipper pair sequences, binding sites for secondary antibodies, metal binding domains, epitope tags).

An antibody (or antigen binding fragment) can also be conjugated with a radiolabeled amino acid. The radiolabel may be used for both diagnostic and therapeutic purposes. For instance, the radiolabel may be used to detect TEM8 and TEM8 expressing cells by x-ray, emission spectra, or other diagnostic techniques. Further, the radiolabel may be used therapeutically as a toxin for treatment of tumors in a subject, for example for treatment of breast carcinoma, lung carcinoma, colorectal carcinoma or melanoma. Examples of labels for polypeptides include, but are not limited to, the following radioisotopes or radionucleotides: $^3H$, $^{14}C$, $^{15}N$, $^{35}S$, $^{90}Y$, $^{99}Tc$, $^{111}In$, $^{125}I$, $^{131}I$.

Means of detecting such detectable markers are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

An antibody (or antigen binding fragment) can also be derivatized with a chemical group such as polyethylene glycol (PEG), a methyl or ethyl group, or a carbohydrate group. These groups may be useful to improve the biological characteristics of the antibody (or antigen binding fragment), such as to increase serum half-life or to increase tissue binding.

The average number of effector molecule or detectable marker moieties per antibody (or antigen binding fragment) in a conjugate can range, for example, from 1 to 20 moieties per antibody (or antigen binding fragment). For some conjugates, the average number of effector molecule or detectable marker moieties per antibody (or antigen binding fragment) may be limited by the number of attachment sites on the antibody (or antigen binding fragment). For example, where the attachment is a cysteine thiol, an antibody (or antigen binding fragment) may have only one or several cysteine thiol groups, or may have only one or several sufficiently reactive thiol groups through which a linker may be attached. In certain embodiments, the average number of effector molecule or detectable marker moieties per antibody (or antigen binding fragment) in a conjugate range from 1 to about 8; from about 2 to about 6; from about 3 to about 5; from about 3 to about 4; from about 3.1 to about 3.9; from about 3.2 to about 3.8; from about 3.2 to about 3.7; from about 3.2 to about 3.6; from about 3.3 to about 3.8; or from about 3.3 to about 3.7. See, for example, U.S. Pat. No. 7,498,298 (herein incorporated by reference in its entirety). The average number of effector molecule or detectable marker moieties per antibody (or antigen binding fragment) in preparations of conjugates may be characterized by conventional means such as mass spectroscopy and, ELISA assay.

The loading (for example, effector molecule/antibody ratio) of an conjugate may be controlled in different ways, for example, by: (i) limiting the molar excess of effector molecule-linker intermediate or linker reagent relative to antibody, (ii) limiting the conjugation reaction time or temperature, (iii) partial or limiting reductive conditions for cysteine thiol modification, (iv) engineering by recombinant techniques the amino acid sequence of the antibody such that the number and position of cysteine residues is modified for control of the number or position of linker-effector molecule attachments (such as thioMab or thioFab prepared as disclosed in WO2006/034488 (herein incorporated by reference in its entirety).

V. Nucleotides, Expression Vectors and Host Cells

Nucleic acids encoding the amino acid sequences of antibodies that specifically bind TEM8 are provided. Nucleic acid molecules encoding these antibodies can readily be produced by one of skill in the art, using the amino acid sequences provided herein, and the genetic code. In addition, one of skill can readily construct a variety of clones containing functionally equivalent nucleic acids, such as nucleic acids which differ in sequence but which encode the same effector molecule, detectable marker or antibody (or antigen binding fragment) sequence.

Nucleic acid sequences encoding the antibodies that specifically bind TEM8 can be prepared by any suitable method including, for example, cloning of appropriate sequences or by direct chemical synthesis by methods such as the phosphotriester method of Narang et al., *Meth. Enzymol.* 68:90-99, 1979; the phosphodiester method of Brown et al., *Meth. Enzymol.* 68:109-151, 1979; the diethylphosphoramidite method of Beaucage et al., *Tetra. Lett.* 22:1859-1862, 1981; the solid phase phosphoramidite triester method described by Beaucage & Caruthers, *Tetra. Letts.* 22(20):1859-1862, 1981, for example, using an automated synthesizer as described in, for example, Needham-VanDevanter et al., *Nucl. Acids Res.* 12:6159-6168, 1984; and, the solid support method of U.S. Pat. No. 4,458,066. Chemical synthesis produces a single stranded oligonucleotide. This can be converted into double stranded DNA by hybridization with a complementary sequence, or by polymerization with a DNA polymerase using the single strand as a template.

Exemplary nucleic acids including sequences encoding an antibody that specifically binds TEM8 (or antigen binding fragment thereof) can be prepared by cloning techniques. Examples of appropriate cloning and sequencing techniques, and instructions sufficient to direct persons of skill through cloning are found in Sambrook et al., supra, Berger and Kimmel (eds.), supra, and Ausubel, supra. Product information from manufacturers of biological reagents and experimental equipment also provide useful information. Such manufacturers include the SIGMA Chemical Company (Saint Louis, Mo.), R&D Systems (Minneapolis, Minn.), Pharmacia Amersham (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), Invitrogen (San Diego, Calif.), and Applied Biosystems (Foster City, Calif.), as well as many other commercial sources known to one of skill.

Nucleic acids can also be prepared by amplification methods Amplification methods include polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill.

In one example, an antibody (or antigen binding fragment) of use is prepared by inserting the cDNA which encodes a variable region from an antibody into a vector which includes the cDNA encoding an effector molecule or detectable marker, such as an enzyme or label. The insertion is made so that the variable region and the effector molecule or detectable marker are read in frame so that one continuous polypeptide is produced. Thus, the encoded polypeptide contains a functional Fv region and a functional effector molecule or detectable marker region. In one embodiment, cDNA encoding an enzyme is ligated to a scFv so that the enzyme is located at the carboxyl terminus of the scFv. In several examples, cDNA encoding a horseradish peroxidase or alkaline phosphatase, or a polypeptide marker of interest is ligated to a scFv so that the enzyme (or polypeptide marker) is located at the amino terminus of the scFv. In another example, the label is located at the amino terminus of the scFv. In a further example, cDNA encoding the protein or polypeptide marker is ligated to a heavy chain variable region of an antibody (or antigen binding fragment), so that the enzyme or polypeptide marker is located at the carboxyl terminus of the heavy chain variable region. The heavy chain-variable region can subsequently be ligated to a light chain variable region of the antibody (or antigen binding fragment) using disulfide bonds. In a yet another example, cDNA encoding an enzyme or a polypeptide marker is ligated to a light chain variable region of an antibody (or antigen binding fragment), so that the enzyme or polypeptide marker is located at the carboxyl terminus of the light chain variable region. The light chain-variable region can subsequently be ligated to a heavy chain variable region of the antibody (or antigen binding fragment) using disulfide bonds.

Once the nucleic acids encoding the conjugate, antibody, or fragment thereof, are isolated and cloned, the protein can be expressed in a recombinantly engineered cell such as bacteria, plant, yeast, insect and mammalian cells using a suitable expression vector. One or more DNA sequences encoding the antibody or fragment thereof can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art.

Polynucleotide sequences encoding the antibody or antigen binding fragment or conjugate thereof, can be operatively linked to expression control sequences. An expression control sequence operatively linked to a coding sequence is ligated such that expression of the coding sequence is achieved under conditions compatible with the expression control sequences. The expression control sequences include, but are not limited to appropriate promoters, enhancers, transcription terminators, a start codon (i.e., ATG) in front of a protein-encoding gene, splicing signal for introns, maintenance of the correct reading frame of that gene to permit proper translation of mRNA, and stop codons.

The polynucleotide sequences encoding the antibody, or antigen binding fragment or conjugate thereof can be inserted into an expression vector including, but not limited to a plasmid, virus or other vehicle that can be manipulated to allow insertion or incorporation of sequences and can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art.

Transformation of a host cell with recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired, or by electroporation.

When the host is a eukaryote, such methods of transfection of DNA as calcium phosphate coprecipitates, conventional mechanical procedures such as microinjection, electroporation, insertion of a plasmid encased in liposomes, or virus vectors may be used. Eukaryotic cells can also be cotransformed with polynucleotide sequences encoding the antibody, labeled antibody, or antigen binding fragment thereof, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, *Eukaryotic Viral Vectors*, Cold Spring Harbor Laboratory, Gluzman ed., 1982). One of skill in the art can readily use expression systems such as plasmids and vectors of use in producing proteins in cells including higher eukaryotic cells such as the COS, CHO, HeLa and myeloma cell lines.

Isolation and purification of recombinantly expressed polypeptide can be carried out by conventional means including preparative chromatography and immunological separations. Once expressed, the conjugate, antibody, or antigen binding fragment thereof, can be purified according to standard procedures of the art, including ammonium sulfate precipitation, affinity columns, column chromatography, and the like (see, generally, R. Scopes, *Protein Purification*, Springer-Verlag, N.Y., 1982). Substantially pure compositions of at least about 90 to 95% homogeneity are disclosed herein, and 98 to 99% or more homogeneity can be used for pharmaceutical purposes. Once purified, partially or to homogeneity as desired, if to be used therapeutically, the polypeptides should be substantially free of endotoxin.

Methods for expression of single chain antibodies and refolding to an appropriate active form, including single chain antibodies, from bacteria such as *E. coli* have been described and are well-known and are applicable to the antibodies disclosed herein. See, Buchner et al., *Anal. Biochem.* 205:263-270, 1992; Pluckthun, *Biotechnology* 9:545, 1991; Huse et al., *Science* 246:1275, 1989 and Ward et al., *Nature* 341:544, 1989, all incorporated by reference herein. Often, functional heterologous proteins from *E. coli* or other bacteria are isolated from inclusion bodies and require solubilization using strong denaturants, and subsequent refolding. During the solubilization step, as is well known in the art, a reducing agent must be present to separate disulfide bonds. An exemplary buffer with a reducing agent is: 0.1 M Tris pH 8, 6 M guanidine, 2 mM EDTA, 0.3 M DTE (dithioerythritol). Reoxidation of the disulfide bonds can occur in the presence of low molecular weight thiol reagents in reduced and oxidized form, as described in Saxena et al., *Biochemistry*, 9: 5015-5021, 1970, incorporated by reference herein, and especially as described by Buchner et al., supra. Renaturation is typically accomplished by dilution (for example, 100-fold) of the denatured and reduced protein into refolding buffer. An exemplary buffer is 0.1 M Tris, pH 8.0, 0.5 M L-arginine, 8 mM oxidized glutathione (GSSG), and 2 mM EDTA.

As a modification to the two chain antibody purification protocol, the heavy and light chain regions are separately solubilized and reduced and then combined in the refolding solution. An exemplary yield is obtained when these two proteins are mixed in a molar ratio such that a 5 fold molar excess of one protein over the other is not exceeded. Excess oxidized glutathione or other oxidizing low molecular weight compounds can be added to the refolding solution after the redox-shuffling is completed.

In addition to recombinant methods, the antibodies, antigen binding fragments and conjugates thereof can be constructed in whole or in part using standard peptide synthesis. Solid phase synthesis of the polypeptides of less than about 50 amino acids in length can be accomplished by attaching the C-terminal amino acid of the sequence to an insoluble support followed by sequential addition of the remaining amino acids in the sequence. Techniques for solid phase synthesis are described by Barmy & Merrifield, *The Peptides: Analysis, Synthesis, Biology. Vol. 2: Special Methods in Peptide Synthesis, Part A*. pp. 3-284; Merrifield et al., *J. Am. Chem. Soc.* 85:2149-2156, 1963, and Stewart et al., *Solid Phase Peptide Synthesis*, 2nd ed., Pierce Chem. Co., Rockford, Ill., 1984. Proteins of greater length may be synthesized by condensation of the amino and carboxyl termini of shorter fragments. Methods of forming peptide bonds by activation of a carboxyl terminal end (such as by the use of the coupling reagent N,N'-dicylohexylcarbodiimide) are well known in the art.

VI. Methods of Detection

Methods are provided for detecting the presence of a cell that expresses TEM8 in a subject. In some embodiments, the methods include contacting a cell from a subject with one or more of the antibodies that specifically bind TEM8 or conjugate thereof to form an immune complex. The presence (or absence) of the immune complex is then detected. The presence of the immune complex indicates the presence of a cell that expresses TEM8 in the subject. The detection methods can involve in vivo detection or in vitro detection of the immune complex. In several embodiments, detection of a cell that expresses TEM8 includes detecting cell-surface expression of TEM8 on the endothelial cell. In several embodiments of the provided methods, detecting a cell that expresses TEM8 in a subject detects pathological angiogenesis in the subject, for example angiogenesis associated with tumor development. The cell can be a endothelial cell or a pericytes.

Thus, methods are provided for detecting a cell that expresses TEM8, for example, an endothelial cell that expresses TEM8 or a pericyte that expresses TEM8. In a specific non-limiting example, the cell is an endothelial cell. In some embodiments, a subject is selected who has, is suspected of having, or is at risk of developing, a tumor, for example, a carcinoma. For example, the subject has, is suspected of having, or is at risk of developing breast carcinoma, lung carcinoma, colorectal carcinoma or melanoma. In some examples the subject has, is suspected of having, or is at risk of developing breast, colorectal, lung or skin cancer. Thus, the presence of an endothelial cell expressing TEM8 can be detected in these subjects. In some examples, detecting an endothelial cell that expresses TEM8 detects a blood vessel comprising at least one endothelial cell that expresses TEM8. In some examples, the endothelial cell is a vascular endothelial cell, for example a vascular endothelial cell in a tumor associated blood vessel.

In one embodiment, a sample is obtained from a subject, and the presence of an endothelial cell that expresses TEM8 is assessed in vitro. For example, such methods include contacting an endothelial cell in a biological sample from the subject with one or more of the conjugates or antibodies provided herein that specifically bind TEM8 to form an immune complex. The presence (or absence) of the immune complex is then detected. The presence of the immune complex on the endothelial cell from the subject indicates the presence of an endothelial cell that expresses TEM8 in the subject. For example, an increase in the presence of the immune complex in the sample as compared to formation of the immune complex in a control sample indicates the presence of an endothelial cell that expresses TEM8 in the subject.

A biological sample is typically obtained from a mammalian subject of interest, such as human. The sample can be any sample, including, but not limited to, tissue from biopsies, autopsies and pathology specimens. Biological samples also include sections of tissues, for example, frozen sections taken for histological purposes.

In some examples of the disclosed methods, the TEM8 specific antibody (or antigen binding fragment) is conjugated to a detectable marker. In some examples, the methods further include contacting a second antibody that specifically binds the TEM8 specific antibody, antigen binding fragment thereof, or a conjugate including these molecules, for a sufficient amount of time to form an immune complex and detecting this immune complex. An increase in the presence of this immune complex in a biological sample from a selected subject (as described above) compared to the presence of the immune complex in a control sample or other standard detects the presence of an endothelial cell that expresses TEM8 in the biological sample. In some examples, the second antibody is conjugated to a detectable marker.

Suitable detectable markers for the antibody or secondary antibody are described and known to the skilled artisan. For example, various enzymes, prosthetic groups, fluorescent materials, luminescent materials, magnetic agents and radioactive materials. Non-limiting examples of suitable enzymes include horseradish peroxidase, alkaline phosphatase, beta-galactosidase, or acetylcholinesterase. Non-limiting examples of suitable prosthetic group complexes include streptavidin/biotin and avidin/biotin. Non-limiting examples of suitable fluorescent materials include umbelliferone, fluorescein, fluorescein isothiocyanate, rhodamine, dichlorotriazinylamine fluorescein, dansyl chloride or phycoerythrin. A non-limiting exemplary luminescent material is luminol; a non-limiting exemplary a magnetic agent is gadolinium, and non-limiting exemplary radioactive labels include $^{125}$I, $^{131}$I, $^{35}$S or $^{3}$H.

The antibodies that specifically bind TEM8 and conjugates thereof can be used in immunohistochemical assays. These assays are well known to one of skill in the art (see Harlow & Lane, *Antibodies, A Laboratory Manual*, Cold Spring Harbor Publications, New York (1988), for a description of immunoassay formats The antibodies disclosed herein can also be used to detect endothelial cells that express TEM8 as well as pericytes that express TEM8 in vivo. In some example, in vivo detection of an endothelial cell that expresses TEM8 detects pathological angiogenesis in the subject. Thus, methods are disclosed for detecting pathological angiogenesis in a subject, such as pathological angiogenesis associated with a tumor, such as a carcinoma; for example, a breast carcinoma, lung carcinoma, colorectal carcinoma or melanoma. In one embodiment, an effective amount of an antibody that specifically binds to TEM8 (or antigen binding fragment thereof) or a conjugate thereof is administered to the subject for a sufficient amount of time for the antibody (or antigen binding fragment) to form an immune complex, which can then be detected. Detection of the immune complex in the subject determines the presence of an endothelial cell that expresses TEM8, which detects pathological angiogenesis in the subject. In one specific, non-limiting example detection of an immune complex is performed by immunoscintography. Other specific, non-limiting examples of immune complex detection include radiolocalization, radioimaging, magnetic resonance imaging (such as using a biotinylated antibody and avidin-iron oxide), positron emission tomography (such as using an $^{111}$indium-labeled monoclonal antibody) or fluorescence imaging (such as using luciferase or green fluorescent protein labeled antibodies). See Paty et al., *Transplantation.*, 77:1133-1137, 2004, herein incorporated by reference. In several examples, the disclosed method detects endothelial cells lining the inner wall of blood vessels in a tumor in the subject, for example, a breast carcinoma, lung carcinoma, colorectal carcinoma or melanoma.

In the setting of magnetic resonance imaging, contrast agent detection can be greatly impacted by magnetic resonance scanner field strength. Increased field strengths provide improvements by orders of magnitude in the ability to detect contrast agents (Hu et al., *Ann. Rev. Biomed. Eng.*, 6:157-184, 2004; Wedeking et al., *Magn. Reson. Imaging.*, 17:569-575, 1999). For example, the limit of detection of gadolinium at 2 tesla (T) is ~30 µM. At 4T the limit of detection is reduced to ~1 µM. With newly available 7 to 12T scanners one would expect to detect low (10-100) nM concentrations of this contrast agent. Similar sensitivity can also be identified using contrast agents such as iron oxide. Once detected the test results can be used to assist in or guide surgical or other excision of a tumor.

In one embodiment, an effective amount of an antibody (or antigen binding fragment) that specifically binds to TEM8 or a conjugate thereof is administered to a subject having a tumor following anti-cancer or anti-angiogenic treatment. After a sufficient amount of time has elapsed to allow for the administered antibody (or antigen binding fragment) or conjugate to form an immune complex with TEM8 on an endothelial cell, the immune complex is detected. For example, an antibody that specifically binds to TEM8 or conjugate thereof can be administered to a subject prior to, or following, treatment of a tumor. The tumor can be (but is not limited to) a breast, colorectal, lung or skin cancer. The presence (or absence) of the immune complex indicates the effectiveness of the treatment. For example, an increase in the immune complex compared to a control taken prior to the treatment indicates that the treatment is not effective, whereas a decrease in the immune complex compared to a control taken prior to the treatment indicates that the treatment is effective.

VII. Methods of Treatment

A therapeutically effective amount of an antibody (or antigen binding fragment) that specifically binds TEM8 or conjugate thereof can be administered to a subject to treat pathological angiogenesis, for example to treat a tumor, for example a carcinoma. In some embodiments, administration of a therapeutically effective amount of an antibody (or antigen binding fragment) that specifically binds TEM8 or conjugate thereof decreases pathological angiogenesis, such as pathological angiogenesis that occurs in various types of cancer, such as breast, colorectal, lung or skin cancer. Thus, a subject can be selected for treatment that has, is suspected of having or is at risk of developing a tumor, such as a carcinoma.

In some examples, the antibodies, compositions and conjugates disclosed herein can be administered to a subject to decrease pathological angiogenesis in the subject, to slow or inhibit the growth or metastasis of a tumor, or treat corneal or retinal degeneration. In these applications, a therapeutically effective amount of an antibody (or antigen binding fragment) that specifically binds TEM8 or a conjugate or composition including such antibody (or antigen binding fragment) is administered to a subject in an amount and under conditions sufficient to form an immune complex with TEM8, thereby slowing or inhibiting the growth or the metastasis of a tumor, or other pathological angiogenesis, or to inhibit a sign or a symptom of a cancer. Examples of suitable subjects include those diagnosed with or suspecting of having cancer (for example, a subject having a tumor), for example subjects having a carcinoma, such as a breast carcinoma, lung carcinoma, colorectal carcinoma or melanoma.

The therapeutically effective amount of the antibody (or antigen binding fragment) or conjugate will depend upon the severity of the disease and the general state of the patient's health. A therapeutically effective amount of the antibody (or antigen binding fragment) or conjugate is that which provides either subjective relief of a symptom(s) or an objectively identifiable improvement as noted by the clinician or other qualified observer. In one embodiment, a therapeutically effective amount of a conjugate or antibody (or antigen binding fragment) is the amount necessary to inhibit tumor growth (such as growth of a breast carcinoma, lung carcinoma, colorectal carcinoma or melanoma), pathological angiogenesis, or the amount that is effective at reducing a sign or a symptom of the tumor. The therapeutically effective amount of the agents administered can vary depending upon the desired effects and the subject to be treated. In some examples, therapeutic amounts are amounts which eliminate or reduce the patient's tumor burden, or which prevent or reduce the proliferation of metastatic cells, or which prevent or reduce pathological angiogenesis.

Subjects that can benefit from the disclosed methods include human and veterinary subjects. Subjects can be screened prior to initiating the disclosed therapies, for example to determine whether the subject has a tumor or pathological angiogenesis, or both. The presence of a tumor or pathological angiogenesis, or both, indicates that the tumor or pathological angiogenesis can be treated using the methods provided herein.

Any method of administration can be used for the disclosed conjugates, antibodies, compositions and additional agents, including local and systemic administration. For example topical, oral, intravascular such as intravenous, intramuscular, intraperitoneal, intranasal, intradermal, intrathecal and subcutaneous administration can be used. The particular mode of administration and the dosage regimen will be selected by the attending clinician, taking into account the particulars of the case (for example the subject, the disease, the disease state involved, and whether the treatment is prophylactic). In cases in which more than one agent or composition is being administered, one or more routes of administration may be used; for example, a chemotherapeutic agent may be administered orally and an antibody (or antigen binding fragment) or conjugate or composition disclosed herein may be administered intravenously. Methods of administration include injection for which the conjugates, antibodies or compositions are provided in a nontoxic pharmaceutically acceptable carrier such as water, saline, Ringer's solution, dextrose solution, 5% human serum albumin, fixed oils, ethyl oleate, or liposomes. In some embodiments, local administration of the disclosed compounds can be used, for instance by applying the antibody (or antigen binding fragment) to a region of tissue from which a tumor has been removed, or a region suspected of being prone to tumor development. In some embodiments, sustained intra-tumoral (or near-tumoral) release of the pharmaceutical preparation that includes a therapeutically effective amount of the antibody (or antigen binding fragment) may be beneficial. In other examples, the conjugate is applied as an eye drop topically to the cornea, or intravitreally into the eye.

The compositions that include an antibody (or antigen binding fragment) that specifically binds TEM8 or conjugate thereof can be formulated in unit dosage form suitable for individual administration of precise dosages. In addition, the compositions may be administered in a single dose or in a multiple dose schedule. A multiple dose schedule is one in which a primary course of treatment may be with more than one separate dose, for instance 1-10 doses, followed by other doses given at subsequent time intervals as needed to maintain or reinforce the action of the compositions. Treatment can involve daily or multi-daily doses of compound(s) over a period of a few days to months, or even years. Thus, the dosage regime will also, at least in part, be determined based on the particular needs of the subject to be treated and will be dependent upon the judgment of the administering practitioner.

Typical dosages of the antibodies, conjugates, compositions or additional agents can range from about 0.01 to about 30 mg/kg, such as from about 0.1 to about 10 mg/kg. In some examples, the dosage is at least about 0.1 mg/kg, at least about 0.2 mg/kg, at least about 0.3 mg/kg, at least about 0.4 mg/kg, at least about 0.5 mg/kg, at least about 1 mg/kg, at least about 4 mg/kg, at least about 3 mg/kg, at least about 5 mg/kg, at least about 6 mg/kg, at least about 7 mg/kg, at least about 8 mg/kg is at least about 9 mg/kg, at least about 10 mg/kg, at least about 11 mg/kg, at least about 12 mg/kg, at least about 13 mg/kg, at least about 14 mg/kg, at least about 15 mg/kg, at least about 16 mg/kg, at least about 17 mg/kg, at least about 18 mg/kg, at least about 19 mg/kg, at least about 20 mg/kg, at least about 21 mg/kg, at least about 22 mg/kg, at least about 23 mg/kg, at least about 24 mg/kg at least about 25 mg/kg, at least about 26 mg/kg, at least about 27 mg/kg, at least about 28 mg/kg, at least about 29 mg/kg, or at least about 30 mg/kg.

In particular examples, the subject is administered a therapeutic composition that includes one or more of the conjugates, antibodies, compositions or additional agents, on a multiple daily dosing schedule, such as at least two consecutive days, 10 consecutive days, and so forth, for example for a period of weeks, months, or years. In one example, the subject is administered the conjugates, antibodies, compositions or additional agents for a period of at least 30 days, such as at least 2 months, at least 4 months, at least 6 months, at least 12 months, at least 24 months, or at least 36 months.

In additional embodiments, the antibodies, compositions and conjugates that specifically bind TEM8 can be used to decrease binding of Anthrax PA to a cell. For example, an effective amount of the provided antibodies, compositions and conjugates can be incubated with a cell under conditions sufficient to form an immune complex with TEM8, thereby decreasing binding of Anthrax PA to the cell. In some examples, an effective amount of the antibodies, compositions and conjugates that specifically bind TEM8 can be administered to a subject to decrease binding of Anthrax PA to a cell in the subject. Suitable subjects may include those diagnosed or at risk of developing with Anthrax infection or suspected of exposure to Anthrax.

VIII. Several Embodiments

Clause 1: An isolated monoclonal antibody, or antigen binding fragment thereof, comprising a heavy chain variable region and a light chain variable region, wherein the heavy chain variable region comprises a heavy chain complementarity determining region (H-CDR)1, a H-CDR2, and a H-CDR3, the H-CDR1, H-CDR2, and H-CDR3, respectively comprising:

(a) the amino acid sequence set forth as amino acids 31-37, 52-67, and 100-106 of SEQ ID NO: 1 (L2);

(b) the amino acid sequence set forth as amino acid residues 31-35, 50-65, and 96-102 of SEQ ID NO: 2 (L1);

(c) the amino acid sequence set forth as amino acid residues 31-37, 52-69, and 102-110 of SEQ ID NO: 3 (L3);

(d) the amino acid sequence set forth as amino acid residues 31-35, 50-66, and 99-106 of SEQ ID NO: 4 (L5); or (e) the amino acid sequence set forth as amino acid residues 31-37, 52-67, and 100-107 of SEQ ID NO: 5 (1D2), wherein the monoclonal antibody, or antigen binding fragment thereof, specifically binds to TEM8 and is neutralizing.

Clause 2: The isolated monoclonal antibody or antigen binding fragment thereof of clause 1, wherein the heavy chain variable region comprises the amino acid sequence set forth as SEQ ID NO: 1, SEQ ID NO: 2, SEQ ID NO: 3, SEQ ID NO: 4, or SEQ ID NO: 5.

Clause 3: The isolated monoclonal antibody or antigen binding fragment thereof of clause 1, wherein:

(a) the heavy chain variable region comprises the amino acid sequence set forth as amino acids 31-37, 52-67, and 100-106 of SEQ ID NO: 1, and the light chain variable region comprises the amino acid sequence set forth as amino acids 23-33, 49-55, and 88-96 of SEQ ID NO: 6;

(b) the heavy chain variable region comprises the amino acid sequence set forth as amino acids 31-35, 50-65, and 96-102 of SEQ ID NO: 2, and the light chain variable region comprises the amino acid sequence set forth as amino acids 23-33, 49-55, and 88-98 of SEQ ID NO: 7;

(c) the heavy chain variable region comprises the amino acid sequence set forth as amino acids 31-37, 52-69, and 102-110 of SEQ ID NO: 3, and the light chain variable region comprises the amino acid sequence set forth as amino acids 23-33, 49-55, and 88-96 of SEQ ID NO: 8;

(d) the heavy chain variable region comprises the amino acid sequence set forth as amino acids 31-35, 50-66, and 99-106 of SEQ ID NO: 4, and the light chain variable region comprises the amino acid sequence set forth as amino acids 23-33, 49-55, and 88-98 of SEQ ID NO: 9; or (e) the heavy chain variable region comprises the amino acid sequence set forth as amino acids 31-37, 52-67, and 100-107 of SEQ ID NO: 5, and the light chain variable region comprises the amino acid sequence set forth as amino acids 23-33, 49-55, and 88-98 of SEQ ID NO: 10.

Clause 4: The isolated monoclonal antibody or antigen binding fragment thereof of clause 1, wherein:

(a) the heavy chain variable region comprises the amino acid sequence set forth as SEQ ID NO: 1 and the light chain variable region comprises the amino acid sequence set forth as SEQ ID NO: 6;

(b) the heavy chain variable region comprises the amino acid sequence set forth as SEQ ID NO: 2 and the light chain variable region comprises the amino acid sequence set forth as SEQ ID NO: 7;

(c) the heavy chain variable region comprises the amino acid sequence set forth as SEQ ID NO: 3 and the light chain variable region comprises the amino acid sequence set forth as SEQ ID NO: 8;

(d) the heavy chain variable region comprises the amino acid sequence set forth as SEQ ID NO: 4 and the light chain variable region comprises the amino acid sequence set forth as SEQ ID NO: 9; or (e) the a heavy chain variable region comprises the amino acid sequence set forth as SEQ ID NO: 5 and the light chain variable region comprises the amino acid sequence set forth as SEQ ID NO: 10.

Clause 5: The isolated monoclonal antibody of any one of clauses 1-4, wherein the monoclonal antibody, or antigen binding fragment thereof, comprises a human framework region.

Clause 6: The isolated monoclonal antibody of any one of clauses 1-5, wherein the antibody is an IgG.

Clause 7: The antigen binding fragment of any one of clauses 1-5.

Clause 8: The antigen binding fragment of clause 7, wherein the antigen binding fragment is a Fv, Fab, F(ab')$_2$, scFV or a scFV$_2$ fragment.

Clause 9: The isolated monoclonal antibody or antigen binding fragment thereof of any one of clauses 1-8, conjugated to an effector molecule.

Clause 10: The isolated monoclonal antibody or antigen binding fragment thereof of clause 9, wherein the effector molecule is a chemotherapeutic agent.

Clause 11: The isolated monoclonal antibody or antigen binding fragment thereof of clause 10, wherein the chemotherapeutic agent is 5-fluorouracil or irinotecan.

Clause 12: The isolated monoclonal antibody or antigen binding fragment thereof of clause 9, wherein the effector molecule is an anti-angiogenic agent.

Clause 13: The isolated monoclonal antibody or antigen binding fragment thereof of clause 9, wherein the effector molecule is a toxin.

Clause 14: The isolated monoclonal antibody or antigen binding fragment thereof of clause 13, wherein the toxin is a maytansinoid toxin.

Clause 15: The isolated monoclonal antibody or antigen binding fragment thereof of clause 14, wherein the maytansinoid toxin is DM1.

Clause 16: The isolated monoclonal antibody or antigen binding fragment thereof of clause 13, wherein the toxin is an auristatin toxin.

Clause 17: The isolated monoclonal antibody or antigen binding fragment thereof of any one of clause 16, wherein the auristatin toxin is Monomethyl Auristatin E (MMAE) or Monomethyl Auristatin F (MMAF).

Clause 18: The isolated monoclonal antibody or antigen binding fragment thereof of any one of clauses 9-17, wherein the isolated monoclonal antibody or antigen binding fragment thereof is conjugated to the effector molecule by a linker.

Clause 19: The isolated monoclonal antibody or antigen binding fragment thereof of clause 18, wherein the linker is a cleavable linker.

Clause 20: The isolated monoclonal antibody or antigen binding fragment thereof of clause 19, wherein the linker is a cathepsin-cleavable linker.

Clause 21: The isolated monoclonal antibody or antigen binding fragment thereof of any one of clauses 1-8, conjugated to a detectable marker.

Clause 22: The isolated monoclonal antibody or antigen binding fragment thereof of clause 21, wherein the detectable marker is a fluorescent, enzymatic, heavy metal or radioactive marker.

Clause 23: A composition comprising an effective amount of the isolated monoclonal antibody or antigen binding fragment thereof of any one of clauses 1-22 and a pharmaceutically acceptable carrier.

Clause 24: An isolated nucleic acid molecule encoding the monoclonal antibody or antigen binding fragment thereof of any of clauses 1-8.

Clause 25: The isolated nucleic acid molecule of clause 24, encoding a heavy chain domain and a light chain domain of the monoclonal antibody, wherein (a) the heavy chain variable region comprises the amino acid sequence set forth as amino acids 31-37, 52-67, and 100-106 of SEQ ID NO: 1, and the light chain variable region comprises the amino acid sequence set forth as amino acids 23-33, 49-55, and 88-96 of SEQ ID NO: 6;

(b) the heavy chain variable region comprises the amino acid sequence set forth as amino acids 31-35, 50-65, and 96-102 of SEQ ID NO: 2, and the light chain variable region comprises the amino acid sequence set forth as amino acids 23-33, 49-55, and 88-98 of SEQ ID NO: 7;

(c) the heavy chain variable region comprises the amino acid sequence set forth as amino acids 31-37, 52-69, and 102-110 of SEQ ID NO: 3, and the light chain variable region comprises the amino acid sequence set forth as amino acids 23-33, 49-55, and 88-96 of SEQ ID NO: 8;

(d) the heavy chain variable region comprises the amino acid sequence set forth as amino acids 31-35, 50-66, and 99-106 of SEQ ID NO: 4, and the light chain variable region comprises the amino acid sequence set forth as amino acids 23-33, 49-55, and 88-98 of SEQ ID NO: 9; or (e) the heavy chain variable region comprises the amino acid sequence set forth as amino acids 31-37, 52-67, and 100-107 of SEQ ID NO: 5, and the light chain variable region comprises the amino acid sequence set forth as amino acids 23-33, 49-55, and 88-98 of SEQ ID NO: 10.

Clause 26: The isolated nucleic acid molecule of clause 24, encoding a heavy chain domain and a light chain domain of the monoclonal antibody, wherein (a) the heavy chain variable region comprises the amino acid sequence set forth as SEQ ID NO: 1 and the light chain variable region comprises the amino acid sequence set forth as SEQ ID NO: 6;

(b) the heavy chain variable region comprises the amino acid sequence set forth as SEQ ID NO: 2 and the light chain variable region comprises the amino acid sequence set forth as SEQ ID NO: 7;

(c) the heavy chain variable region comprises the amino acid sequence set forth as SEQ ID NO: 3 and the light chain variable region comprises the amino acid sequence set forth as SEQ ID NO: 8;

(d) the heavy chain variable region comprises the amino acid sequence set forth as SEQ ID NO: 4 and the light chain variable region comprises the amino acid sequence set forth as SEQ ID NO: 9; or (e) the a heavy chain variable region comprises the amino acid sequence set forth as SEQ ID NO: 5 and the light chain variable region comprises the amino acid sequence set forth as SEQ ID NO: 10.

Clause 27. A method of treating a subject with a tumor, comprising:

selecting a subject with a tumor; and administering to the subject a therapeutically effective amount of the composition of clause 23 under conditions sufficient to form an immune complex, wherein formation of the immune complex treats the tumor in the subject.

Clause 28: The method of clause 27, further comprising administering to the subject a therapeutically effective amount of an additional agent.

Clause 29: The method of clause 28, wherein the additional agent is an anti-angiogenic agent.

Clause 30: The method of clause 29, wherein the additional agent is a chemotherapeutic agent.

Clause 31: The method of clause 30, wherein the chemotherapeutic agent is 5-fluorouracil or irinotecan.

Clause 32: The method of clause 27, wherein the tumor is breast cancer, colorectal cancer, lung cancer or skin cancer.

Clause 33: The method of clause 27, wherein the tumor is a carcinoma.

Clause 34: The method of clause 27, wherein treating the tumor comprises a reduction in tumor burden.

Clause 35: The method of clause 27, wherein the isolated monoclonal antibody is conjugated to an effector molecule, wherein the effector molecule is a toxin and wherein the toxin is a maytansinoid toxin or an auristatin toxin.

Clause 36: The method of clause 35, wherein the maytansinoid toxin is DM1.

Clause 37: The method of clause 36, wherein the auristatin toxin is Monomethyl Auristatin E (MMAE).

Clause 38. A method of detecting the presence of an endothelial cell expressing TEM8 in a subject, comprising:

contacting an endothelial cell from the subject with an effective amount of the composition of clause 23 under conditions sufficient to form an immune complex; and detecting the presence of the immune complex on the endothelial cell from the subject, wherein the presence of the immune complex on the endothelial cell from the subject indicates the presence of an endothelial cell expressing TEM8 in the subject.

Clause 39: The method of clause 35, wherein the contacting is in vivo.

Clause 40: The method of clause 35, wherein the contacting is in vitro.

Clause 41: The method of clause 35, wherein detecting the presence of an endothelial cell expressing TEM8 in a subject detects pathological angiogenesis in the subject.

Clause 42: The method of clause 35, wherein the endothelial cell is in a biological sample from the subject.

Clause 43: The method of clause 35, wherein the endothelial cell expressing TEM8 is in a carcinoma.

Clause 44: A method of decreasing the binding of Anthrax protective antigen to a cell, comprising:

contacting the cell with an effective amount of the isolated monoclonal antibody or antigen binding fragment thereof of any one of clauses 1-20 under conditions sufficient to form an immune complex, wherein formation of the immune complex decreases the binding of Anthrax protective antigen to the cell.

Clause 45: The method of clause 41, wherein contacting the cell with an effective amount of the monoclonal antibody, or antigen binding fragment thereof, comprises administering a therapeutically effective amount of the monoclonal antibody, or antigen binding fragment thereof, to a subject.

Clause 46: A kit for detecting pathological angiogenesis in a subject, treating a tumor in a subject, or decreasing the binding of Anthrax protective antigen to a cell, comprising a container comprising the isolated monoclonal antibody or antigen binding fragment thereof of any one of clauses 1-22 or the composition of clause 23 and instructions for using the kit.

Administration of the antibodies and conjugates can also be accompanied by administration of other anti-cancer or anti-angiogenesis agents or therapeutic treatments (such as surgical resection of a tumor or radiation therapy). For example, prior to, during, or following administration of a therapeutic amount of the antibodies or conjugates, the subject can receive one or more additional therapies. In one example, the subject receives one or more treatments to remove or reduce the tumor or pathological angiogenesis prior to administration of a therapeutic amount of one or more agents for treatment of the tumor or pathological angiogenesis. For example, the additional agent may include, but is not limited to, a chemotherapeutic agent, an anti-angiogenic agent, or a combination thereof. In another example, at least part of the tumor is surgically or otherwise excised or reduced in size or volume prior to administering the therapeutically effective amount of the antibody (or antigen binding fragment) or conjugate.

Particular examples of additional therapeutic agents that can be used include microtubule binding agents, DNA intercalators or cross-linkers, DNA synthesis inhibitors, DNA and RNA transcription inhibitors, antibodies, enzymes, enzyme inhibitors, gene regulators, and angiogenesis inhibitors. These agents (which are administered at a therapeutically effective amount) and treatments can be used alone or in combination. For example, any suitable anti-cancer or anti-angiogenic agent can be administered in combination with the antibodies, conjugates disclosed herein. Methods and therapeutic dosages of such agents are known to those skilled in the art, and can be determined by a skilled clinician. In one example the chemotherapeutic agent includes 5-FU or IRT or both.

Microtubule binding agent refers to an agent that interacts with tubulin to stabilize or destabilize microtubule formation thereby inhibiting cell division. Examples of microtubule binding agents that can be used in conjunction with the disclosed therapy include, without limitation, paclitaxel, docetaxel, vinblastine, vindesine, vinorelbine (navelbine), the epothilones, colchicine, dolastatin 15, nocodazole, podophyllotoxin and rhizoxin. Analogs and derivatives of such compounds also can be used and are known to those of ordinary skill in the art. For example, suitable epothilones and epothilone analogs are described in International Publication No. WO 2004/018478. Taxoids, such as paclitaxel and docetaxel, as well as the analogs of paclitaxel taught by U.S. Pat. Nos. 6,610,860; 5,530,020; and 5,912,264, can be used.

Suitable DNA and RNA transcription regulators, including, without limitation, actinomycin D, daunorubicin, doxorubicin and derivatives and analogs thereof also are suitable for use in combination with the disclosed therapies. DNA intercalators and cross-linking agents that can be administered to a subject include, without limitation, cisplatin, carboplatin, oxaliplatin, mitomycins, such as mitomycin C, bleomycin, chlorambucil, cyclophosphamide and derivatives and analogs thereof. DNA synthesis inhibitors suitable for use as therapeutic agents include, without limitation, methotrexate, 5-fluoro-5'-deoxyuridine, 5-FU and analogs thereof. Examples of suitable enzyme inhibitors include, without limitation, camptothecin, etoposide, formestane, trichostatin and derivatives and analogs thereof. Suitable compounds that affect gene regulation include agents that result in increased or decreased expression of one or more genes, such as raloxifene, 5-azacytidine, 5-aza-2'-deoxycytidine, tamoxifen, 4-hydroxytamoxifen, mifepristone and derivatives and analogs thereof.

Examples of the commonly used chemotherapy drugs include Adriamycin, Alkeran, Ara-C, BiCNU, Busulfan, CCNU, Carboplatinum, Cisplatinum, Cytoxan, Daunorubicin, DTIC, 5-FU, Fludarabine, Hydrea, Idarubicin, Ifosfamide, Methotrexate, Mithramycin, Mitomycin, Mitoxantrone, Nitrogen Mustard, Taxol (or other taxanes, such as docetaxel), Velban, Vincristine, VP-16, while some more newer drugs include Gemcitabine (Gemzar), Herceptin, IRT (Camptosar, CPT-11), Leustatin, Navelbine, Rituxan STI-571, Taxotere, Topotecan (Hycamtin), Xeloda (Capecitabine), Zevelin and calcitriol.

Non-limiting examples of immunomodulators that can be used include AS-101 (Wyeth-Ayerst Labs.), bropirimine (Upjohn), gamma interferon (Genentech), GM-CSF (granulocyte macrophage colony stimulating factor; Genetics Institute), IL-2 (Cetus or Hoffman-LaRoche), human immune globulin (Cutter Biological), IMREG (from Imreg of New Orleans, La.), SK&F 106528, and TNF (tumor necrosis factor; Genentech).

Thus, non-limiting examples of chemotherapeutic agents for use in combination with the disclosed TEM8 specific antibodies, antigen binding fragments, or conjugates thereof, include chemotherapeutic agents such as erlotinib (TARCEVA®, Genentech/OSI Pharm.), bortezomib (VELCADE®, Millenium Pharm.), fulvestrant (FASLODEX®, AstraZeneca), sutent (SU11248, Pfizer), letrozole (FEMARA®, Novartis), imatinib mesylate (GLEEVEC®, Novartis), PTK787/ZK 222584 (Novartis), oxaliplatin (Eloxatin®, Sanofi), 5-FU (5-fluorouracil), leucovorin, Rapamycin (Sirolimus, RAPAMUNE®, Wyeth), lapatinib (TYKERB®, GSK572016, GlaxoSmithKline), lonafarnib (SCH 66336), sorafenib (BAY43-9006, Bayer Labs.), and gefitinib (IRESSA®, AstraZeneca), AG1478, AG1571 (SU 5271; Sugen), alkylating agents such as thiotepa and CYTOXAN® cyclosphosphamide; alkyl sulfonates such as busulfan, improsulfan and piposulfan; antifolate antineoplastic such as pemetrexed (ALIMTA® Eli Lilly), aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics, calicheamicin, calicheamicin gamma1I and calicheamicin omegaI1; dynemicin, including dynemicin A; bisphosphonates, such as clodronate; an esperamicin; as well as neocarzinostatin chromophore and related chromoprotein enediyne antibiotic chromophores, aclacinomysins, actinomycin, anthramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, for example, paclitaxel (TAXOL®, Bristol-Myers Squibb Oncology, Princeton, N.J.), ABRAXANE™ Cremophor-free, albumin, nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; CPT-11; topoisomerase inhibitor RFS 2000; difluoromethylornithine (DMFO); retinoids such as retinoic acid; capecitabine; and pharmaceutically acceptable salts, acids or derivatives of any of the above.

Non-limiting examples of anti-angiogenic agents include molecules, such as proteins, enzymes, polysaccharides, oligonucleotides, DNA, RNA, and recombinant vectors, and small molecules that function to reduce or even inhibit blood vessel growth. Examples of suitable angiogenesis inhibitors include, without limitation, angiostatin K1-3, staurosporine, genistein, fumagillin, medroxyprogesterone, suramin, interferon-alpha, metalloproteinase inhibitors, platelet factor 4, somatostatin, thrombospondin, endostatin, thalidomide, and derivatives and analogs thereof. For example, in some embodiments the anti-angiogenesis agent is an antibody that specifically binds to VEGF (for example, AVASTIN®, Roche) or a VEGF receptor (for example, a VEGFR2 antibody). In one example the anti-angiogenic agent includes a VEGFR2 antibody, or DMXAA (also known as Vadimezan or ASA404; available commercially, for example, from Sigma Corp., St. Louis, Mo.) or both. Exemplary kinase inhibitors include GLEEVAC®, IRESSA®, and TARCEVA® that prevent phosphorylation and activation of growth factors. Antibodies that can be used include HERCEPTIN® and AVASTIN® that block growth factors and the angiogenic pathway.

In some examples, the additional agent is a monoclonal antibody, for example, 3F8, Abagovomab, Adecatumumab, Afutuzumab, Alacizumab, Alemtuzumab, Altumomab pentetate, Anatumomab mafenatox, Apolizumab, Arcitumomab, Bavituximab, Bectumomab, Belimumab, Besilesomab, Bevacizumab, Bivatuzumab mertansine, Blinatumomab, Brentuximab vedotin, Cantuzumab mertansine, Capromab pendetide, Catumaxomab, CC49, Cetuximab, Citatuzumab bogatox, Cixutumumab, Clivatuzumab tetraxetan, Conatumumab, Dacetuzumab, Detumomab, Ecromeximab, Eculizumab, Edrecolomab, Epratuzumab, Ertumaxomab, Etaracizumab, Farletuzumab, Figitumumab, Galiximab, Gemtuzumab ozogamicin, Girentuximab, Glembatumumab vedotin, Ibritumomab tiuxetan, Igovomab, Imciromab, Intetumumab, Inotuzumab ozogamicin, Ipilimumab, Iratumumab, Labetuzumab, Lexatumumab, Lintuzumab, Lorvotuzumab mertansine, Lucatumumab, Lumiliximab, Mapatumumab, Matuzumab, Mepolizumab, Metelimumab, Milatuzumab, Mitumomab, Morolimumab, Nacolomab tafenatox, Naptumomab estafenatox, Necitumumab, Nimotuzumab, Nofetumomab merpentan, Ofatumumab, Olaratumab, Oportuzumab monatox, Oregovomab, Panitumumab, Pemtumomab, Pertuzumab, Pintumomab, Pritumumab, Ramucirumab, Rilotumumab, Rituximab, Robatumumab, Satumomab pendetide, Sibrotuzumab, Sonepcizumab, sorafenib, sunitinib, Tacatuzumab tetraxetan, Taplitumomab paptox, Tenatumomab, TGN1412, Ticilimumab (=tremelimumab), Tigatuzumab, TNX-650, Trastuzumab, Tremelimumab, Tucotuzumab celmoleukin, Veltuzumab, Volociximab, Votumumab, Zalutumumab.

Another common treatment for some types of cancer is surgical treatment, for example surgical resection of the cancer or a portion of it. Another example of a treatment is radiotherapy, for example administration of radioactive material or energy (such as external beam therapy) to the tumor site to help eradicate the tumor or shrink it prior to surgical resection.

Other therapeutic agents, for example anti-tumor agents, that may or may not fall under one or more of the classifications above, also are suitable for administration in combination with the disclosed therapies. By way of example, such agents include adriamycin, apigenin, rapamycin, zebularine, cimetidine, and derivatives and analogs thereof.

Preparation and dosing schedules for the additional agent may be used according to manufacturer's instructions or as determined empirically by the skilled practitioner. Preparation and dosing schedules for such chemotherapy are also described in Chemotherapy Service, (1992) Ed., M. C. Perry, Williams & Wilkins, Baltimore, Md.

The combination therapy may provide synergy and prove synergistic, that is, the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, for example by different injections in separate syringes. In general, during alternation therapy, an effective dosage of each active ingredient is administered sequentially, i.e. serially, whereas in combination therapy, effective dosages of two or more active ingredients are administered together.

VIII. Compositions

Compositions are provided that include one or more of the disclosed conjugates, antibodies, or antigen binding fragment thereof, that specifically bind TEM8, in a carrier (such as a pharmaceutically acceptable carrier). The compositions can be prepared in unit dosage forms for administration to a subject. The amount and timing of administration are at the discretion of the treating clinician to achieve the desired outcome. The compositions can be formulated for systemic (such as intravenus) or local (such as intra-tumor) administration. In one example, the antibody that specifically binds TEM8 or an antigen binding fragment thereof, or conjugate including such an antibody or antigen binding fragment, is formulated for parenteral administration, such as intravenous administration. Compositions including a conjugate, antibody or antigen binding fragment as disclosed herein are of use, for example, for the treatment and detection of a tumor, for example a tumor occurring in breast, colorectal, lung or skin cancer. In some examples, the compositions are useful for the treatment or detection of a carcinoma. The compositions including a conjugate, antibody or antigen binding fragment as disclosed herein are also of use, for example, for the detection of pathological angiogenesis. The compositions including a conjugate, antibody or antigen binding fragment as disclosed herein are also of use, for example, for inhibiting the binding of Anthrax PA to TEM8.

The compositions for administration can include a solution of the conjugate, antibody or antigen binding fragment dissolved in a pharmaceutically acceptable carrier, such as an aqueous carrier. A variety of aqueous carriers can be used, for example, buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of antibody (or antigen binding fragment) or conjugate in these formulations can vary widely, and will be selected primarily based on fluid volumes, viscosities, body weight and the like in accordance with the particular mode of administration selected and the subject's needs. Actual methods of preparing such dosage forms are known, or will be apparent, to those skilled in the art.

A typical composition for intravenous administration includes about 0.01 to about 30 mg/kg of antibody (or antigen binding fragment) per subject per day (or the corresponding dose of a conjugate including the antibody (or antigen binding fragment)). Actual methods for preparing administrable compositions will be known or apparent to those skilled in the art and are described in more detail in such publications as *Remington's Pharmaceutical Science*, 19th ed., Mack Publishing Company, Easton, Pa. (1995).

Antibodies or conjugates may be provided in lyophilized form and rehydrated with sterile water before administration, although they are also provided in sterile solutions of known concentration. The antibody (or antigen binding fragment) or conjugate solution is then added to an infusion bag containing 0.9% sodium chloride, USP, and in some cases administered at a dosage of from 0.5 to 15 mg/kg of body weight. Considerable experience is available in the art in the administration of antibody (or antigen binding fragment) and conjugate drugs; for example, antibody drugs have been marketed in the U.S. since the approval of RITUXAN® in 1997. Antibodies or conjugates can be administered by slow infusion, rather than in an intravenous push or bolus. In one example, a higher loading dose is administered, with subsequent, maintenance doses being administered at a lower level. For example, an initial loading dose of 4 mg/kg antibody (or antigen binding fragment) (or the corresponding dose of a conjugate including the antibody (or antigen binding fragment)) may be infused over a period of some 90 minutes, followed by weekly maintenance doses for 4-8 weeks of 2 mg/kg infused over a 30 minute period if the previous dose was well tolerated.

Controlled release parenteral formulations can be made as implants, oily injections, or as particulate systems. For a broad overview of protein delivery systems see, Banga, A. J., *Therapeutic Peptides and Proteins: Formulation, Processing, and Delivery Systems*, Technomic Publishing Company, Inc., Lancaster, Pa., (1995). Particulate systems include microspheres, microparticles, microcapsules, nanocapsules, nanospheres, and nanoparticles. Microcapsules contain the therapeutic protein, such as a cytotoxin or a drug, as a central core. In microspheres the therapeutic is dispersed throughout the particle. Particles, microspheres, and microcapsules smaller than about 1 μm are generally referred to as nanoparticles, nanospheres, and nanocapsules, respectively. Capillaries have a diameter of approximately 5 μm so that only nanoparticles are administered intravenously. Microparticles are typically around 100 μm in diameter and are administered subcutaneously or intramuscularly. See, for example, Kreuter, J., *Colloidal Drug Delivery Systems*, J. Kreuter, ed., Marcel Dekker, Inc., New York, N.Y., pp. 219-342 (1994); and Tice & Tabibi, *Treatise on Controlled Drug Delivery*, A. Kydonieus, ed., Marcel Dekker, Inc. New York, N.Y., pp. 315-339, (1992).

Polymers can be used for ion-controlled release of the antibody (or antigen binding fragment) or conjugate compositions disclosed herein. Various degradable and nondegradable polymeric matrices for use in controlled drug delivery are known in the art (Langer, *Accounts Chem. Res.* 26:537-542, 1993). For example, the block copolymer, polaxamer 407, exists as a viscous yet mobile liquid at low temperatures but forms a semisolid gel at body temperature. It has been shown to be an effective vehicle for formulation and sustained delivery of recombinant interleukin-2 and urease (Johnston et al., *Pharm. Res.* 9:425-434, 1992; and Pec et al., *J. Parent. Sci. Tech.* 44(2):58-65, 1990). Alternatively, hydroxyapatite has been used as a microcarrier for controlled release of proteins (Ijntema et al., *Int. J. Pharm.* 112:215-224, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa. (1993)). Numerous additional systems for controlled delivery of therapeutic proteins are known (see U.S. Pat. No. 5,055,303; U.S. Pat. No. 5,188,837; U.S. Pat. No. 4,235,871; U.S. Pat. No. 4,501,728; U.S. Pat. No. 4,837,028; U.S. Pat. No. 4,957,735; U.S. Pat. No. 5,019,369; U.S. Pat. No. 5,055,303; U.S. Pat. No. 5,514,670; U.S. Pat. No. 5,413,797; U.S. Pat. No. 5,268,164; U.S. Pat. No. 5,004,697; U.S. Pat. No. 4,902,505; U.S. Pat. No. 5,506,206; U.S. Pat. No. 5,271,961; U.S. Pat. No. 5,254,342 and U.S. Pat. No. 5,534,496).

IX. Kits

Kits are also provided. For example, kits for detecting a cell (such as an endothelial cell or a pericytes) that expresses TEM8 in a subject, treating a tumor in a subject, or decreasing binding of Anthrax PA to a cell. The kits will typically include an antibody (or antigen binding fragment) that specifically binds TEM8 or a conjugate thereof.

More than one of the conjugates or antibodies that specifically bind TEM8 can be included in the kit. Thus, the kit can include two or more antibodies that specifically bind TEM8, or an antibody (or antigen binding fragment) that specifically binds TEM8 and a conjugate thereof, or a combination thereof. In some embodiments, an antibody fragment or conjugate including an antibody fragment, such as an Fv fragment, is included in the kit. In one example, such as for in vivo uses, the antibody can be a scFv fragment.

In one embodiment, a kit includes instructional materials disclosing means of use of an antibody that specifically binds TEM8, or a conjugate thereof. The instructional materials may be written, in an electronic form (such as a computer diskette or compact disk) or may be visual (such as video files). The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

EXAMPLES

The following examples are provided to illustrate certain particular features and embodiments and should not be construed as limiting.

Example 1

Genetic Depletion of TEM8 Inhibits Tumor Growth in an Animal Model

This example illustrates the effect of genetic depletion of TEM8 on tumor growth in vivo. TEM8 knockout mice were crossed onto an athymic nude background (TEM8 KO) to create immunodeficient mice for in vivo studies and the resulting mice were challenged with various tumor types including melanoma, breast, lung, and colon cancer. The results show that TEM8 depletion inhibits growth of each of these tumor types in an animal model.

Athymic TEM8 KO mice on an immunodeficient background (TEM8$^{-/-}$, nu/nu) were generated by crossing TEM8 KO mice on a C57BL/6 background (Cullen et al., *Cancer Research*, 69:6-21-6026, 2009) with athymic NCr-nu/nu mice. For tumor studies involving TEM8 KO mice, only TEM8 WT and KO littermates derived from TEM8 heterozygous intercrosses were used for comparison. Tumor studies not involving TEM8 KO mice were performed on athymic NCr-nu/nu mice.

TEM8-KO/nude mice or control animals were inoculated with various tumor cell lines. DLD-1, HCT116, LS174T and SW620 cells were obtained from ATCC, and NCI-H460, LOX IMVI (LOX), and UACC-64 (UACC) were from the DCTD Tumor Repository at NCI (Frederick, Md.). MDA-MB-231 cells are available from ATCC (Cat No: HTB-26). Cells were cultured in RPMI 1640 supplemented with 10% FBS. $2.5 \times 10^6$ to $5 \times 10^6$ tumor cells were injected into the mammary fat pad or subcutaneously into the flank. Tumors were measured with a digital caliper, and tumor volumes were calculated using the formula $L \times W^2 \times 0.5$ and presented as mean±SE. Tumor weights were calculated following surgical removal.

Figure 1B:
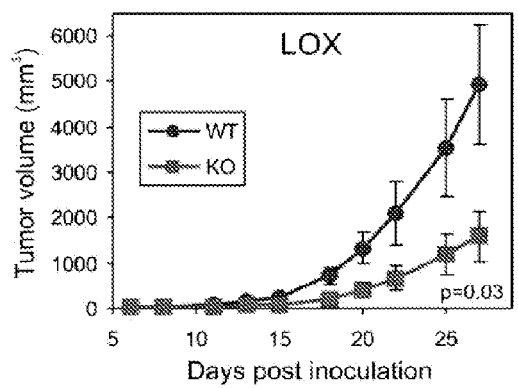
Figure 1C:
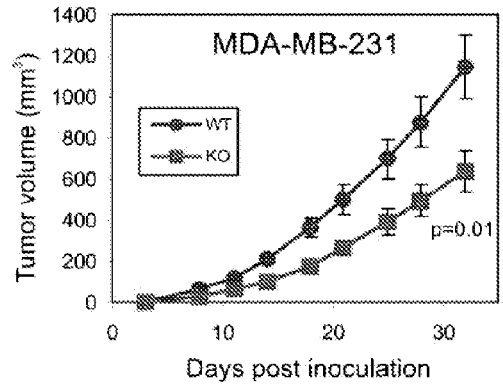
Figure 2C:
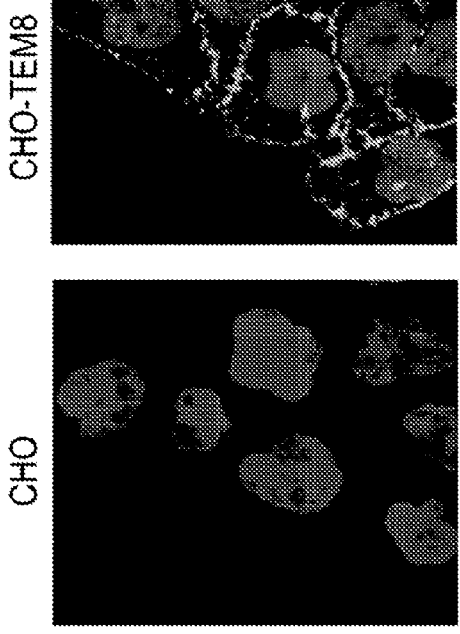
Figure 2D:
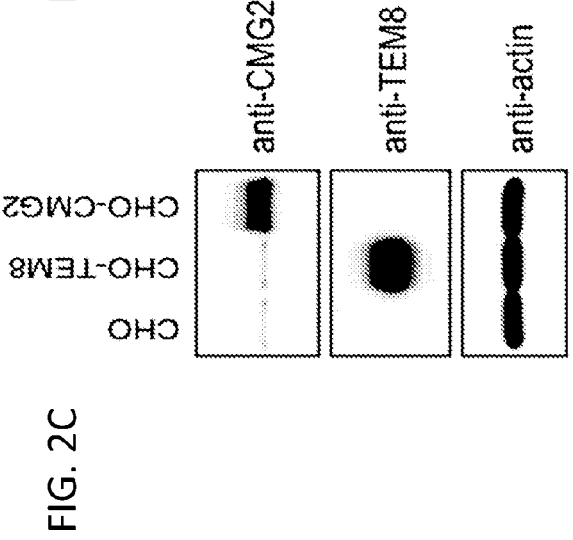
Figure 2E:
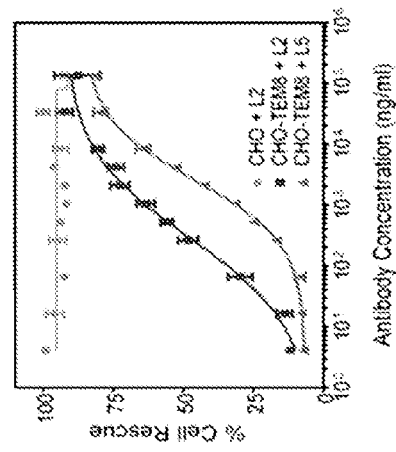
Figure 2F:
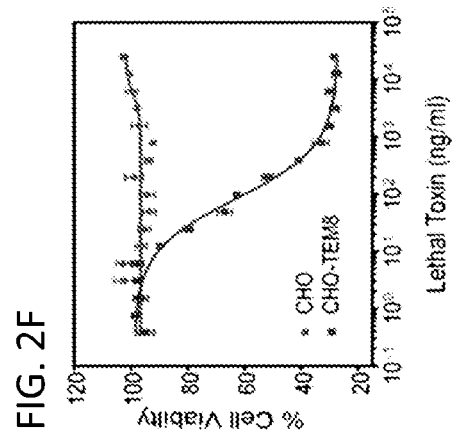
Figure 2G:
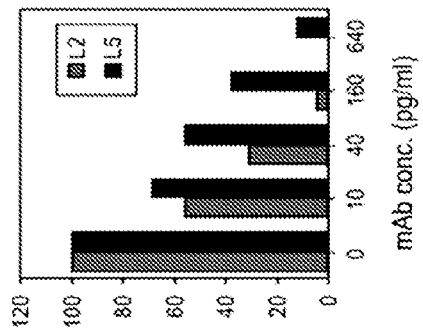

As shown in FIG. 1, tumor growth was inhibited in the TEM8$^{-/-}$ (also known as TEM8 knockout or KO) mice compared to TEM8$^{+/+}$ (also known as TEM8 wildtype or WT) littermate controls when challenged with various tumor types including melanoma (UACC and LOX), breast (MDA-MB-231), lung (NCI-H460), and colon cancer (SW620, HCT116 and DLD-1). The MDA-MB-231 breast tumors (FIG. 1C) were grown orthotopically in the mammary fat pad, while the melanoma and other tumor types (FIGS. 1A-1B and 1D-1G) were implanted subcutaneously. Tumor growth was consistently slower in KO versus WT mice, and SW620 tumors required over 100 days to reach an average size of 800 mm$^3$, compared to only 35 days for WT littermates (FIG. 1G). These studies reveal that host-derived TEM8 functions to promote the subcutaneous and orthotopic growth of human tumor xenografts of diverse origin.

Example 2

Development of Anti-TEM8 mAbs

This example illustrates the development a panel of fully human anti-TEM8 Fabs using antibody phage display. The selection strategy involved serial panning of the Fab libraries on both TEM8-transfected mammalian cells and purified recombinant TEM8-ED protein derived from mammalian cells, and resulted in the identification of five TEM8 Fabs, termed L1, L2, L3, L5 and ID2.

Methods

Construction and Purification of TEM8-Fc and TEM8-AP

Testing of candidate Fabs required purified TEM8 extracellular domain (ED). A TEM8(ED)-Fc/pFuse vector encoding a TEM8(ED)-Fc fusion protein was constructed by cloning the extracellular domain of human TEM8 (amino acids 1 to 321 of SEQ ID NO: 13) in frame with the Fc domain of mouse IgG2a in the pFuse-mIgG2Aa-Fc1 vector (InvivoGen, San Diego, Calif.). After sequence verification, the mutation-free plasmid was stably transfected into Human Embryonic Kidney 293 (293) cells. The TEM8(ED)-Fc fusion protein was purified from the culture supernatant using affinity purification on protein G agarose (Roche). Only proteins that were at least 95% pure by coomassie gel staining were used for immunoselection of phage libraries. TEM8-AP was constructed as previously described (Nanda et al., Cancer Res., 64:817-820, 2004).

Antibody Phage Display

A fully human, synthetic phage display library was screened for anti-human TEM8 antibodies. This library, being totally synthetic, is not subject to tolerance mechanisms found in normal immune responses and allowed the generation of antibodies against regions of the TEM8 extracellular domain that are 100% conserved between mouse and human. In vitro selection of the phage display library involved two rounds of sequential panning on biotinylated, purified recombinant TEM8(ED)-Fc fusion proteins and one round of panning on 293 cells transfected with human TEM8 (293/Flag-hTEM8). After the final round of panning, DNA inserts for the Fab heavy and light chains were subcloned as pools into an expression vector and transformant clones were evaluated for expression of TEM8-binding Fabs by ELISA (described below).

Cell Lines and Culture Conditions 293 cells were obtained from ATCC. 293 cells were cultured in DMEM supplemented with 10% FBS. 293 cells expressing mouse (293-mTEM8) or a flag-tagged human TEM8 (293/Flag-huTEM8) were generated by lipofectamine 2000 mediated stable transfection of 293 cells with a mTEM8/pcDNA3 or a Flag-huTEM8/pcDNA3 expression vector (Yang et al., Biochim Biophys Acta 1813(1):39-49, 2011). Because transfected cells expressed variable levels of TEM8 (see 293/mTEM8 cells in FIG. 8C) they were subsequently enriched for surface expression by florescence activated cell sorting (FACS) using anti-AF344 (293/mTEM8) (Yang et al., Biochim Biophys Acta 1813(1):39-49, 2011) or anti-FLAG antibodies (293/Flag-hTEM8) (M2 clone, Sigma).

Flow Cytometry

Trypsinized cells were rinsed in cold PBS/0.5% BSA (PBS/BSA) and labeled with anti-TEM8 Fabs (human) or full IgG (human-mouse) primary antibodies in PBS/BSA containing 10% goat serum at 4° C. Cells were rinsed with PBS/BSA and incubated with FITC-conjugated goat anti-human Fab or anti-mouse IgG secondary antibodies (Jackson Immunoresearch, West Grove, Pa.), rinsed again, and analyzed on a FACScalibur flow cytometer (Becton Dickinson, Franklin Lakes, N.J.) using CellQuest™ Software.

ELISA

NUNC® IMMULON® plates were coated overnight with 1 μg/ml neutravidin. The next day, plates were washed with PBST, blocked with 1% BSA and loaded with 25 ng biotinylated human TEM8-Fc. Control plates received no human TEM8-Fc protein. After incubation, plates were washed and incubated with periplasmic extracts from E. coli TG-1 transformants that contained Fab inserts from the phage library. Periplasmic extracts of IPTG-induced clones were prepared by lysozyme digestion of bacterial pellets (PBS, 1 mg/ml lysozyme, 2 mM MgCl2, benzonase) and non-specific binding was blocked by the addition of 1% BSA. Target and control ELISA plates were incubated with equivalent amounts of extract for 1 hour, washed with PBST and Fab binding was detected by the addition of HRP-conjugated goat anti-human kappa light chain (Sigma, A7164) and lambda light chain (Sigma, A5175) antibodies. After addition of HRP substrate, absorbance (A450 nm) was measured in a spectrophotometer. $EC_{50}$ ELISAs were performed similarly using dilutions of purified Fabs.

Results

A previously generated series of anti-TEM8 antibodies (the SB series of antibodies; Nanda et al., 2004) did not bind the predominant native form of TEM8 on the cell surface. To overcome these obstacles and circumvent potential difficulties associated with breaking tolerance, another panel of fully human anti-TEM8 antibodies was developed in vitro using antibody phage display. The selection strategy was designed to include panning of Fab libraries on Tem8-transfected mammalian cells and purified recombinant mammalian-derived TEM8-ED. This resulted in the identification of five independent Fabs, L1, L2, L3, L5 and ID2. These clones were sequenced and found to possess unique heavy and light variable domain regions, the sequences of which are disclosed herein as SEQ ID NOs: 1-10. The sequences of the heavy and light chains for the L1, L2, L3, L5 and 1D2 Fabs are also disclosed herein as SEQ ID NOs: 24-33.

Figure 8B:
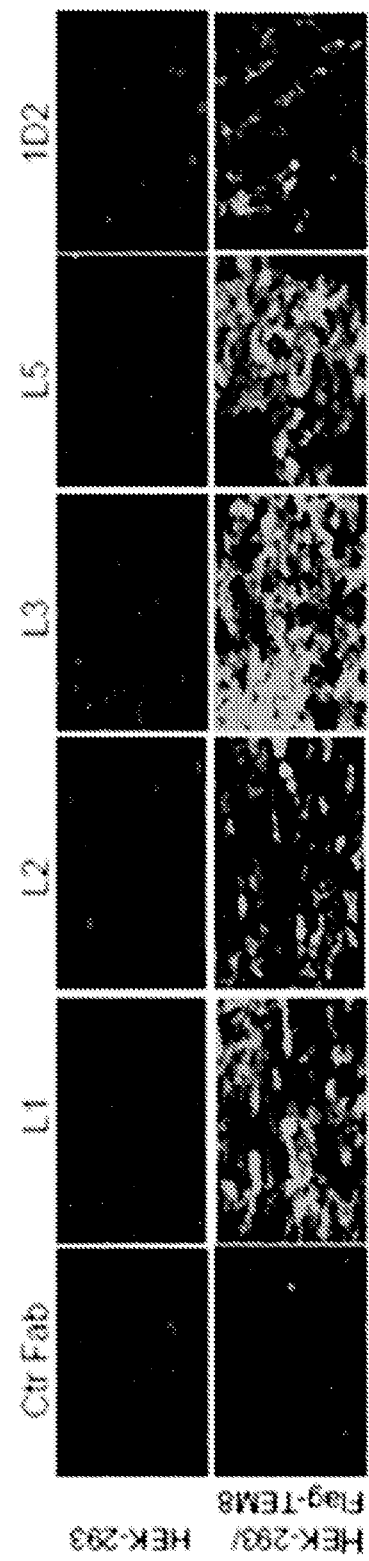
Figure 8C:
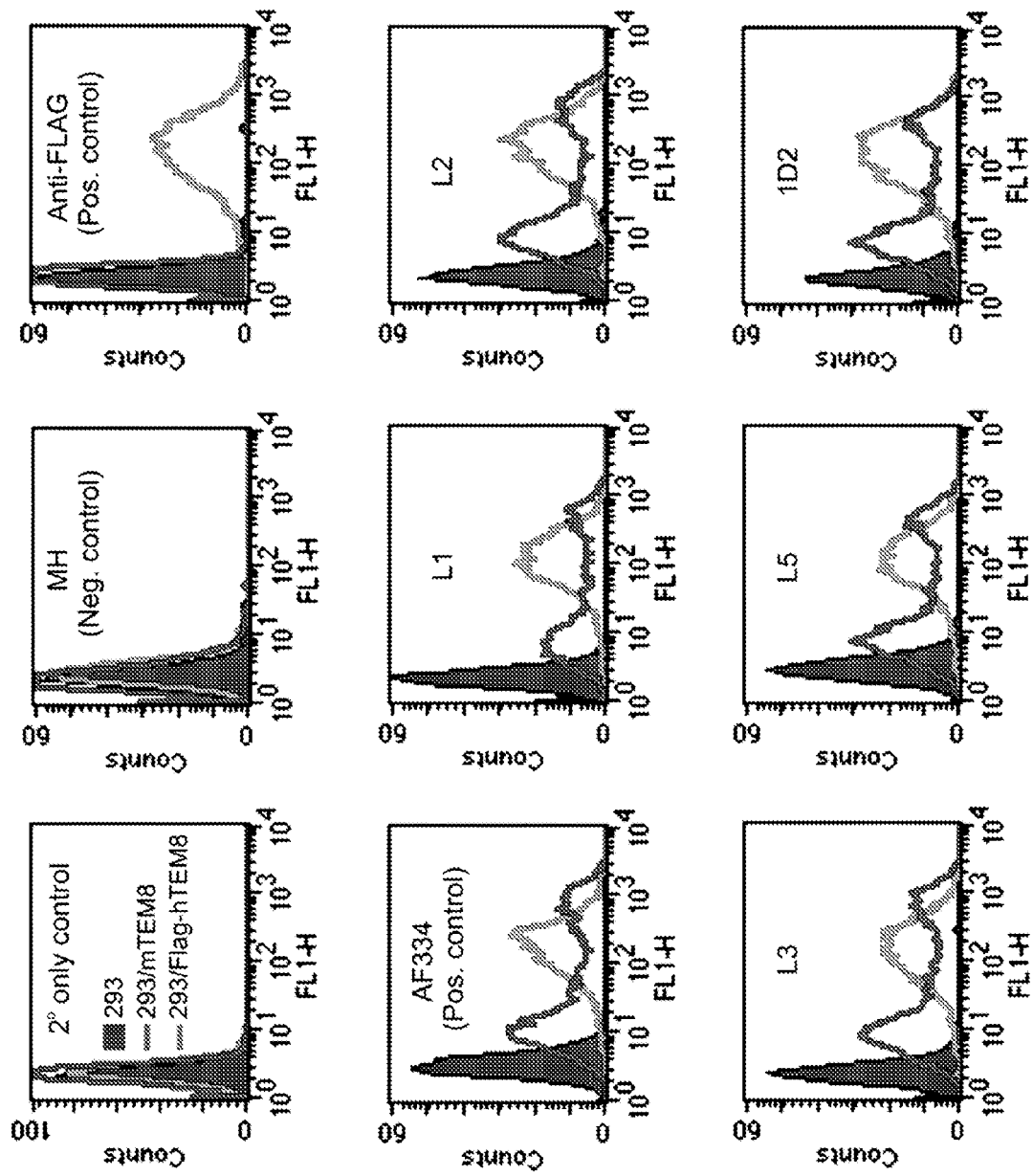

As shown in FIG. 8, each of the L1, L2, L3, L5 and 1D2 Fabs were found to react with both mouse and human TEM8 protein in an ELISA (FIG. 8A), on the surface of live TEM8-positive cells by immunofluorescence staining (FIG. 8B) and flow cytometry (FIG. 8C). Thus, five human anti-TEM8 Fabs positive in each of the initial screens and containing unique variable domains were identified. The locations of the CDRs for these antibodies were determined.

Example 3

TEM8 Fabs Neutralize Anthrax PA Binding to TEM8

This example illustrates that the TEM8 Fabs disclosed herein neutralize the cytotoxic effects of Anthrax toxin binding to TEM8. Anthrax lethal toxin is a multi-functional virulence factor produced by Bacillus anthracis that enters cells by binding the TEM8 or CMG2 receptor, and plays a central role in all stages of Anthrax infection, from germination to the induction of vascular collapse leading to host death (Moayeri and Leppla, Curr Opin Microbiol 7(1):19-24, 2004). The L1, L2, L3 and L5 Fabs were screened for their ability to block the binding of FITC-labeled Anthrax toxin PA to the surface of TEM8 expressing cells.

CHO-TEM8 cells (described below) were trypsinized and kept on ice for the remainder of the assay. Cells were incubated with serial dilutions of the anti-TEM8 Fabs or full IgGs in DMEM containing 0.5% BSA (DMEM/BSA). 1 μg of PA-FITC (List Biologicals, Campbell, Calif.) was added and incubated for 30 min. Cells were rinsed with DMEM/BSA and analyzed by flow cytometry (as described above). The geometric mean of each histogram was plotted against the concentration of Fabs to calculate the $EC_{50}$ using GraphPad Prism software (San Diego, Calif.).

Figure 9A:
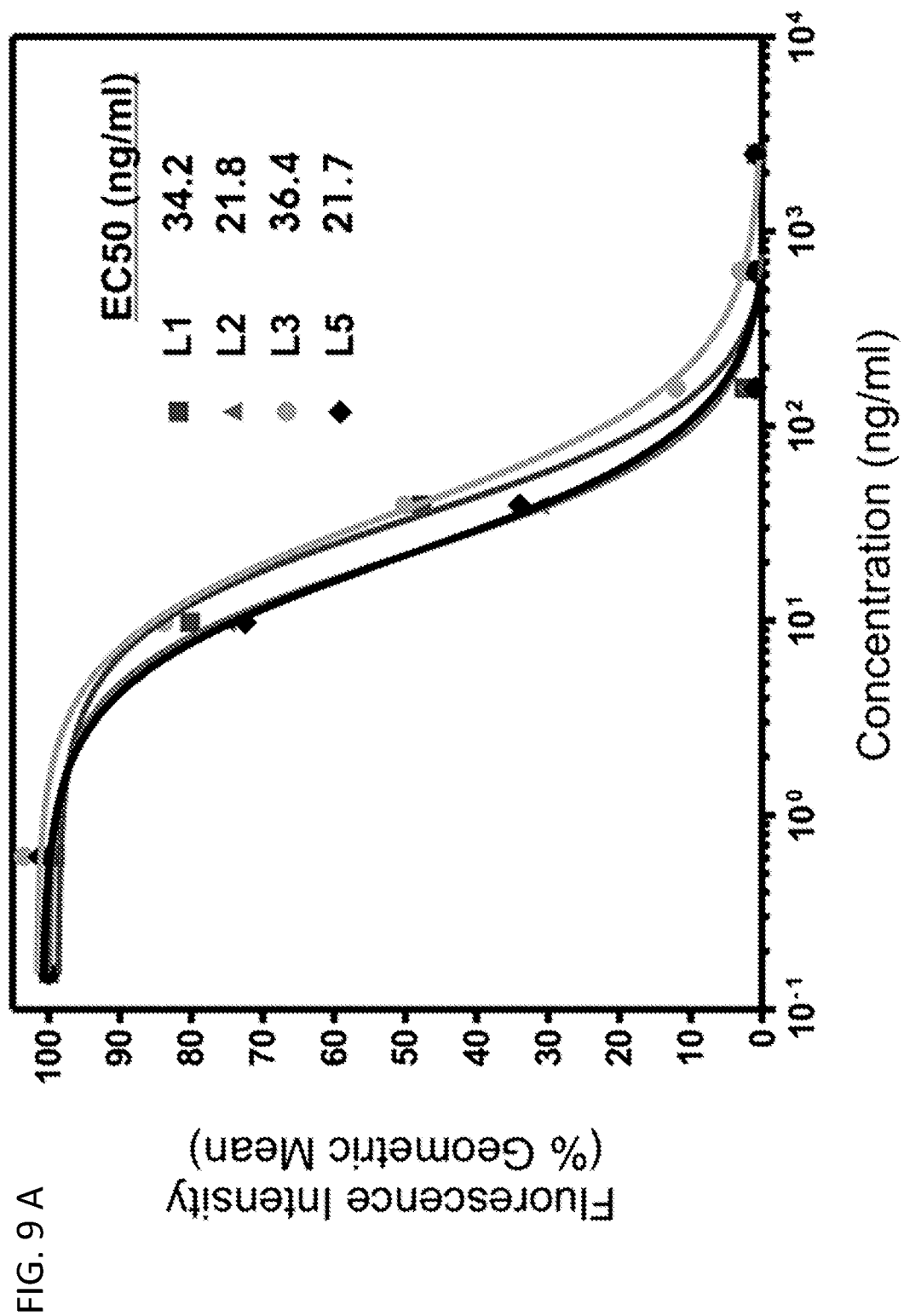
FIGS. 9A and 9B are a set of graphs illustrating that the TEM8 Fabs and full IgGs bind to TEM8 and bock binding of Anthrax PA to TEM8.
Figure 9:
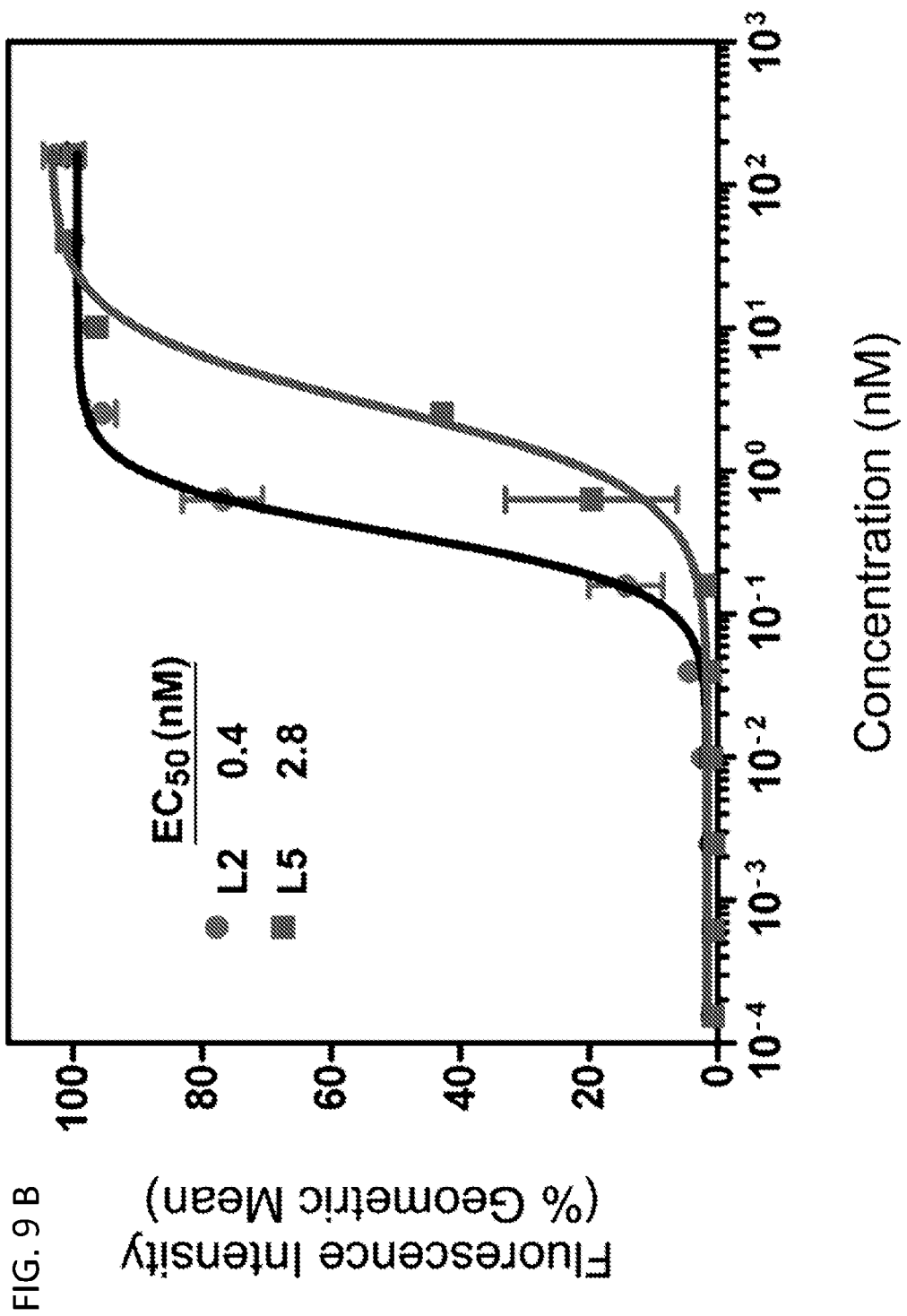
Figure 10B:
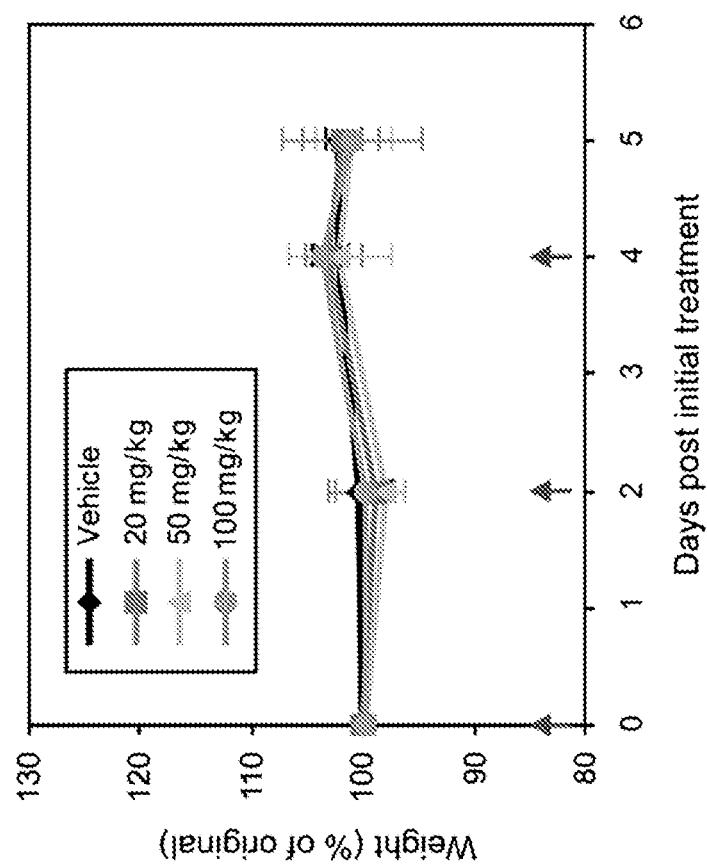
FIGS. 10A-10B show a set of graphs illustrating that the L2-mIgG2a anti-TEM8 antibody is non-toxic to a mouse. Total food consumption (A) and body weights (B) were unchanged in mice treated three times with 0 (vehicle control), 20, 50, or 100 mg/kg of L2-mIgG2a over a 5-day period.
Figure 10A:
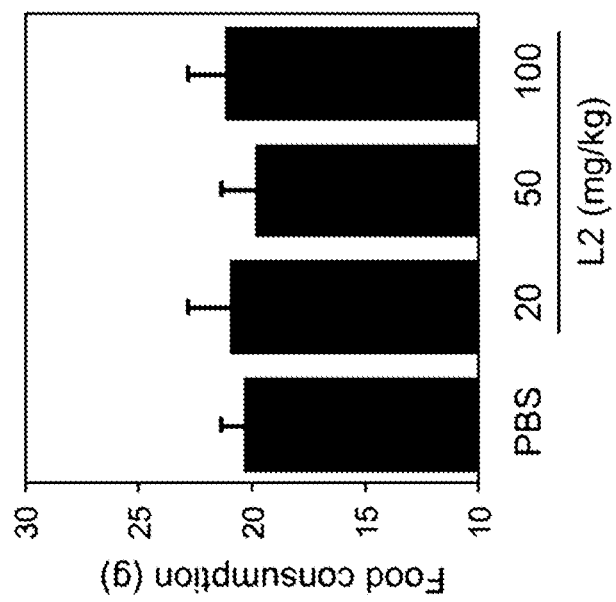

As shown in FIG. 9A, each of the Fabs blocked FITC-PA binding to CHO-TEM8 cells in a dose dependent manner, demonstrating that the L1, L2, L3 and L5 Fabs neutralize binding of PA to its cell surface receptor, TEM8. Additionally, these results further indicate the specificity of the identified Fabs for TEM8.

Example 4

Reformatting L2 and L5 Fabs to Generate Mouse/Human Chimeric IgGs

This example describes reformatting the L2 and L5 Fabs to generate mouse/human chimeric IgGs. Two Fabs (L2 and L5) were reformatted to full IgG with mouse IgG2a to increase half life, in order to use in a mouse model. The results show that the reformatted L2-mIgG2a and L5-mIgG2a chimeric antibodies specifically interact with TEM8. Also described is the use of these chimeric antibodies to neutralize the cytotoxic effect of Anthrax toxin on CHO cells expressing TEM8.

The results show that both the L2 and L5 chimeric antibodies neutralized the cytotoxic effect of Anthrax toxin.

The L2 and L5 Fabs were reformatted to generate mouse/human chimeric IgGs by fusing the constant domains of mouse IgG2a (CH1, CH2, CH3, and CL) with the human VH variable domain of the Fab heavy chain and the VL of the lambda light chain gene. The murine constant regions were added for the preclinical mouse studies to reduce potential immune responses, increase overall stability and maximize the in vivo half-lives of the antibodies. Vectors containing the chimeric heavy (geneticin-resistance gene) and light (zeocin-resistance gene) chains were stably co-transfected into HEK293T cells. Clones were tested for expression of the chimeric IgG utilizing a mouse IgG-Fc ELISA (Bethyl Laboratories, Montgomery, Tex.). Anti-TEM8 antibodies were collected from culture supernatants grown in serum free medium and purified by Protein A and size exclusion chromatography. Antibody preparations used for in vivo studies possessed <5% aggregates and endotoxin levels were below 10 EU/mg. 293 cells were cultured as above. CHO cells were maintained in Ham's F12 medium supplemented with 10% fetal bovine serum (FBS).

After reformatting, both reformatted L2 (L2-mIgG2a) and reformatted L5 (L5-mIgG2a) were found to maintain their activity towards TEM8 in the same screens used to test the Fabs (above), but failed to react with CMG2, the closest homologue of TEM8, when tested against CMG2 transfectants of the Anthrax toxin receptor-deficient CHO cell line, CHO/PR230 (FIG. 2A-D). Surprisingly, upon titration and comparison at non-saturating concentrations, L2 bound TEM8 expressing cells with 7-fold higher affinity than L5 ($EC_{50}$ 0.4 nM and 2.8 nM, respectively, see FIG. 9B). Similarly, L2 was ~4-fold more potent at blocking the binding of FITC-labeled PA to TEM8 and ~9-fold more potent at preventing cytotoxicity caused by Anthrax lethal toxin (FIGS. 2E-2G).

Example 5

L2 Antibody Treatment is Non-Toxic to an Animal Model

This example illustrates that the L2-mIgG2a antibody is non-toxic to an animal model. Dose-escalation and serial dose toxicology studies using a mouse model were performed.

In the dose-escalation treatment, C57BL/6 mice were administered PBS (vehicle control), 20, 50 or 100 mg/kg L2-mIgG2a every other day for three treatments. 24 hours after the last treatment, samples were processed for complete blood counts (CBC), serum chemistry, organ weights, and H&E staining. For histopathological assessment of the H&E-stained sections, a comprehensive set of 44 organs or tissues were evaluated from the PBS control group and the 100 mg/kg L2-mIgG2a treatment group (3 males and 3 females, total 6 mice/group) by a boarded veterinary pathologist. As shown in FIGS. 10A and 10B and Table 5, no significant difference was observed between the control or treatment group. Table 5 shows selected parameters for the 100 mg/kg and control (PBS) dosing. All serum chemistry and blood cell counts were similar to that in the control group, and no dose-dependent alterations were observed. Treated mice consumed food and socialized similar to control animals, and both body and organ weights were unchanged. Further, the comprehensive histopathologic analysis of H&E sections from 44 organs or tissues derived from 6 mice/group failed to reveal any abnormalities.

In a longer-term single-dose toxicology study, mice were treated with 20 mg/kg of L2-mIgG2a 3× per week for up to 6 weeks, followed by an analysis of the same toxicology parameters as those in the dose escalation study. CBCs, serum chemistry profiles and H&E evaluations were also performed on athymic NCr nude mice bearing either HCT-116 or SW620 tumors that had been treated for either 6 weeks (L2-mIgG2a alone) or longer (combination groups) with 20 mg/kg of L2-mIgG2a. Again, no abnormalities were noted (Table 6).

TABLE 5

Toxicity parameters and organ weights were unchanged in mice following treatment with 100 mg/kg of L2-mIgG2a.

| | Control | 100 mg/kg L2-mIgG2a |
|---|---|---|
| Selected Toxicological Results: Mean ± SD. | | |
| Selected Parameters | | |
| WBC (K/μL) | 5.9 ± 2.5 | 6.3 ± 2.4 |
| RBC (M/μL) | 9.5 ± 0.4 | 9.6 ± 0.4 |
| Albumin (g/dL) | 4.0 ± 0.4 | 3.9 ± 0.1 |
| ALT (U/L) | 52.7 ± 10.1 | 51.9 ± 27.4 |
| Total Bilirubin (mg/dL) | ≤0.2 | ≤0.2 |
| Creatine (mg/dL) | ≤0.2 | ≤0.2 |
| Hemoglobin (g/dL) | 13.9 ± 0.6 | 13.9 ± 0.4 |
| Total Protein (g/dL) | 5.6 ± 0.2 | 5.7 ± 0.4 |
| BUN (mg/dL) | 19.7 ± 2.0 | 17.5 ± 3.4 |
| Selected Organ Weights (mg): Mean ± SD. | | |
| Selected organ | | |
| Brain | 462 ± 19 | 465 ± 15 |
| Heart | 137 ± 15 | 155 ± 21 |
| Kidney | 312 ± 58 | 308 ± 63 |
| Liver | 1173 ± 180 | 1152 ± 271 |
| Lung | 153 ± 20 | 168 ± 34 |
| Spleen | 80 ± 13 | 83 ± 15 |

TABLE 6

Toxicity parameters and organ weights were unchanged in mice following 6 weeks of treatment with 20 mg/kg of L2-mIgG2a.

| | Control | 20 mg/kg (6 weeks) L2-mIgG2a |
|---|---|---|
| Selected Toxicological Results: Mean ± SD. | | |
| Selected Parameters | | |
| Food consumption (g/wk) | 34.2 ± 1.7 | 33.6 ± 3.6 |
| WBC (K/μL) | 6.4 ± 1.7 | 4.5 ± 1.5 |
| RBC (M/μL) | 8.6 ± 0.3 | 8.5 ± 1.0 |
| Albumin (g/dL) | 4.9 ± 0.6 | 4.6 ± 0.3 |
| ALT (U/L) | 44.6 ± 7.1 | 40.2 ± 16.6 |
| Total Bilirubin (mg/dL) | ≤0.3 | ≤0.3 |
| Creatine (mg/dL) | ≤0.2 | ≤0.2 |
| Hemoglobin (g/dL) | 12.4 ± 0.7 | 12.4 ± 1.2 |
| Total Protein (g/dL) | 7.1 ± 1.1 | 7.6 ± 0.9 |
| BUN (mg/dL) | 17.8 ± 3.5 | 18.6 ± 2.4 |
| Selected Organ Weights (mg): Mean ± SD. | | |
| Selected organ | | |
| Brain | 450 ± 23 | 468 ± 21 |
| Heart | 142 ± 4 | 130 ± 12 |
| Kidney | 344 ± 39 | 366 ± 35 |
| Liver | 1298 ± 107 | 1382 ± 201 |
| Lung | 166 ± 27 | 172 ± 8 |
| Spleen | 118 ± 26 | 124 ± 33 |

Example 6

TEM8 Specific Antibody Treatment Inhibits Tumor Growth and Augments Cancer Therapy in a Mouse Model This example illustrates that L2- and L5-mIgG2a chimeric antibody treatment inhibits tumor growth, augments multiple cancer therapies and detects tumor associated vasculature in a mouse model. The example also provides an illustration of a conjugate including a mAb that specifically binds to TEM8 and a detectable marker.

Methods

Animal and Tumor Studies

Athymic nude TEM8 KO mice on an immunedeficient background (TEM8$^{-/-}$, nu/nu) are described above. Like the C57BL/6 Tem8 KO mice, nude Tem8 KO mice also develop misaligned incisors. The misalignment of incisors is a particular problem for rodents because their incisors grow continuously throughout life, and proper alignment is necessary for shearing that ensures maintenance of tooth length. To prevent potential interference with food consumption, the incisors of Tem8 KO mice are routinely clipped beginning at approximately three months of age. For tumor studies involving TEM8 KO mice, only TEM8 WT and KO littermates derived from TEM8 heterozygous intercrosses were used for comparison. Tumor studies not involving TEM8 KO mice were performed on athymic NCr-nu/nu mice. $2.5 \times 10^6$ to $5 \times 10^6$ tumor cells were injected subcutaneously into the flank of athymic nude mice. For B16 tumor cell injections, $5 \times 10^5$ cells were injected subcutaneously into C57BL/6 mice. Tumors were measured with a digital caliper, and tumor volumes were calculated using the formula $L \times W^2 \times 0.5$ and presented as mean±SE. Tumor weights were calculated following surgical removal.

For the L2-mIgG2a treatment involving KO mice, treatment was initiated one day following tumor cell injection. For all other therapeutic studies, mice were sorted into groups containing the same average size tumors prior to initiation of therapy. To minimize tumor variation in these studies, at the time of sorting, mice were excluded from the analysis if their tumors were less than half the average tumor size for the group or more than double the average tumor size. Mice were treated with L2-mIgG2a or L5-mIgG2a anti-TEM8 antibody at various doses ranging from 2 mg/kg to 100 mg/kg. DC101 or various doses of L2-mIgG2a or L5-mIgG2a antibodies were administered 3× per week, typically on a Monday, Wednesday, Friday schedule, or at the time points indicated in the individual figures. DC101 was administered at 40 mg/kg (Prewett et al., *Cancer Res.*, 59(20):5209-5218, 1999), DMXAA (Sigma) was administered once at 25 mg/kg (MTD) followed with 5 mg/kg/day for 2 days (Zhao et al., *Clin. Cancer Res.*, 9(17):6545-6550, 2003), 5-FU was given once per week for three weeks at 100 mg/kg (MTD) and IRT was given once per week for three weeks at 80 mg/kg (⅔ MTD). The IRT treatment schedule was repeated following a two-week break period. The DC101 hybridoma was obtained from ATCC and DC101 was purified from conditioned medium by Protein A chromatography. L2-mIgG2a and L5-mIgG2a antibody was prepared as described above.

Immunofluorescence and Microvascular Density Studies

For in vivo target identification, 75 μg of L2-mIgG2a conjugated to FITC (FLUOREPORTER FITC PROTEIN KIT®, Invitrogen) was co-injected with 1 mg non-specific mouse IgG intraperitoneally into DLD-1 tumor-bearing TEM8 WT and TEM8 KO mice Animals were euthanized 3 hours later, and normal and tumor tissues were excised, frozen, cryosectioned, rinsed with TBST, and fixed with Leukoperm (AdB Serotec, Raleigh, N.C.). Endothelial cells were labeled with either rat anti-PV-1 (Meca-32) or rat anti-CD31 (Becton Dickenson, Franklin Lakes, N.J.) antibodies followed by biotin-labeled donkey anti-rat (Jackson Immunoresearch Laboratories, West Grove, Pa.) and Texas red-streptavidin (Vector laboratories, Burlingame, Calif.). L2-mIgG2a-FITC was amplified with 488 goat anti-FITC followed by 488 donkey anti-goat. For microvascular density studies, frozen sections fixed with LEUKOPERM® were stained with rat anti-CD31 (BD) followed by FITC-labeled goat anti-rat (Jackson Immunoresearch Laboratories, West Grove, Pa.). The mean MVD was determined using MIPAV (medical image processing, analysis, and visualization) software package (CIT, NIH, mipav.cit.nih.gov) by averaging the CD31-positive area taken from the areas with the highest vascular density (four microscopic fields from 3 different tumors). A one-way ANOVA was used to calculate statistical differences.

To measure proliferation or apoptosis of tumor endothelial cells following L2 treatment in vivo, L2 (20 mg/kg) or vehicle (PBS) were administered intraperitoneally to mice with DLD1 tumors (average tumor size 500 mm$^3$) After 24 hours, tumors were excised, frozen and cryosectioned. Vessels were labeled with both rat anti-PV-1 (Meca-32) and rat anti-CD31 (BD) antibodies. Proliferating cells were stained with the rabbit anti-phosphohistone H3 (Ser10) mitosis marker (Millipore) and cells undergoing apoptosis were labeled with the APOPTAG™ Fluorescein Direct In Situ Apoptosis Detection Kit (Millipore). Quantitative colocalization analyses were performed using the IMARIS™ software suite (Bitplane AG, Zurich, Switzerland).

For immunofluorescence staining of human colon cancer samples (Cooperative Human Tissue Network), tissue sections taken from frozen blocks were sectioned and blocked with an excess of non-specific chimeric (human-Fab, mouse Fc) antibody generated against a foreign antigen (cyclosporine A). TEM8 was detected with L2-mIgG2a-labeled FITC as described above, and co-stained with rabbit anti-von Willebrand factor (Dako, Carpinteria, Calif.) followed by biotinylated donkey anti-rabbit and Texas Red-streptavidin. All immunofluorescent images were captured using a Carl Zeiss LSM 510 laser scanning confocal microscope. Flow cytometry was performed as described above.

Western Blotting

Western blotting was performed using SB5 anti-TEM8 antibodies (Nanda et al., *Cancer Res* 64(3):817-820, 2004), CMG2 antibodies or anti-actin antibodies (Chemicon) as previously described (Cullen et al., *Proc. Natl. Acad. Sci. USA.*, 108:5759-5764, 2011).

Wound Healing Assay

C57LB6 mice with B16 tumors growing on one flank were shaved and wounded on the opposite flank with a 6 mm diameter uni-punch biopsy instrument (Premier). Wounds were measured with a digital caliper daily. On day six, wounds were removed for immunofluorescence staining of blood vessels using anti-CD31 antibodies. Using MIPAV software, the CD31 positive surface area in the region of interest (ROI, granulation area) was averaged from five wounds per group (four sections per wound), and reported as a percent of the ROI area.

MATRIGEL™ Plug Assay

Athymic nude mice were injected subcutaneously with 500l of MATRIGEL™ (BD Biosciences) containing 300 ng of mFGF (Peprotech). Mice were treated with 20 mg/kg of non-specific mouse IgG or L2 (n=6 mice/group) by i.p. injection every other day for total three treatments. After 6 days mice were sacrificed, and the MATRIGEL™ plugs were removed and fixed in 4% paraformaldehyde. The plugs were embedded in paraffin, sectioned, and stained with hematoxylin and eosin. Sections were examined by light microscopy, and the blood vessel density was calculated using MIPAV software from 4-5 fields per plug.

ADCC Assay

Mouse mononuclear cells were isolated from the spleens of athymic nude mice by density centrifugation using lympholyte-M (Cedarlane Laboratories) according to the manufacturer's instructions and resuspended in PF-DMEM; phenol-free DMEM containing 10% low IgG FBS (Invitrogen). NK cells were enriched from the mononuclear fraction through negative selection using a cocktail of streptavidin M-280 magnetic DYNABEADS® (Invitrogen) that had been pre-armed separately with biotinylated antibodies against CD3e, CD4, CD5, CD8a, CD19, Ly-6G and Ter-119 (eBioscience) (see description of magnetic bead assay below). The NK enriched fraction was at least 50% pure as assessed by flow cytometry using anti-CD49b antibodies (eBioscience). 293-TEM8 (target, T) cells were trypsinized, rinsed, suspended in PF-DMEM and incubated with the indicated concentrations of antibodies (control IgG or L2) for 30 minutes on ice. 10,000 target cells were mixed with various numbers of NK (effector, E) cells in wells of a 96-well plate. After 20 hours, cell viability was measured using the CYTOTOX-GLO® cytotoxicity assay (Promega). The percentage of specific cell lysis was calculated by using the following formula: $100 \times [(A-C)/(B-D)]$, where A represents luminescence obtained in the test well (experimental release), B represents luminescence obtained by lysing all of the target cells with 1% TRITON X-100™ (maximum release), C represents luminescence obtained when no antibody is added to effector and target cells, and D is spontaneous release from target cells. When this calculation provided a negative value, 0.0% was assigned to the result.

CDC Assay

293-TEM8 cells were trypsinized, rinsed, suspended in PF-DMEM and incubated with the indicated concentrations of antibodies (control IgG or L2) for 30 minutes on ice. Next, 50,000 cells were incubated with 5, 10 and 20% rabbit complement (LOW-TOX-M™ rabbit complement; Cedarlane) for 2 hours at 37° C. Cell viability was measured using the CYTOTOX-ONE™ homogenous membrane integrity assay (Promega). The percentage of specific cell lysis was calculated by using the following formula: $100 \times [(A-C)/(B-C)]$, where A represents the fluorescence (560 nm Ex, 595 nm Em) obtained in the experimental well, B represents the fluorescence obtained by lysing all of the target cells with 1% TRITONX100™ (maximum release), and C represents the fluorescence obtained when target cells were incubated with rabbit complement in the absence of antibody. When this calculation provided a negative value, 0.0% was assigned to the result.

Results

Figure 3A:
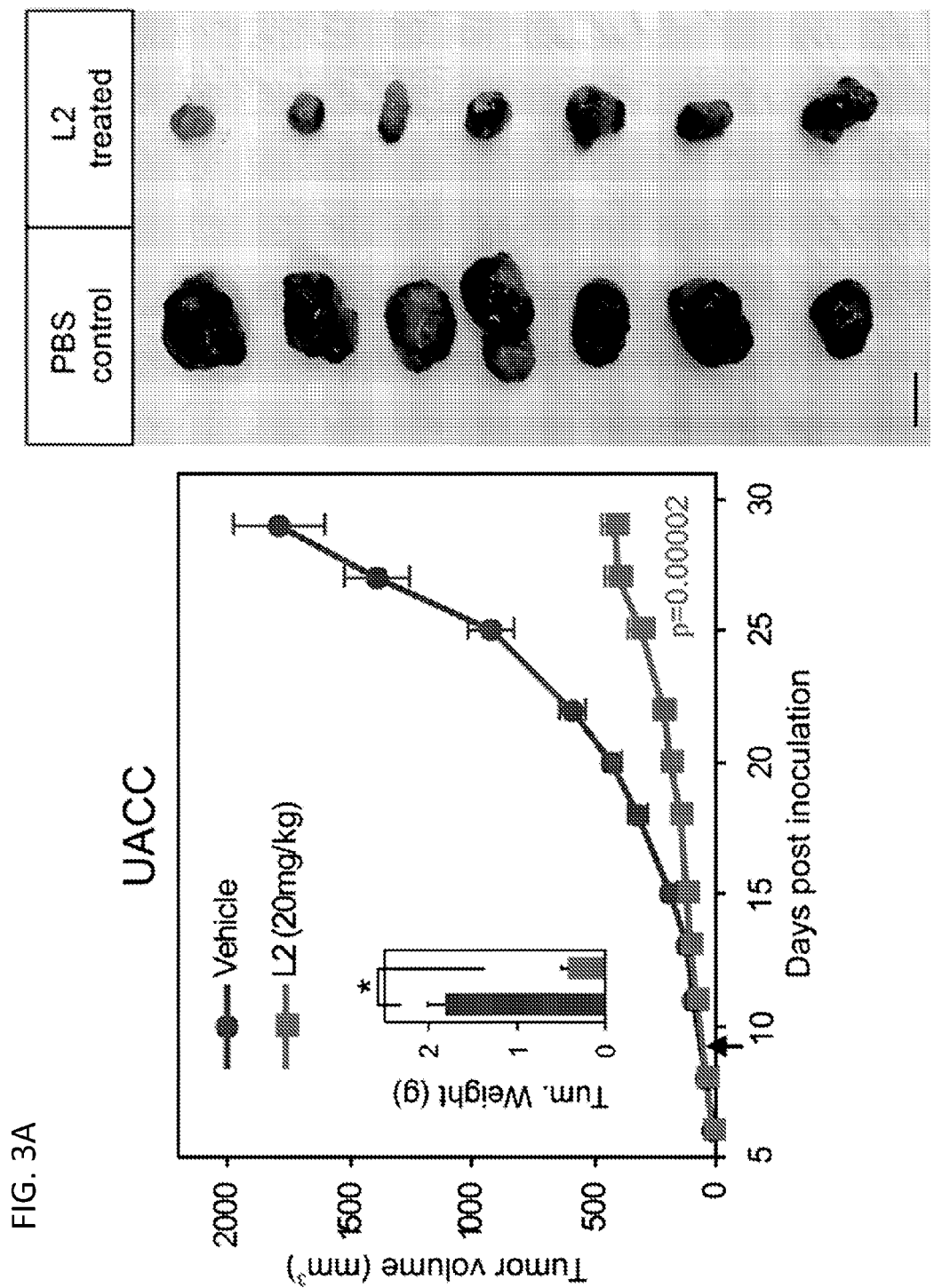
Figure 3B:
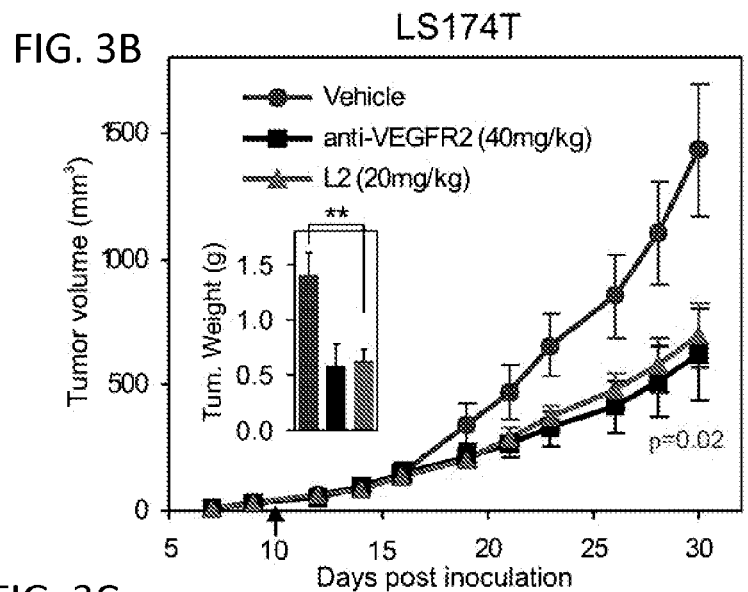
Figure 3C:
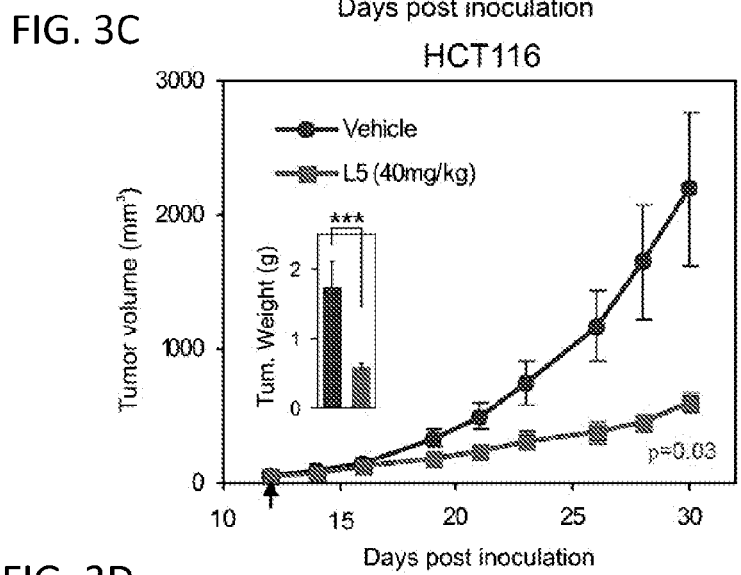
Figure 3D:
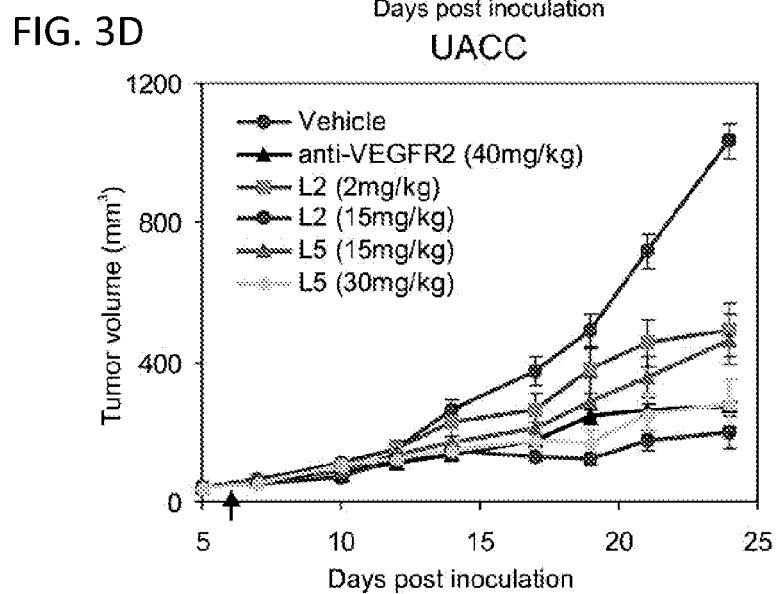

The L2- and L5-mIgG2a chimeric antibodies were tested in vivo for activity against UACC, HCT-116, and DLD-1 colon tumor xenografts in athymic nude mice. In these studies, mice were treated three times per week with L2- or L5-mIgG2a starting when tumors reached an average size of 50 mm$^3$. As shown in FIG. 3, for each tumor type analyzed, a marked tumor growth inhibition was observed in each of the L2-mIgG2a treated groups compared to vehicle (PBS) alone. The antitumor activity was comparable to that of anti-VEGFR2 antibodies (FIG. 3B). Next, the L2- and L5-mIgG2a antibodies were compared in a dose-escalation study to determine the amount of antibody required for optimal tumor growth inhibition. In this study, UACC tumor-bearing mice were separated into groups which were given 2, 15 or 30 mg/kg of antibody 3× per week. When mice were given 2 mg/kg of L2-mIgG2a, partial growth inhibition was observed, while maximum growth inhibition was observed with 15 mg/kg (FIG. 3D). L5-mIgG2a showed partial growth inhibition at 15 mg/kg, similar to that observed in the 2 mg/kg L2-mIgG2a treatment group, and in each tumor study required 30 to 40 mg/kg to achieve its optimal biologic dose (OBD). Although L5-mIgG2a required a higher dose than L2-mIgG2a to achieve maximum efficacy, at their OBD both antibodies showed similar anti-tumor activity. Taken together, these studies demonstrate a marked in vivo anti-tumor activity of two independent anti-TEM8 antibodies.

The above studies were conducted in immune compromised mice. To determine if L2 could suppress tumor growth in the presence of an intact immune system, murine B16 melanoma cells were injected into syngeneic C57BL6 mice and began treating mice with L2 at a tumor size of 50 mm$^3$. The L2-treated group had a 60% reduction in tumor growth by the end of the study (FIG. 5C). Midway through the therapeutic course 6 mm diameter wounds were inflicted into each of the tumor bearing mice to determine if L2 treatment would interfere with wound healing. Wound closure rates were not significantly altered by L2 (FIG. 5D), despite its clear anti-tumor activity in the same mice. Immunofluorescence staining for CD31 showed no alteration in the amount of vasculature present within the healing wound granulation tissue (FIG. 5E). MATRIGEL®-induced vascularization was also unaffected by L2 treatment (FIG. 5F). Thus, L2 antibodies inhibited chronic pathological tumor growth while not interfering with normal healing processes dependent on physiological angiogenesis.

Figure 4A:
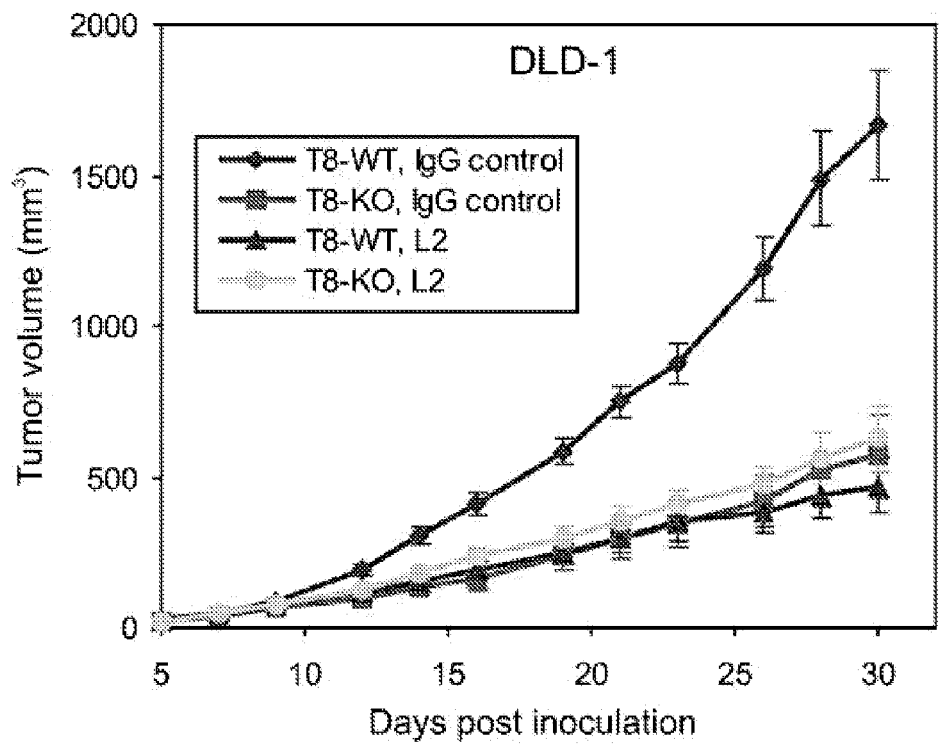
Figure 11A:
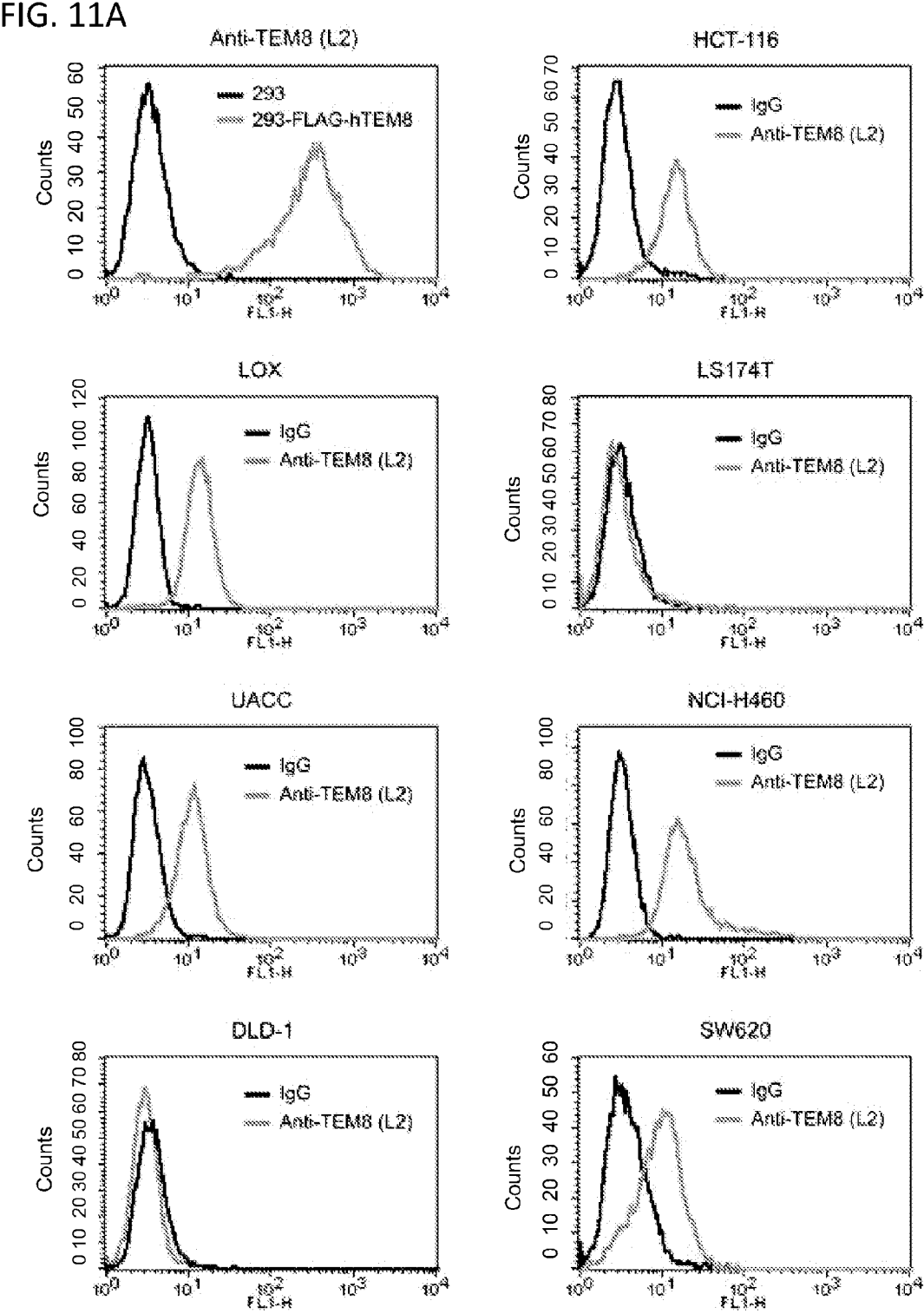
FIGS. 11A-11B show a series of graphs illustrating that TEM8 is expressed in some, but not all, human tumor cell lines in culture. (A) TEM8 expression in several human tumor cell lines was evaluated by flow cytometry. The 293 and 293/hFlag-TEM8 cells served as specificity controls. Only two of the cell lines evaluated, DLD-1 and LS174T, were negative for TEM8, whereas HCT-116, LOX, UACC, NCI-H460, and SW-620 cell lines were TEM8 positive. (B) TEM8 mRNA, as detected by quantitative RT-PCR, was absent in cultured DLD-1 tumor cells, and BerEP4-positive human tumor cells isolated from DLD-1 tumor xenografts. The TEM8 positive human HCT-116 tumor cells served as a positive control.
Figure 11B:
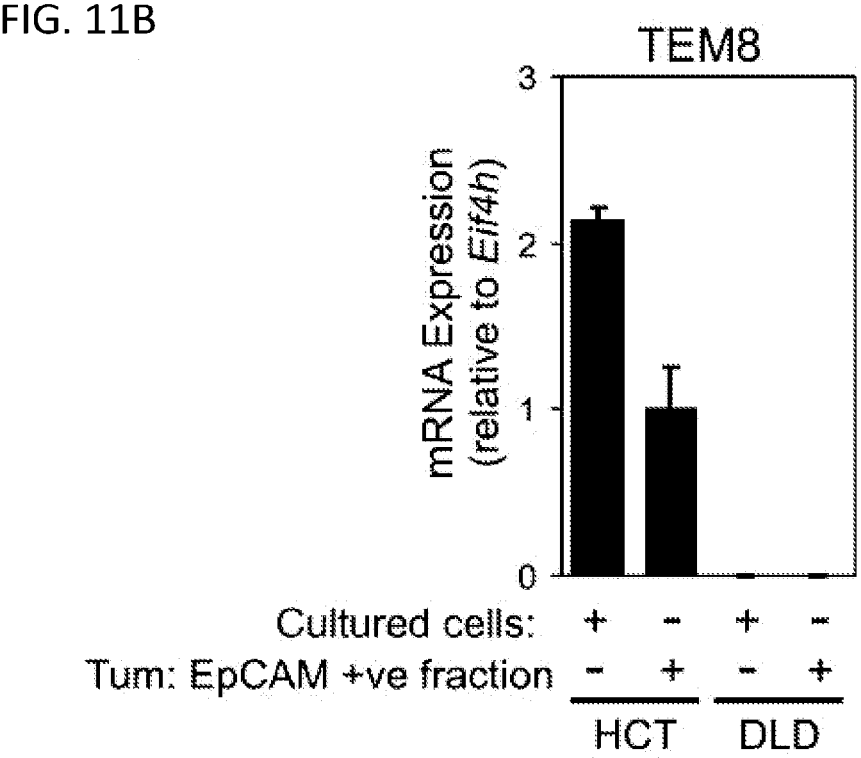

If L2-mIgG2a's anti-tumor activity depends on its ability to inhibit the function of host-derived TEM8, then L2-mIgG2a should only have activity against tumors in TEM8 WT mice but not TEM8 KO mice, provided the tumor cells employed do not themselves depend upon endogenous TEM8 for their growth in vivo. RT-PCR and flow cytometry analysis revealed variability of TEM8 expression among cultured tumor cell lines (FIG. 11A), but DLD-1 tumor cells were found to be TEM8-negative both in cell culture and following purification from established tumors in vivo (FIGS. 11A and 11B). Therefore, to test the specificity of the L2-mIgG2a antibody in vivo, TEM8 WT and KO mice were challenged with TEM8 negative DLD-1 tumor cells and treated with L2-mIgG2a or control IgG three times per week (FIG. 4A). As expected, tumors grew slower in TEM8 KO compared to WT mice treated with control IgG. When the L2-mIgG2a antibody was administered to TEM8 WT mice, tumor growth was inhibited relative to the IgG control group, but was indistinguishable from that in the KO group. Importantly, L2-mIgG2a treatment of TEM8 KO tumor-bearing mice did not result in any further tumor growth inhibition. Taken together, these results indicate that TEM8 is the target of L2 in vivo, and that L2-mIgG2a is a function-blocking (neutralizing) monoclonal antibody.

Figure 4B:
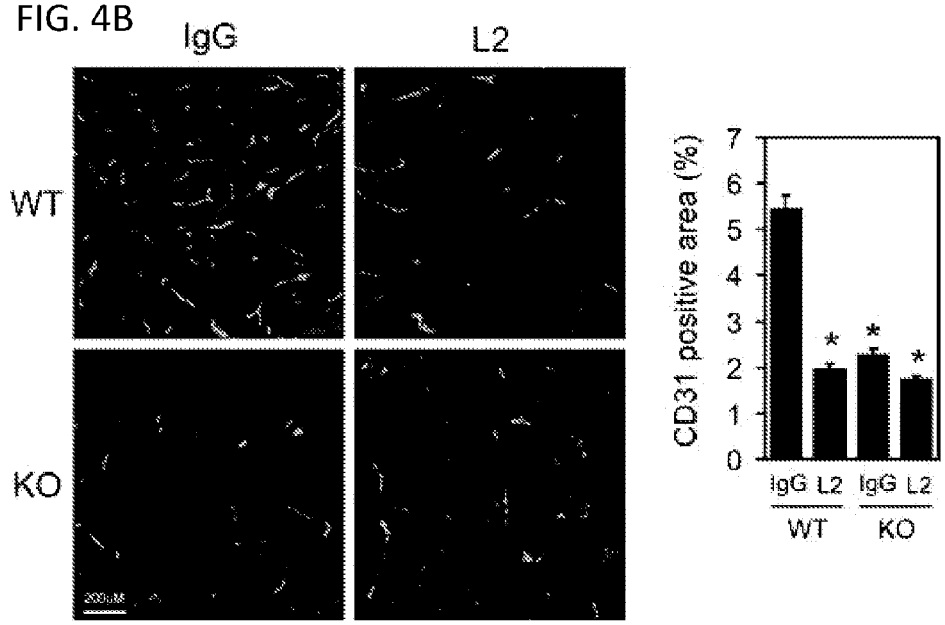
Figure 4C:
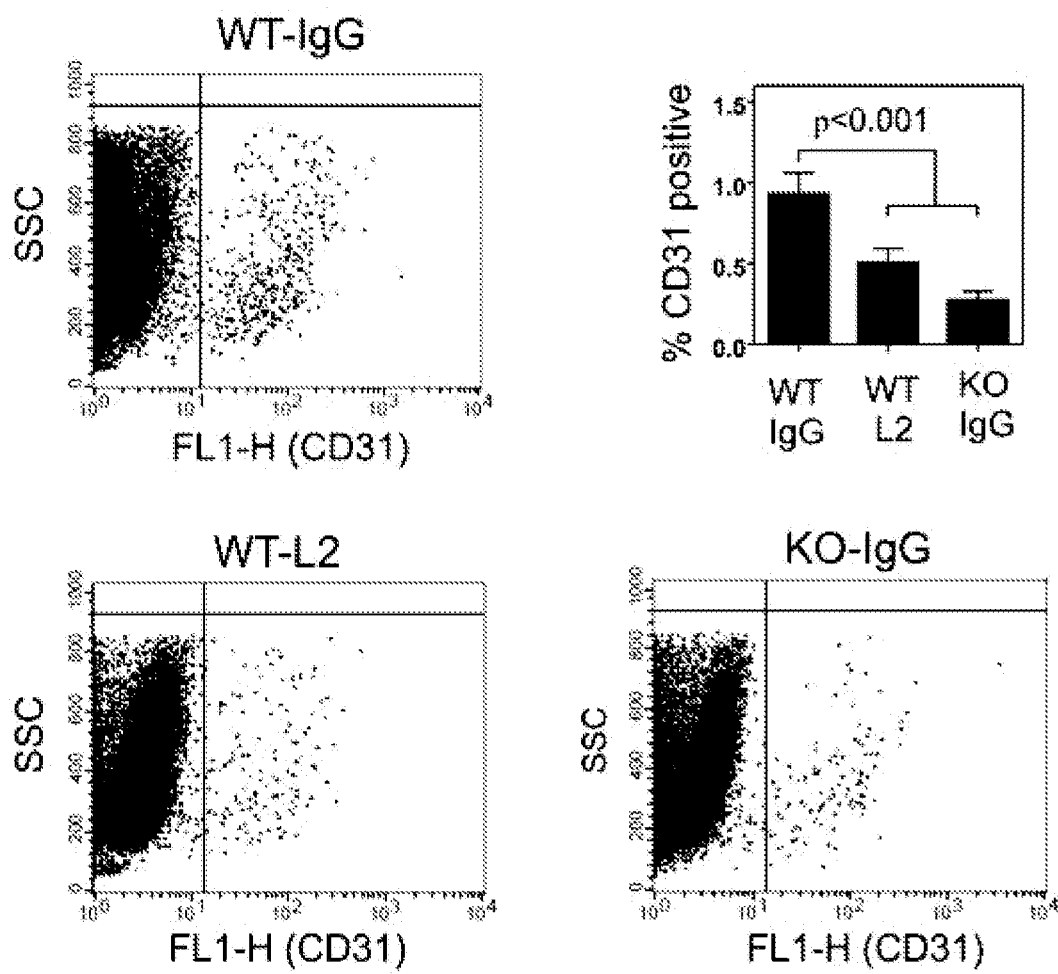
Figure 4D:
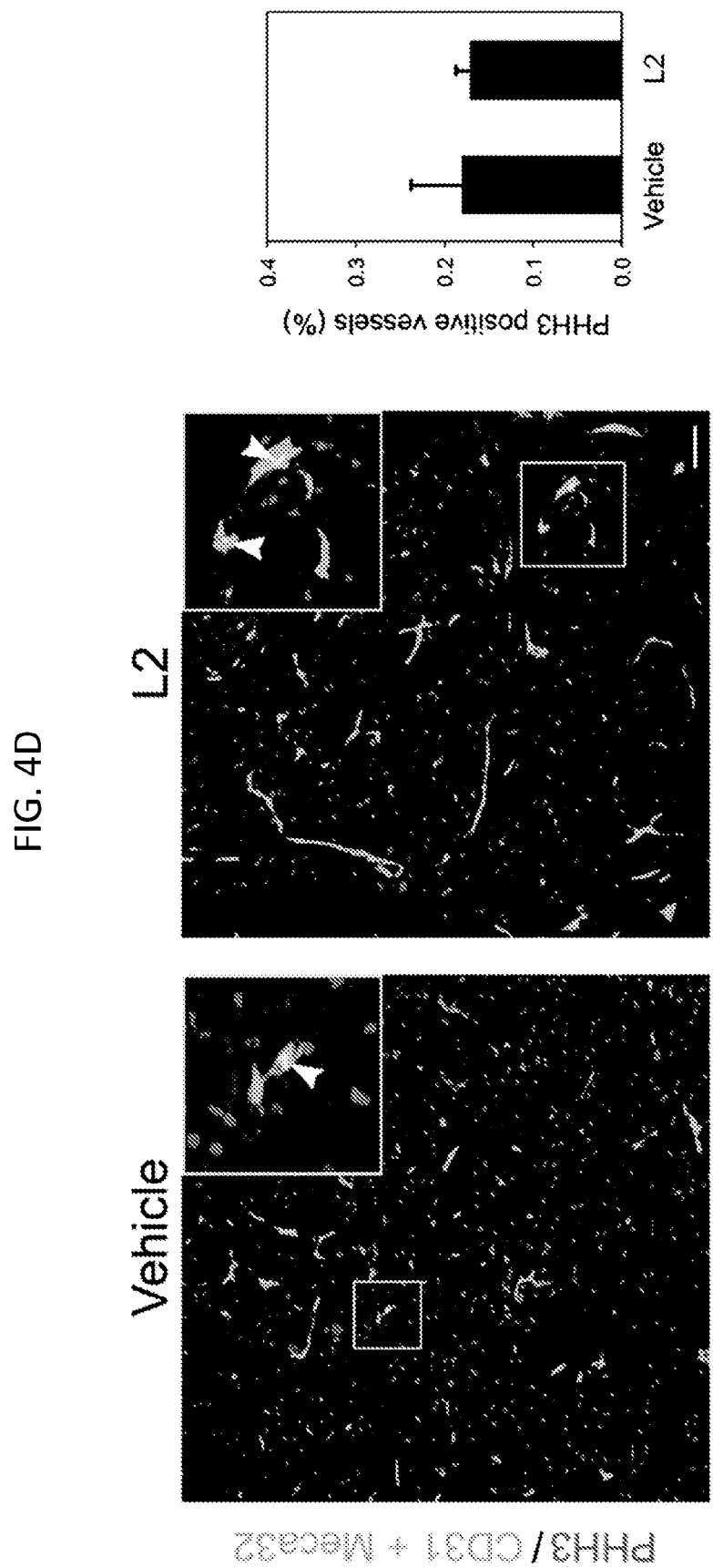

To assess if the target of L2-IgG2a in vivo is tumor associated vasculature, CD31 vessel staining in the DLD-1 tumor groups was performed, and a reduced number of vessels in tumors derived from TEM8 KO or L2-mIgG2a-treated mice was found (FIG. 4B). Quantification of the number of CD31-positive endothelial cells in tumors using flow cytometry revealed significantly lower endothelial cell numbers following both pharmacologic and genetic ablation of TEM8 (FIG. 4C). Based on previous studies that showed a role for CMG2 in promoting endothelial proliferation (Reeves et al., Oncogene, 29:789-801, 2010) the possibility that TEM8 promotes proliferation of tumor endothelial cells was investigated. However, endothelial proliferation in DLD1 tumors was not altered in response to L2 treatment (FIG. 4D), although the number of apoptotic ECs was significantly increased (p<0.02, FIG. 4E).

Figures 5A, 5B:
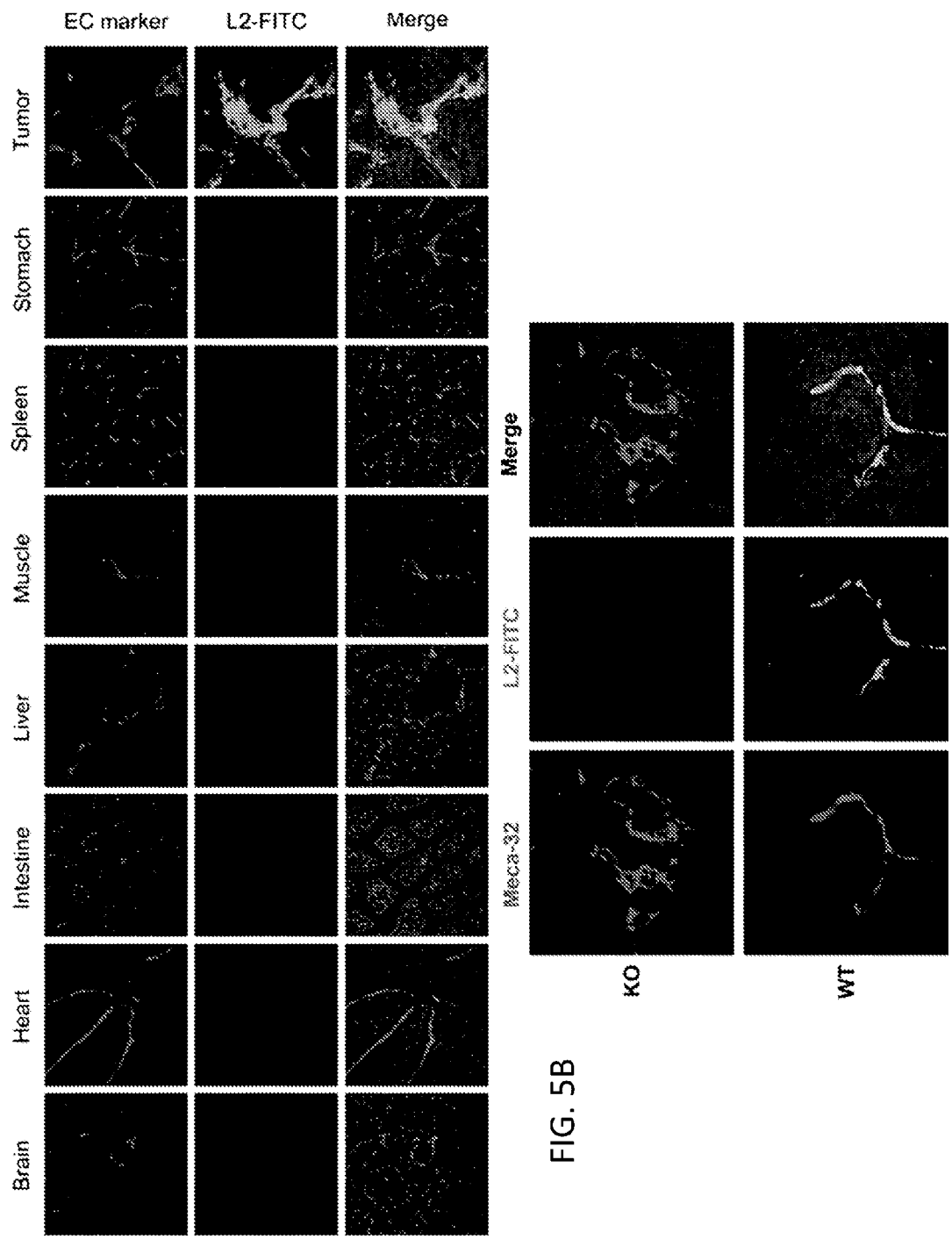

To further assess the specificity of L2-mIgG2a in vivo, L2-mIgG2a was conjugated with FITC (as described above) and injected into the tail vein of tumor-bearing mice. Immunofluorescence analysis revealed localization of TEM8 selectively in tumor associated vasculature, but not in any of the normal control tissues analyzed including brain, heart, intestine, liver, muscle, spleen and stomach (FIG. 5A). In addition to tumor endothelium, tumor associated perivascular cells surrounding the endothelium, possibly pericytes, were also frequently positive, consistent with previous reports documenting TEM8 expression in tumor-associated perivascular stromal cells and smooth muscle cells in cell culture (Yang et al., *Biochim Biophys Acta* 1813(1):39-49, 2011; Fernando and Fletcher, *Cancer Res* 69(12):5126-5132, 2009). Stromal cell staining was confined to the tumor region in TEM8 WT mice and was absent from the tumors in TEM8 KO mice, confirming the specificity of antibody staining (FIG. 5B). This result shows that an L2 antibody specifically detects tumor associated vasculature.

To determine if TEM8 could potentially function as a target of antibody-dependent cellular cytotoxicity (ADCC), effector NK cells were mixed with TEM8-expressing 293 target cells at various ratios, and found that L2, but not control IgG, was able to elicit cytotoxicity that was dependent on both the antibody and effector cell concentration (FIGS. 5F and 5G). Similarly, L2 elicited complement dependent cytotoxicity (CDC) in both an antibody and complement-dependent manner (FIGS. 5H and 5I). A non-limiting explanation for this finding is that TEM8 functions in ADCC and CDC.

The delayed tumor growth in the TEM8 KO and the encouraging anti-tumor activity of L2-mIgG2a against relatively small established 50 mm$^3$ tumors prompted us to determine the activity of L2-mIgG2a against larger tumors (FIG. 6). Importantly, tumors that were 200 mm$^3$ in size prior to treatment with L2-mIgG2a still showed a significant response to the antibody such that when the control tumors reached an average size of 2000 mm$^3$, treated tumors had an average size of 1288 mm$^3$ (FIG. 6A). However, because the L2-mIgG2a-mediated growth inhibition was incomplete, the combination of L2-mIgG2a with other classes of anticancer agents was tested to determine if this would result in enhanced antitumor efficacy. L2-mIgG2a treatment was combined with the anti-VEGFR2 antibody DC101, an anti-angiogenic agent that prevents VEGF from binding VEGFR2. As shown in FIG. 6A, L2-mIgG2a significantly enhanced the activity of DC101 against UACC melanoma when mice with established tumors were treated with both antibodies three times per week (p<0.05). Next, the combination of L2-mIgG2a with DMXAA (ASA404), a vascular targeting agent, against the NCI-H460 lung cancer xenografts was tested (FIG. 6B). DMXAA is a vascular targeting agent that has shown promising activity in early clinical trials against lung cancer (Baguley and McKeage, *Future Oncol.*, 6(10):1537-1543, 2010). In this study, DMXAA was administered on day 7 and day 30 (lower arrows), whereas L2-mIgG2a was given 3× per week (upper arrows). Both L2-mIgG2a and DMXAA significantly delayed tumor growth, but the combination was even more efficacious, and the second treatment with DMXAA revealed a continued sensitivity of the tumors to this agent. Finally, the combination of L2-mIgG2a with 5-FU or IRT, chemotherapeutic agents that are currently used to treat patients with colorectal cancer, was tested. L2-mIgG2a significantly enhanced the efficacy of 5-FU and IRT against HCT116 tumors (FIG. 6C-6D). L2-mIgG2a also enhanced the efficacy of IRT against another colon cancer tumor model (SW620, FIG. 6E) demonstrating the generality of this response. The combination of L2 with IRT was highly efficacious, such that tumors in 5 of 11 mice in the HCT116 study and 4 of 11 mice in the SW620 study had completely regressed by 100 days post-inoculation, and these mice remained tumor-free for the duration of the study—an additional 7 months (FIGS. 6D and 6E). No complete tumor responses were observed in any of the monotherapy treatment arms. To further assess the inhibitory activity of L2 in combination with IRT following long term therapy, treatment was discontinued after 100 days, which resulted in rapid expansion of the remaining tumors that had not completely regressed.

Figure 6A:
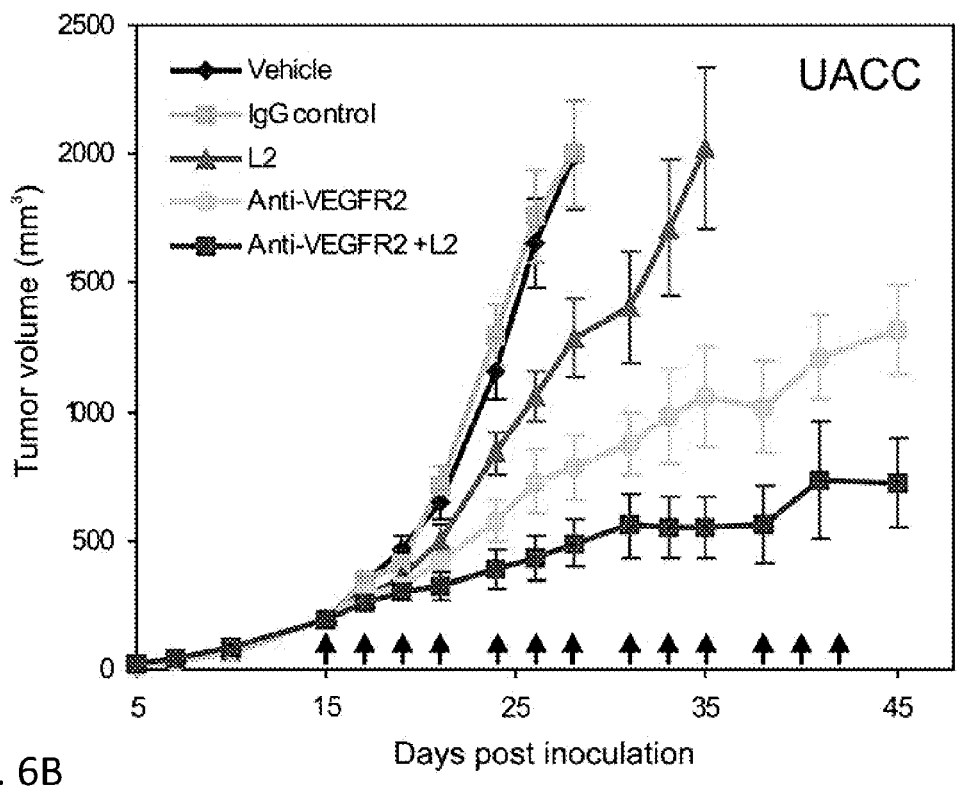
FIGS. 6A-6F show a series of graphs illustrating that the L2-mIgG2a anti-TEM8 antibody augments the efficacy of multiple classes of anti-cancer agents for reduction of tumor volume in a mouse model. (A) UACC tumors were treated with vehicle (PBS), non-specific mouse IgG (20 mg/kg), L2-mIgG2a anti-TEM8 (20 mg/kg), anti-Vascular Endothelial Froth Factor Receptor 2 (VEGFR2) (40 mg/kg) or a combination of L2-mIgG2a (20 mg/kg) and anti-VEGFR2 (40 mg/kg) three times per week (arrows) beginning 15 days post tumor cell inoculation when tumors reached a size of 200 mm³ in volume. L2-mIgG2a in combination with anti-VEGFR2 suppressed tumor growth more than anti-VEGFR2 alone (P<0.05). (B) NCI-H460 tumors were treated with vehicle, L2-mIgG2a anti-TEM8, DMXAA (5,6-Dimethyl-9-oxo-9H-xanthen-4-yl)-acetic acid) or a combination of L2-mIgG2a and DMXAA beginning 15 days post tumor inoculation when tumors reached an average size of 100 mm³ in volume. The L2-mIgG2a (20 mg/kg) was administered 3 times per week (upper arrows) for the duration of the study whereas DMXAA was administered at a high dose of 25 mg/kg (the two lower arrows), followed by 5 mg/kg/day the following two days. DMXAA in combination with L2-mIgG2a suppressed tumor growth more than DMXAA alone (P<0.001). (C) HCT-116 tumors were treated with vehicle, L2-mIgG2a anti-TEM8 (20 mg/kg), 5-fluorouracil (5-FU) (100 mg/kg) or a combination of L2-mIgG2a and 5-FU beginning 11 days post tumor inoculation when tumors reached an average size of 100 mm$^3$ in volume. The L2-mIgG2a was administered 3 times per week (upper arrows) whereas 5-FU was administered once/week for three weeks (the three lower arrows). 5-FU in combination with L2-mIgG2a suppressed tumor growth more than 5-FU alone (P<0.0001). (D) HCT-116 tumors were treated with vehicle, L2-mIgG2a anti-TEM8 (20 mg/kg), irinotecan (IRT) (80 mg/kg) or a combination of L2-mIgG2a and IRT beginning 11 days post tumor inoculation when tumors reached a size of 100 mm$^3$ in volume. The L2-mIgG2a was administered 3 times per week (upper arrows) until 100 days post-inoculation whereas IRT was administered once/week for three weeks (the nine lower arrows) followed by a two-week break period. IRT in combination with L2-mIgG2a suppressed tumor growth more than IRT alone (P<0.02). The HCT-116 tumor studies shown in FIGS. 6C and 6D were conducted at the same time and both contain the same vehicle and L2-mIgG2a groups which were duplicated for ease of comparison. (E) SW620 tumors were treated with vehicle, L2-IgG2a anti-TEM8 (20 mg/kg), IRT (80 mg/kg) or a combination of L2-mIgG2a and IRT beginning 14 days post tumor inoculation when tumors reached a size of 100 mm$^3$ in volume. The treatments in this study were the same as those described for HCT-116 above. IRT in combination with L2-mIgG2a suppressed tumor growth more than IRT alone (P<0.02). The IRT in combination with L2-mIgG2a combination therapy also resulted in complete tumor regression in 5 of 11 (D; HCT116) or 4 of 11 (E; SW620) of the treated mice. No complete tumor regressions were observed in any of the monotherapy treatment arms. For ease of comparison, only half of the error bars are shown in D and E. Data in A-E are represented as mean±SE. (F) Body weights in HCT116 tumor-bearing mice from the 5-FU study (upper panel, corresponding to C) or the IRT study (lower panel, corresponding to D) were monitored from the start of therapy until the tumors in the control groups reached their maximum allowable size and mice had to be euthanized. Note that 5-FU and IRT treatment appeared to cause a small, albeit non-significant, reduction in body weight, but L2-mIgG2a did not result in any change in body weight. Data in F represent mean values. The SD ranged from 2 to 8% and error bars were omitted for clarity.
Figure 6B:
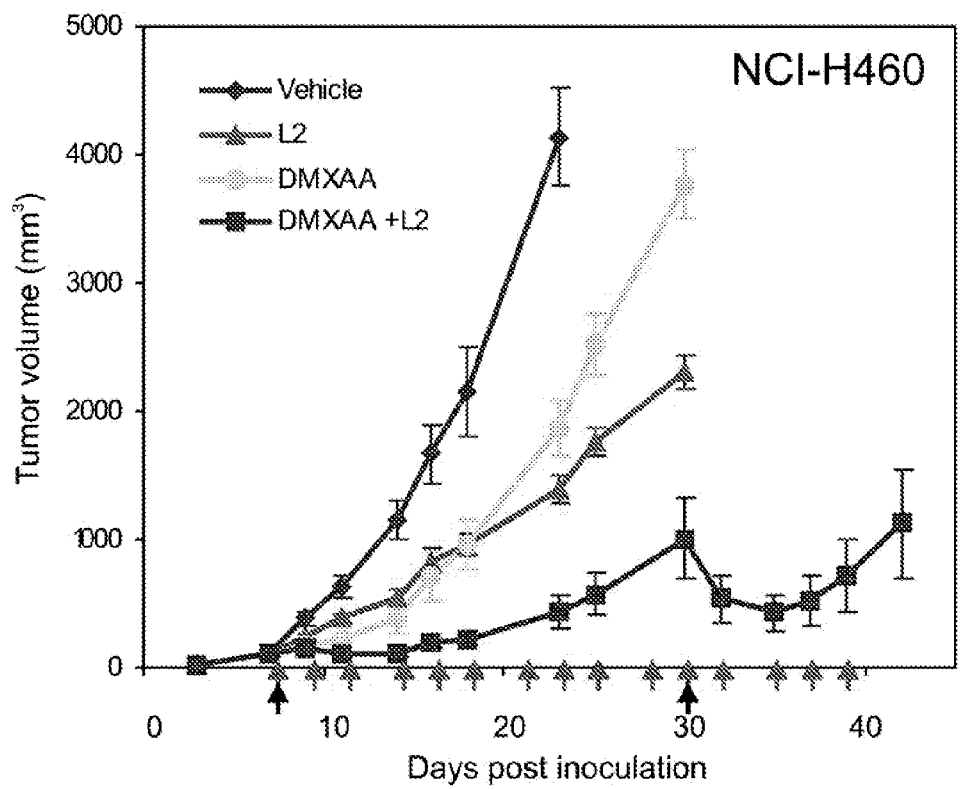
Figure 6D:
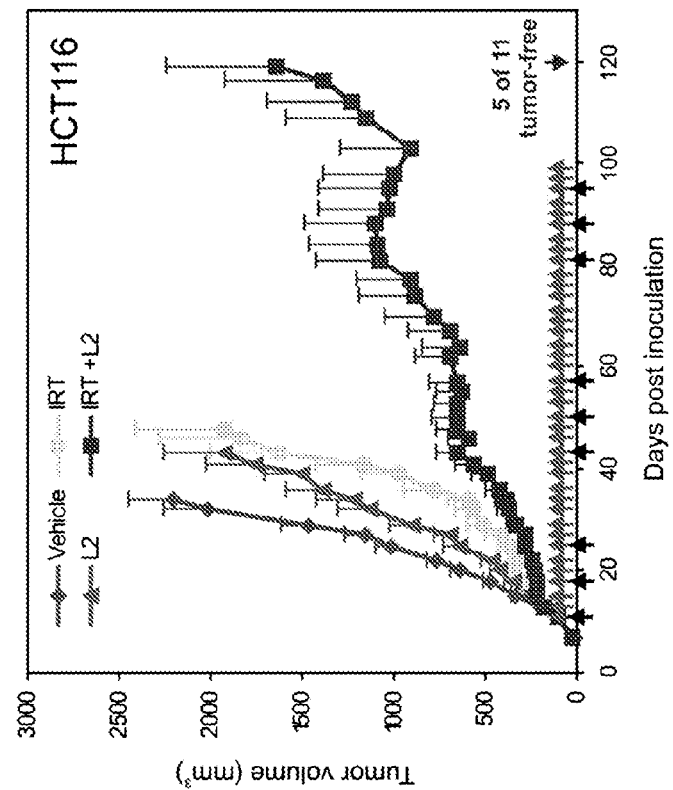
Figure 6C:
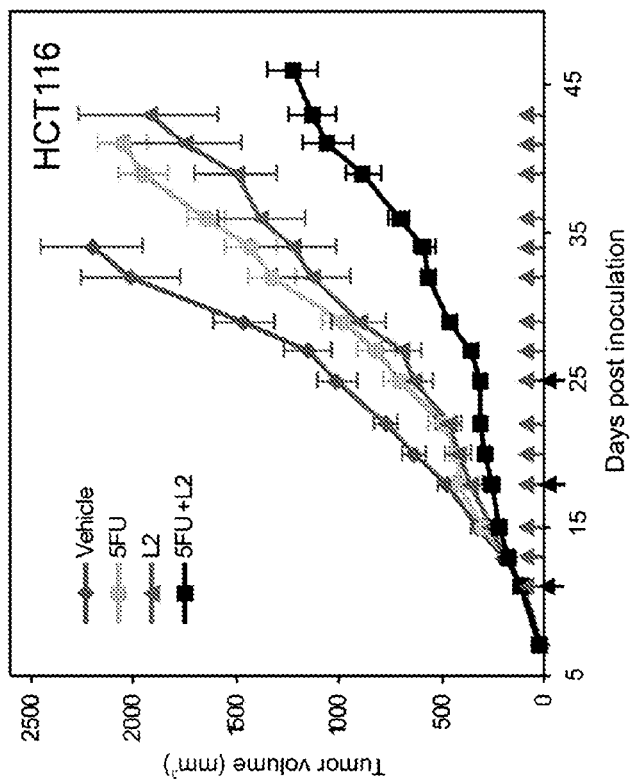
Figure 6F:
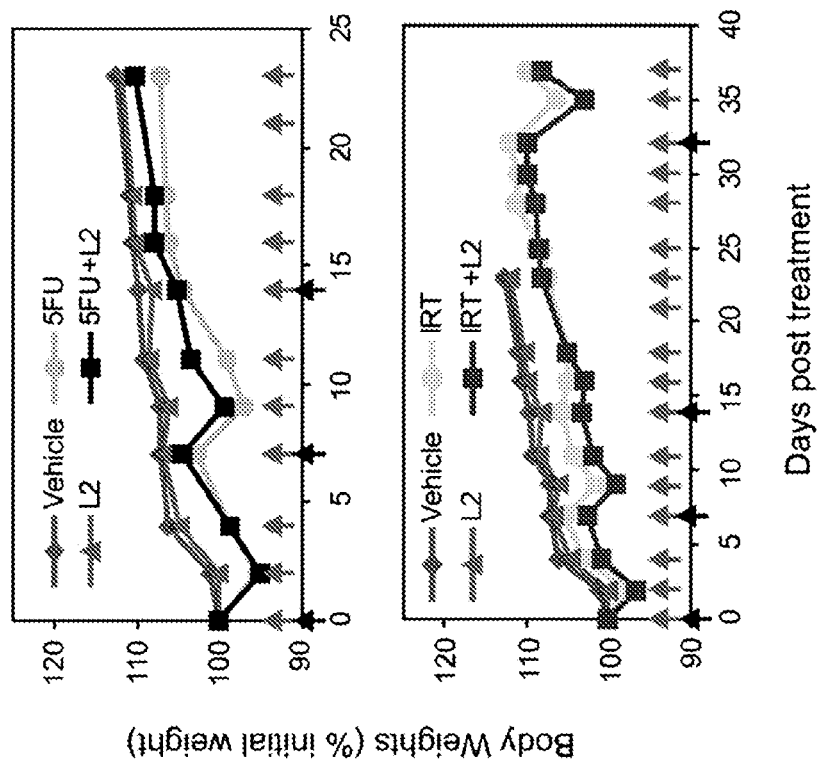
Figure 6E:
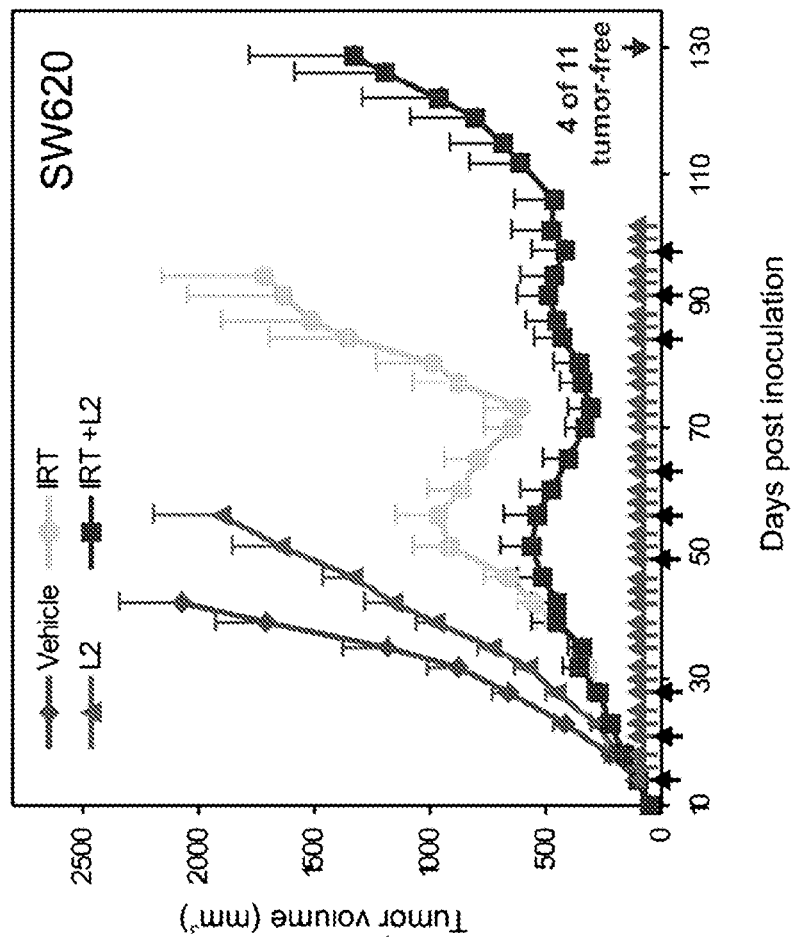

Analysis of body weights, food consumption, serum chemistry and hematological profiles in these combination drug trials failed to reveal a change in toxicity caused by the addition of L2-mIgG2a to the chemotherapeutic agent (FIG. 6F and Table 7). As shown in Table 7, toxicology studies failed to reveal any added toxicity in mice treated with L2-mIgG2a and chemotherapy versus chemotherapy alone. Various toxicological parameters (Table 7A) and organ weights (Table 7B) were unchanged by the addition of 20 mg/kg L2 3× per week to the 5-FU or IRT treatment schedules. Taken together, these studies demonstrate that L2 treatment can enhance the anti-tumor responses of various classes of anti-cancer agents without added toxicity.

TABLE 7

Toxicology studies failed to reveal any added toxicity in mice treated with L2-mIgG2a and chemotherapy versus chemotherapy alone.

| | 5-FU | 5-FU + L2 | IRT | IRT + L2 |
|---|---|---|---|---|
| A. Selected Toxicological Results: Mean ± SD. | | | | |
| Selected Parameters | | | | |
| Food consumption (g/wk) | 29.7 ± 1.9 | 30.6 ± 1.7 | 31.9 ± 2.7 | 28.1 ± 1.8 |
| WBC (K/µL) | 9.4 ± 4.4 | 7.6 ± 4.1 | 4.0 ± 0.9 | 6.6 ± 2.0 |
| RBC (M/µL) | 8.6 ± 0.4 | 9.1 ± 0.6 | 8.1 ± 1.1 | 8.9 ± 0.3 |
| Albumin (g/dL) | 2.7 ± 0.5 | 3.6 ± 0.8 | 3.7 ± 0.4 | 3.0 ± 1.1 |
| ALT (U/L) | 59.2 ± 62.6 | 42.2 ± 7.9 | 48.6 ± 25.7 | 42.2 ± 12.1 |
| Total Bilirubin (mg/dL) | ≤0.3 | ≤0.3 | ≤0.3 | ≤0.3 |
| Creatine (mg/dL) | ≤0.2 | ≤0.2 | ≤0.2 | ≤0.2 |
| Hemoglobin (g/dL) | 12.4 ± 0.4 | 14.4 ± 1.1 | 12.3 ± 1.7 | 12.2 ± 1.3 |
| Total Protein (g/dL) | 6.0 ± 0.6 | 5.9 ± 0.5 | 5.8 ± 0.3 | 5.33 ± 0.5 |
| BUN (mg/dL) | 19.4 ± 1.5 | 18.0 ± 3.7 | 20.6 ± 2.7 | 19.3 ± 3.9 |
| B. Selected Organ Weights (mg): Mean ± SD. | | | | |
| Selected organs | | | | |
| Brain | 460 ± 23 | 464 ± 15 | 464 ± 26 | 460 ± 26 |
| Heart | 126 ± 5 | 134 ± 9 | 134 ± 13 | 130 ± 10 |
| Kidney | 398 ± 27 | 346 ± 27 | 354 ± 53 | 367 ± 49 |
| Liver | 1412 ± 88 | 1168 ± 116 | 1334 ± 226 | 1430 ± 243 |
| Lung | 168 ± 15 | 174 ± 15 | 166 ± 31 | 213 ± 109 |
| Spleen | 170 ± 37 | 144 ± 38 | 134 ± 34 | 273 ± 145 |

Figure 7:
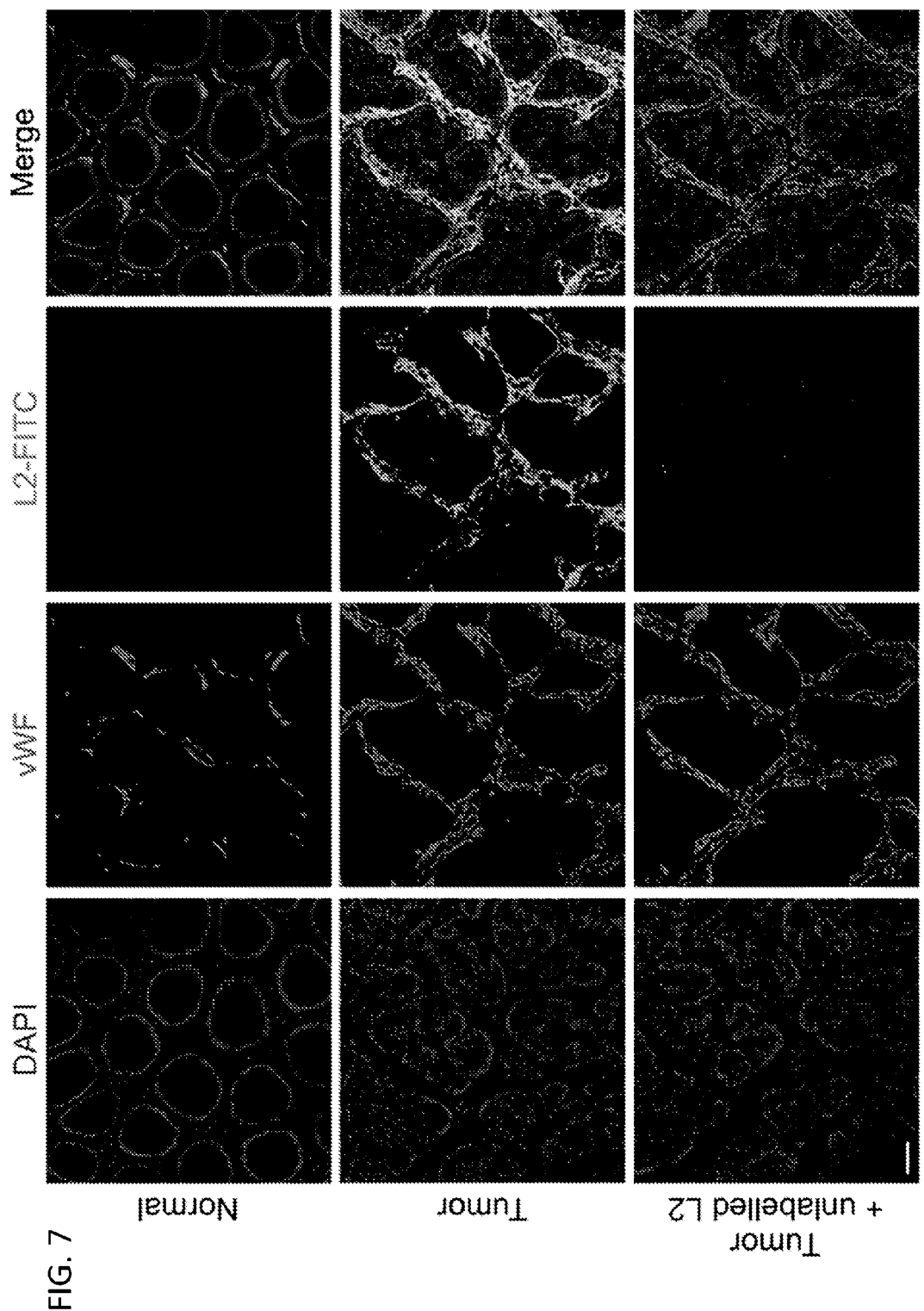
FIG. 7 shows a series of digital images illustrating that L2-mIgG2a anti-TEM8 antibodies bind to the vasculature of human colorectal cancer. Patient matched tumor and normal tissue samples were harvested from colon cancer patients, frozen, sectioned, and processed in parallel for immunofluorescence staining with FITC-conjugated L2-mIgG2a, von Willebrand Factor (vWF) and DAPI, and examined using immunofluorescence microscopy. As a control (bottom panel), some samples were blocked with unlabeled L2-mIgG2a prior to adding the L2-FITC. FITC-conjugated L2-mIgG2a strongly labeled the tumor stroma from human colorectal cancer patients, including vWF positive vasculature, but failed to show any reactivity with normal colonic mucosa. The middle and bottom panel were taken from serial sections. Bar=100 µm.

The L2-mIgG2a anti-TEM8 antibody was developed to recognize both mouse and human TEM8 protein. To further investigate human TEM8 expression patterns in vivo, immunofluorescence staining with L2-mIgG2a of colorectal tumors or adjacent normal colonic mucosa derived from six cases of late stage colorectal cancer, four of which were patient-matched, was tested. For these studies samples were stained with FITC-conjugated L2-mIgG2a in the presence of excess isotype-matched non-specific IgG to block any potential non-specific binding. Although staining was undetectable in all cases of normal colonic mucosa, in each of the tumor samples L2-mIgG2a-FITC strongly labeled the tumor stroma, including vWF positive endothelial cells, vascular pericytes, as well as fibroblast-like cells (FIG. 7). The staining was considered specific because it was completely blocked by the addition of unlabeled L2-mIgG2a. Thus, in tumors from both mice and humans, TEM8 is found in tumor-associated vasculature and perivascular stromal cells.

Example 7

Detection of an Endothelial Cell that Expresses TEM8 in a Human

This example describes particular methods that can be used to detect an endothelial cell that expresses TEM8 in a subject. However, one skilled in the art will appreciate that similar methods can be used. Such detection may be performed, for example, before, during, or after, treating the subject (or combination thereof) with an antibody that specifically binds TEM8 or conjugate thereof A conjugate including a TEM8 specific monoclonal antibody (such, but not limited to, as a TEM8 specific monoclonal antibody including a heavy chain variable region including a H-CDR1, H-CDR2, and H-CDR3 including the amino acid sequence set forth as amino acids 31-37, 52-67 and 100-106 of SEQ ID NO: 1, respectively, and a light chain variable region including a L-CDR1, L-CDR2, and L-CDR3 including the amino acid sequence set forth as amino acids 23-33, 49-55 and 88-96 of SEQ ID NO: 6, respectively) and a detectable marker is administered to the subject. Administration can be achieved by any sufficient method known in the art, but is typically intravenous administration. Typically, the conjugate is administered as a component of a composition including the conjugate and a pharmaceutically acceptable carrier.

An effective amount of the conjugate is administered to the subject. The amount of conjugate administered is sufficient to form a detectable immune complex with TEM8 in the subject. A effective amount can being readily determined by one skilled in the art, for example using routine trials establishing dose response curves. In addition, particular exemplary dosages are provided above. The conjugate can be administered in single or multiple dose delivery or via continuous delivery over an extended time period.

The conjugate utilized for detection of pathological angiogenesis in a subject includes a detectable marker useful for diagnostic imaging. For example, a detectable marker used for magnetic resonance imaging, such as super paramagnetic iron oxide nanocrystals. The particular detectable marker will depend on the particular type of diagnostic imaging utilizes, as will be appreciated by the skilled artisan.

Detection of the endothelial cell that expresses TEM8 is accomplished by detecting the conjugate immobilized in the subject using the diagnostic imaging method corresponding to the detectable marker used. For example, if the detectable marker is super paramagnetic iron oxide nanocrystals, then the diagnostic imaging methods will typically include magnetic resonance imaging.

Example 8

Figure 12:
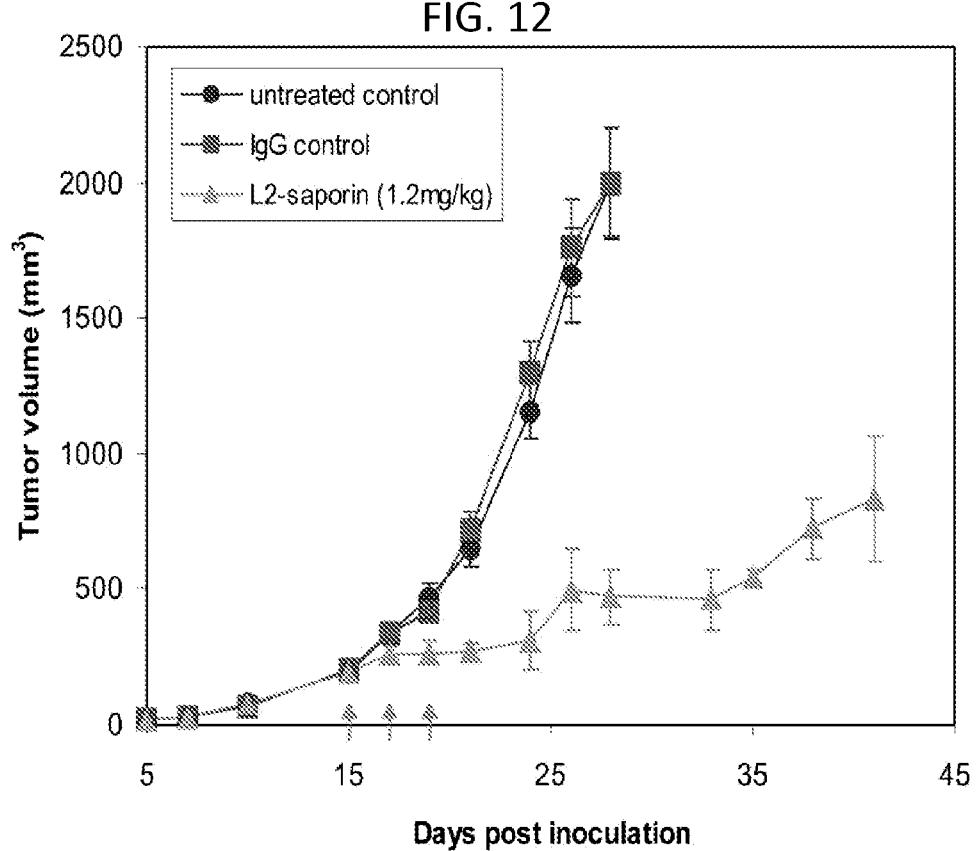
FIG. 12 shows a graph illustrating that the L2-mIgG2a-saporin conjugate inhibits the growth of human tumor xenografts. Nude mice were inoculated subcutaneously with UACC tumor cells and the resulting tumor growth monitored. When tumors reached a size of 200 mm$^3$ (arrows), treatments with 1.2 mg/ml L2-mIgG2a-saporin or non-specific IgG-control were administered three times per week.

Treatment with a Conjugate Including TEM8 Specific Antibody and a Toxin Inhibits Large Tumor Growth in a Mouse Model This example illustrates that a conjugate including the L2-mIgG2a chimeric antibody and saporin inhibits tumor growth in a mouse model. Mice were inoculated with UACC human melanoma xenografts as described above. When tumor size reached 200 mm$^3$, 1.2 mg/kg L2-mIgG2a-saporin or non-specific IgG control was administered; administration was repeated every second day for a total of three treatments. As shown in FIG. 12, treatment with L2-mIgG2a-saporin inhibited tumor growth compared to the control or untreated conditions.

Example 9

TEM8 Functions in Pathological but not Physiological Angiogenesis

This example illustrates that TEM8 functions in pathological, but not physiological angiogenesis.
Quantitative RT-PCR
mRNA was isolated and quantitative RT-PCR performed according to standard methods and as described previously (Cullen et al., Proc. Natl. Acad. Sci. USA., 108:5759-5764, 2011). Eukaryotic translation initiation factor 4H (Eif4h) was selected as the housekeeping gene for normalization because transcriptome studies revealed that this gene was uniformly expressed among diverse cell types (Velculescu et al., Nat. Genet., 23:387-388, 1999) and its use as a housekeeping gene has been validated in earlier studies (Cullen et al., Proc. Natl. Acad. Sci. USA., 108:5759-5764, 2011; Seaman, et al., Cancer cell, 11:539-554, 2007).
Co-Culture and Hypoxia Assays
Human dermal microvascular endothelial cells (HMEC-1 or HMEC) were obtained from the Centers for Disease Control (CDC). HMECs and DLD1 cells ($1 \times 10^6$ each) were co-cultured for 48 hours. DLD1 cells were isolated from the mixtures by magnetic separation using DYNABEADS® bound to the BerEP4 antibody (Epithelial Enrich beads, Invitrogen, Carlsbad, Calif.). HMECs were isolated from the mixtures using streptavidin M-280 DYNABEADS® that had been pre-armed with biotin-labeled goat anti-human VE-cadherin polyclonal antibody (R&D Systems). Following cell lysis, beads were magnetically removed. For the hypoxia experiment, HMECs were incubated in EGM-2 complete medium for 24 hours with either 1% $O_2$ or 150 µM cobalt chloride ($CoCl_2$). Cell lysates were analyzed for TEM8, β-actin and HIF-1α by western blotting as previously described (Cullen et al., Proc. Natl. Acad. Sci. USA., 108:5759-5764, 2011).
Cell Separation Using Magnetic Beads
Endothelial cells were isolated from various tumors, quiescent liver, or regenerating livers using streptavidin M-280 magnetic beads (Invitrogen) that had been pre-armed with biotin labeled anti-CD105 antibodies (eBioscience) as previously described Seaman, et al., Cancer cell, 11:539-554, 2007). All endothelial cells used in the analysis where at least 100-fold enriched in endothelial markers such as VE-cadherin compared to unfractionated control tissues. Myeloid cells and hematopoietic cells were isolated from tumors using streptavidin M-280 beads that had been pre-armed with biotin-linked anti-CD11b and biotin-linked anti-CD45, respectively (eBioscience). For HCT116 and DLD1 tumor cell isolation (FIG. 11B), tumor cells were isolated from dispersed tumors using Epithelial Enrich magnetic DYNA-BEADS® (Invitrogen) that specifically react with the human pan-epithelial EpCAM receptor.

Growth Factor Studies

For the time course studies, HMECs were plated in complete endothelial growth medium (EBM-2 (Lonza) supplemented with 100 ng/ml basic fibroblast growth factor (FGF/FGF2) (PeproTech), 50 ng/ml VEGF$_{165}$ (PeproTech), and 5% fetal bovine serum). 24 hours later (day 0), the medium was replaced with either complete medium, or basal medium (EBM-2 alone). Complete or basal medium was replenished every day to minimize any potential fluctuation in growth factor levels over time and cells were collected for RNA or protein isolation on day 0, 2, 4, 6, 8 and 10. The cells were photographed under brightfield microscopy on day 2, 6 and 10. To determine the effect of VEGF, FGF and serum on TEM8 expression, HMECs were plated in complete medium overnight. 24 hours later, the medium was replaced with basal medium (EBM-2 alone), or basal medium supplemented with either 100 ng/ml FGF, 50 ng/ml VEGF, 5% serum, or all three (i.e. FGF, VEGF and serum). Medium was replenished daily, and cells were collected for RNA and protein analysis 96 hours later. For the VEGF and FGF time course, HMECs maintained in EBM-2 basal medium containing 1% FBS were stimulated with 50 ng/ml VEGF or 100 ng/ml FGF for 0 hours (control), 24 hours, 48 hours or 72 hours.

Results

To obtain further evidence that TEM8 is selectively associated with pathological angiogenesis, the Tem8 expression pattern between tumor endothelial cells (ECs) and adult regenerating liver ECs was compared. Following 70% partial hepatectomy the remaining liver grows rapidly in a highly regulated angiogenesis-dependent process (Seaman, et al., Cancer cell, 11:539-554, 2007; Drixler et al., Ann Surg., 236: 703-711, 2002). In this model, quiescent ECs enter the cell cycle synchronously at around 24 hours post-surgery and cease proliferation about 72 hours later. To examine gene expression, quantitative RT-PCR (QPCR) on ECs purified from tumor xenografts derived from DLD1, HCT116 or LS174T cells, or ECs isolated from quiescent resting liver (0 hours) or regenerating liver taken at various post-surgical time-points (6, 18, 48, 72, or 96 hours) was performed. Although markers of proliferation, such as Ki67, protein regulator of cytokinesis 1 (Prc1), and thymidine kinase (TK) were highly induced in liver ECs by 48 hours post-partial hepatectomy, Tem8 expression levels remained baseline in regenerating liver ECs. In contrast, Tem8 was expressed 32 to 55-fold higher in each of the tumor EC fractions compared to resting liver ECs (FIG. 13A). The peak expression levels of the cell cycle genes in regenerating liver ECs were higher than that in tumor ECs presumably because of the synchronous nature of the proliferating liver EC population.

To investigate whether Tem8 is expressed by tumor associated inflammatory cells, such as CD11b+ myeloid cells or other bone marrow derived cells that have been shown to promote tumor angiogenesis and may be involved in the refractoriness of tumors to VEGF inhibition (Shojaei et al., Nat. Biotechnol., 25: 911-920, 2007), TEM8 expression in CD45+ (pan hematopoietic), CD11b+ (myeloid), and CD105+ (endothelial) cells isolated from tumors was examined. Tem8 was highly expressed only in the endothelial fraction (FIG. 14A). To determine potential tumor microenvironmental factors that induce TEM8 expression on tumor vasculature, cultured human microvascular endothelial cells (HMECs) were examined in response to several conditions. Neither co-culture with tumor cells nor exposure to hypoxia induced TEM8 (FIGS. 14B and 14C). However, upon serum starvation, TEM8 levels steadily increased in these cells which normally express low endogenous TEM8 levels, resulting in a 4-fold increase in TEM8 mRNA (FIG. 13B) and a 5-fold increase in TEM8 protein (FIG. 13C) by day 10. In contrast, TEM8 levels remained low in cells maintained in complete medium, and the slight increase in TEM8 expression noted at later time points (FIGS. 13B and 13C) may have been due to rapid growth factor depletion caused by increasing cell numbers (FIG. 13D, top panel). The increase in TEM8 expression upon growth factor starvation was not influenced by the amount of cell-cell contact based on comparisons of sparse versus confluent cells wherein the cell numbers were held constant but surface area altered. Importantly, TEM8 elevation in growth factor starved cells could be inhibited by FGF, VEGF or serum treatment, and the combination of all three resulted in the lowest TEM8 levels (FIGS. 13E and 13F and 14D). Thus, TEM8 may be part of a compensatory angiogenic or survival pathway that is activated, at least in part, by insufficient local angiogenic growth factors.

Example 10

Treatment of Cancer in a Human

This example describes a particular method that can be used to treat a primary or metastatic tumor in humans by administration of one or more antibodies that specifically bind TEM8 or a conjugate thereof. Although particular methods, dosages, and modes of administrations are provided, one skilled in the art will appreciate that variations can be made without substantially affecting the treatment.

Human patients are treated intravenously with at least 1 µg (such as 0.001-1000 mg) of one or more antibodies that specifically bind TEM8 or conjugate thereof, such as, but not limited to, an antibody including a heavy chain variable region including a H-CDR 1, H-CDR2, and H-CDR3 including the amino acid sequence set forth as amino acids 31-37, 52-67 and 100-106 of SEQ ID NO: 1, respectively, and a light chain variable region including a L-CDR1, L-CDR2, and L-CDR3 including the amino acid sequence set forth as amino acids 23-33, 49-55 and 88-96 of SEQ ID NO: 6, respectively, for example for a period of at least 1 day, 1 week, 1 month, at least 2 months, at least 3 months, at least 6 months, at least one year, at least 2 years, or at least five years or more or less time. Administration of the conjugate can be used in conjunction with normal cancer therapy (for example rather than replacing the therapy). Thus, the conjugate can be added to the usual and customary anti-angiogenic, chemotherapy, surgery, radiation treatments (or combination thereof) conventionally used for the particular tumor type. Administration of the conjugates can be continued after customary therapy was stopped and can be taken long term (for example over a period of months or years).

Briefly, the method includes screening subjects to determine if they have a tumor, such as a primary or metastatic tumor. Subjects having a tumor are selected. In a clinical trial, half of the subjects would follow the established protocol for treatment of the tumor (such as a normal anti-angiogenic/chemotherapy/radiotherapy/surgery regimen). The other half would follow the established protocol for treatment of the tumor (such as a normal anti-angiogenic/chemotherapy/radiotherapy/surgery regimen) in combination with administration of the antibodies or conjugates described above. In some examples, the tumor is surgically excised (in whole or part) prior to treatment with the conjugate.

Screening Subjects

The subject is first screened to determine if they have a tumor. Examples of methods that can be used to screen for tumors include a combination of ultrasound, tissue biopsy, or detection of tumor-associated vasculature. However, such pre-screening is not required prior to administration of the antibodies or conjugates disclosed herein.

Pre-Treatment of Subjects

The subject is treated prior to administration of an antibody that specifically binds TEM8 or conjugate thereof. However, such pre-treatment is not always required, and can be determined by a skilled clinician. For example, the tumor can be surgically excised (in total or in part) prior to administration of one or more antibodies or conjugates. In addition, the subject can be treated with an established protocol for treatment of the particular tumor present (such as a normal anti-angiogenesis/chemotherapy/radiotherapy regimen).

Administration

Administration can be achieved by any sufficient method known in the art, but is typically intravenous administration. Typically, the antibody or conjugate is administered as a component of a composition including the antibody or conjugate and a pharmaceutically acceptable carrier.

A therapeutically effective amount of the antibody or conjugate is administered to the subject. The amount of antibody or conjugate administered is sufficient to treat a subject having a tumor. A therapeutically effective amount can being readily determined by one skilled in the art, for example using routine trials establishing dose response curves. In addition, particular exemplary dosages are provided above. The conjugate can be administered in a single dose delivery, via continuous delivery over an extended time period, in a repeated administration protocol (for example, by a daily, weekly, or monthly repeated administration protocol).

Assessment

Following the administration of one or more therapies, subjects having a tumor can be monitored for tumor treatment, such as regression or reduction in tumor burden (for example, reduction in metastatic lesions). In particular examples, subjects are analyzed one or more times, starting seven days following treatment Subjects can be monitored using any method known in the art. For example, diagnostic imaging can be used (such as x-rays, CT scans, MRIs, ultrasound, fiber optic examination, and laparoscopic examination), as well as analysis of biological samples from the subject (for example analysis of blood, tissue biopsy, or other biological samples), such as analysis of the type of cells present, or analysis for a particular tumor marker. In one example, if the subject has a metastatic tumor, assessment can be made using ultrasound, MRI, or CAT scans and analysis of the type of cells contained in a tissue biopsy.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. An isolated monoclonal antibody or antigen binding fragment thereof, comprising a heavy chain variable region comprising a heavy chain complementarity determining region (HCDR)1, a HCDR2, and a HCDR3, and a light chain variable region comprising a light chain complementarity determining region (LCDR)1, a LCDR2, and a L-CDR3, of the amino acid sequences set forth as one of:
   (a) SEQ ID NO: 1 and SEQ ID NO: 6, respectively (L2);
   (b) SEQ ID NO: 2 and SEQ ID NO: 7, respectively (L1);
   (c) SEQ ID NO: 3 and SEQ ID NO: 8, respectively (L3);
   (d) SEQ ID NO: 4 and SEQ ID NO: 9, respectively (L5); or
   (e) SEQ ID NO: 5 and SEQ ID NO: 10, respectively (1D2); and
   wherein the monoclonal antibody or antigen binding fragment specifically binds to TEM8.

2. The antibody or antigen binding fragment of claim 1, wherein:
   (a) the heavy chain variable region comprises the amino acid sequence set forth as amino acids 31-37, 52-67, and 100-106 of SEQ ID NO: 1, and the light chain variable region comprises the amino acid sequence set forth as amino acids 23-33, 49-55, and 88-96 of SEQ ID NO: 6;
   (b) the heavy chain variable region comprises the amino acid sequence set forth as amino acids 31-35, 50-65, and 96-102 of SEQ ID NO: 2, and the light chain variable region comprises the amino acid sequence set forth as amino acids 23-33, 49-55, and 88-98 of SEQ ID NO: 7;
   (c) the heavy chain variable region comprises the amino acid sequence set forth as amino acids 31-37, 52-69, and 102-110 of SEQ ID NO: 3, and the light chain variable region comprises the amino acid sequence set forth as amino acids 23-33, 49-55, and 88-96 of SEQ ID NO: 8;
   (d) the heavy chain variable region comprises the amino acid sequence set forth as amino acids 31-35, 50-66, and 99-106 of SEQ ID NO: 4, and the light chain variable region comprises the amino acid sequence set forth as amino acids 23-33, 49-55, and 88-98 of SEQ ID NO: 9; or
   (e) the heavy chain variable region comprises the amino acid sequence set forth as amino acids 31-37, 52-67, and 100-107 of SEQ ID NO: 5, and the light chain variable region comprises the amino acid sequence set forth as amino acids 23-33, 49-55, and 88-98 of SEQ ID NO: 10.

3. The antibody or antigen binding fragment of claim 1, wherein
   the heavy chain variable region comprises the amino acid sequence set forth as SEQ ID NO: 1, SEQ ID NO: 2, SEQ ID NO: 3, SEQ ID NO: 4, or SEQ ID NO: 5; or
   the light chain variable region comprises the amino acid sequence set forth as SEQ ID NO: 6, SEQ ID NO: 7, SEQ ID NO: 8, SEQ ID NO: 9, or SEQ ID NO: 10.

4. The antibody or antigen binding fragment of claim 1, wherein the heavy and light chain variable regions comprise the amino acid sequences set forth as one of:
   (a) SEQ ID NO: 1 and SEQ ID NO: 6, respectively;
   (b) SEQ ID NO: 2 and SEQ ID NO: 7, respectively;
   (c) SEQ ID NO: 3 and SEQ ID NO: 8, respectively;
   (d) SEQ ID NO: 4 and SEQ ID NO: 9, respectively; or
   (e) SEQ ID NO: 5 and SEQ ID NO: 10, respectively.

5. The antibody or antigen binding fragment of claim 1, comprising a human framework region.

6. The antibody of claim 1, wherein the antibody is an IgG.

7. The antibody or antigen binding fragment of claim 1, wherein the antibody or antigen binding fragment is neutralizing.

8. The antigen binding fragment of claim 1.

9. The antigen binding fragment of claim 8, wherein the antigen binding fragment is a Fv, Fab, F(ab')$_2$, scFV or a scFV$_2$ fragment.

10. The antibody or antigen binding fragment of claim 1, conjugated to an effector molecule or a detectable marker.

11. The antibody or antigen binding fragment of claim 10, wherein the effector molecule is an anti-angiogenic agent or a chemotherapeutic agent.

12. The antibody or antigen binding fragment of claim 10, wherein the detectable marker is a fluorescent, enzymatic, heavy metal or radioactive marker.

13. The antibody or antigen binding fragment of claim 10, wherein the chemotherapeutic agent is a toxin.

14. The antibody or antigen binding fragment of claim 13, wherein the toxin is a maytansinoid toxin or an auristatin toxin.

15. The antibody or antigen binding fragment of claim 14, wherein
the maytansinoid toxin is DM1; or
the auristatin toxin is Monomethyl Auristatin E (MMAE) or Monomethyl Auristatin F (MMAF).

16. The antibody or antigen binding fragment thereof of claim 10, wherein the isolated monoclonal antibody or antigen binding fragment is conjugated to the effector molecule by a cleavable linker.

17. A composition comprising an effective amount of the antibody or antigen binding fragment of claim 1 and a pharmaceutically acceptable carrier.

18. An isolated nucleic acid molecule encoding the antibody or antigen binding fragment of claim 1.

19. A vector comprising the nucleic acid molecule of claim 18.

20. A host cell, comprising the nucleic acid molecule of claim 18.

21. A method of treating a subject with a TEM8-expressing tumor, comprising:
administering to the subject a therapeutically effective amount of the antibody or antigen binding fragment of claim 1 under conditions sufficient to form an immune complex, wherein formation of the immune complex treats the tumor in the subject.

22. The method of claim 21, further comprising selecting the subject with the tumor.

23. The method of claim 22, wherein selecting the subject comprises detecting an endothelial cell that expresses TEM8 in the subject.

24. The method of claim 21, further comprising administering to the subject a therapeutically effective amount of an anti-angiogenic agent or a chemotherapeutic agent.

25. The method of claim 24, wherein the anti-angiogenic agent comprises bevacizumab.

26. The method of claim 21, wherein the tumor is breast cancer, colorectal cancer, lung cancer or skin cancer.

27. The method of claim 21, wherein treating the tumor comprises a reduction in tumor burden.

28. The method of claim 21, wherein the isolated monoclonal antibody or antigen binding fragment is conjugated to a chemotherapeutic agent.

29. The method of claim 28, wherein the chemotherapeutic agent is a maytansinoid toxin or an auristatin toxin.

30. A method of detecting an endothelial cell expressing TEM8 in a subject, comprising:
contacting an endothelial cell from the subject with an effective amount of the antibody or antigen binding fragment of claim 1 under conditions sufficient to form an immune complex; and
detecting the immune complex on the endothelial cell from the subject, wherein the presence of the immune complex on the endothelial cell from the subject detects the endothelial cell expressing TEM8 in the subject.

31. The method of claim 30, wherein the contacting is in vivo.

32. The method of claim 30, wherein the contacting is in vitro.

33. The method of claim 30, wherein detecting the presence of an endothelial cell expressing TEM8 in the subject detects pathological angiogenesis in the subject.

34. The method of claim 30, wherein the endothelial cell is in a biological sample from the subject.

35. A method of decreasing the binding of Anthrax protective antigen to a cell, comprising:
contacting the cell with an effective amount of the antibody or antigen binding fragment of claim 1 under conditions sufficient to form an immune complex, wherein formation of the immune complex decreases the binding of Anthrax protective antigen to the cell.

36. The method of claim 35, wherein contacting the cell with an effective amount of the monoclonal antibody or antigen binding fragment comprises administering a therapeutically effective amount of the monoclonal antibody or antigen binding fragment to a subject.

37. A kit for detecting pathological angiogenesis in a subject, treating a tumor in a subject, or decreasing the binding of Anthrax protective antigen to a cell, comprising a container comprising the antibody or antigen binding fragment of claim 1 and instructions for using the kit.

* * * * *

UNITED STATES PATENT AND TRADEMARK OFFICE
CERTIFICATE OF CORRECTION

PATENT NO. : 9,181,340 B2
APPLICATION NO. : 14/126372
DATED : November 10, 2015
INVENTOR(S) : St. Croix et al.

It is certified that error appears in the above-identified patent and that said Letters Patent is hereby corrected as shown below:

On the Title Page

Left Column, at Item (72) Inventors: "Brad St. Croix, Frederick, MD (US);"
Should read -- Bradley St. Croix, Frederick, MD (US); --

Signed and Sealed this
Twenty-first Day of November, 2023

Katherine Kelly Vidal
*Director of the United States Patent and Trademark Office*